US012534434B2

(12) United States Patent
Takeda et al.

(10) Patent No.: US 12,534,434 B2
(45) Date of Patent: Jan. 27, 2026

(54) ORGANIC COMPOUND, LIGHT-EMITTING ELEMENT, LIGHT-EMITTING DEVICE, ELECTRONIC APPARATUS, AND LIGHTING DEVICE

(71) Applicant: Semiconductor Energy Laboratory Co., Ltd., Kanagawa-ken (JP)

(72) Inventors: Kyoko Takeda, Kanagawa (JP); Harue Osaka, Kanagawa (JP); Satoshi Seo, Kanagawa (JP); Tsunenori Suzuki, Kanagawa (JP); Naoaki Hashimoto, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 471 days.

(21) Appl. No.: 16/636,732

(22) PCT Filed: Jul. 30, 2018

(86) PCT No.: PCT/IB2018/055660
§ 371 (c)(1),
(2) Date: Feb. 5, 2020

(87) PCT Pub. No.: WO2019/030604
PCT Pub. Date: Feb. 14, 2019

(65) Prior Publication Data

US 2020/0216428 A1 Jul. 9, 2020

(30) Foreign Application Priority Data

Aug. 10, 2017 (JP) ................................. 2017-155324

(51) Int. Cl.
*C07D 209/82* (2006.01)
*C07D 407/14* (2006.01)
(Continued)

(52) U.S. Cl.
CPC ......... *C07D 209/82* (2013.01); *C07D 407/14* (2013.01); *H10K 85/636* (2023.02);
(Continued)

(58) Field of Classification Search
CPC .. C07D 407/14; C07D 209/82; C07D 209/80; C07D 405/14; H01L 51/0061;
(Continued)

(56) References Cited

U.S. PATENT DOCUMENTS 6,660,410 B2 * 12/2003 Hosokawa ........... H10K 85/636 313/506
8,986,857 B2 3/2015 Suzuki et al.
(Continued)

FOREIGN PATENT DOCUMENTS

CN 103052624 A 4/2013
CN 105103327 A 11/2015
(Continued)

OTHER PUBLICATIONS

Tetradhedron, 72, (2016), pp. 7081-7092. (Year: 2016).*
(Continued)

*Primary Examiner* — Dawn L Garrett
(74) *Attorney, Agent, or Firm* — Husch Blackwell LLP

(57) ABSTRACT

A novel compound is provided. In addition, a light-emitting element with high emission efficiency and a long lifetime is provided. An organic compound represented by General Formula (G0), including a dibenzocarbazole skeleton and two amine skeletons. In General Formula (G0), A represents a substituted or unsubstituted dibenzocarbazole skeleton. The dibenzocarbazole skeleton and the amine skeletons may be bonded to each other through or not through an arylene group. In addition, a light-emitting element including the compound is provided.

9 Claims, 46 Drawing Sheets

(51) Int. Cl.
*H10K 50/11* (2023.01)
*H10K 85/60* (2023.01)

(52) U.S. Cl.
CPC ..... *H10K 85/6572* (2023.02); *H10K 85/6574* (2023.02); *H10K 50/11* (2023.02)

(58) Field of Classification Search
CPC ............. H01L 51/0072; H01L 51/0073; H01L 51/5012; H01L 27/32; H01L 51/5024; H01L 51/50; C09K 11/06; G02B 5/20; G09F 9/00; G09F 9/30; H05B 33/12; H10K 85/636; H10K 85/6572; H10K 85/6574; H10K 50/11; H10K 50/12; H10K 59/00; H10K 50/00; Y02E 10/549
See application file for complete search history.

(56) References Cited

U.S. PATENT DOCUMENTS

| | | | |
|---|---|---|---|
| 9,240,558 B2 | 1/2016 | Suzuki et al. | |
| 9,905,782 B2 | 2/2018 | Inoue et al. | |
| 10,193,086 B2 | 1/2019 | Inoue et al. | |
| 10,207,992 B2 | 2/2019 | Suzuki et al. | |
| 10,439,146 B2 | 10/2019 | Ogita et al. | |
| 10,573,820 B2 | 2/2020 | So et al. | |
| 10,700,291 B2 | 6/2020 | Inoue et al. | |
| 10,886,474 B2 | 1/2021 | Moon et al. | |
| 2003/0170491 A1* | 9/2003 | Liao | H05B 45/60 257/88 |
| 2008/0122344 A1 | 5/2008 | Shin et al. | |
| 2014/0319510 A1* | 10/2014 | Kageyama | H10K 85/633 564/429 |
| 2017/0012212 A1 | 1/2017 | Lee et al. | |
| 2017/0062728 A1 | 3/2017 | Mun et al. | |
| 2017/0250346 A1 | 8/2017 | Seo et al. | |
| 2017/0294590 A1* | 10/2017 | Moon | C07D 405/04 |
| 2018/0182972 A1 | 6/2018 | So et al. | |
| 2019/0341551 A1 | 11/2019 | Ogita et al. | |
| 2020/0131124 A1* | 4/2020 | Suh | H01L 51/0073 |
| 2021/0013428 A1 | 1/2021 | Inoue et al. | |

FOREIGN PATENT DOCUMENTS

| | | | | |
|---|---|---|---|---|
| CN | 106187859 A | 12/2016 | | |
| CN | 106631981 A | 5/2017 | | |
| CN | 107787314 A | 3/2018 | | |
| JP | 2002-193952 A | 7/2002 | | |
| JP | 2012-077069 A | 4/2012 | | |
| JP | 2017-036267 A | 2/2017 | | |
| KR | 2008-0047210 A | 5/2008 | | |
| KR | 2010-0108924 A | 10/2010 | | |
| KR | 2015-0004099 A | 1/2015 | | |
| KR | 20150098062 A | * | 8/2015 | C07D 209/56 |
| KR | 2016-0013692 A | 2/2016 | | |
| KR | 2016-0027940 A | 3/2016 | | |
| KR | 2016-0037107 A | 4/2016 | | |
| KR | 20160059609 A | * | 5/2016 | |
| KR | 2016-0146351 A | 12/2016 | | |
| KR | 10-1740858 B1 | 5/2017 | | |
| KR | 2017-0056425 A | 5/2017 | | |
| WO | WO 2010/114264 A2 | 10/2010 | | |
| WO | WO 2013/015144 A1 | 1/2013 | | |
| WO | WO 2014/157599 A1 | 10/2014 | | |
| WO | WO 2016/048109 A1 | 3/2016 | | |
| WO | WO 2016/200070 A2 | 12/2016 | | |
| WO | WO-2019022562 A1 | * | 1/2019 | C07D 209/56 |

OTHER PUBLICATIONS

Machine translation for KR 20150004099 A (publication date: Jan. 2015) (Year: 2015).*

Machine translation of KR 20160059609 A (publication date May 2016). (Year: 2016).*

Justin Thomas, K. R., Lin, J. T., Tao, Y. T., & Ko, C. W. (2001). Light-emitting carbazole derivatives: potential electroluminescent materials. Journal of the American Chemical Society, 123(38), 9404-9411. (Year: 2001).*

International Search Report re Application No. PCT/IB2018/055660, dated Oct. 23, 2018.

Written Opinion re Application No. PCT/IB2018/055660, dated Oct. 23, 2018.

Chinese Office Action (Application No. 201880051352.6) Dated Oct. 25, 2022.

* cited by examiner

ORGANIC COMPOUND, LIGHT-EMITTING ELEMENT, LIGHT-EMITTING DEVICE, ELECTRONIC APPARATUS, AND LIGHTING DEVICE

This application is a 371 of international application PCT/IB2018/055660 filed on Jul. 30, 2018 which is incorporated herein by reference.

TECHNICAL FIELD

One embodiment of the present invention relates to a novel organic compound. Specifically, one embodiment of the present invention relates to an organic compound having a dibenzocarbazole skeleton and a diamine skeleton. In addition, one embodiment of the present invention relates to a light-emitting element, a light-emitting device, an electronic apparatus, and a lighting device each of which includes the organic compound.

Note that one embodiment of the present invention is not limited to the above technical field. One embodiment of the present invention relates to an object, a method, or a manufacturing method. The present invention also relates to a process, a machine, manufacture, or a composition of matter. In particular, one embodiment of the present invention relates to a semiconductor device, a light-emitting device, a display device, a lighting device, a light-emitting element, or a manufacturing method thereof. One embodiment of the present invention relates to a novel method for synthesizing an organic compound having a dibenzocarbazole skeleton and a diamine skeleton. Thus, specific examples of one embodiment of the present invention disclosed in this specification include manufacturing methods of a light-emitting element, a light-emitting device, a display device, an electronic apparatus, and a lighting device, each of which includes the organic compound.

BACKGROUND ART

Light-emitting elements (organic EL elements) that include organic compounds and utilize electroluminescence (EL) have been put to more practical use. In general, such light-emitting elements each have a structure in which an organic compound layer containing a light-emitting material (an EL layer) is interposed between a pair of electrodes. Carriers are injected by application of voltage to this element, and recombination energy of the carriers is used, whereby light emission can be obtained from the light-emitting material.

Such light-emitting elements are of self-light-emitting type, and have advantages such as high visibility and no need for backlight when used for pixels of a display; accordingly, the light-emitting elements are suitable as flat panel display elements. Displays including such light-emitting elements are also highly advantageous in that they can be thin and lightweight. Moreover, such a light-emitting element also has a feature that response speed is extremely fast.

Since light-emitting layers of such light-emitting elements can be successively formed two-dimensionally, planar light emission can be obtained. This is a feature difficult to obtain with point light sources typified by incandescent lamps and LEDs or linear light sources typified by fluorescent lamps. Furthermore, light emission from an organic compound can be light emission which does not include UV light by selecting a material; thus, the light-emitting elements also have great potential as planar light sources used in lighting devices and the like.

Displays and lighting devices including organic EL elements can be suitably used for a variety of electronic apparatuses as described above; thus, research and development of light-emitting elements have progressed in seeking for higher efficiency or longer element lifetimes. White light is required for the above display and lighting device; therefore, three colors of red (R), green (G), and blue (B) are mixed. Here, a fluorescent material is used for blue light because a blue phosphorescent material at present is insufficient in color purity and reliability. Thus, blue fluorescent materials with high color purity, reliability, and emission efficiency have been actively developed (e.g., Patent Document 1 and Patent Document 2).

REFERENCE

Patent Document

[Patent Document 1] Japanese Published Patent Application No. 2012-77069

[Patent Document 2] Japanese Published Patent Application No. 2002-193952

SUMMARY OF THE INVENTION

Problems to be Solved by the Invention

Along with the demand for higher performance of electronic apparatuses and lighting devices, a variety of properties is required for light-emitting elements, and in particular, a blue fluorescent material with high color purity is desired. In addition, higher emission efficiency and higher reliability are required for a material used for a light-emitting element.

Thus, an object of one embodiment of the present invention is to provide a novel organic compound. In particular, an object is to provide a novel organic compound exhibiting blue fluorescence. Another object of one embodiment of the present invention is to provide a novel organic compound having an aromatic amine skeleton. Another object of one embodiment of the present invention is to provide a light-emitting element with high color purity. Another object of one embodiment of the present invention is to provide a light-emitting element having a long lifetime. Another object of one embodiment of the present invention is to provide a light-emitting element having high emission efficiency. Another object of one embodiment of the present invention is to provide a light-emitting element with low driving voltage.

Another object of one embodiment of the present invention is to provide a light-emitting element, a light-emitting device, and an electronic apparatus each with high reliability. Another object of one embodiment of the present invention is to provide a light-emitting element, a light-emitting device, and an electronic apparatus each having low power consumption.

Note that the descriptions of these objects do not disturb the existence of other objects. In one embodiment of the present invention, there is no need to achieve all of these objects. Other objects will be apparent from the description of the specification, the drawings, the claims, and the like, and other objects can be derived from the description of the specification, the drawings, the claims, and the like.

One embodiment of the present invention is an organic compound represented by General Formula (G0) below.

[Chemical Formula 1]

(G0)

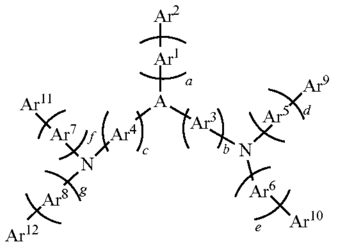

In General Formula (G0), A represents a substituted or unsubstituted dibenzocarbazole skeleton; $Ar^1$ is bonded to the N-position of the dibenzocarbazole skeleton; each of $Ar^1$ and $Ar^3$ to $Ar^8$ independently represents a substituted or unsubstituted arylene group having 6 to 25 carbon atoms; $Ar^2$ represents a substituted or unsubstituted aryl group having 6 to 25 carbon atoms; each of a, b, c, d, e, f and g independently represents an integer of 0 to 3; and each of $Ar^9$ to $Ar^{12}$ independently represents a substituted or unsubstituted aryl group having 6 to 100 carbon atoms or a substituted or unsubstituted heteroaryl group having 3 to 100 carbon atoms.

In the above structure, the dibenzocarbazole skeleton is preferably a dibenzo[c,g]carbazole skeleton.

In the above structure, $Ar^3$ is preferably bonded to either one of two naphthalene skeletons included in the dibenzocarbazole skeleton, and $Ar^4$ is preferably bonded to the other naphthalene skeleton.

Another embodiment of the present invention is an organic compound represented by General Formula (G1) below.

[Chemical Formula 2]

(G1)

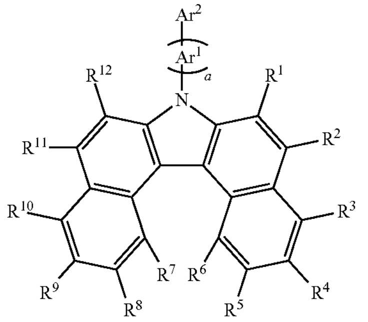

In General Formula (G1), $Ar^1$ represents a substituted or unsubstituted arylene group having 6 to 25 carbon atoms; $Ar^2$ represents a substituted or unsubstituted aryl group having 6 to 25 carbon atoms; any one of $R^1$ to $R^6$ is a substituent represented by General Formula (G1-1); any one of $R^7$ to $R^{12}$ is a substituent represented by General Formula (G1-2); each of the other $R^1$ to $R^{12}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms; and a represents an integer of 0 to 3.

[Chemical Formula 3]

(G1-1)

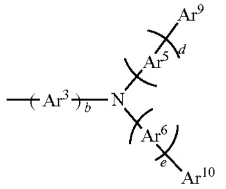

(G1-2)

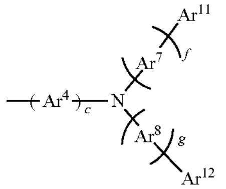

In General Formulae (G1-1) and (G1-2), each of $Ar^3$ to $Ar^8$ independently represents a substituted or unsubstituted arylene group having 6 to 25 carbon atoms; each of b, c, d, e, f and g independently represents an integer of 0 to 3; and each of $Ar^5$ to $Ar^8$ independently represents a substituted or unsubstituted aryl group having 6 to 100 carbon atoms or a substituted or unsubstituted heteroaryl group having 3 to 100 carbon atoms.

Another embodiment of the present invention is an organic compound represented by General Formula (G2) below.

[Chemical Formula 4]

(G2)

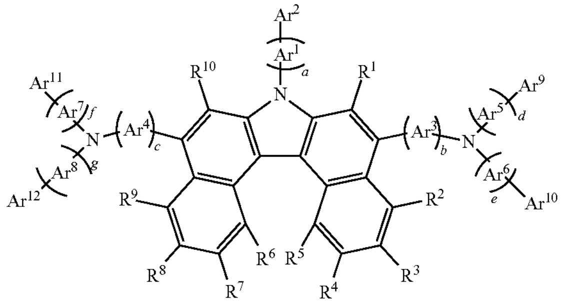

In General Formula (G2), each of $Ar^1$ and $Ar^3$ to $Ar^8$ independently represents a substituted or unsubstituted arylene group having 6 to 25 carbon atoms; $Ar^2$ represents a substituted or unsubstituted aryl group having 6 to 25 carbon atoms; each of a, b, c, d, e, f and g independently represents an integer of 0 to 3; each of $Ar^9$ to $Ar^{12}$ independently represents a substituted or unsubstituted aryl group having 6 to 100 carbon atoms or a substituted or unsubstituted heteroaryl group having 3 to 100 carbon atoms; and each of $R^1$ to $R^{10}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

Another embodiment of the present invention is an organic compound represented by General Formula (G3) below.

[Chemical Formula 5]

(G3)

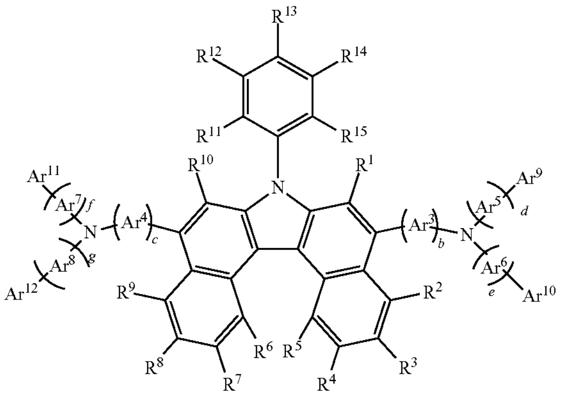

In General Formula (G3), each of $Ar^3$ to $Ar^8$ independently represents a substituted or unsubstituted arylene group having 6 to 25 carbon atoms; each of b, c, d, e, f and g independently represents an integer of 0 to 3; each of $Ar^9$ to $Ar^{12}$ independently represents a substituted or unsubstituted aryl group having 6 to 100 carbon atoms or a substituted or unsubstituted heteroaryl group having 3 to 100 carbon atoms; and each of $R^1$ to $R^{15}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

In the above structure, each of b and c is preferably 0.

It is preferable that, in the above structure, each of $Ar^9$ and $Ar^{11}$ be independently any one of a substituted or unsubstituted phenyl group, biphenyl group, naphthyl group, triphenylyl group, fluorenyl group, carbazolyl group, dibenzothiophenyl group, dibenzofuranyl group, benzofluorenyl group, benzocarbazolyl group, naphthobenzothiophenyl group, naphthobenzofuranyl group, dibenzofluorenyl group, dibenzocarbazolyl group, dinaphthothithiophenyl group, and dinaphthofuranyl group.

An organic compound in the above structure, in which each of $Ar^{10}$ and $Ar^{12}$ is independently any one of substituents represented by General Formulae (Ht-1) to (Ht-7).

[Chemical Formula 6]

(Ht-1)

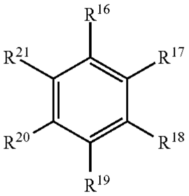

-continued (Ht-2)

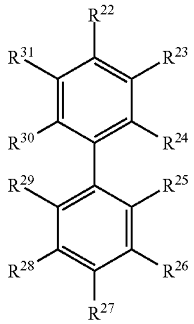

(Ht-3)

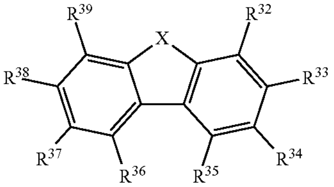

(Ht-4)

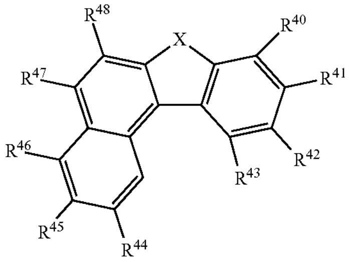

(Ht-5)

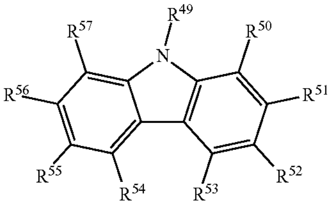

(Ht-6)

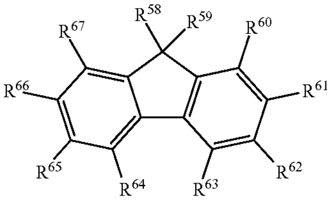

(Ht-7)

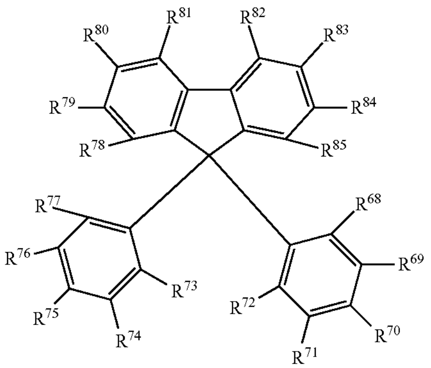

In General Formulae (Ht-3) and (Ht-4), X represents oxygen or sulfur, and, in General Formulae (Ht-1) to (Ht-7), any one of $R^{16}$ to $R^{21}$, any one of $R^{22}$ to $R^{31}$, any one of $R^{32}$ to $R^{39}$, any one of $R^{40}$ to $R^{48}$, any one of $R^{49}$ to $R^{57}$, any one of $R^{58}$ to $R^{67}$, and any one of $R^{68}$ to $R^{77}$ each represent a single bond to $Ar^5$ or $Ar^8$; and the other $R^{16}$ to $R^{85}$ each independently represent hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

Another embodiment of the present invention is an organic compound represented by Structural Formulae (100) to (105) and Structural Formula (168) below.

[Chemical Formula 7]

(100)

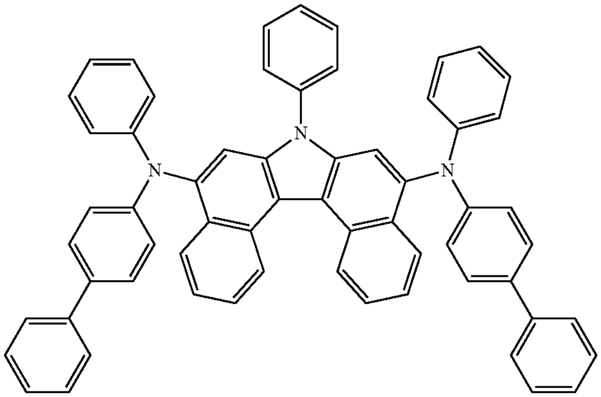

(101)

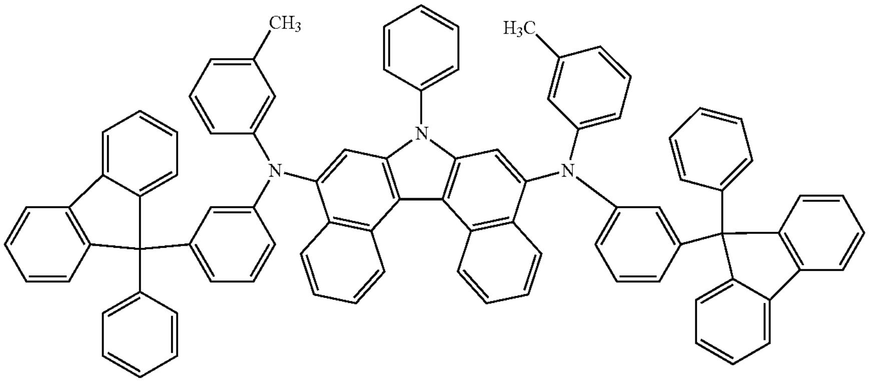

(102)

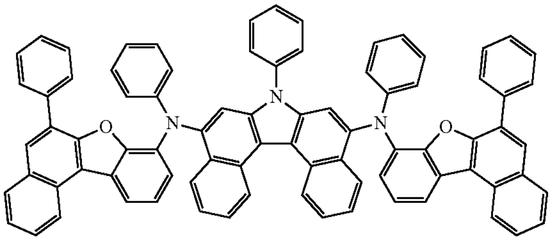

(103)

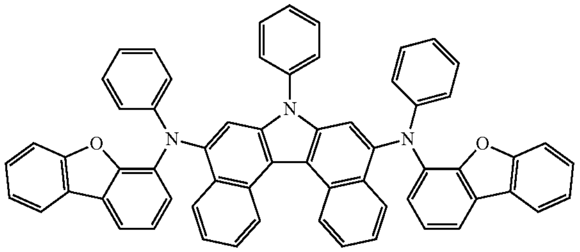

[Chemical Formula 8]

-continued (104)

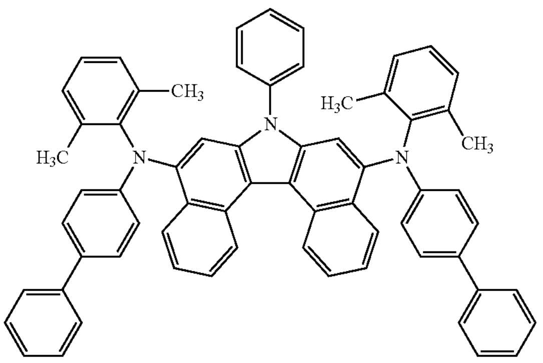

(105)

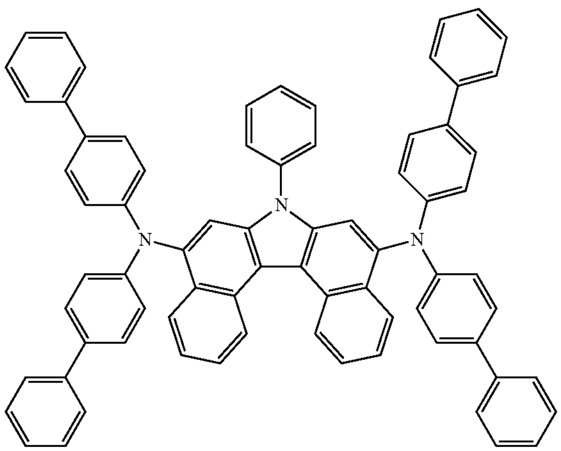

(168)

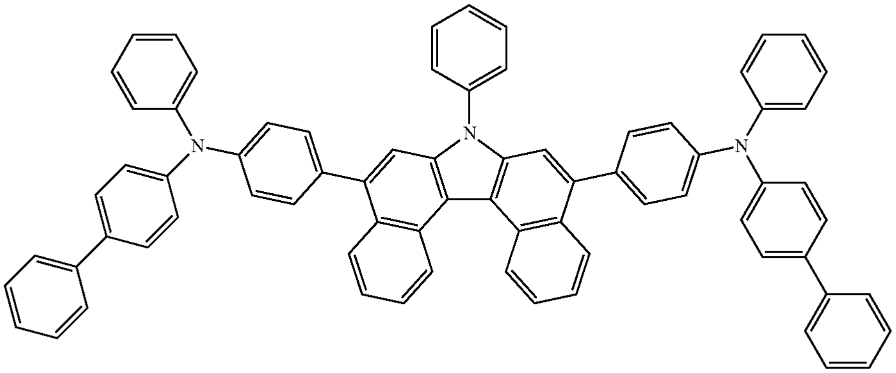

Another embodiment of the present invention is an electronic device containing the organic compound according to any one of the above structures.

In the above structure, the light-emitting element preferably emits light derived from the organic compound according to any one of the above structures.

Note that the light-emitting element having the above structure includes an EL layer between an anode and a cathode. The EL layer preferably includes at least a light-emitting layer. In addition, the EL layer may include a hole-injection layer, a hole-transport layer, an electron-transport layer, an electron-injection layer, and other functional layers.

Another embodiment of the present invention is a display device including the light-emitting element having any of the above structures, and at least one of a color filter and a transistor. Another embodiment of the present invention is an electronic apparatus including the display device, and at least one of a housing and a touch sensor. Another embodiment of the present invention is a lighting device including the light-emitting element having any of the above structures, and at least one of a housing and a touch sensor. The category of one embodiment of the present invention includes not only a light-emitting device including a light-emitting element but also an electronic apparatus including a light-emitting device. Accordingly, a light-emitting device in this specification refers to an image display device or a light source (including a lighting device). A display module in which a connector such as an FPC (Flexible Printed Circuit) or a TCP (Tape Carrier Package) is connected to a light-emitting element, a display module in which a printed wiring board is provided on the tip of a TCP, and a display module in which an IC (integrated circuit) is directly mounted on a light-emitting element by a COG (Chip On Glass) method are also embodiments of the present invention.

Effect of the Invention

According to one embodiment of the present invention, a novel organic compound can be provided. In particular, a novel organic compound exhibiting blue fluorescence can be provided. Alternatively, in one embodiment of the present invention, a novel organic compound having an aromatic amine skeleton can be provided. Alternatively, according to one embodiment of the present invention, a light-emitting element with high color purity can be provided. Alternatively, according to one embodiment of the present invention, a light-emitting element having a long lifetime can be provided. Alternatively, according to one embodiment of the present invention, a light-emitting element with high emission efficiency can be provided. Alternatively, according to one embodiment of the present invention, a light-emitting element with low driving voltage can be provided.

According to another embodiment of the present invention, a light-emitting element, a light-emitting device, and an electronic apparatus each with high reliability can be provided. According to another embodiment of the present invention, a light-emitting element, a light-emitting device, and an electronic apparatus each having low power consumption can be provided.

Note that the description of these effects does not disturb the existence of other effects. Note that one embodiment of the present invention does not necessarily achieve all of these effects. Other effects will be apparent from the description of the specification, the drawings, the claims, and the like, and other effects can be derived from the description of the specification, the drawings, the claims, and the like.

MODE FOR CARRYING OUT THE INVENTION

Figure 1A:
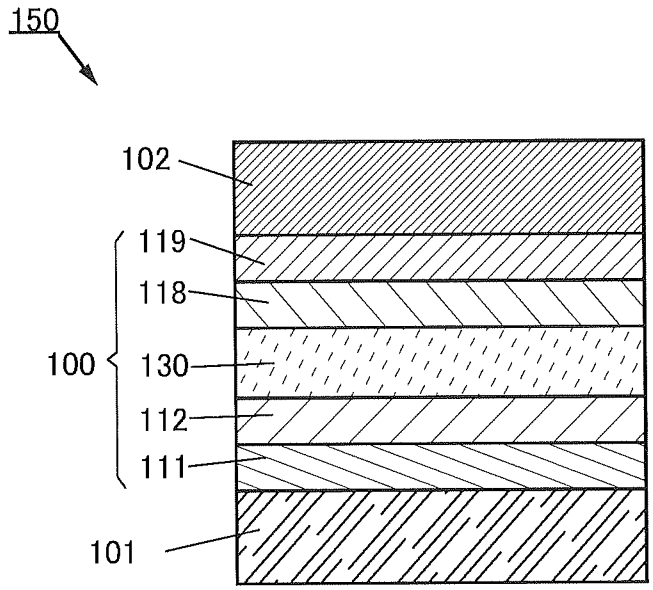
FIGS. 1A-1C are schematic views of a light-emitting element of one embodiment of the present invention, and a diagram showing the correlation of energy levels in a light-emitting layer.

Hereinafter, embodiments of the present invention will be described. However, the present invention can be implemented in many different modes, and it is easily understood by those skilled in the art that modes and details thereof can be changed in various ways without departing from the spirit and scope thereof. Thus, the present invention should not be interpreted as being limited to description of the embodiments.

Note that in each drawing described in this specification, the size and the thickness of an anode, an EL layer, an intermediate layer, a cathode, and the like are exaggerated for clarity in some cases. Therefore, the sizes of the components are not limited to the sizes in the drawings and relative sizes between the components.

Note that the ordinal numbers such as "first", "second", and "third" in this specification and the like are used for convenience and do not denote the order of steps, the positional relation, or the like. Therefore, for example, description can be made even when "first" is replaced with "second" or "third", as appropriate. In addition, the ordinal numbers in this specification and the like are not necessarily the same as the ordinal numbers which specify one embodiment of the present invention.

Note that in structures of the present invention described in this specification and the like, the same portions or portions having similar functions are denoted by common reference numerals in different drawings, and descriptions thereof are not repeated. Further, the same hatching pattern is applied to portions having similar functions, and the portions are not especially denoted by reference numerals in some cases.

Note that the terms "film" and "layer" can be interchanged with each other depending on the case or according to the circumstances. For example, the term "conductive layer" can be changed into the term "conductive film" in some cases. For another example, the term "insulating film" can be changed into the term "insulating layer" in some cases.

Embodiment 1

In this embodiment, an organic compound of one embodiment of the present invention will be described.

An organic compound of one embodiment of the present invention is an organic compound represented by General Formula (G0) below.

[Chemical Formula 9]

(G0)

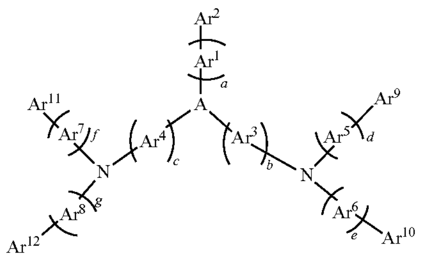

In General Formula (G0), A represents a substituted or unsubstituted dibenzocarbazole skeleton; $Ar^1$ is bonded to the N-position of the dibenzocarbazole skeleton; each of $Ar^1$ and $Ar^3$ to $Ar^8$ independently represents a substituted or unsubstituted arylene group having 6 to 25 carbon atoms; $Ar^2$ represents a substituted or unsubstituted aryl group having 6 to 25 carbon atoms; each of a, b, c, d, e, f and g independently represents an integer of 0 to 3; and each of $Ar^9$ to $Ar^{12}$ independently represents a substituted or unsubstituted aryl group having 6 to 100 carbon atoms or substituted or unsubstituted heteroaryl group having 3 to 100 carbon atoms.

The organic compound of one embodiment of the present invention is an organic compound including one dibenzocarbazole skeleton and two amine skeletons in one molecule. The present inventors found out that a blue fluorescent material with high color purity and a high quantum yield can be obtained with this structure. The organic compound of one embodiment of the present invention includes a dibenzocarbazole skeleton and therefore has a high quantum yield. Furthermore, the dibenzocarbazole skeleton is preferable because of higher heat resistance than a carbazole skeleton.

The dibenzocarbazole skeleton is preferably a dibenzo[c, g]carbazole skeleton. With this structure, when the organic compound of one embodiment of the present invention is used for a light-emitting element, a light-emitting element having high reliability can be obtained.

It is preferable that, in the organic compound of one embodiment of the present invention, a substituent having one amine skeleton be bonded to each of two naphthalene skeletons included in the dibenzocarbazole skeleton in General Formula (G0). That is, it is preferable that $Ar^3$ be bonded to either one of the two naphthalene skeletons included in the dibenzocarbazole skeleton and $Ar^4$ be bonded to the other naphthalene skeleton. This structure is preferable because steric hindrance of the two amine skeletons can be inhibited and therefore the organic compound of one embodiment of the present invention can be easily synthesized. Moreover, emission efficiency of a light-emitting element can be improved as compared to the case of using an organic compound having one dibenzocarbazole skeleton and one amine skeleton in one molecule. This effect can be obtained because a structure change between excitation and light emission can be reduced in such a manner that the dibenzocarbazole skeleton is sandwiched between the two amine skeletons, so that both the highest occupied molecular orbital (HOMO) and the lowest unoccupied molecular orbital (LUMO) orbital are distributed in the dibenzocarbazole skeleton.

The organic compound of one embodiment of the present invention preferably includes a substituted or unsubstituted aryl group or a substituted or unsubstituted aryl group through a substituted or unsubstituted arylene group at the N-position of the dibenzocarbazole skeleton. With this structure, an aromatic hydrocarbon group which has higher reliability and heat resistance as compared to the case where hydrogen is bonded can be introduced into the N-position, whereby an organic compound with high heat resistance and reliability can be obtained.

It is preferable that, in the organic compound of one embodiment of the present invention, a substituted or unsubstituted aryl group having 6 to 100 carbon atoms or a substituted or unsubstituted heteroaryl group having 3 to 100 carbon atoms be independently introduced into each of $Ar^9$ to $Ar^{12}$ in General Formula (G0). With this structure, an aromatic hydrocarbon skeleton which has high heat resistance and high reliability can be introduced into the amine skeleton, and further the amine skeleton can be a tertiary amine skeleton having high reliability and a high sublimation property, whereby an organic compound with high heat resistance and reliability can be obtained.

Examples of the aryl group having 6 to 100 carbon atoms and the heteroaryl group having 3 to 100 carbon atoms includes a substituted or unsubstituted phenyl group, biphenyl group, naphthyl group, triphenylyl group, fluorenyl group, carbazolyl group, dibenzothiophenyl group, dibenzofuranyl group, benzofluorenyl group, benzocarbazolyl group, naphthobenzothiophenyl group, naphthobenzofuranyl group, dibenzofluorenyl group, dibenzocarbazolyl group, dinaphthothiophenyl group, dinaphthofuranyl group, phenanthryl group, triadinyl group, pyrimidinyl group, pyrazinyl group, triazolyl group, pyridinyl group, benzofuropyrimidinyl group, benzothiopyrimidinyl group, benzofuropyrazinyl group, benzothiopyrazinyl group, benzofuropyridinyl group, benzothiopyridinyl group, and bicarbazolyl group. Note that the aryl group having 6 to 100 carbon atoms and the heteroaryl group having 3 to 100 carbon atoms are not limited thereto.

An organic compound of one embodiment of the present invention is an organic compound represented by General Formula (G1) below.

[Chemical Formula 10]

(G1)

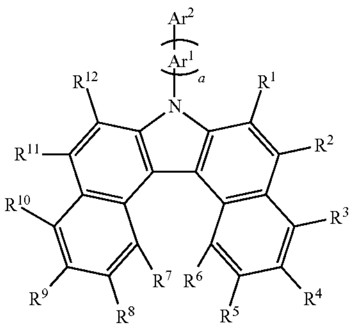

In General Formula (G1), $Ar^1$ represents a substituted or unsubstituted arylene group having 6 to 25 carbon atoms; $Ar^2$ represents a substituted or unsubstituted aryl group having 6 to 25 carbon atoms; any one of $R^1$ to $R^6$ is a substituent represented by General Formula (G1-1); any one of $R^7$ to $R^{12}$ is a substituent represented by General Formula (G1-2); each of the other $R^1$ to $R^{12}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms; and a represents an integer of 0 to 3.

[Chemical Formula 11]

(G1-1)

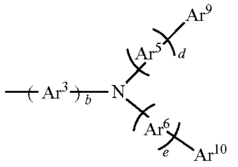

(G1-2)

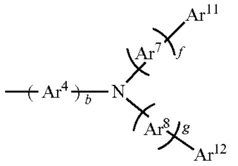

In General Formulae (G1-1) and (G1-2), each of $Ar^3$ to $Ar^8$ independently represents a substituted or unsubstituted arylene group having 6 to 25 carbon atoms; each of b, c, d, e, f, and g independently represents an integer of 0 to 3; and each of $Ar^5$ to $Ar^8$ independently represents a substituted or unsubstituted aryl group having 6 to 100 carbon atoms or a substituted or unsubstituted heteroaryl group having 3 to 100 carbon atoms.

It is preferable that, in the organic compound of one embodiment of the present invention, $Ar^3$ be bonded to any one of the 1-position to 6-position of the dibenzo[c,g] carbazole skeleton and $Ar^4$ be bonded to any one of the 6-position to 13-position of the dibenzo[c,g]carbazole skeleton in General Formula (G1). That is, a substituent having one amine skeleton is preferably bonded to each of the two naphthalene skeletons included in the dibenzo[c,g]carbazole. With this structure, emission efficiency of a light-emitting element can be improved as compared to the case of using an organic compound having one dibenzo[c,g] carbazole skeleton and one amine skeleton in one molecule. This effect can be obtained probably because symmetry of the whole molecule is improved.

An organic compound of one embodiment of the present invention is an organic compound represented by General Formula (G2) below.

[Chemical Formula 12]

(G2)

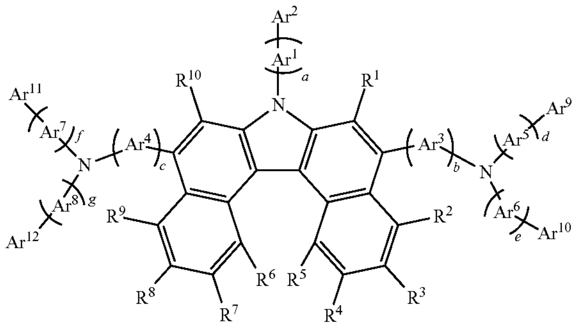

In General Formula (G2), each of $Ar^1$, and $Ar^3$ to $Ar^8$ independently represents a substituted or unsubstituted arylene group having 6 to 25 carbon atoms; $Ar^2$ represents a substituted or unsubstituted aryl group having 6 to 25 carbon atoms; each of a, b, c, d, e, f, and g independently represents an integer of 0 to 3; each of $Ar^9$ to $Ar^{12}$ independently represents a substituted or unsubstituted aryl group having 6 to 100 carbon atoms or a substituted or unsubstituted heteroaryl group having 6 to 100 carbon atoms; and each of $R^1$ to $R^{10}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

It is preferable that, in General Formula (G2), $Ar^3$ and $Ar^4$ be bonded to the 5-position and 9-position of the dibenzo [c,g]carbazole skeleton, respectively. That is, a substituent having an amine skeleton is preferably bonded to each of the 5-position and 9-position of the dibenzo[c,g]carbazole skeleton. With this structure, the organic compound of one embodiment of the present invention can be obtained at low cost because synthesis can be performed easily as will be described later.

An organic compound of one embodiment of the present invention is an organic compound represented by General Formula (G2) below.

[Chemical Formula 13]

G3

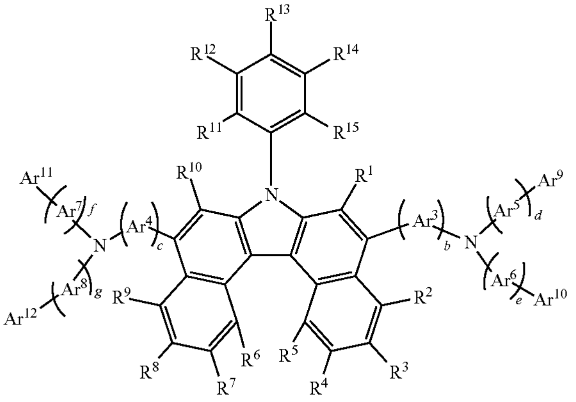

In General Formula (G3), each of $Ar^3$ to $Ar^8$ independently represents a substituted or unsubstituted arylene group having 6 to 25 carbon atoms; each of b, c, d, e, f and g independently represents an integer of 0 to 3; each of $Ar^9$ to $Ar^{12}$ independently represents a substituted or unsubstituted aryl group having 6 to 100 carbon atoms or a substituted or unsubstituted heteroaryl group having 6 to 100 carbon atoms; and each of $R^1$ to $R^{15}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

The organic compound of one embodiment of the present invention preferably includes a substituted or unsubstituted phenyl group at the N-position. The phenyl group can be introduced into the N-position of the dibenzocarbazole skeleton at low cost, whereby this structure enables the organic compound of one embodiment of the present invention to be synthesized at low cost. When the phenyl group is introduced into the N-position of the dibenzocarbazole skeleton, the sublimation property can be improved.

In addition, in General Formulae (G0) to (G 3), (G1-1), and (G1-2) described above, each of b and c is preferably 0. In other words, the dibenzocarbazole skeleton is preferably bonded directly to the amine skeletons. With this structure, an organic compound having a favorable quantum yield can be obtained.

Alternatively, in General Formulae (G0) to (G3), (G1-1), and (G1-2), each of d, e, f and g may be independently greater than or equal to 1 and less than or equal to 3. That is, $Ar^8$ to $Ar^{12}$ may be bonded to the amine skeleton through the arylene group. With this structure, the length of the conjugated system can be adjusted; thus, an emission color can be adjusted. Furthermore, an organic compound with high heat resistance can be obtained because the molecular weight can be increased.

Alternatively, in General Formulae (G0) to (G3), (G1-1), and (G1-2), each of a, d, e, f, and g may be 0. That is, $Ar^8$ to $Ar^{12}$ may be bonded to the amine skeleton directly. With this structure, the organic compound of one embodiment of the present invention can be obtained at lower cost.

It is preferable that, in General Formulae (G0) to (G3), (G1-1), and (G1-2) described above, each of $Ar^9$ and $Ar^{11}$ be independently any one of a substituted or unsubstituted phenyl group, biphenyl group, naphthyl group, triphenylyl group, fluorenyl group, carbazolyl group, dibenzothiophenyl group, dibenzofuranyl group, benzofluorenyl group, benzocarbazolyl group, naphthobenzothiophenyl group, naphthobenzofuranyl group, dibenzofluorenyl group, dibenzocarbazolyl group, dinaphthothiophenyl group, dinaphthofuranyl group, and phenanthryl group. These substituents are easily introduced into the amine skeletons and electrochemically stable, whereby a highly reliable organic compound can be obtained at low cost.

In addition, it is preferable that, in General Formulae (G0) to (G3), (G1-1), and (G1-2), each of $Ar^{10}$ and $Ar^{12}$ be independently any one of the substituents represented by General Formulae (Ht-1) to (Ht-7).

[Chemical Formula 14]

(Ht-1)

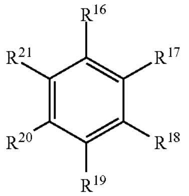

(Ht-2)

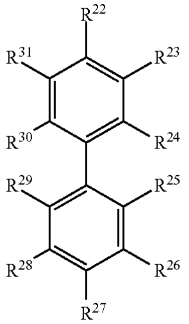

(Ht-3)

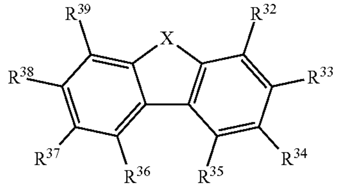

(Ht-4)

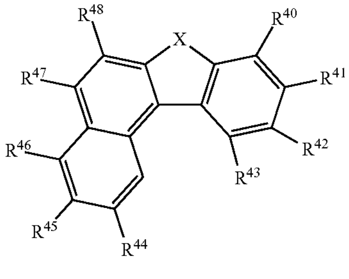

-continued (Ht-5)

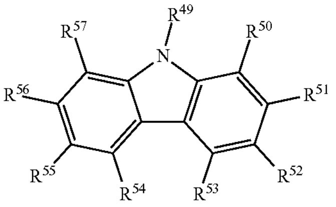

(Ht-6)

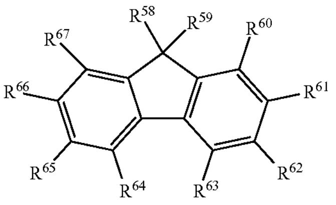

-continued (Ht-7)

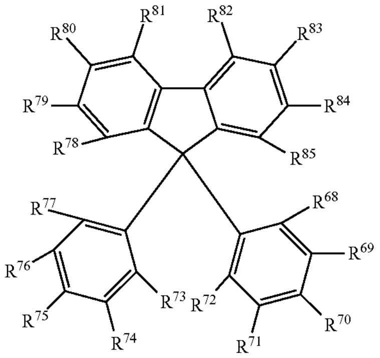

In General Formulae (Ht-3) and (Ht-4), X represents oxygen or sulfur, and, in General Formulae (Ht-1) to (Ht-7), any one of $R^{16}$ to $R^{21}$, any one of $R^{22}$ to $R^{31}$, any one of $R^{32}$ to $R^{39}$, any one of $R^{40}$ to $R^{48}$, any one of $R^{49}$ to $R^{57}$, and any one of $R^{58}$ to $R^{67}$ represent a single bond to nitrogen; and each of the other $R^{16}$ to $R^{85}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

An organic compound of one embodiment of the present invention is an organic compound represented by Structural Formulae (100) to (105) and (168) below.

[Chemical Formula 15]

(100)

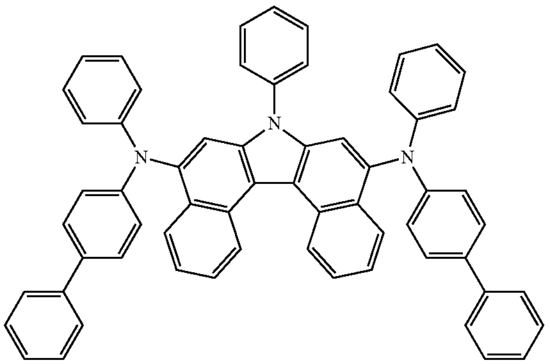

(101)

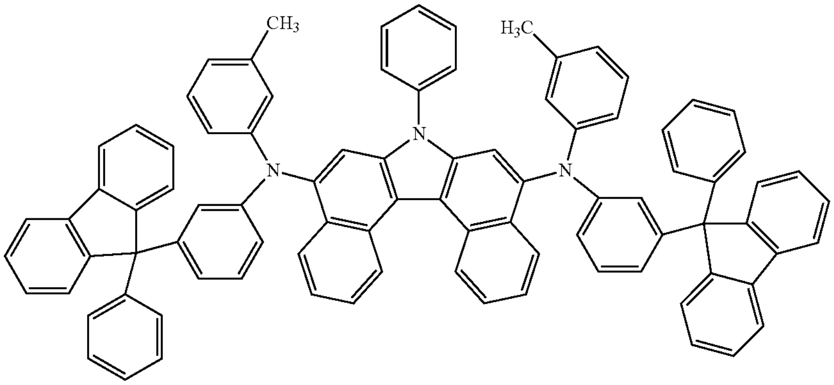

-continued (102)

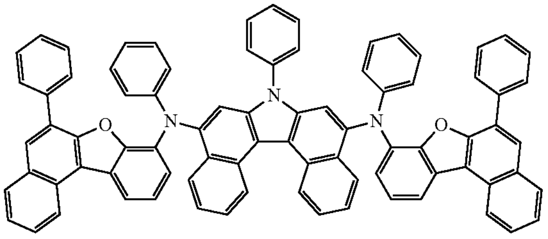

(103)

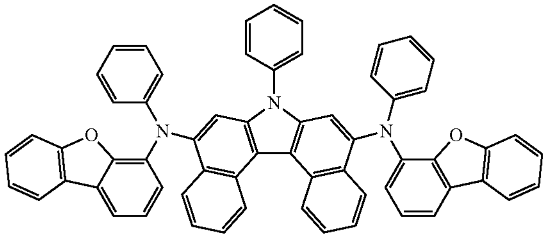

[Chemical Formula 16]

(104)

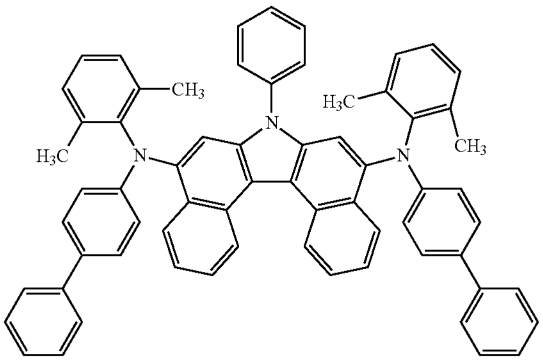

(105)

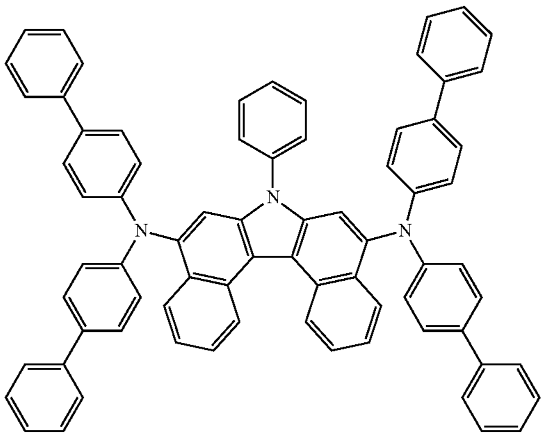

(168)

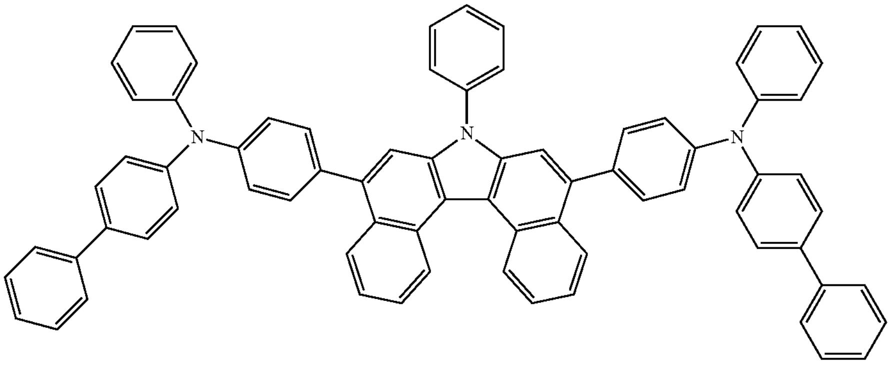

Examples of Substituents

In General Formulae (G0) to (G3), (G1-1), and (G1-2), examples of the substituted or unsubstituted arylene group having 6 to 25 carbon atoms, represented by $Ar^1$ and $Ar^3$ to $Ar^8$, include a phenylene group, a naphthylenediyl group, a fluorenediyl group, a biphenyldiyl group, a spirofluorenediyl group, and a terphenyldiy group. It is particularly preferable to use a phenylene group and a biphenyldiyl group because a high sublimation property can be obtained at low cost and with a smaller molecular weight as compared to the other arylene groups. Specifically, groups represented by Structural Formulae (Ar-1) to (Ar-27) below can be used. Note that the group represented by Ar is not limited thereto and may include a substituent.

[Chemical Formula 17]

(Ar-1)

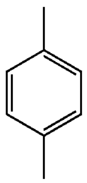

(Ar-2)

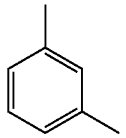

-continued
(Ar-3)
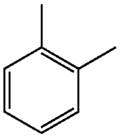
(Ar-4)
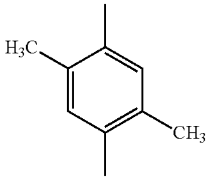
(Ar-5)
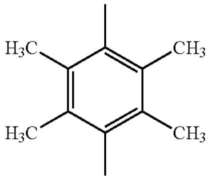
(Ar-6)
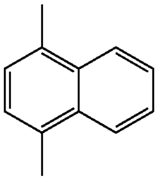
(Ar-7)
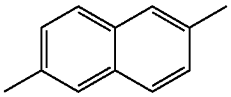
(Ar-8)
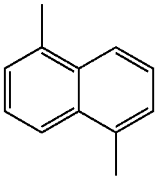
(Ar-9)
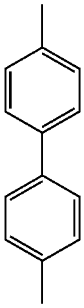
(Ar-10)
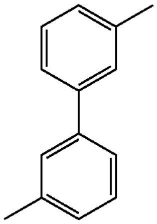
-continued
(Ar-11)
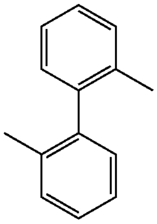
(Ar-12)
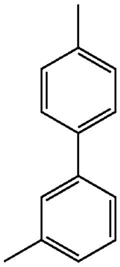
(Ar-13)
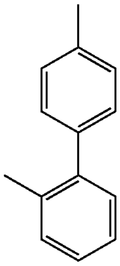
(Ar-14)
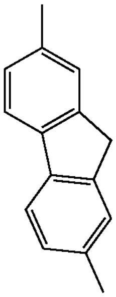
(Ar-15)
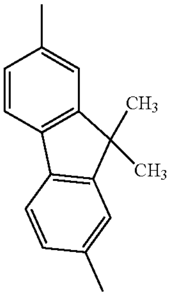

-continued
(Ar-16)
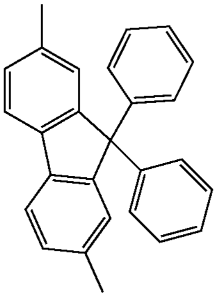
(Ar-17)
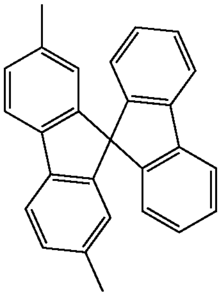
(Ar-18)
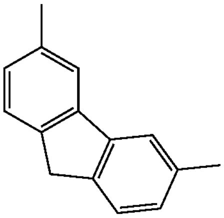
(Ar-19)
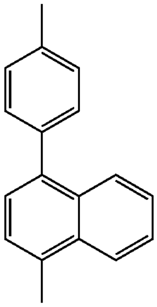
(Ar-20)
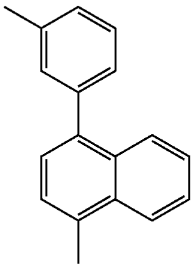
-continued
(Ar-21)
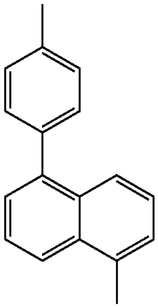
(Ar-22)
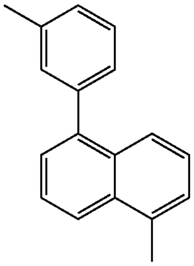
(Ar-23)
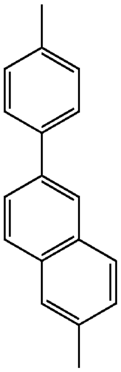
(Ar-24)
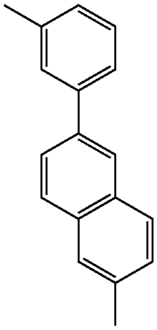
(Ar-25)
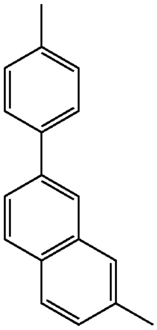

-continued (Ar-26)

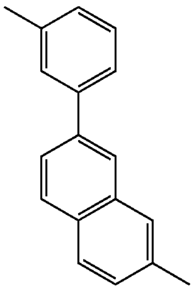

(Ar-27)

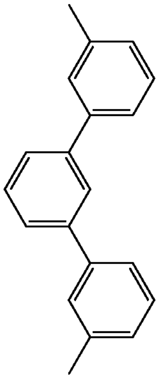

Moreover, in General Formulae (G0) to (G3), (G1-1), and (G1-2), $Ar^9$ to $Ar^{12}$ represents, for example, a substituted or unsubstituted aryl group having 6 to 100 carbon atoms or a substituted or unsubstituted heteroaryl group having 6 to 100 carbon atoms. Specific examples of the aryl group or the heteroaryl group include a phenyl group, a naphthyl group, a biphenyl group, a fluorenyl group, a spirofluorenyl group, and a phenanthryl group. A substituent including a condensed heteroaromatic ring including a carbazole ring, a dibenzofuran ring, or a dibenzothiophene ring (e.g., a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring) can also be given. More specific examples include groups represented by Structural Formulae (Ar-28) to (Ar-79) below. Note that the groups represented by $Ar^9$ to $Ar^{12}$ are not limited thereto.

[Chemical Formula 18]

(Ar-28)

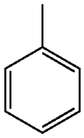

(Ar-29)

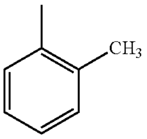

-continued (Ar-30)

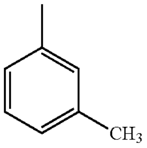

(Ar-31)

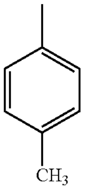

(Ar-32)

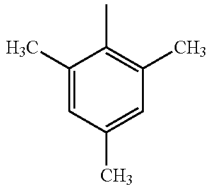

(Ar-33)

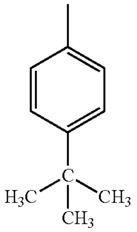

(Ar-34)

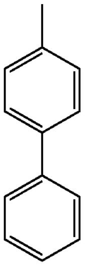

(Ar-35)

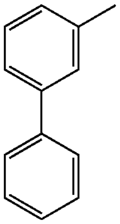

(Ar-36)

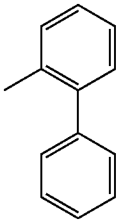

-continued
(Ar-37)
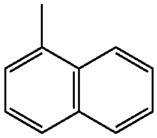
(Ar-38)
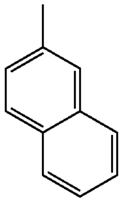
(Ar-39)
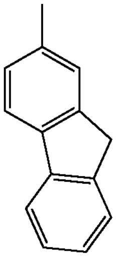
(Ar-40)
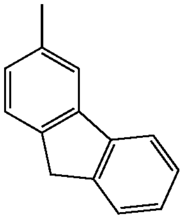
(Ar-41)
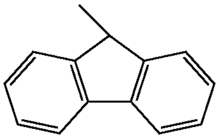
(Ar-42)
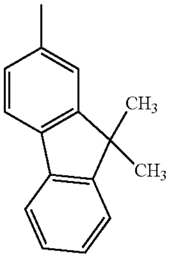
(Ar-43)
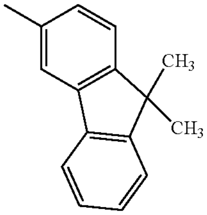
-continued
(Ar-44)
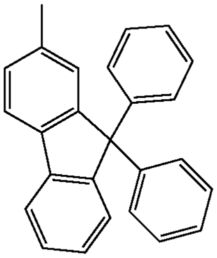
(Ar-45)
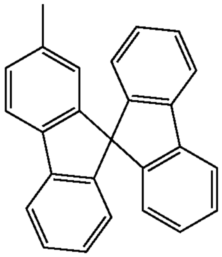
(Ar-46)
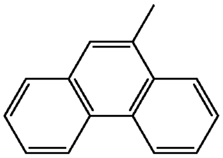
(Ar-47)
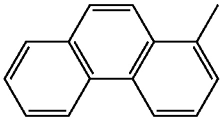
(Ar-48)
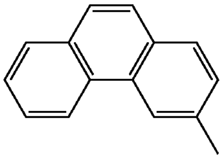
(Ar-49)
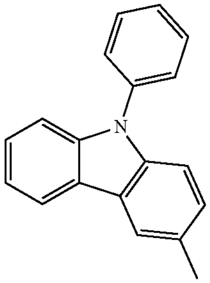
(Ar-50)
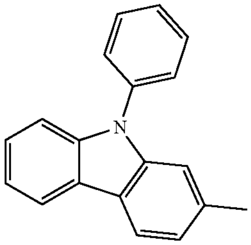

-continued
(Ar-51)
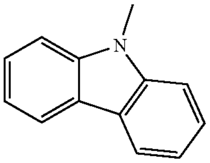
(Ar-52)
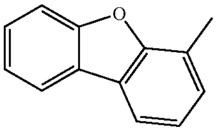
(Ar-53)
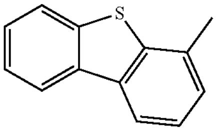
(Ar-54)
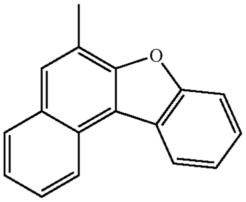
(Ar-55)
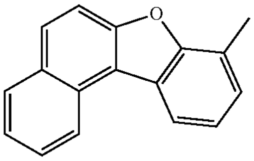
(Ar-56)
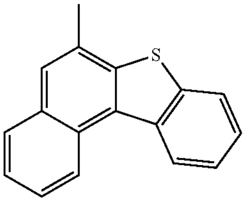
(Ar-57)
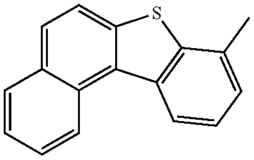
(Ar-58)
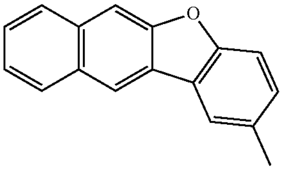
[Chemical Formula 19]
(Ar-59)
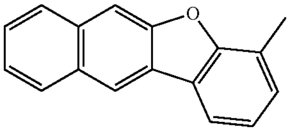
-continued
(Ar-60)
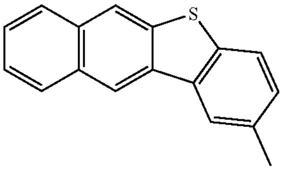
(Ar-61)
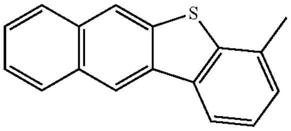
(Ar-62)
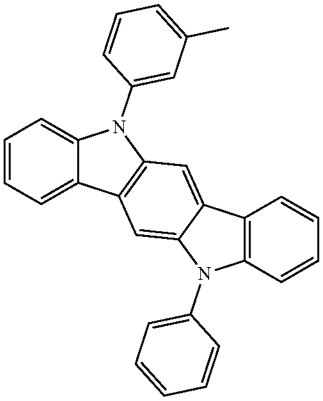
(Ar-63)
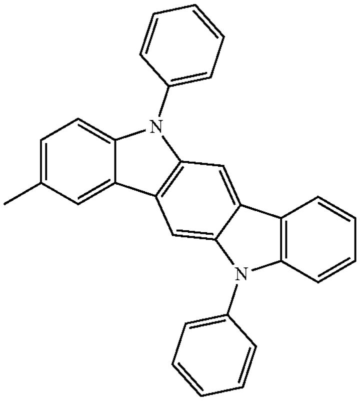
(Ar-64)
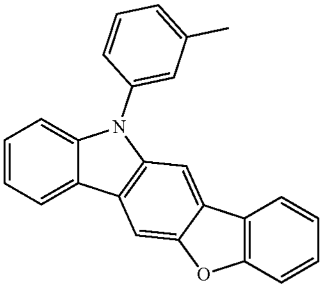

-continued
(Ar-65)
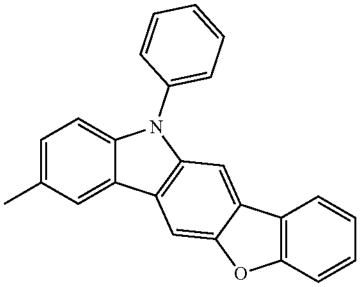
(Ar-66)
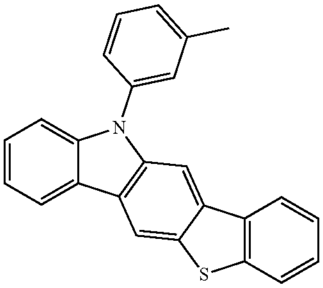
(Ar-67)
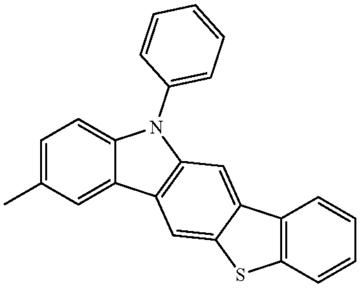
(Ar-68)
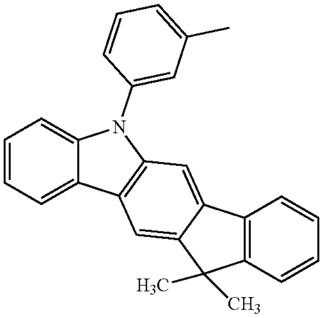
(Ar-69)
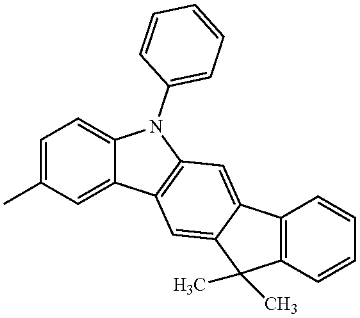
-continued
(Ar-70)
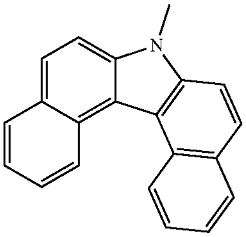
(Ar-71)
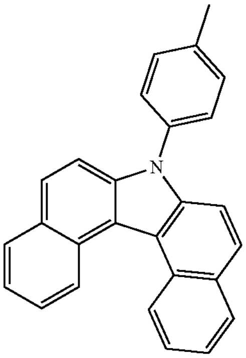
(Ar-72)
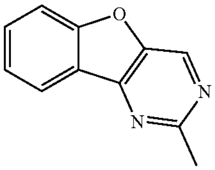
(Ar-73)
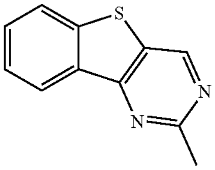
(Ar-74)
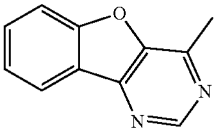
(Ar-75)
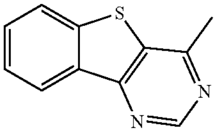
(Ar-76)
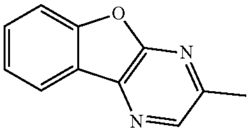
(Ar-77)
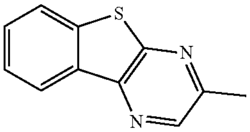

-continued (Ar-78)

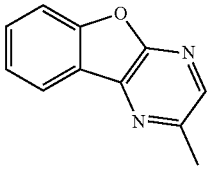

(Ar-79)

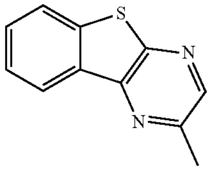

Note that, as in (Ar-28) to (Ar-36), the case where $Ar^9$ to $Ar^{12}$ are a phenyl group, an alkylphenyl group, or a biphenyl group is preferable because the emitted light has a short wavelength. The substituents have a high volume; therefore, molecular interaction is suppressed and sublimation and evaporation temperatures can be lowered. In addition, as in (Ar-29) and (Ar-32), the case where an alkyl group is introduced at the ortho-position is preferable because the emitted light has a short wavelength. Moreover, the emitted light of the fluorenyl group represented by (Ar-39) to (Ar-45) is preferable because of a shorter wavelength than that of an aryl group to which two or more six-membered rings are fused.

In General Formulae (G0) to (G2), examples of the substituted or unsubstituted aryl group having 6 to 25 carbon atoms, represented by $Ar^2$, include a phenylene group, a naphthylene group, a biphenyl group, a fluorenyl group, a biphenyldiyl group, and a spirofluorenyl group. Specifically, groups represented by Structural Formulae (Ar-28) to (Ar-51) below can be used. Note that the group represented by $Ar^2$ is not limited thereto and may include a substituent.

Moreover, each of $R^1$ to $R^{15}$ in General Formulae (G1) to (G3) and $R^{16}$ to $R^{85}$ in General Formulae (Ht-1) to (Ht-7) represents, for example, hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms. Specific examples of the alkyl group include a methyl group, an ethyl group, a propyl group, an isopropyl group, a butyl group, an isobutyl group, a tert-butyl group, and an n-hexyl group; specific examples of the cycloalkyl group include a cyclopropyl group, a cyclobutyl group, a cyclopentyl group, and a cyclohexyl group; and specific examples of the aryl group include a phenyl group, a naphthyl group, a biphenyl group, a fluorenyl group, and a spirofluorenyl group. More specific examples include groups represented by Structural Formulae (R-1) to (R-35) below. Note that the groups represented by $R^1$ to $R^{15}$ and $R^{16}$ to $R^{85}$ are not limited thereto.

[Chemical Formula 20]

(R-1)

(R-2)

-continued (R-3)

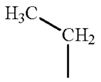

(R-4)

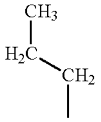

(R-5)

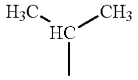

(R-6)

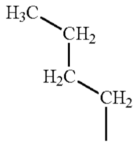

(R-7)

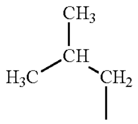

(R-8)

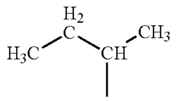

(R-9)

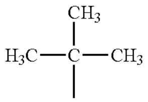

(R-10)

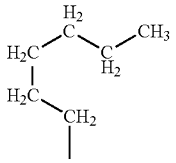

(R-11)

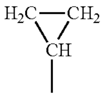

(R-12)

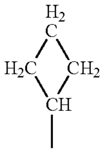

(R-13)

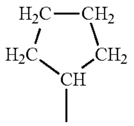

(R-14)

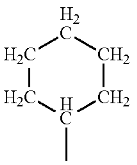

-continued
(R-15)
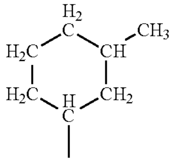
(R-16)
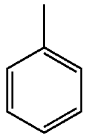
(R-17)
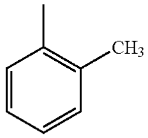
(R-18)
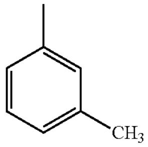
(R-19)
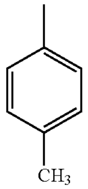
(R-20)
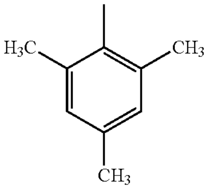
(R-21)
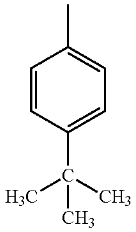
(R-22)
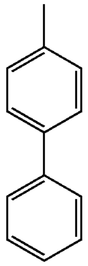
-continued
(R-23)
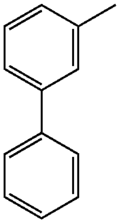
(R-24)
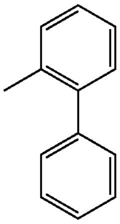
(R-25)
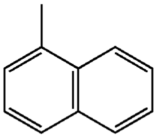
(R-26)
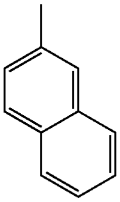
(R-27)
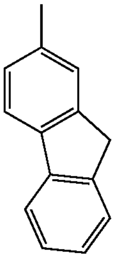
(R-28)
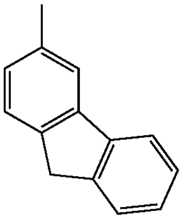
(R-29)
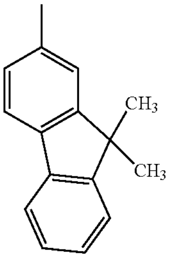

-continued (R-30)

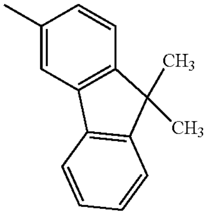

(R-31)

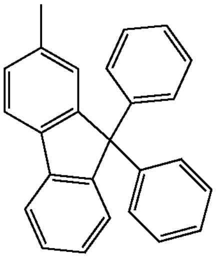

(R-32)

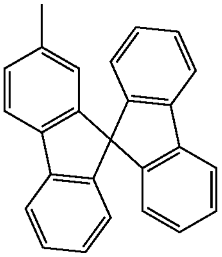

(R-33)

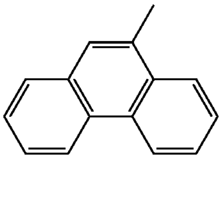

(R-34)

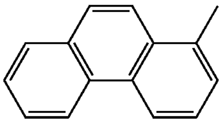

-continued (R-35)

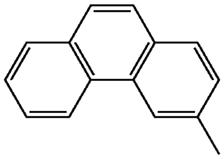

In the case where $R^{16}$ to $R^{85}$ are hydrogen, the organic compound of one embodiment of the present invention can be synthesized easily and at low cost, which is preferable because the organic compound achieves electrochemical stability and high reliability. In addition, in the case of a substituent other than hydrogen, the heat resistance of the organic compound of one embodiment of the present invention can be increased. As in (R-2) to (R-15), (R-17) to (R-21), (R-29), and (R-30), in the case of an alkyl group, a cycloalkyl group, or an aryl group having an alkyl group, solubility in an organic solvent becomes high, whereby purification of the organic compound of one embodiment of the present invention can be easily performed. When the molecular has a high volume by an aryl group, the sublimation temperature can be lowered. As in (R-16), (R-22) to (R-26), and (R-31) to (R-35), in the case of an aryl group which does not include an alkyl group or a cycloalkyl group, electrochemical stability and highly reliability can be obtained.

In the case where A, $A^1$ to $Ar^{12}$, and $R^1$ to $R^{85}$ in General Formulae (G0) to (G3), (G-1), and (G1-2) and General Formulae (Ht-1) to (Ht-7) above further include a substituent, examples of the substituent include an alkyl group having 1 to 6 carbon atoms, a substituted or unsubstituted cycloalkyl group having 3 to 7 carbon atoms, and a substituted or unsubstituted aryl group having 6 to 25 carbon atoms. Specific examples of the alkyl group include a methyl group, an ethyl group, a propyl group, an isopropyl group, a butyl group, an isobutyl group, a tert-butyl group, and an n-hexyl group; specific examples of the cycloalkyl group include a cyclopropyl group, a cyclobutyl group, a cyclopentyl group, and a cyclohexyl group; and specific examples of the aryl group include a phenyl group, a naphthyl group, a biphenyl group, a fluorenyl group, and a spirofluorenyl group.

In addition, the molecular weight of the organic compound of one embodiment of the present invention is preferably less than or equal to 1500 because the sublimation property is high. More preferably, the molecular weight is less than or equal to 1200, further preferably less than or equal to 1000. Furthermore, the molecular weight is preferably greater than or equal to 600 because of high heat resistance.

Specific Examples of Compounds

Specific examples of the compounds represented by General Formulae (G0) to (G3) include organic compounds represented by Structural Formulae (100) to (175) below. Note that the organic compounds represented by General Formulae (G0) to (G3) are not limited to the following examples.

[Chemical Formula 21]
(100)
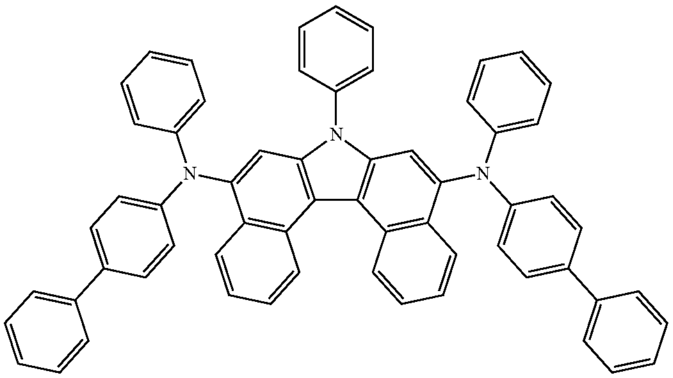
(101)
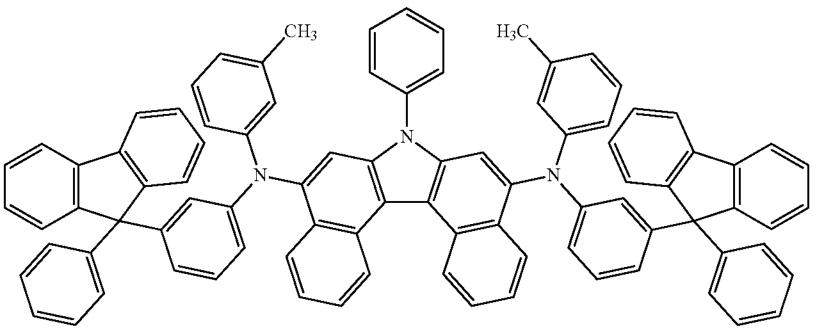
(102)
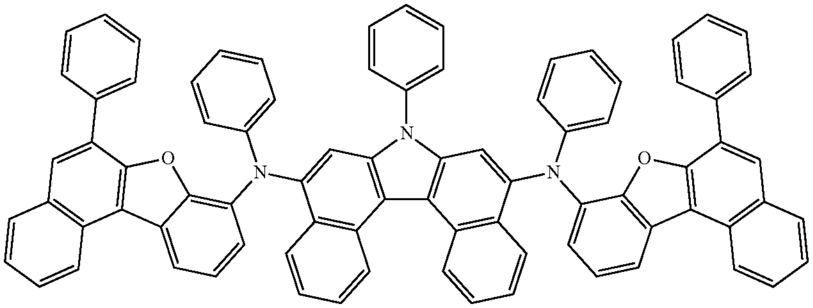
(103)
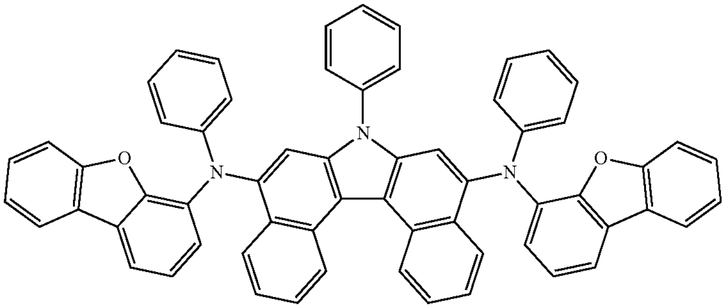

-continued
(104)
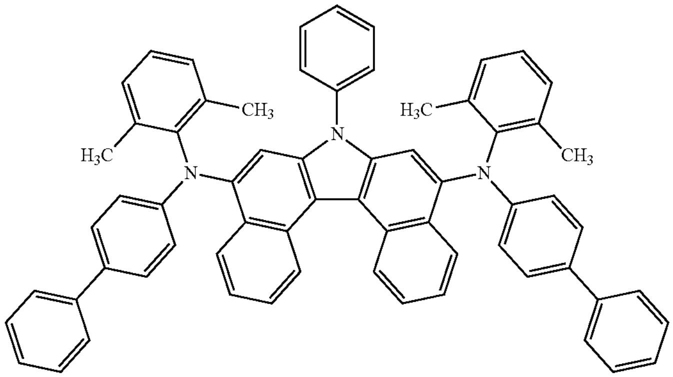
(105)
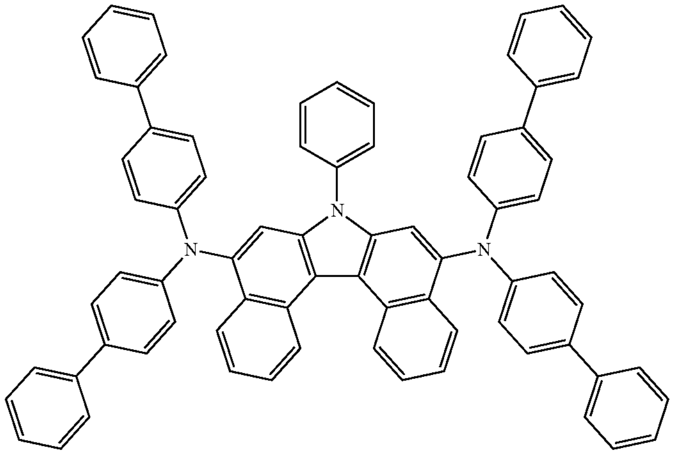
(106)
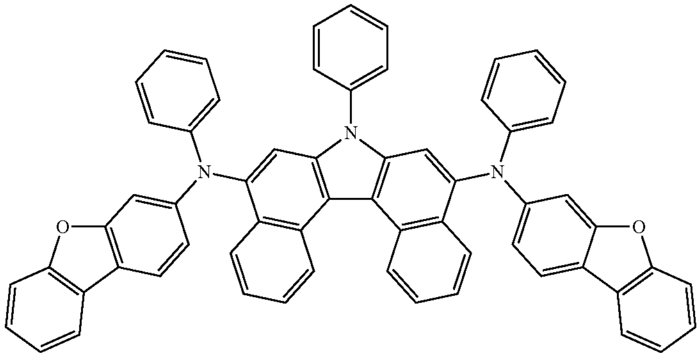
(107)
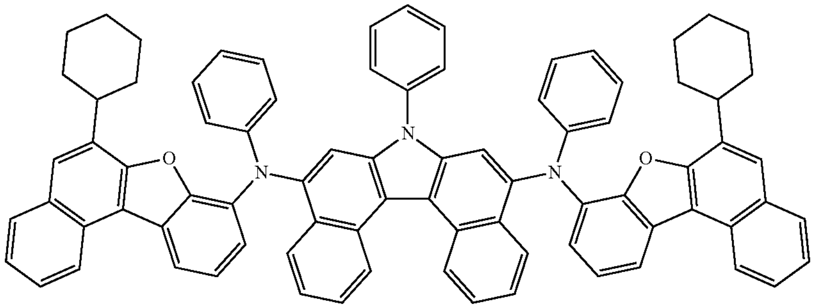

-continued
(108)
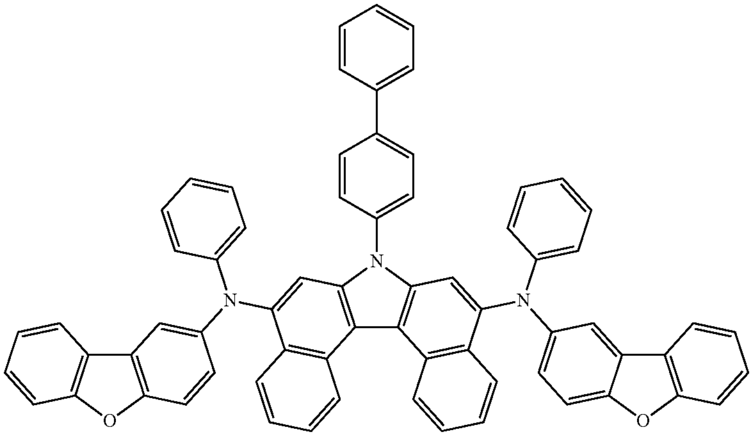
(109)
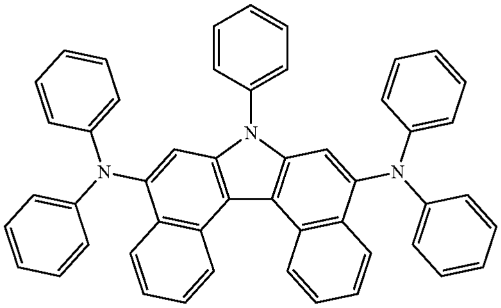
[Chemical Formula 22]
(110)
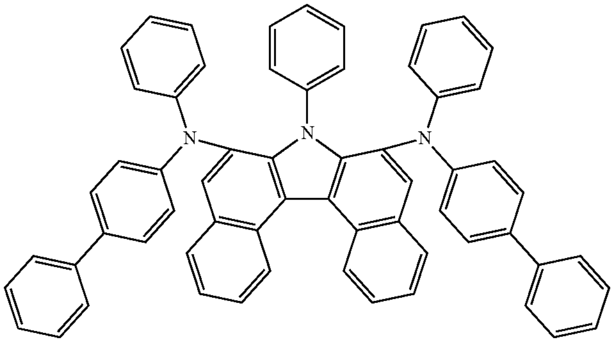
(111)
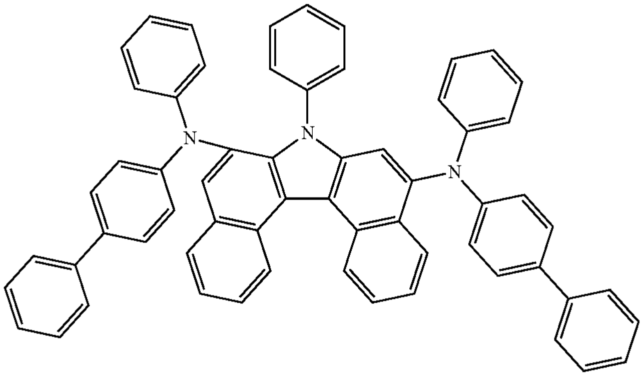

-continued
(112)
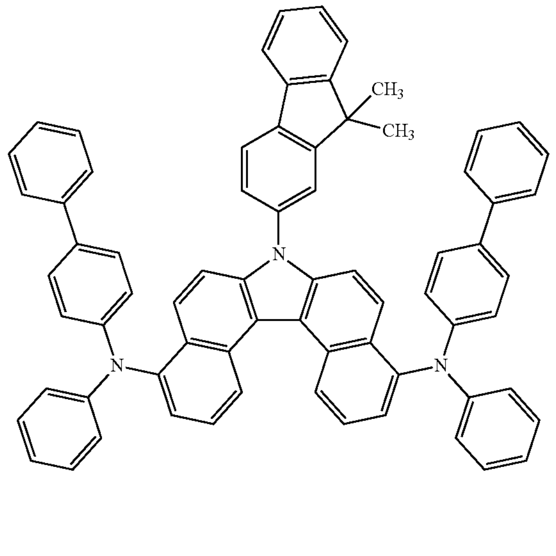
(113)
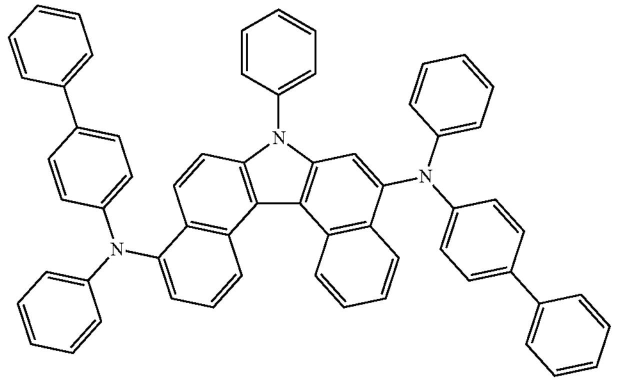
(114)
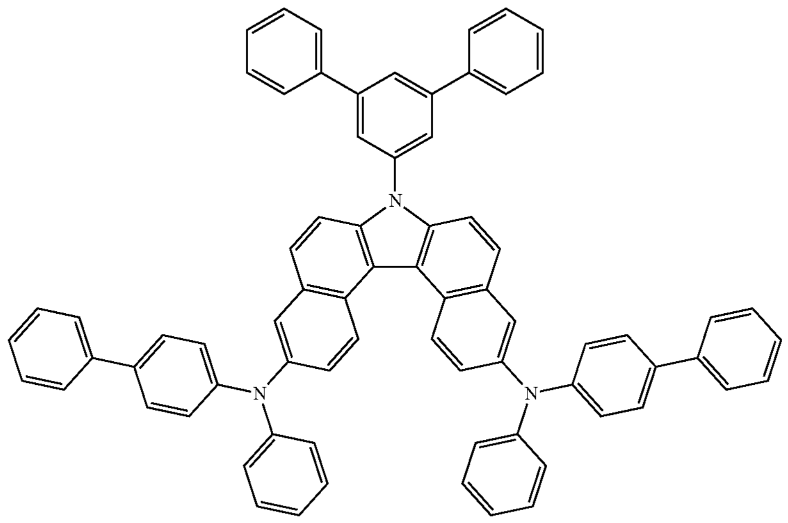

-continued
(115)
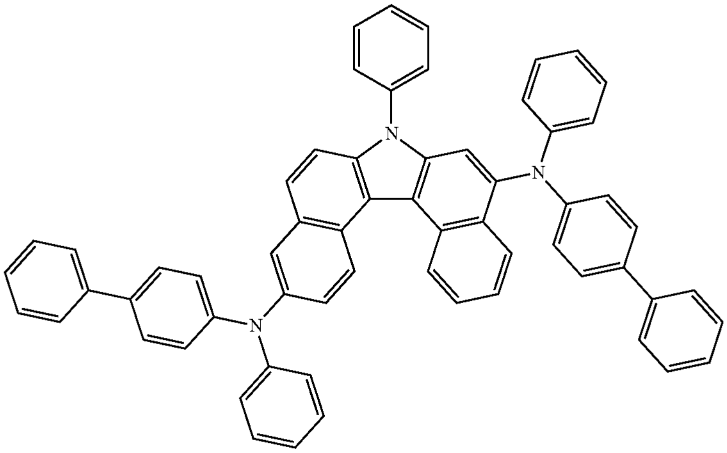
(116)
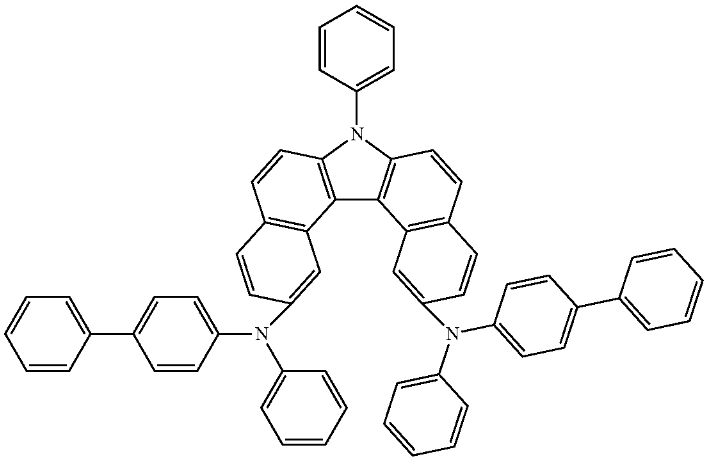
(117)
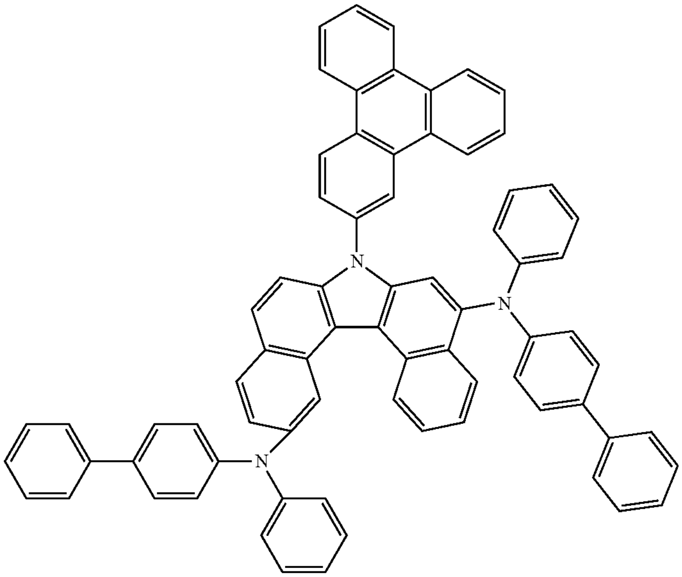

-continued
[Chemical Formula 23]
(118)
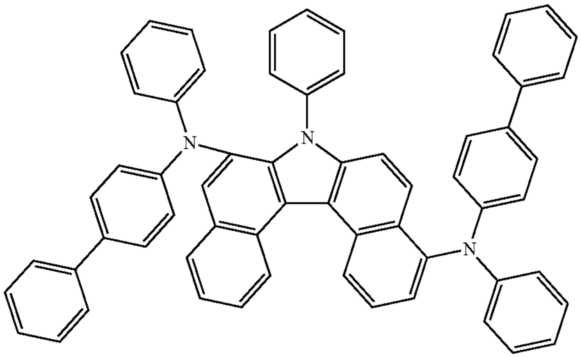
(119)
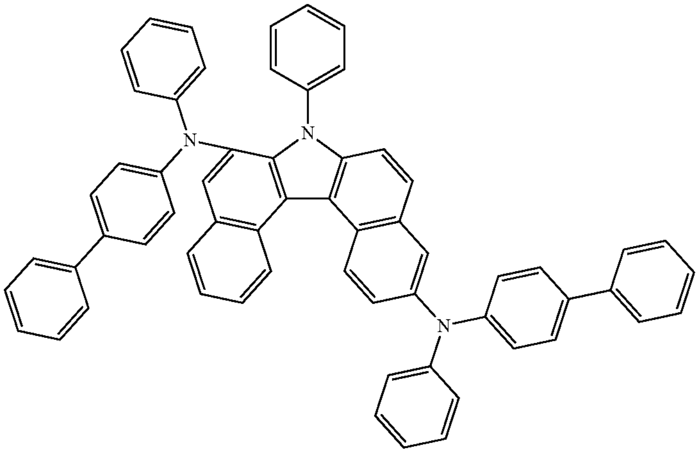
(120)
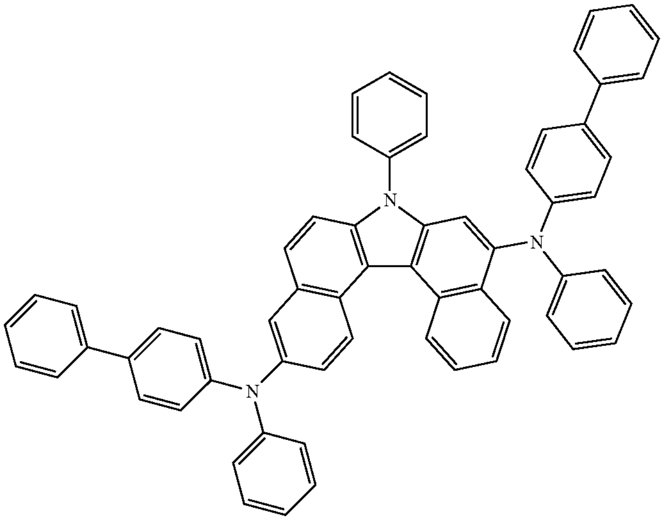

-continued
(121)
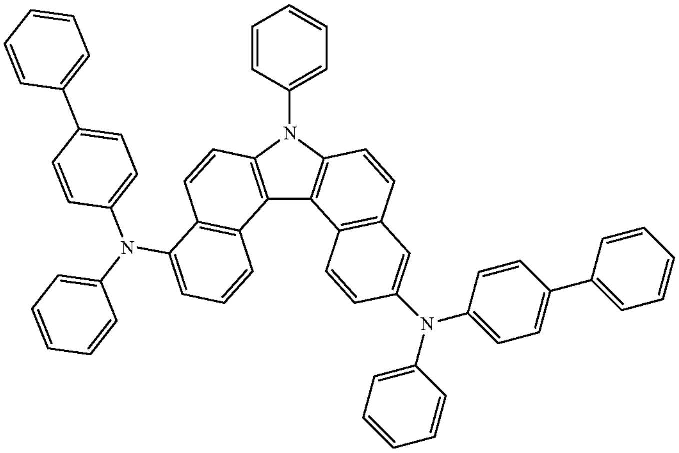
(122)
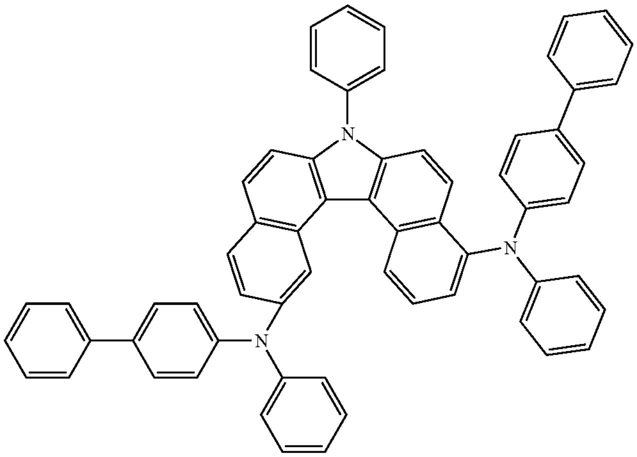
(123)
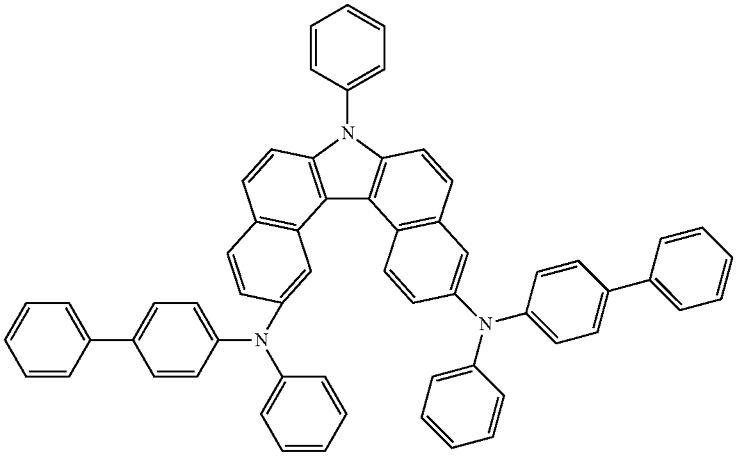

-continued
(124)
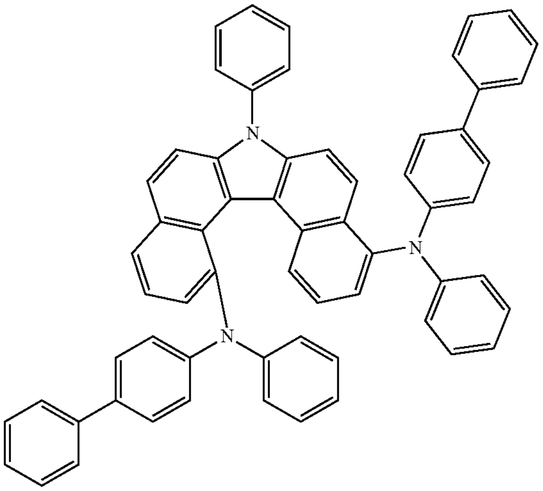
(125)
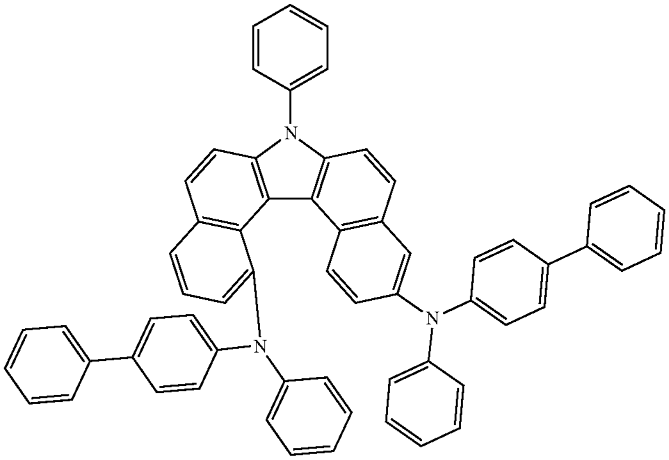
[Chemical Formula 24]
(126)
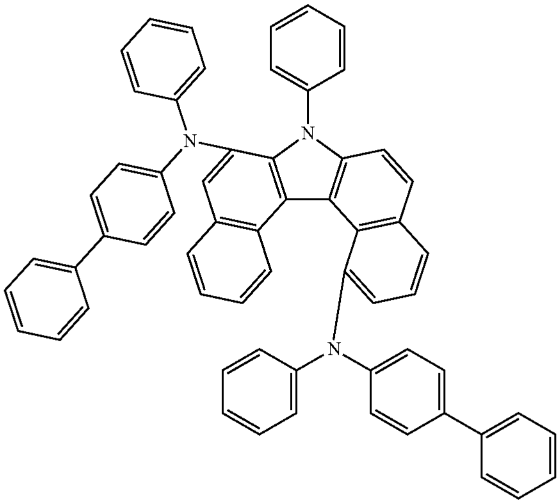
(127)
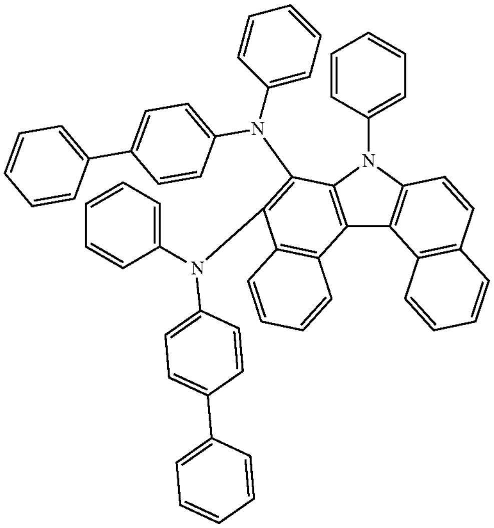

-continued
(128)
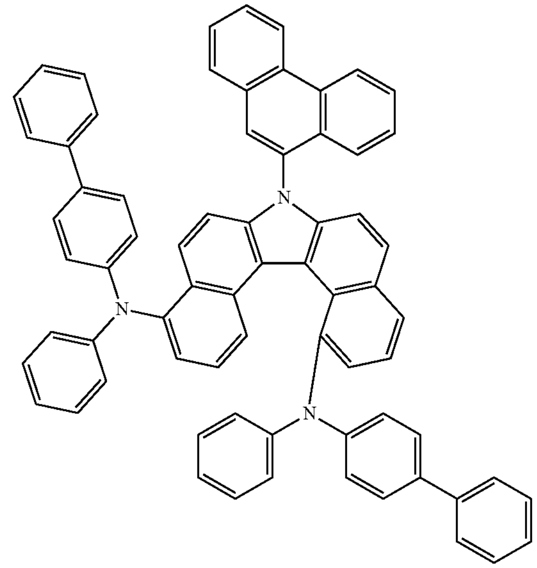
(129)
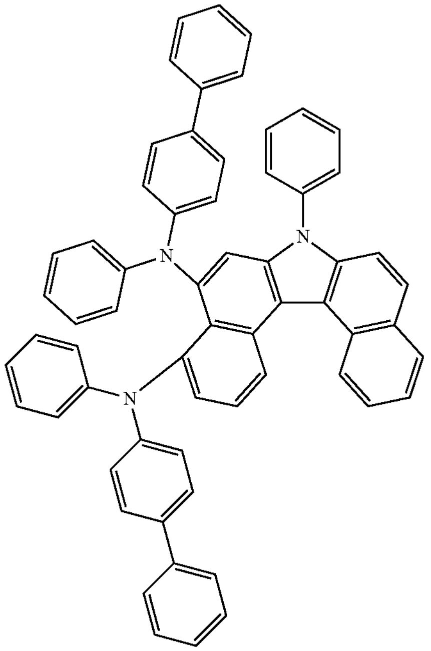
(130)
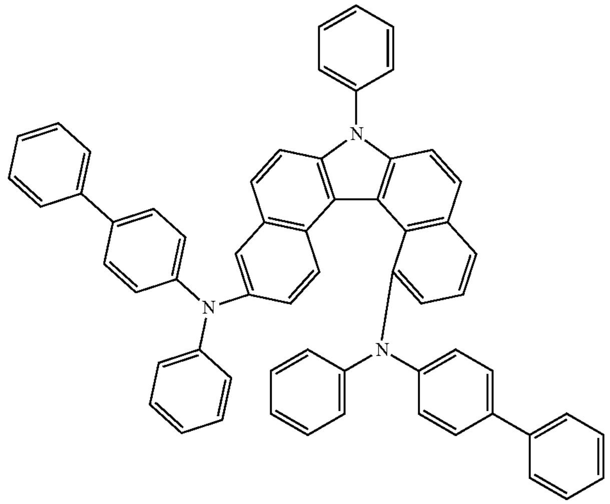
(131)
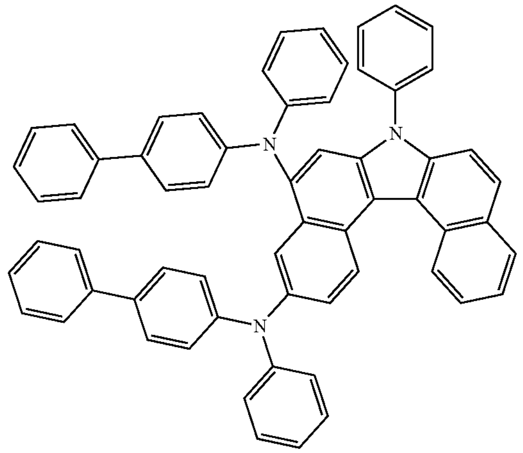

-continued
(132)
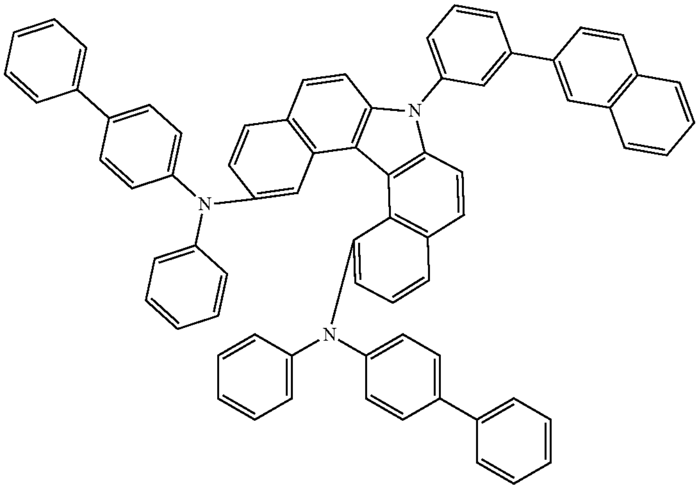
(133)
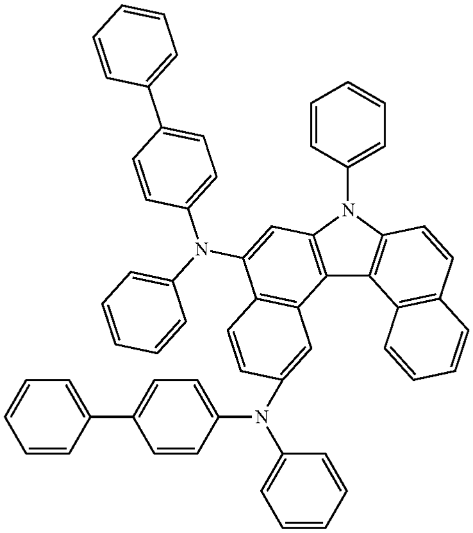
[Chemical Formula 25]
(134)
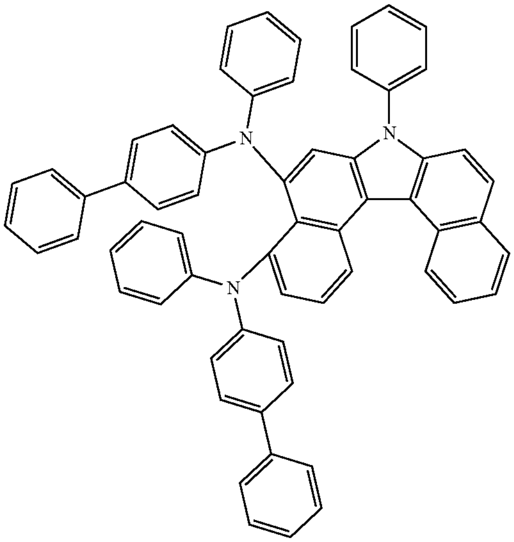
(135)
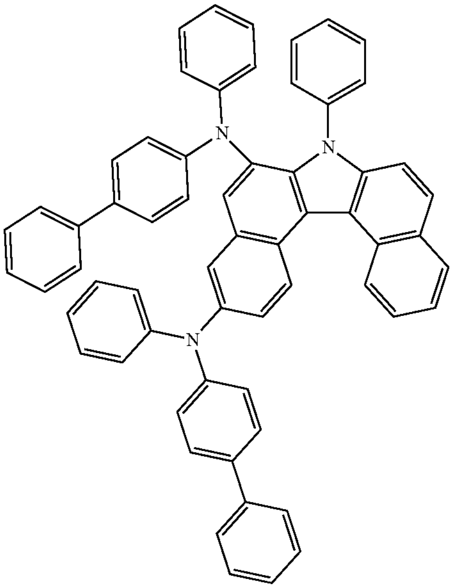

-continued
(136)
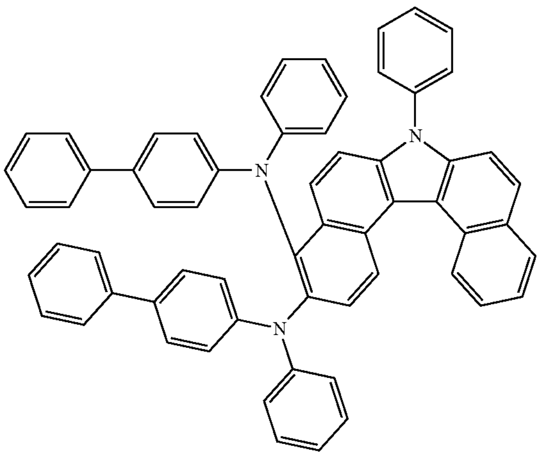
(137)
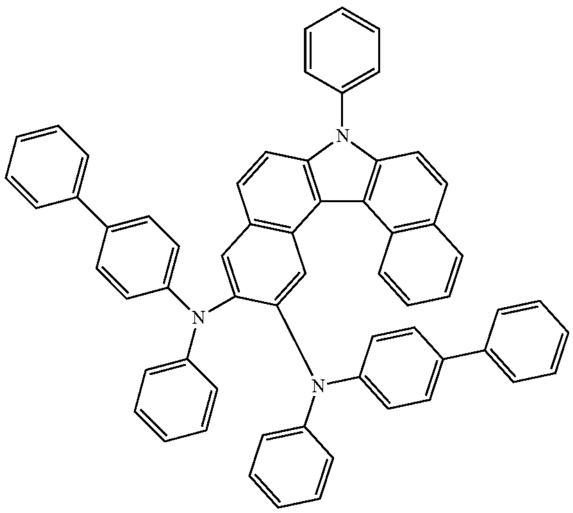
(138)
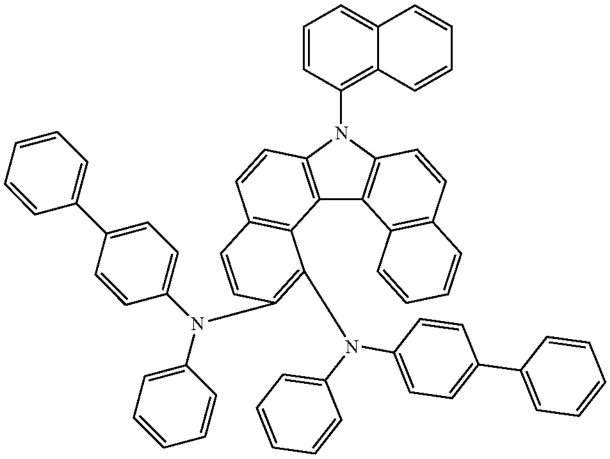
(139)
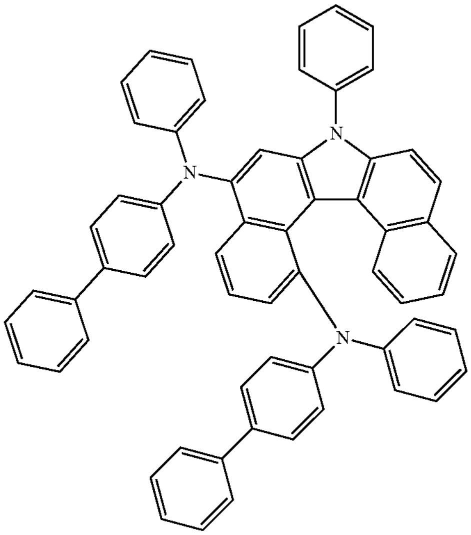
(140)
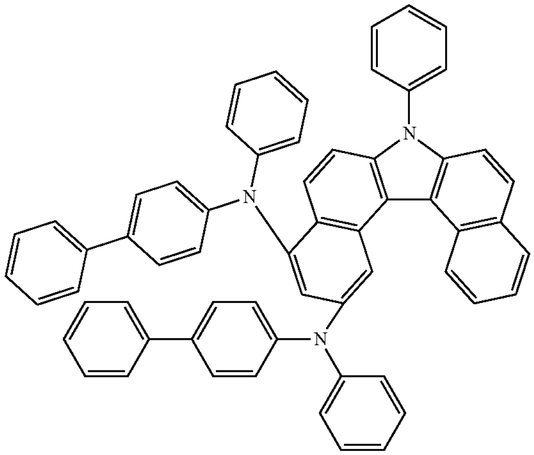

-continued
(141)
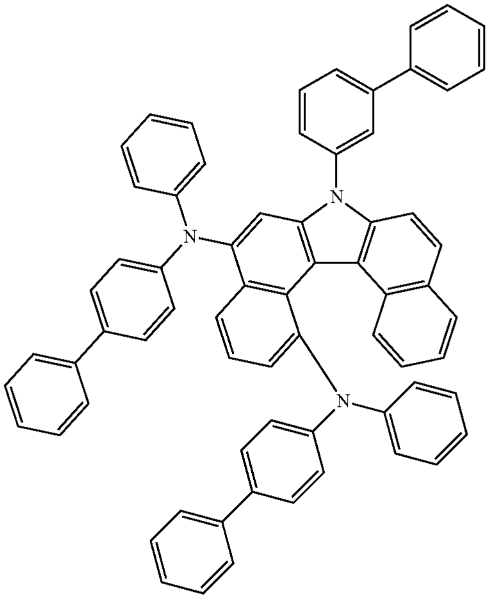
[Chemical Formula 26]
(142)
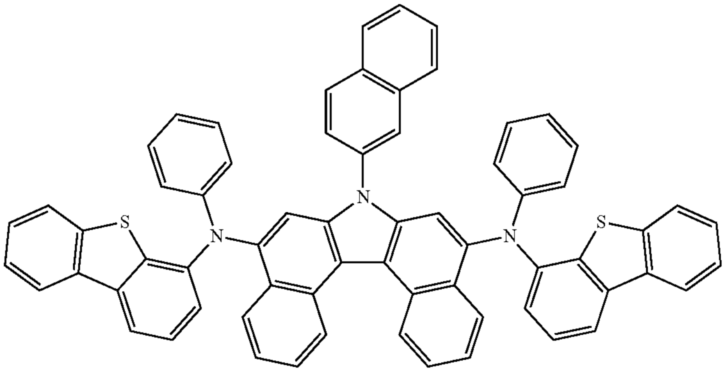
(143)
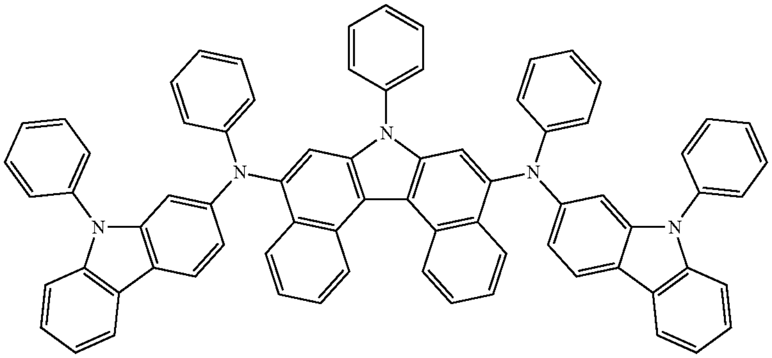

-continued
(144)
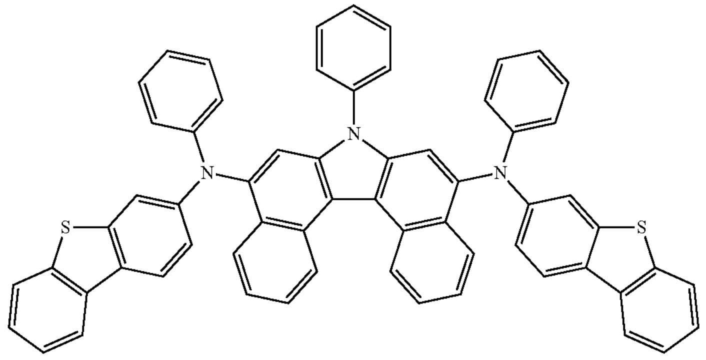
(145)
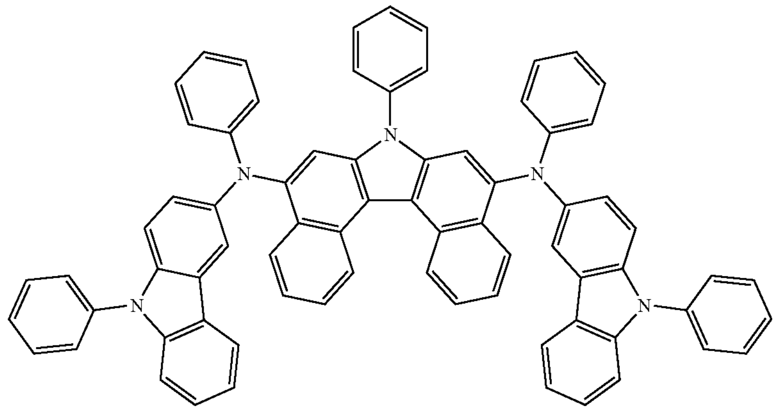
(146)
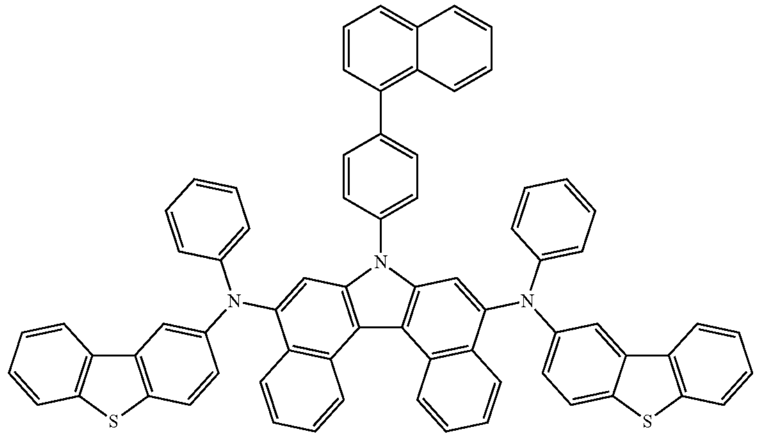
(147)
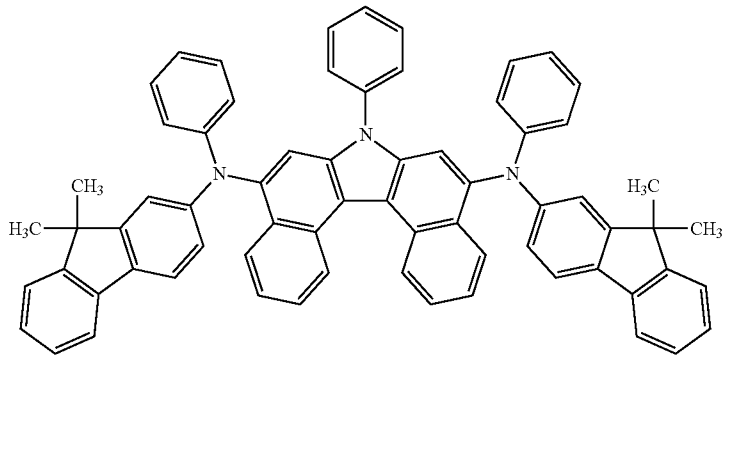

-continued
(148)
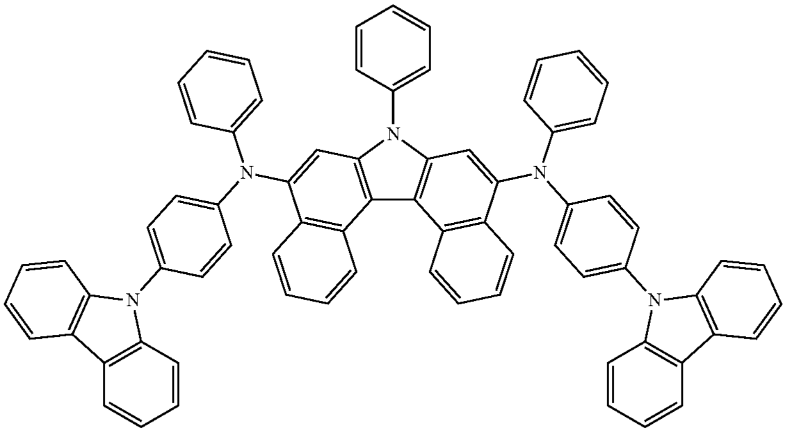
(149)
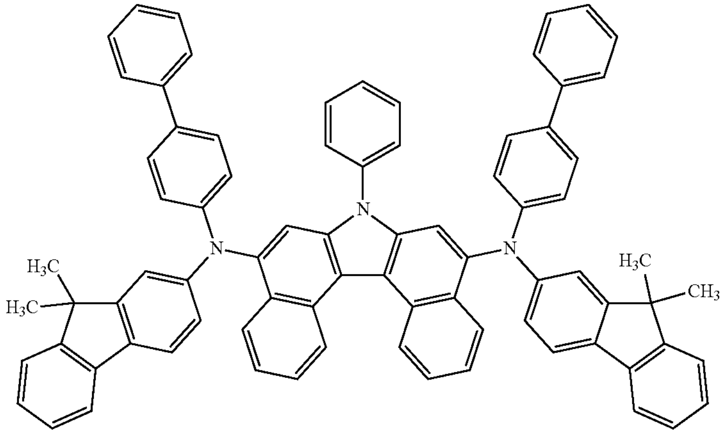
[Chemical Formula 27]
(150)
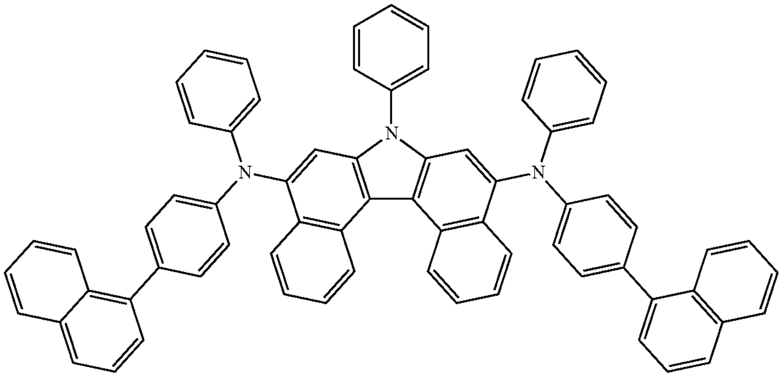
(151)
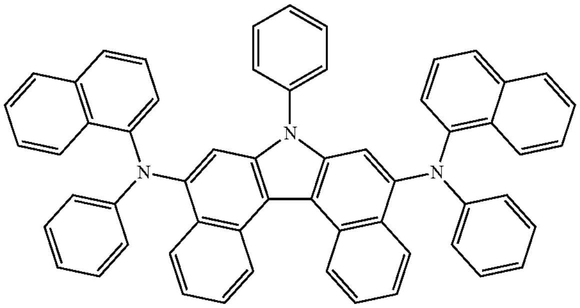

-continued
(152)
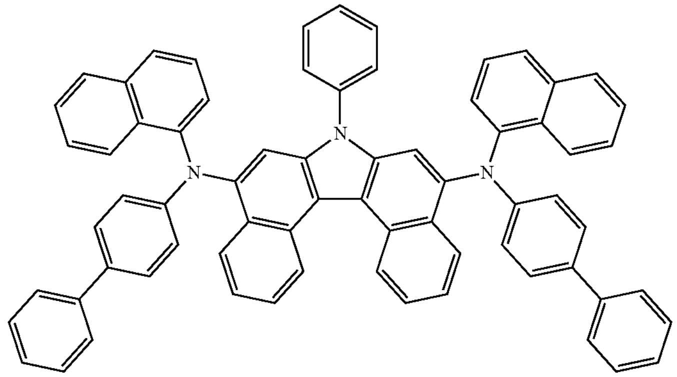
(153)
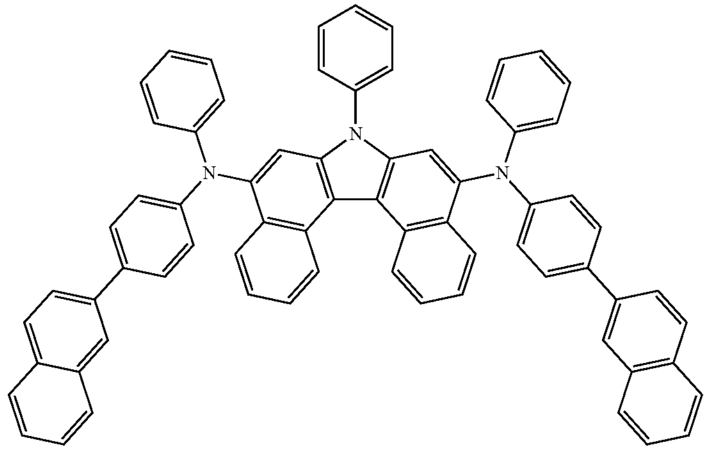
(154)
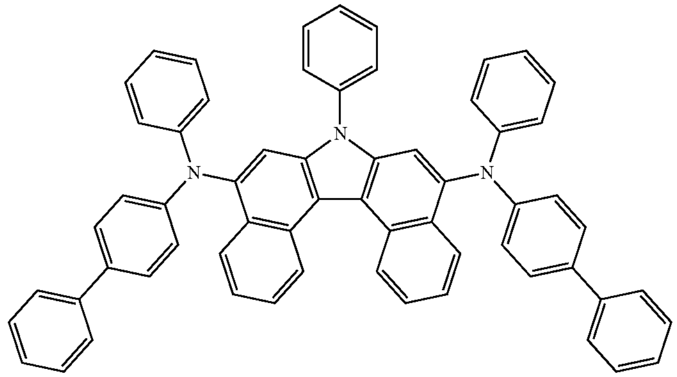
(155)
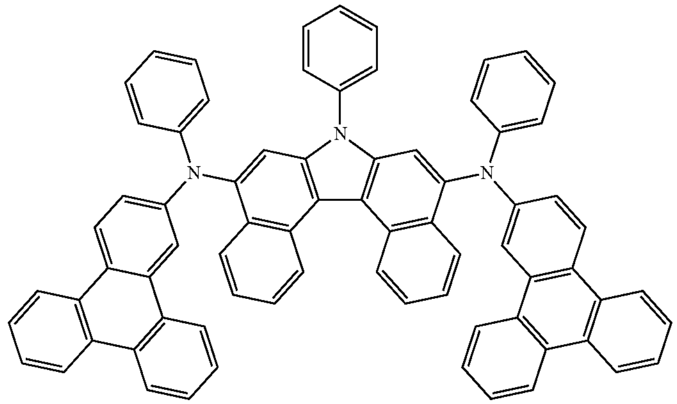

-continued
(156)
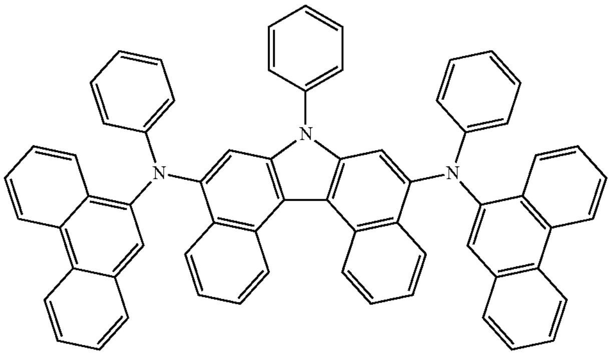
(157)
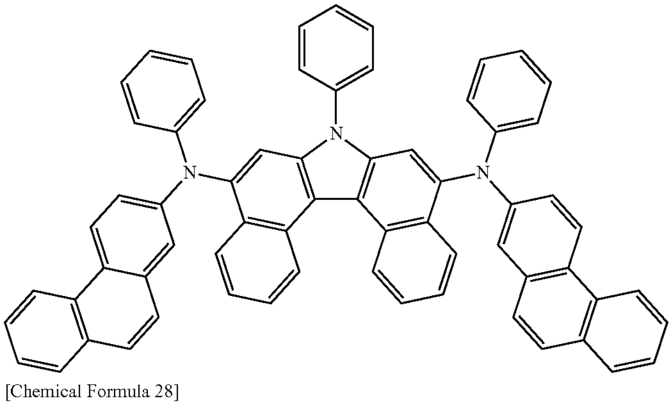
[Chemical Formula 28]
(158)
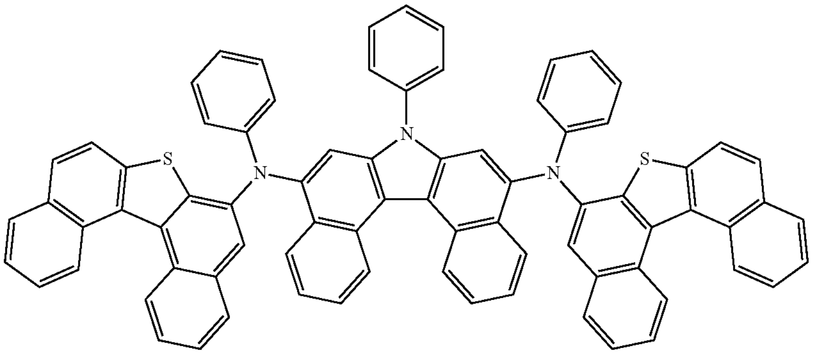
(159)
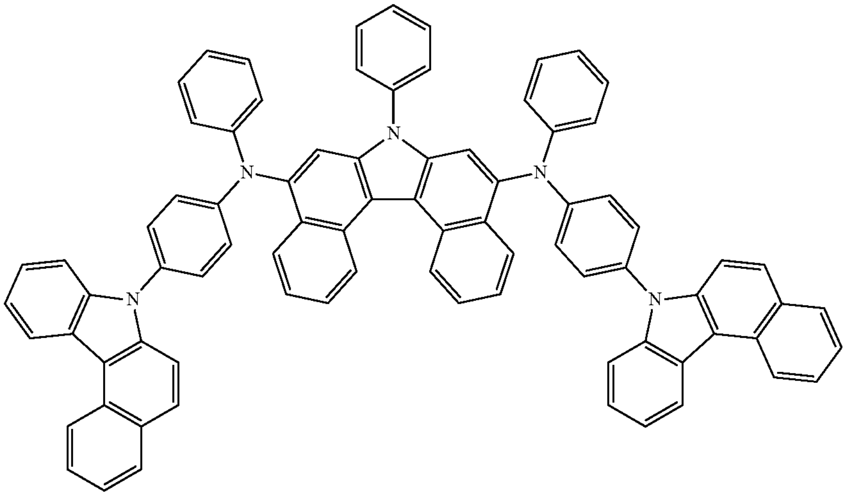

-continued
(160)
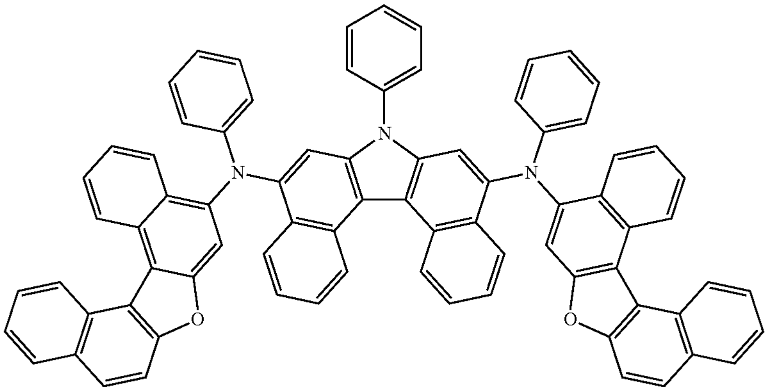
(161)
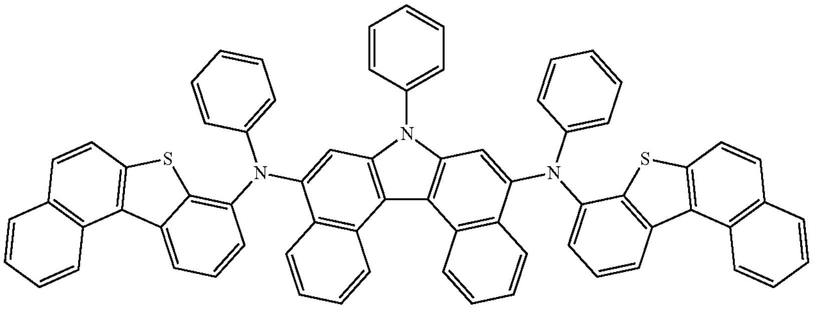
(162)
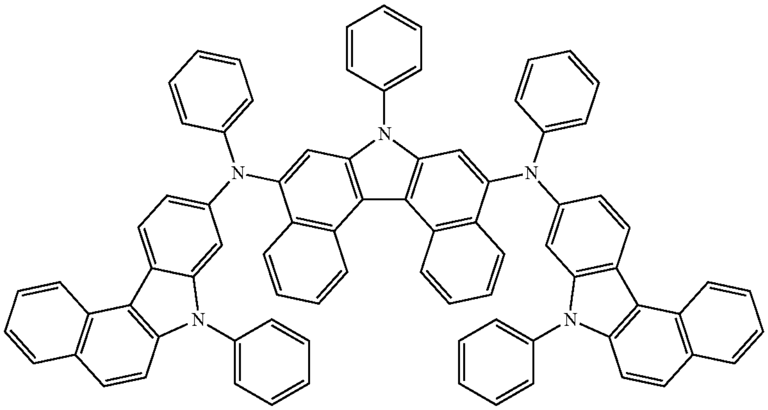
(163)
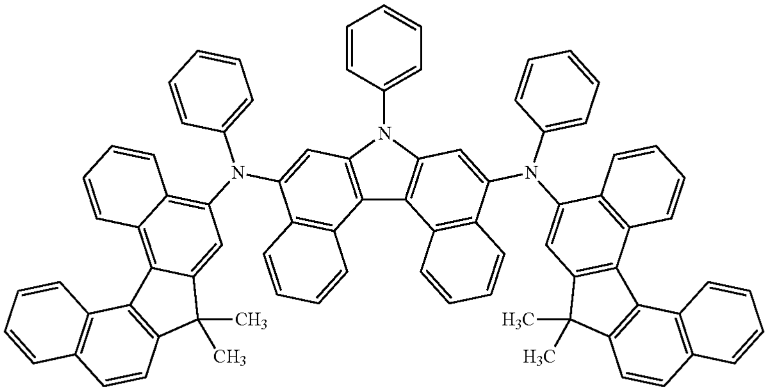

-continued
(164)
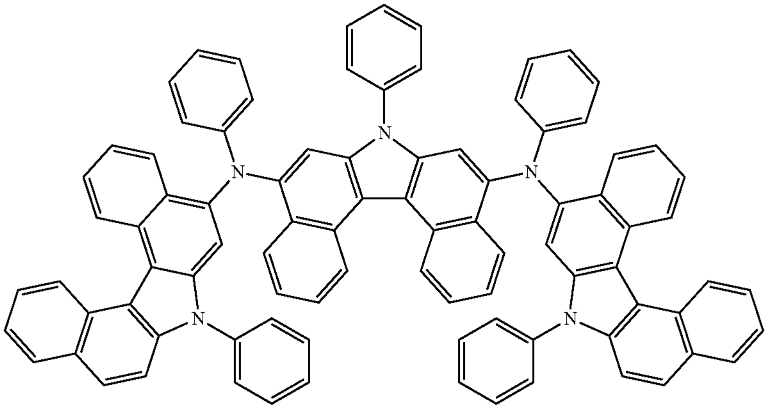
(165)
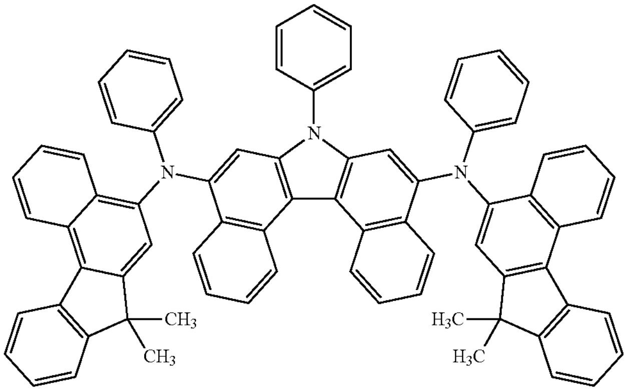
[Chemical Formula 29]
(166)
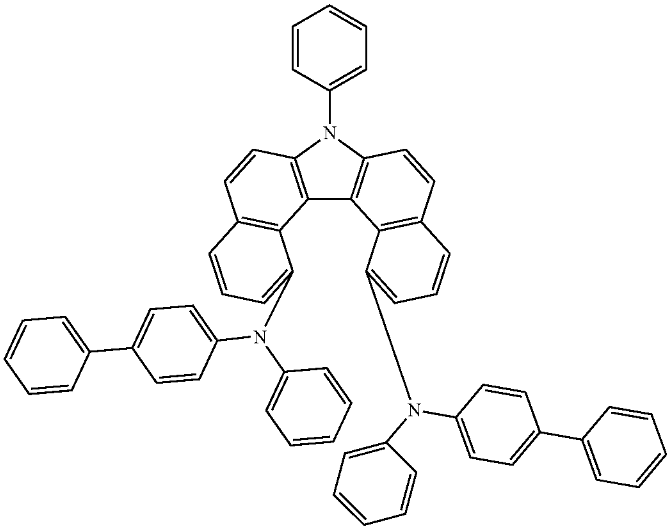

-continued
(167)
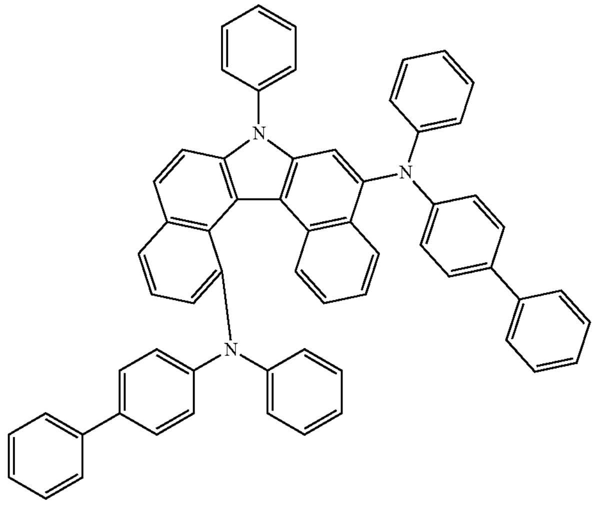
(168)
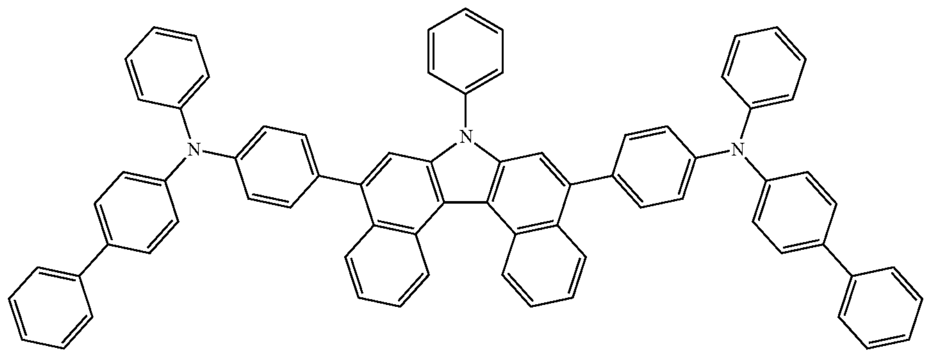
(169)
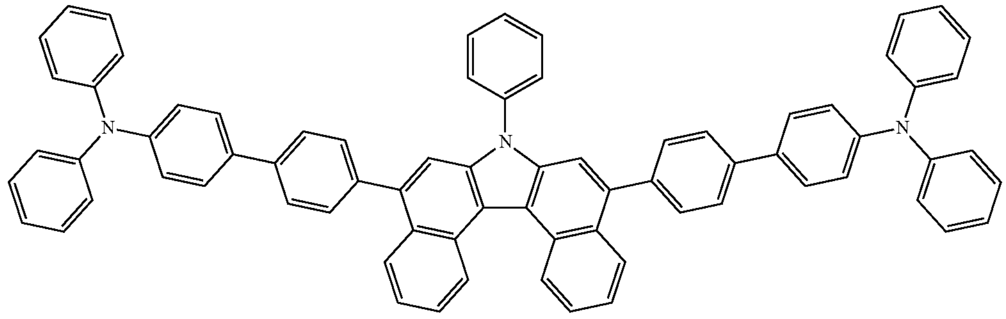
(170)
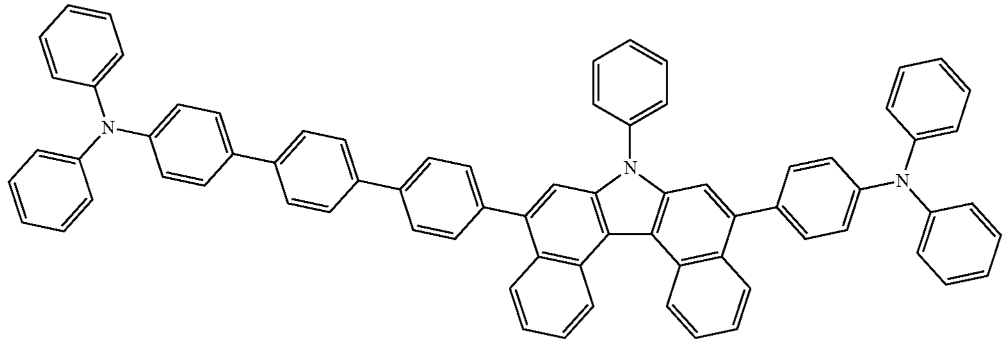

-continued
[Chemical Formula 30]
(171)
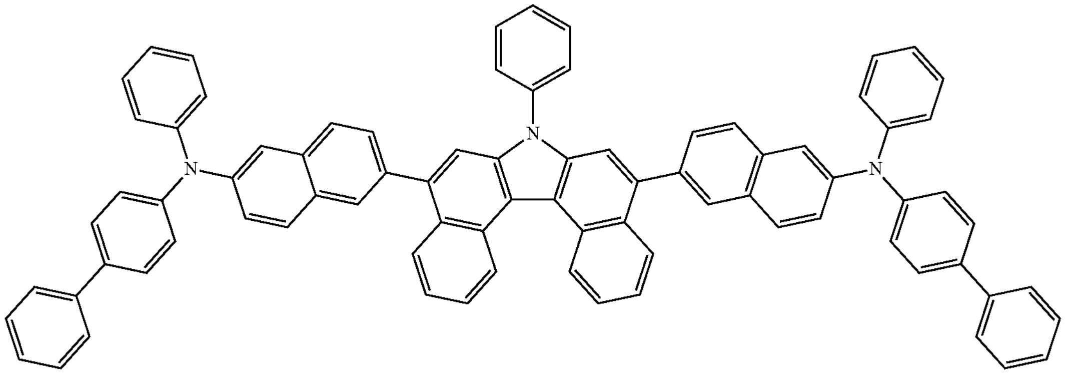
(172)
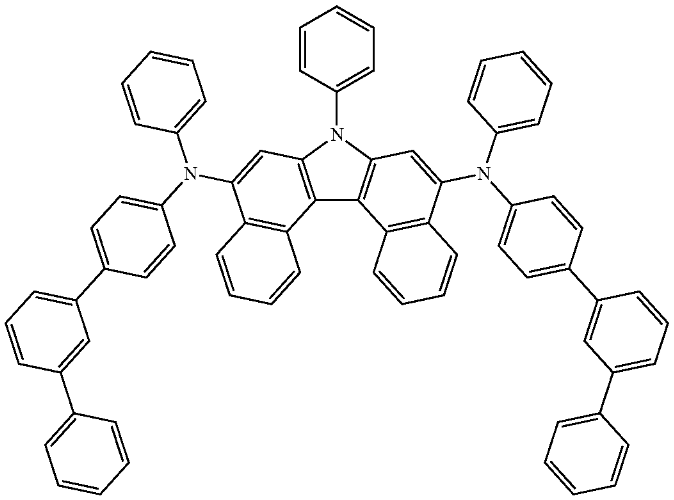
(173)
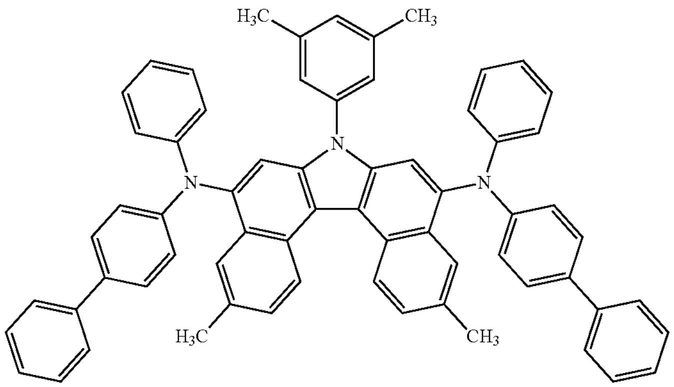

-continued (174)

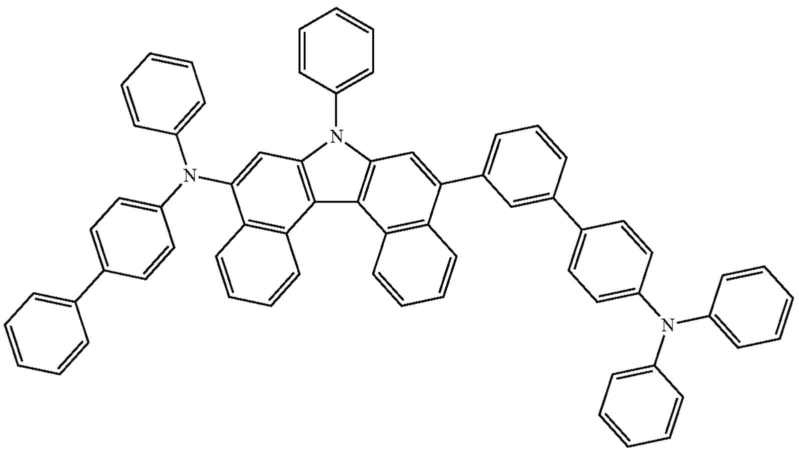

(175)

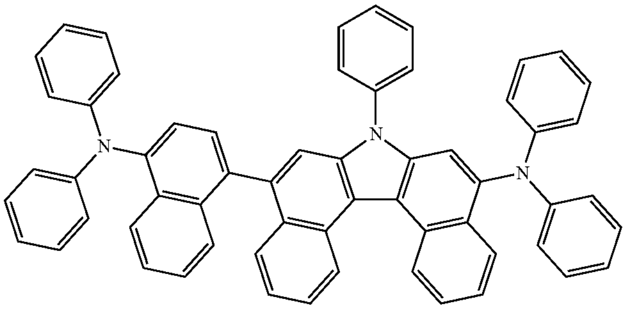

Note that, as in the organic compound represented by Structural Formula (174), in the case where each of b, c, d, e, f and g in General Formulae (G0), (G1), (G1-1), (G1-2), (G2), and (G3) is an integer of 1 to 3, $Ar^1$ and $Ar^3$ to $Ar^8$ may be bonds of different substitutes. For example, Structural Formula (174) is an example in which c is 2 in General Formula (G0); 1,3-phenylene is used for one $Ar^3$ and 1,4-phenylene is used for the other $Ar^3$.

Note that the organic compound of this embodiment can be deposited by an evaporation method (including a vacuum evaporation method), an inkjet method, a coating method, a gravure printing method, or the like.

Note that this embodiment can be combined as appropriate with any of the other embodiments.

Embodiment 2

In this embodiment, examples of a method for synthesizing an organic compound of one embodiment of the present invention will be described giving the organic compounds represented by General Formula (G0) as an example.

The organic compound represented by General Formula (G0) can be obtained by a cross coupling reaction of an organic compound (a1), an arylamine compound (a2), and an arylamine compound (a3) as shown in a synthesis scheme (F-1) below. Examples of $X^1$ and $X^2$ include a halogen group such as chlorine, bromine, or iodine and a sulfonyloxy group. When b or c is 0, that is, when the organic compound (a2) or the organic compound (a3) is a secondary amine, $D^1$ represents hydrogen; when b or c is 1 or larger, that is, when the organic compound (a2) or the organic compound (a3) is a tertiary amine, $D^1$ represents boronic acid, dialkoxyboronic acid, aryl aluminum, aryl zirconium, aryl zinc, aryl tin, or the like.

[Chemical Formula 31]

(F-1)

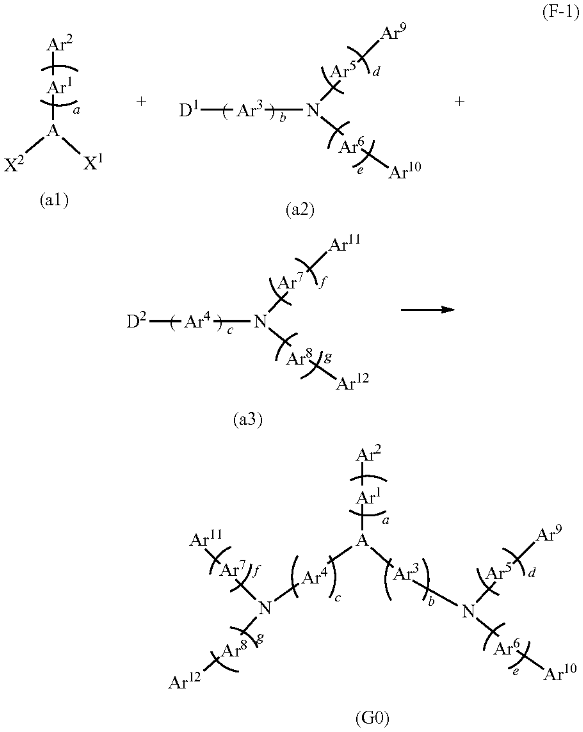

(a1) (a2) (a3) (G0)

In General Formulae (a1) to (a3) and (G0), A represents a substituted or unsubstituted dibenzocarbazole skeleton; $Ar^1$ is bonded to the N-position of the dibenzocarbazole skeleton; each of $Ar^1$ and $Ar^3$ to $Ar^8$ independently represents a substituted or unsubstituted arylene group having 6 to 25 carbon atoms; $Ar^2$ represents a substituted or unsubstituted aryl group having 6 to 25 carbon atoms; each of a, b, c, d, e, f and g independently represents an integer of 0 to 3; and each of $Ar^9$ to $Ar^{12}$ independently represents a substituted or unsubstituted aryl group having 6 to 100 carbon atoms or a substituted or unsubstituted heteroaryl group having 6 to 100 carbon atoms.

The above reaction can proceed under various conditions. For example, a synthesis method in which a metal catalyst is used under the presence of a base can be employed. For example, Ullmann coupling or the Buchwald-Hartwig reaction can be used in the case where b or c is 0. In the case where b or c is 1 or larger, the Suzuki-Miyaura reaction can be used.

Note that the organic compound (a2) and the organic compound (a3) are reacted at the same time with the organic compound (a1); however, in the case where the organic compound (a2) and the organic compound (a3) are different organic compounds, it is preferable to react the organic compound (a2) and the organic compound (a3) sequentially with the organic compound (a1) one kind by one kind because a target substance having a high yield and high purity can be obtained. In the case where the organic compound (a2) and the organic compound (a3) are the same, they are preferably reacted at the same time with the organic compound (a1) because a target substance having a high yield and high purity can be obtained.

In the case where b or c is 1 or larger, the functional groups to be reacted may be opposite, i.e., each of X1 and X2 in the organic compound (a1) may represent boronic acid, and each of D1 in the organic compound (a2) and D2 in the organic compound (a3) may represent a halogen group.

The organic compound of one embodiment of the present invention can be synthesized in the above-described manner.

In this embodiment, an example of a method for synthesizing an intermediate that can be used for synthesis of the organic compound of one embodiment of the present invention will be described.

As will be shown in Synthesis Scheme (F-2) below, an organic compound (b2) can be obtained by halogenation of the organic compound (b1) as the source materials of the organic compound represented by General Formula (G2).

As will be shown in Synthesis Scheme (F-2) below, the source materials of the organic compound represented by General Formula (G2) can obtain an organic compound (b2) by halogenation of the organic compound (b1).

[Chemical Formula 32]

(F-2)

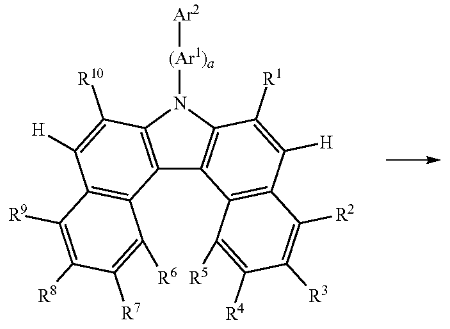

(b1)

-continued

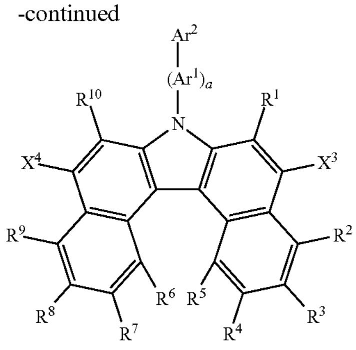

(b2)

In General Formulae (b1) and (b2), $Ar^1$ represents a substituted or unsubstituted arylene group having 6 to 25 carbon atoms; $Ar^2$ represents a substituted or unsubstituted aryl group having 6 to 25 carbon atoms; each of $R^1$ to $R^{10}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms; and a represents an integer of 0 to 3. Examples of $X^3$ and $X^4$ include a halogen group such as chlorine, bromine, or iodine.

The above reaction can proceed under various conditions. For example, a reaction using a halogenating agent can be used in the presence of a polar solvent. As the above halogenating agent, N-bromosuccinimide (NBS), N-iodosuccinimide (NIS), bromine, iodine, potassium iodide, or the like can be used. A bromide is preferably used as the halogenating agent because synthesis can be performed at lower cost. When an iodide is used as a halogenating agent, the generated target substance is preferably used as a source material because the reaction proceeds more easily owing to higher activation of an iodine-substituted portion.

In the above scheme, when N-bromosuccinimide (NBS) or N-iodosuccinimide (NIS) is reacted in the presence of ethyl acetate or chloroform, the 5-position and 9-position of the dibenzo[c,g]carbazole skeleton are selectively halogenated at room temperature easily. Therefore, the above scheme can be suitably used for the synthesis of the organic compound of one embodiment of the present invention. In addition, a solvent of ethyl acetate, chloroform, or the like which is used in the above reaction is unlikely to be mixed with water, so that the solution after the reaction is preferably cleaned with water because unnecessary succinimide, unreacted NBS or NIS, or the like can be easily removed and purification can be easily performed.

The organic compound (b2) obtained by the scheme (F-2) can be used as the organic compound (a1) in the scheme (F-1).

Although an example of a method for synthesizing the organic compound of one embodiment of the present invention is described above, the present invention is not limited thereto and synthesis may be performed by any other synthesis method.

Embodiment 3

In this embodiment, structure examples of light-emitting elements including an organic compound of one embodiment of the present invention will be described below with reference to FIG. 1.

FIG. 1(A) is a schematic cross-sectional view of a light-emitting element 150 of one embodiment of the present invention. The light-emitting element 150 includes at least a pair of electrodes (an electrode 101 and an electrode 102) and an EL layer 100 provided between the pair of electrodes.

The EL layer 100 includes at least a light-emitting layer 130 and a hole-transport layer 112. In addition, functional layers such as a hole-injection layer 111, an electron-transport layer 118, and an electron-injection layer 119 are included.

Although description is given assuming that the electrode 101 serves as an anode and the electrode 102 serves as a cathode in this embodiment, the structure of the light-emitting element is not limited thereto. That is, a structure in which the electrode 101 serves as a cathode and the electrode 102 serves as an anode may be employed. In that case, the stacking order of layers is reversed. In other words, the hole-injection layer, the hole-transport layer, the light-emitting layer, the electron-transport layer, and the electron-injection layer may be stacked in this order from the anode side.

The structure of the EL layer 100 is not limited thereto, and another functional layer, for example, a functional layer that is capable of improving or inhibiting an electron- or hole-transport property or a functional layer inhibiting diffusion of excitons may be included. The functional layers may be each a single layer or have a stacked-layer structure of a plurality of layers.

In the light-emitting element 150, any of the layers in the EL layer 100 contains the organic compound of one embodiment of the present invention. Note that the organic compound has a favorable quantum yield. Therefore, a light-emitting element with high emission efficiency can be obtained by using the organic compound as a guest material of the light-emitting layer 130. Further, blue light emission with high color purity can be obtained.

Structure Example 1 of Light-Emitting Element

Figure 1B:
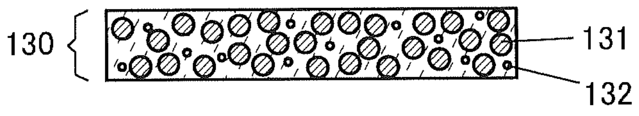

Next, a structure example of the above blue fluorescent element will be described with reference to FIGS. 1(A), 1(B), and 1(C).

A light-emitting element 150 illustrated in FIG. 1(A) is an element in which the organic compound of one embodiment of the present invention is used for at least the light-emitting layer 130. FIG. 1(B) illustrates a structure example of materials in the light-emitting layer 130, and FIG. 1(C) is a schematic diagram showing the correlation of energy levels of the materials in the light-emitting layer 130.

Here, the case where a T1 level of a host material 131 is lower than a T1 level of a guest material 132 is described. The following explains what terms and numerals in FIG. 1(C) represent. Note that the T1 level of the host material 121 may be higher than the T1 level of the guest material 122.

Host (131): the host material 131;

Guest (132): the guest material 132 (fluorescent material);

$S_{FH}$: the S1 level of the host material 131;

$T_{FH}$: the T1 level of the host material 131;

$S_{FG}$: the S1 level of the guest material 132 (fluorescent material); and $T_{FG}$: the T1 level of the guest material 132 (fluorescent material).

The host material 131 preferably has a function of converting triplet excitation energy into singlet excitation energy by causing triplet-triplet annihilation (TTA). Thus, the triplet excitation energy which normally does not contribute to fluorescence and is generated in the light-emitting layer 130 can be partly converted into singlet excitation energy in the host material 131, and the singlet excitation energy can be transferred to the guest material 132 (see Route $E_1$ in FIG. 1(C)) and extracted as fluorescence. Accordingly, the emission efficiency of the fluorescent element can be improved. Note that the fluorescence caused by TTA is obtained through a triplet excited state having a long lifetime; thus, delayed fluorescence is observed.

Figure 1C:
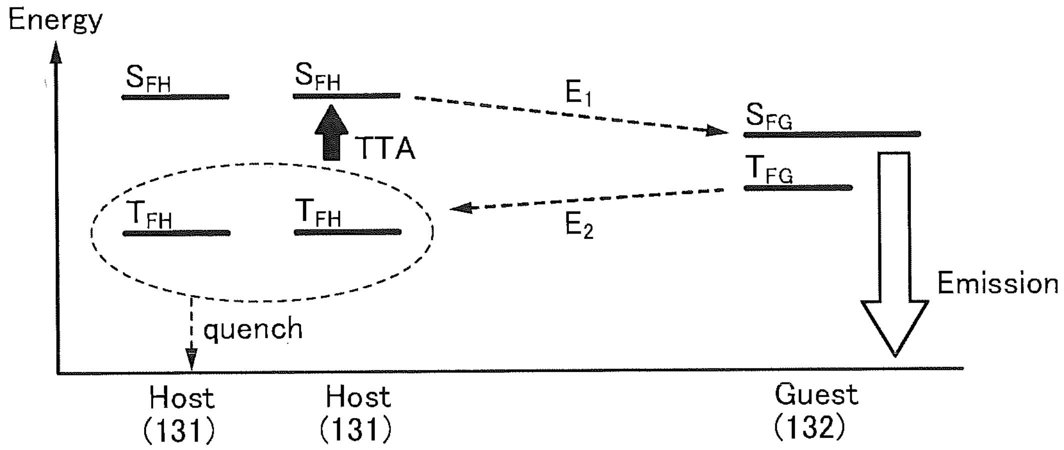

In order to transfer the singlet excitation energy to the guest material 132 efficiently in the light-emitting layer 130, the lowest level of the singlet excitation energy (S1 level) of the host material 131 is preferably higher than the S1 level of the guest material 132 as shown in FIG. 1(C). In addition, the lowest level of the triplet excitation energy (T1 level) of the host material 131 is preferably lower than the T1 level of the guest material 132 (see Route $E_2$ in FIG. 1(C)). With such a structure, TTA can be efficiently caused in the light-emitting layer 130.

Furthermore, the T1 level of the host material 131 is preferably lower than the T1 level of a material used for the hole-transport layer 112 that is in contact with the light-emitting layer 130. That is, the hole-transport layer 112 preferably has a function of inhibiting diffusion of excitons. Such a structure can inhibit diffusion of triplet excitons generated in the light-emitting layer 130 to the light-emitting layer 130, so that an element with high emission efficiency can be provided.

Having a favorable quantum yield, the organic compound of one embodiment of the present invention can be suitably used as a guest material utilizing the TTA in a light-emitting element.

Note that the lowest singlet excitation energy level of an organic compound can be observed from an absorption spectrum at a transition from the singlet ground state to the lowest singlet excited state in the organic compound. Alternatively, the lowest singlet excitation energy level may be estimated from a peak wavelength of a fluorescence spectrum of the organic compound. Furthermore, the lowest triplet excitation energy level can be observed from an absorption spectrum at a transition from the singlet ground state to the lowest triplet excited state in the organic compound, but is difficult to observe in some cases because this transition is a forbidden transition. In such cases, the lowest triplet excitation energy level may be estimated from a peak wavelength of a phosphorescence spectrum of the organic compound.

Note that the organic compound of one embodiment of the present invention can be used for an electronic apparatus such as an organic thin film solar cell. Specifically, the organic compound can be used in a carrier-transport layer or a carrier-injection layer because the organic compound has a carrier-transport property. In addition, a mixed film of the organic compound and an acceptor substance can be used as a charge generation layer. The organic compound can be photoexcited and hence can be used for a power generation layer.

<Material>

Next, components of a light-emitting element of one embodiment of the present invention will be described in detail below.

<<Light-Emitting Layer>>

In the light-emitting layer 130, the host material 131 is present in a higher proportion by weight than at least the guest material 132, and the guest material 132 (fluorescent material) is dispersed in the host material 131. Note that in the light-emitting layer 130, the host material 131 may be composed of one kind of compound or a plurality of compounds.

In the light-emitting layer 130, the organic compound of one embodiment of the present invention is preferably used as the guest material 132. As the guest material 132, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like can be used, and for example, the following materials can be used.

Specific examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9-phenyl-9H-fluoren-9-yl)phenyl]-N,N'-bis(4-tert-butylphenyl)-pyrene-1,6-diamine (abbreviation: 1,6tBu-FLPAPrn), N,N'-bis[4-(9-phenyl-9H-fluoren-9-yl)phenyl]-N,N'-diphenyl-3,8-dicyclohexylpyrene-1,6-diamine (abbreviation: ch-1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(1-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N"',N"'-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 6, coumarin 545T, N,N'-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and 5,10,15,20-tetraphenylbisbenzo[5,6]indeno[1,2,3-cd: 1',2',3'-lm]perylene.

Note that the light-emitting layer 130 may contain a material other than the host material 131 and the guest material 132.

In addition, the organic compound of one embodiment of the present invention can be used as the host material 131 in the light-emitting layer 130.

Although there is no particular limitation on a material that can be used in the light-emitting layer 130, examples include condensed polycyclic aromatic compounds such as anthracene derivatives, phenanthrene derivatives, pyrene derivatives, chrysene derivatives, and dibenzo[g,p]chrysene derivatives, and specific examples include metal complexes such as tris(8-quinolinolato)aluminum(III) (abbreviation: Alq), tris(4-methyl-8-quinolinolato)aluminum(III) (abbreviation: $Almq_3$), bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). Other examples include condensed polycyclic aromatic compounds such as anthracene derivatives, phenanthrene derivatives, pyrene derivatives, chrysene derivatives, and dibenzo[g,p]chrysene derivatives, and specific examples include 9,10-diphenylanthracene (abbreviation: DPAnth), N,N'-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 7-[4-(10-phenyl-9-anthryl)phenyl]-7H-dibenzo[c,g]carbazole (abbreviation: cgDBCzPA), 6,12-dimethoxy-5,11-diphenylchrysene, N,N,N',N',N",N",N"',N"'-octaphenyldibenzo[g,p]chrysene-2,7,10,15-tetraamine (abbreviation: DBC1), 9-phenyl-3-[4-(10-phenyl-9-anthryl)phenyl]-9H-carbazole (abbreviation: PCzPA), 3,6-diphenyl- 9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). One or more substances having a wider energy gap than the guest material 132 are selected from these substances and known substances.

Note that the light-emitting layer 130 can also have a structure in which two or more layers are stacked. For example, in the case where the light-emitting layer 130 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material.

Next, details of other components of the light-emitting element 150 in FIG. 1(A) will be described below.

<<Hole-Injection Layer>>

The hole-injection layer 111 has a function of reducing a barrier for hole injection from one of the pair of electrodes (the electrode 101 or the electrode 102) to promote hole injection and is formed using a transition metal oxide, a phthalocyanine derivative, an aromatic amine, or the like, for example. Examples of the transition metal oxide include molybdenum oxide, vanadium oxide, ruthenium oxide, tungsten oxide, and manganese oxide. Examples of the phthalocyanine derivative include phthalocyanine and metal phthalocyanine. Examples of the aromatic amine include a benzidine derivative and a phenylenediamine derivative. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron accepting property and a layer containing a hole-transport material may be used. In a steady state or in the presence of an electric field, electric charge can be transferred between these materials. Examples of the material having an electron-accepting property include organic acceptors such as a quinodimethane derivative, a chloranil derivative, and a hexaazatriphenylene derivative. A specific example is a compound having an electron-withdrawing group (a halogen group or a cyano group), such as 7,7,8,8-tetracyano-2,3,5,6-tetrafluoroquinodimethane (abbreviation: $F_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of metal from Group 4 to Group 8 can be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because of stability in the air, a low hygroscopic property, and easiness of handling.

A material having a property of transporting more holes than electrons can be used as the hole-transport material, and a material having a hole mobility of $1\times10^{-6}$ $cm^2/Vs$ or higher is preferable. Specifically, an aromatic amine compound, a carbazole derivative, an aromatic hydrocarbon, a stilbene derivative, or the like can be used. Furthermore, the hole-transport material may be a high molecular compound.

Note that the organic compound of one embodiment of the present invention can also be suitably used as the hole-transport material.

Examples of the aromatic amine compound, which is a material having a high hole-transport property, include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis {4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Specific examples of the carbazole derivative include 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples of the carbazole derivative include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Moreover, examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples include pentacene and coronene. The aromatic hydrocarbon having a hole mobility of $1\times10^{-6}$ $cm^2/Vs$ or higher and having 14 to 42 carbon atoms is further preferable.

Note that the aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

Other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD).

Furthermore, examples of the material having a high hole-transport property include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N"-triphenyl-N,N',N"-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Moreover, amine compounds, carbazole compounds, thiophene compounds, furan compounds, fluorene compounds, triphenylene compounds, phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), 2,8-di(9H-carbazol-9-yl)-dibenzothiophene (abbreviation: Cz2DBT), 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)-benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II), or the like can be used. Among the above compounds, compounds including at least one of a pyrrole skeleton, a furan skeleton, a thiophene skeleton, and an aromatic amine skeleton are preferred because of their high stability and reliability. In addition, the compounds having such skeletons have a high hole-transport property to contribute to a reduction in driving voltage.

<<Hole-Transport Layer>>

The hole-transport layer 112 is a layer containing a hole-transport material and can be formed using any of the hole-transport materials described as examples of the material of the hole-injection layer 111. In order that the hole-transport layer 112 has a function of transporting holes injected into the hole-injection layer 111 to the light-emitting layer 130, the hole-transport layer 112 preferably has the HOMO level equal or close to the HOMO level of the hole-injection layer 111.

A substance having a hole mobility of $1\times10^{-6}$ $cm^2/Vs$ or higher is preferable. However, other substances may also be used as long as they have a property of transporting more holes than electrons. Note that the layer containing a substance having a high hole-transport property is not limited to a single layer, and two or more layers containing the aforementioned substances may be stacked.

In addition, the organic compound of one embodiment of the present invention can also be suitably used.

<<Electron-Transport Layer>>

The electron-transport layer 118 has a function of transporting, to the light-emitting layer 130, electrons injected from the other of the pair of electrodes (the electrode 101 or the electrode 102) through the electron-injection layer 119. A material having a property of transporting more electrons than holes can be used as the electron-transport material, and a material having an electron mobility of $1\times10^{-6}$ $cm^2/Vs$ or higher is preferable. As a compound that easily accepts electrons (a material having an electron-transport property), a π-electron deficient heteroaromatic compound such as a nitrogen-containing heteroaromatic compound or a metal complex can be used, for example. Specific examples include a metal complex having a quinoline ligand, a benzoquinoline ligand, an oxazole ligand, or a thiazole ligand; an oxadiazole derivative; a triazole derivative, a benzimidazole derivative; a quinoxaline derivative; a dibenzoquinoxaline derivative; a phenanthroline derivative; a pyridine derivative; a bipyridine derivative; a pyrimidine derivative; and a triazine derivative. Note that other substances may also be used for the electron-transport layer as long as they have a property of transporting more electrons than holes. The electron-transport layer 118 is not limited to a single layer, and two or more layers containing the aforementioned substances may be stacked.

Specific examples include metal complexes including a quinoline skeleton or a benzoquinoline skeleton, such as tris(8-quinolinolato)aluminum(III) (abbreviation: Alq), tris(4-methyl-8-quinolinolato)aluminum(III) (abbreviation: $Almq_3$), bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), and bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ) can be used. Furthermore, other than metal complexes, the following can be used: heterocyclic compounds such as 2-(4-biphenylyl)-5-(4-tert-butylphenyl)-1,3,4-oxadiazole (abbreviation:

PBD), 1,3-bis[5-(p-tert-butylphenyl)-1,3,4-oxadiazol-2-yl] benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), bathophenanthroline (abbreviation: Bphen), 2,9-bis(naphthalen-2-yl)-4,7-diphenyl-1,10-phenanthroline (abbreviation: NBPhen), and bathocuproine (abbreviation: BCP); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3-(3,9'-bi-9H-carbazol-9-yl)phenyl] dibenzo[f,h]quinoxaline (abbreviation: 2mCzCzPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); heterocyclic compounds having a pyridine skeleton such as 3,5-bis[3-(9H-carbazol-9-yl)phenyl] pyridine (abbreviation: 35DCzPPy) and 1,3,5-tri[3-(3-pyridyl)phenyl]benzene (abbreviation: TmPyPB); and heteroaromatic compounds such as 4,4'-bis(5-methylbenzoxazol-2-yl)stilbene (abbreviation: BzOs). Among the above-described heterocyclic compounds, the heterocyclic compounds having at least one of a triazine skeleton, a diazine (pyrimidine, pyrazine, pyridazine) skeleton, and a pyridine skeleton are preferred because of their high stability and reliability. In addition, the heterocyclic compounds having such skeletons have a high electron-transport property to contribute to a reduction in driving voltage. Alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances listed here are mainly substances having an electron mobility of $1\times10^{-6}$ $cm^2/Vs$ or higher.

Note that other substances may also be used for the electron-transport layer as long as they have a property of transporting more electrons than holes. The electron-transport layer 118 is not limited to a single layer, and two or more layers containing the aforementioned substances may be stacked.

A layer that controls transfer of carriers may be provided between the electron-transport layer 118 and the light-emitting layer 130. This is a layer formed by addition of a small amount of a substance having a high electron-trapping property to the above-described material having a high electron-transport property, and the layer is capable of adjusting carrier balance by suppressing transport of carriers. Such a structure is very effective in preventing a problem (such as a reduction in element lifetime) that occurs when electrons pass through the light-emitting layer.

An n-type compound semiconductor may also be used, and an oxide such as titanium oxide, zinc oxide, silicon oxide, tin oxide, tungsten oxide, tantalum oxide, barium titanate, barium zirconate, zirconium oxide, hafnium oxide, aluminum oxide, yttrium oxide, or zirconium silicate; a nitride such as silicon nitride; cadmium sulfide; zinc selenide; or zinc sulfide can be used, for example.

<<Electron-Injection Layer>>

The electron-injection layer 119 has a function of reducing a barrier for electron injection from the electrode 102 to promote electron injection and can be formed using a Group 1 metal or a Group 2 metal, or an oxide, a halide, or a carbonate of them, for example. Alternatively, a composite material of the electron-transport material described above and a material having a property of donating electrons thereto can be used. Examples of the material having an electron-donating property include a Group 1 metal, a Group 2 metal, and an oxide of any of them. Specifically, an alkali metal, an alkaline earth metal, or a compound thereof, such as lithium fluoride, sodium fluoride, cesium fluoride, calcium fluoride, or lithium oxide, can be used. A rare earth metal compound like erbium fluoride can also be used. Electride may also be used for the electron-injection layer 119. Examples of the electride include a substance in which electrons are added at high concentration to calcium oxide-aluminum oxide. The electron-injection layer 119 can be formed using the substance that can be used for the electron-transport layer 118.

A composite material in which an organic compound and an electron donor (donor) are mixed may also be used for the electron-injection layer 118. Such a composite material is excellent in an electron-injection property and an electron-transport property because electrons are generated in the organic compound by the electron donor. In this case, the organic compound is preferably a material that is excellent in transporting the generated electrons; specifically, the above-described substances contained in the electron-transport layer 118 (the metal complexes, heteroaromatic compounds, and the like) can be used, for example. As the electron donor, a substance showing an electron-donating property with respect to the organic compound may be used. Specifically, an alkali metal, an alkaline earth metal, and a rare earth metal are preferable, and examples include lithium, sodium, cesium, magnesium, calcium, erbium, and ytterbium. Furthermore, an alkali metal oxide and an alkaline earth metal oxide are preferable, and examples include lithium oxide, calcium oxide, and barium oxide. Alternatively, a Lewis base such as magnesium oxide can be used. Further alternatively, an organic compound such as tetrathiafulvalene (abbreviation: TTF) can be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, gravure printing, or the like. Besides the above-described materials, an inorganic compound such as a quantum dot or a high molecular compound (an oligomer, a dendrimer, a polymer, or the like) may be used for the light-emitting layer, the hole-injection layer, the hole-transport layer, the electron-transport layer, and the electron-injection layer described above.

<<Quantum Dot>>

As a light-emitting material, a quantum dot can also be used. A quantum dot is a semiconductor nanocrystal with a size of several nanometers and contains approximately $1\times10^3$ to $1\times10^6$ atoms. Since energy shift of quantum dots depend on their size, quantum dots made of the same substance emit light with different wavelengths depending on their size, and emission wavelengths can be easily adjusted by changing the size of quantum dots.

Since a quantum dot has an emission spectrum with a narrow peak, emission with high color purity can be obtained. In addition, a quantum dot is said to have a theoretical internal quantum efficiency of approximately 100%, which far exceeds that of a fluorescent organic compound, i.e., 25%, and is comparable to that of a phosphorescent organic compound. Therefore, the use of a quantum dot as a light-emitting material enables a light-emitting element with high emission efficiency to be obtained. Furthermore, since a quantum dot, which is an inorganic compound, has high inherent stability, a light-emitting element that is favorable also in terms of lifetime can be obtained.

Examples of a material of a quantum dot include a Group 14 element, a Group 15 element, a Group 16 element, a compound of a plurality of Group 14 elements, a compound of an element belonging to any of a Group 4 to a Group 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, and semiconductor clusters.

Specific examples include, but are not limited to, cadmium selenide; cadmium sulfide; cadmium telluride; zinc selenide; zinc oxide; zinc sulfide; zinc telluride; mercury sulfide; mercury selenide; mercury telluride; indium arsenide; indium phosphide; gallium arsenide; gallium phosphide; indium nitride; gallium nitride; indium antimonide; gallium antimonide; aluminum phosphide; aluminum arsenide; aluminum antimonide; lead selenide; lead telluride; lead sulfide; indium selenide; indium telluride; indium sulfide; gallium selenide; arsenic sulfide; arsenic selenide; arsenic telluride; antimony sulfide; antimony selenide; antimony telluride; bismuth sulfide; bismuth selenide; bismuth telluride; silicon; silicon carbide; germanium; tin; selenium; tellurium; boron; carbon; phosphorus; boron nitride; boron phosphide; boron arsenide; aluminum nitride; aluminum sulfide; barium sulfide; barium selenide; barium telluride; calcium sulfide; calcium selenide; calcium telluride; beryllium sulfide; beryllium selenide; beryllium telluride; magnesium sulfide; magnesium selenide; germanium sulfide; germanium selenide; germanium telluride; tin sulfide; tin selenide; tin telluride; lead oxide; copper fluoride; copper chloride; copper bromide; copper iodide; copper oxide; copper selenide; nickel oxide; cobalt oxide; cobalt sulfide; iron oxide; iron sulfide; manganese oxide; molybdenum sulfide; vanadium oxide; tungsten oxide; tantalum oxide; titanium oxide; zirconium oxide; silicon nitride; germanium nitride; aluminum oxide; barium titanate; a compound of selenium, zinc, and cadmium; a compound of indium, arsenic, and phosphorus; a compound of cadmium, selenium, and sulfur; a compound of cadmium, selenium, and tellurium; a compound of indium, gallium, and arsenic; a compound of indium, gallium, and selenium; a compound of indium, selenium, and sulfur; a compound of copper, indium, and sulfur; and combinations thereof. What is called an alloyed quantum dot, whose composition is represented by a given ratio, may be used. For example, an alloyed quantum dot of cadmium, selenium, and sulfur is a means effective in obtaining blue light because the emission wavelength can be changed by changing the content ratio of elements.

As the structure of the quantum dot, any of a core type, a core-shell type, a core-multishell type, and the like may be used. When a core is covered with a shell formed of another inorganic material having a wider band gap, the influence of defects and dangling bonds existing at the surface of a nanocrystal can be reduced. Since such a structure can significantly improve the quantum efficiency of light emission, it is preferable to use a core-shell or core-multishell quantum dot. Examples of the material of a shell include zinc sulfide and zinc oxide.

Quantum dots have a high proportion of surface atoms and thus have high reactivity and easily cohere together. For this reason, it is preferable that a protective agent be attached to, or a protective group be provided at the surfaces of quantum dots. The attachment of the protective agent or the provision of the protective group can prevent cohesion and increase solubility in a solvent. It is also possible to reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxyethylene n-nonylphenyl ether; tertiary amines such as tri(n-hexyl)amine, tri(n-octyl) amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolines; aminoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

Since band gaps of quantum dots are increased as their size is decreased, the size is adjusted as appropriate so that light with a desired wavelength can be obtained. Light emission from the quantum dots is shifted to a blue color side, i.e., a high energy side, as the crystal size is decreased. Thus, emission wavelengths of the quantum dots can be adjusted over a wavelength region of a spectrum of an ultraviolet region, a visible light region, and an infrared region by changing the size of quantum dots. The range of size (diameter) of quantum dots which is usually used is greater than or equal to 0.5 nm and less than or equal to 20 nm, preferably greater than or equal to 1 nm and less than or equal to 10 nm. The emission spectra are narrowed as the size distribution of the quantum dots gets smaller, and thus light can be obtained with high color purity. The shape of the quantum dots is not particularly limited and may be a spherical shape, a rod shape, a circular shape, or the like. Quantum rods which are rod-like shape quantum dots have a function of emitting directional light; thus, quantum rods can be used as a light-emitting material to obtain a light-emitting element with higher external quantum efficiency.

In most organic EL elements, to improve emission efficiency, concentration quenching of the light-emitting materials is suppressed by dispersing light-emitting materials in host materials. The host materials need to be materials having singlet excitation energy levels or triplet excitation energy levels higher than or equal to those of the light-emitting materials. In the case of using blue phosphorescent materials as light-emitting materials, it is particularly difficult to develop host materials which have triplet excitation energy levels higher than or equal to those of the blue phosphorescent materials and which are excellent in terms of a lifetime. Even when a light-emitting layer is composed of quantum dots and made without a host material, the quantum dots enable emission efficiency to be ensured; thus, a light-emitting element that is favorable in terms of a lifetime can be obtained. In the case where the light-emitting layer is composed of quantum dots, the quantum dots preferably have core-shell structures (including core-multi-shell structures).

In the case of using quantum dots as the light-emitting material in the light-emitting layer, the thickness of the light-emitting layer is set to be greater than or equal to 3 nm and less than or equal to 100 nm, preferably greater than or equal to 10 nm and less than or equal to 100 nm, and the quantum dot content of the light-emitting layer is greater than or equal to 1 volume % and less than or equal to 100 volume %. Note that it is preferable that the light-emitting layer be composed of the quantum dots. To form a light-emitting layer in which the quantum dots are dispersed as light-emitting materials in host materials, the quantum dots may be dispersed in the host materials, or the host materials and the quantum dots may be dissolved or dispersed in an appropriate liquid medium, and then a wet process (e.g., a spin coating method, a casting method, a die coating method, a blade coating method, a roll coating method, an inkjet method, a printing method, a spray coating method, a curtain coating method, or a Langmuir-Blodgett method) may be employed. For a light-emitting layer containing a phosphorescent material, a vacuum evaporation method, as well as the wet process, can be suitably employed.

As the liquid medium used for the wet process, for example, an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); or dimethyl sulfoxide (DMSO) can be used.

<<Pair of Electrodes>>

The electrode 101 and the electrode 102 each function as an anode or a cathode of the light-emitting element. The electrode 101 and the electrode 102 can each be formed using a metal, an alloy, a conductive compound, a mixture or a stack thereof, or the like.

One of the electrode 101 and the electrode 102 is preferably formed using a conductive material having a function of reflecting light. Examples of the conductive material include aluminum (Al) and an alloy containing Al. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, it is possible to reduce costs for manufacturing a light-emitting element with aluminum. Alternatively, silver (Ag), an alloy containing Ag and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), and gold (Au)), or the like may be used. Examples of the alloy containing silver include an alloy containing silver, palladium, and copper, an alloy containing silver and copper, an alloy containing silver and magnesium, an alloy containing silver and nickel, an alloy containing silver and gold, an alloy containing silver and ytterbium, and the like. Besides, a transition metal such as tungsten, chromium (Cr), molybdenum (Mo), copper, or titanium can be used.

Light emitted from the light-emitting layer is extracted through one or both of the electrode 101 and the electrode 102. Thus, at least one of the electrode 101 and the electrode 102 is preferably formed using a conductive material having a function of transmitting light. As the conductive material, a conductive material having a visible light transmittance higher than or equal to 40% and lower than or equal to 100%, preferably higher than or equal to 60% and lower than or equal to 100%, and a resistivity lower than or equal to $1\times10^{-2}$ Ω·cm can be used.

The electrode 101 and the electrode 102 may each be formed using a conductive material having a function of transmitting light and a function of reflecting light. As the conductive material, a conductive material having a visible light reflectivity higher than or equal to 20% and lower than or equal to 80%, preferably higher than or equal to 40% and lower than or equal to 70%, and a resistivity lower than or equal to $1\times10^{-2}$ Ω·cm can be used. For example, one or more kinds of conductive metals and alloys, conductive compounds, and the like can be used. Specifically, a metal oxide such as indium tin oxide (hereinafter, ITO), indium tin oxide containing silicon or silicon oxide (abbreviation: ITSO), indium oxide-zinc oxide (Indium Zinc Oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and Yb, or the like can be used.

In this specification and the like, the material having a function of transmitting light may be a material that has a function of transmitting visible light and has conductivity, and examples of the material include, in addition to the above-described oxide conductor typified by an ITO, an oxide semiconductor and an organic conductor containing an organic substance. Examples of the organic conductor containing an organic substance include a composite material in which an organic compound and an electron donor (donor) are mixed and a composite material in which an organic compound and an electron acceptor (acceptor) are mixed. Alternatively, an inorganic carbon-based material such as graphene may be used. The resistivity of the material is preferably lower than or equal to $1\times10^{5}$ Ω·cm, further preferably lower than or equal to $1\times10^{4}$ Ω·cm.

Alternatively, one or both of the electrode 101 and the electrode 102 may be formed by stacking a plurality of the above-described materials.

In order to improve the light extraction efficiency, a material whose refractive index is higher than that of an electrode having a function of transmitting light may be formed in contact with the electrode. The material may be conductive or non-conductive as long as it has a function of transmitting visible light. In addition to the oxide conductors described above, an oxide semiconductor and an organic substance are given as examples. Examples of the organic substance include the materials for the light-emitting layer, the hole-injection layer, the hole-transport layer, the electron-transport layer, and the electron-injection layer. Alternatively, an inorganic carbon-based material or a metal film thin enough to transmit light can be used, and a plurality of layers with a thickness of several nanometers to several tens of nanometers may be stacked.

In the case where the electrode 101 or the electrode 102 functions as the cathode, the electrode preferably contains a material having a low work function (3.8 eV or lower). For example, it is possible to use an element belonging to Group 1 or Group 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, or an alloy containing aluminum and silver.

In the case where the electrode 101 or the electrode 102 is used as an anode, the electrode preferably contains a material having a high work function (4.0 eV or higher).

The electrode 101 and the electrode 102 may each be a stack of a conductive material having a function of reflecting light and a conductive material having a function of transmitting light. That case is preferred because the electrode 101 and the electrode 102 can each have a function of adjusting the optical length so that desired light from each light-emitting layer resonates and is intensified.

As the method for forming the electrode 101 and the electrode 102, a sputtering method, an evaporation method, a printing method, a coating method, an MBE (Molecular Beam Epitaxy) method, a CVD method, a pulsed laser deposition method, an ALD (Atomic Layer Deposition) method, or the like can be used as appropriate.

<<Substrate>>

The light-emitting element of one embodiment of the present invention may be formed over a substrate of glass, plastic, or the like. As the way of stacking layers over the substrate, layers may be sequentially stacked from the electrode 101 side or sequentially stacked from the electrode 102 side.

For the substrate over which the light-emitting element of one embodiment of the present invention can be formed, glass, quartz, or plastic can be used, for example. Alternatively, a flexible substrate may be used. The flexible substrate means a substrate that can be bent, such as a plastic substrate made of polycarbonate or polyarylate, for example. A film, an inorganic vapor deposition film, or the like can also be used. Another material may be used as long as the substrate functions as a support in a manufacturing process of the light-emitting elements or the optical elements. Another material having a function of protecting the light-emitting elements or the optical elements may be used.

In the present invention and the like, a light-emitting element can be formed using any of a variety of substrates, for example. The type of the substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film. Examples of a glass substrate include a barium borosilicate glass substrate, an aluminoborosilicate glass substrate, and a soda lime glass substrate. Examples of the flexible substrate, the attachment film, the base material film, and the like are as follows. Examples include substrates of plastics typified by polyethylene terephthalate (PET), polyethylene naphthalate (PEN), polyether sulfone (PES), and polytetrafluoroethylene (PTFE). Another example is a resin such as acrylic. Another example is polypropylene, polyester, polyvinyl fluoride, or polyvinyl chloride. Another example is polyamide, polyimide, aramid, epoxy, an inorganic vapor deposition film, or paper.

A flexible substrate may be used as the substrate, and the light-emitting element may be formed directly on the flexible substrate. A separation layer may be provided between the substrate and the light-emitting element. The separation layer can be used when part or the whole of the light-emitting element formed thereover is completed, separated from the substrate, and transferred to another substrate. In such a case, the light-emitting element can be transferred to a substrate having low heat resistance or a flexible substrate as well. For the above separation layer, a stacked-layer structure of inorganic films, which are a tungsten film and a silicon oxide film, or a structure in which a resin film of polyimide or the like is formed over a substrate can be used, for example.

In other words, after the light-emitting element is formed using a substrate, the light-emitting element may be transferred to another substrate. Examples of a substrate to which the light-emitting element is transferred include, in addition to the above-described substrates, a cellophane substrate, a stone substrate, a wood substrate, a cloth substrate (including a natural fiber (silk, cotton, or hemp), a synthetic fiber (nylon, polyurethane, or polyester), a regenerated fiber (acetate, cupra, rayon, or regenerated polyester), or the like), a leather substrate, and a rubber substrate. By using such a substrate, a light-emitting element with high durability, a light-emitting element with high heat resistance, a lightweight light-emitting element, or a thin light-emitting element can be obtained.

The light-emitting element 150 may be formed over an electrode electrically connected to a field-effect transistor (FET), for example, that is formed over any of the above-described substrates. Accordingly, an active matrix display device in which the FET controls the driving of the light-emitting element 150 can be manufactured.

Note that, in this embodiment, one embodiment of the present invention has been described. Furthermore, in any of the other embodiments, one embodiment of the present invention is described. However, embodiments of the present invention are not limited thereto. In other words, since various embodiments of the invention are described in this embodiment and the other embodiments, one embodiment of the present invention is not limited to a particular embodiment. Although an example in which one embodiment of the present invention is used in a light-emitting element is described, for example, one embodiment of the present invention is not limited thereto. For example, depending on the case or according to the circumstances, one embodiment of the present invention is not necessarily used in a light-emitting element.

The structure described above in this embodiment can be used in combination as appropriate with any of the other embodiments.

Embodiment 4

In this embodiment, a light-emitting element having a structure different from the structure of the light-emitting element described in Embodiment 3 will be described below with reference to FIG. 2. Note that in FIG. 2, a portion having a function similar to that of a portion denoted by a reference numeral shown in FIG. 1(A) is represented by the same hatch pattern and the reference numeral is omitted in some cases. In addition, common reference numerals are used for portions having similar functions, and a detailed description thereof is omitted in some cases.

Structure Example 2 of Light-Emitting Element

Figure 2:
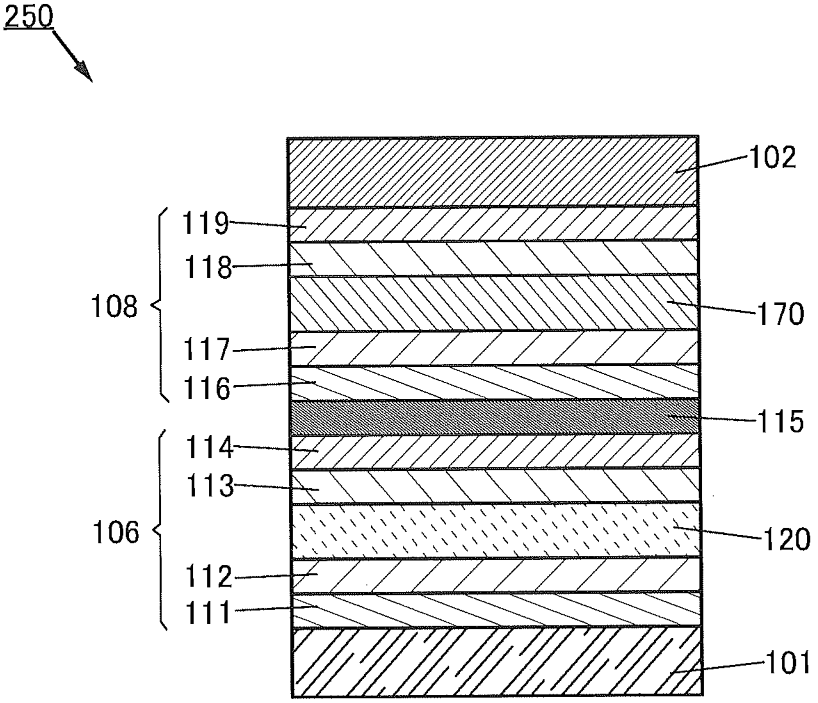
FIG. 2 is a schematic view of a light-emitting element of one embodiment of the present invention.

FIG. 2 is a schematic cross-sectional view of a light-emitting element 250.

The light-emitting element 250 illustrated in FIG. 2 includes a plurality of light-emitting units (a light-emitting unit 106 and a light-emitting unit 108) between a pair of electrodes (the electrode 101 and the electrode 102). Any one of the plurality of light-emitting units preferably has a structure similar to that of the EL layer 100 illustrated in FIG. 1(A). That is, the light-emitting element 150 illustrated in FIG. 1(A) includes one light-emitting unit, while the light-emitting element 250 includes a plurality of light-emitting units. Note that the electrode 101 functions as an anode and the electrode 102 functions as a cathode in the light-emitting element 250 in the following description; however, the functions of the electrodes may be reversed as the structure of the light-emitting element 250.

Moreover, in the light-emitting element 250 illustrated in FIG. 2, the light-emitting unit 106 and the light-emitting unit 108 are stacked, and a charge-generation layer 115 is provided between the light-emitting unit 106 and the light-emitting unit 108. Note that the light-emitting unit 106 and the light-emitting unit 108 may have the same structure or different structures. For example, it is preferable to use a structure similar to that of the EL layer 100 for the light-emitting unit 108.

The light-emitting element 250 includes a light-emitting layer 120 and a light-emitting layer 170. The light-emitting unit 106 includes the hole-injection layer 111, the hole-transport layer 112, an electron-transport layer 113, and an electron-injection layer 114 in addition to the light-emitting layer 120. The light-emitting unit 108 includes a hole-injection layer 116, a hole-transport layer 117, the electron-transport layer 118, and the electron-injection layer 119 in addition to the light-emitting layer 170.

In the light-emitting element 250, any layer of each of the light-emitting unit 106 and the light-emitting unit 108 contains the organic compound of one embodiment of the present invention. Note that the layer containing the organic compound is preferably the light-emitting layer 120 or the light-emitting layer 170.

The charge-generation layer 115 may have either a structure in which a substance having an acceptor property, which is an electron acceptor, is added to a hole-transport material or a structure in which a substance having a donor property, which is an electron donor, is added to an electron-transport material. Moreover, both of these structures may be stacked.

In the case where the charge-generation layer 115 contains a composite material of an organic compound and a substance having an acceptor property, the composite material that can be used for the hole-injection layer 111 described in Embodiment 3 is used as the composite material. As the organic compound, a variety of compounds such as an aromatic amine compound, a carbazole compound, an aromatic hydrocarbon, and a high molecular compound (an oligomer, a dendrimer, a polymer, or the like) can be used. Note that a substance having a hole mobility of $1\times10^{-6}$ $cm^2/Vs$ or higher is preferably used as the organic compound. However, other substances may also be used as long as they have a property of transporting more holes than electrons. Since the composite material of an organic compound and a substance having an acceptor property has excellent carrier-injection and carrier-transport properties, low-voltage driving or low-current driving can be achieved. Note that in the case where a surface of a light-emitting unit on the anode side is in contact with the charge-generation layer 115, the charge-generation layer 115 can also serve as a hole-injection layer or a hole-transport layer of the light-emitting unit; thus, a structure in which a hole-injection layer or a hole-transport layer is not provided in the light-emitting unit may be employed. Alternatively, in the case where a surface of a light-emitting unit on the cathode side is in contact with the charge-generation layer 115, the charge-generation layer 115 can also serve as an electron-injection layer or an electron-transport layer of the light-emitting unit; thus, a structure in which an electron-injection layer or an electron-transport layer is not provided in the light-emitting unit may be employed.

Note that the charge-generation layer 115 may have a stacked-layer structure combining a layer containing the composite material of an organic compound and a substance having an acceptor property and a layer formed of another material. For example, a layer containing the composite material of an organic compound and a substance having an acceptor property and a layer containing one compound selected from electron-donating substances and a compound having a high electron-transport property may be combined. Moreover, a layer containing the composite material of an organic compound and a substance having an acceptor property and a layer containing a transparent conductive film may be combined.

Note that the charge-generation layer 115 sandwiched between the light-emitting unit 106 and the light-emitting unit 108 injects electrons into one of the light-emitting units and injects holes into the other of the light-emitting units when voltage is applied to the electrode 101 and the electrode 102. For example, in FIG. 2, the charge-generation layer 115 injects electrons into the light-emitting unit 106 and injects holes into the light-emitting unit 108 when voltage is applied such that the potential of the electrode 101 is higher than the potential of the electrode 102.

Note that in terms of light extraction efficiency, the charge-generation layer 115 preferably has a property of transmitting visible light (specifically, the transmittance of visible light through the charge-generation layer 115 is higher than or equal to 40%). Moreover, the charge-generation layer 115 functions even when it has lower conductivity than the pair of electrodes (the electrode 101 and the electrode 102).

Forming the charge-generation layer 115 using the above-described materials can inhibit an increase in driving voltage in the case where the light-emitting layers are stacked.

The light-emitting element having two light-emitting units has been described with reference to FIG. 2; however, a light-emitting element in which three or more light-emitting units are stacked can be similarly employed. When a plurality of light-emitting units partitioned by the charge-generation layer are arranged between a pair of electrodes as in the light-emitting element 250, it is possible to achieve a light-emitting element that can emit high-luminance light with the current density kept low and has a long lifetime. Moreover, a light-emitting element having low power consumption can be achieved.

Note that in each of the above structures, the emission colors exhibited by the guest materials used in the light-emitting unit 106 and the light-emitting unit 108 may be the same or different. In the case where guest materials having a function of exhibiting light emission of the same color are used for the light-emitting unit 106 and the light-emitting unit 108, the light-emitting element 250 can exhibit high emission luminance at a small current value, which is preferred. In the case where guest materials having a function of exhibiting light emission of different colors are used for the light-emitting unit 106 and the light-emitting unit 108, the light-emitting element 250 can exhibit multi-color light emission, which is preferred. In this case, with the use of a plurality of light-emitting materials with different emission wavelengths in one or both of the light-emitting layer 120 and the light-emitting layer 170, the light-emitting element 250 emits light obtained by synthesizing light emission having different emission peaks; thus, its emission spectrum has at least two maximum values.

The above structure is also suitable for obtaining white light emission. When the light-emitting layer 120 and the light-emitting layer 170 emit light of complementary colors, white light emission can be obtained. It is particularly suitable to select the guest materials so that white light emission with high color rendering properties or light emission of at least red, green, and blue can be obtained.

In the case of a light-emitting element in which three or more light-emitting units are stacked, colors of light emitted from guest materials used in the light-emitting units may be the same or different from each other. In the case where a plurality of light-emitting units that exhibit the same emission color are included, the emission color of the plurality of light-emitting units can have higher emission luminance at a smaller current value than another color. Such a structure can be suitably used for adjustment of emission colors. The structure is particularly suitable when guest materials that emit light of different colors with different luminous efficiencies are used. For example, when three layers of light-emitting units are included, the intensity of fluorescence and phosphorescence can be adjusted with two layers of light-emitting units that contain a fluorescent material for the same color and one layer of a light-emitting unit that contains a phosphorescent material that emits light of a color different from the emission color of the fluorescent material. That is, the intensity of emitted light of each color can be adjusted with the number of light-emitting units.

In the case of the light-emitting element including two layers of fluorescent units and one layer of a phosphorescent unit, it is preferable that the light-emitting element include the two layers of the light-emitting units including a blue fluorescent material and the one layer of the light-emitting unit including a yellow phosphorescent material; that the light-emitting element include the two layers of the light-emitting units including a blue fluorescent material and the one layer of the light-emitting-layer unit including a red phosphorescent material and a green phosphorescent material; or that the light-emitting element include the two layers of the light-emitting units including a blue fluorescent material and the one layer of the light-emitting-layer unit including a red phosphorescent material, a yellow phosphorescent material, and a green phosphorescent material, in which case white light emission can be obtained efficiently.

At least one of the light-emitting layer 120 and the light-emitting layer 170 may further be divided into layers and the divided layers may contain different light-emitting materials. That is, at least one of the light-emitting layer 120 and the light-emitting layer 170 can consist of two or more layers. For example, in the case where the light-emitting layer is formed by stacking a first light-emitting layer and a second light-emitting layer in this order from the hole-transport layer side, the first light-emitting layer is formed using a material having a hole-transport property as the host material and the second light-emitting layer is formed using a material having an electron-transport property as the host material. In this case, the light-emitting materials contained in the first light-emitting layer and the second light-emitting layer may be the same or different, and may have functions of exhibiting light emission of the same color or exhibiting light emission of different colors. White light emission with high color rendering properties that is formed of three primary colors or four or more emission colors can also be obtained by using a plurality of light-emitting materials having functions of exhibiting light emission of different colors.

In addition, it is suitable that the light-emitting layer of the light-emitting unit 108 include a phosphorescent compound. When the organic compound of one embodiment of the present invention is used for at least one of the plurality of units, a light-emitting element with high emission efficiency and reliability can be provided.

Note that this embodiment can be combined as appropriate with any of the other embodiments.

Embodiment 5

In this embodiment, a light-emitting device including the light-emitting element described in Embodiment 3 and Embodiment 4 will be described with reference to FIGS. 3(A) and 3(B).

Figure 3A:
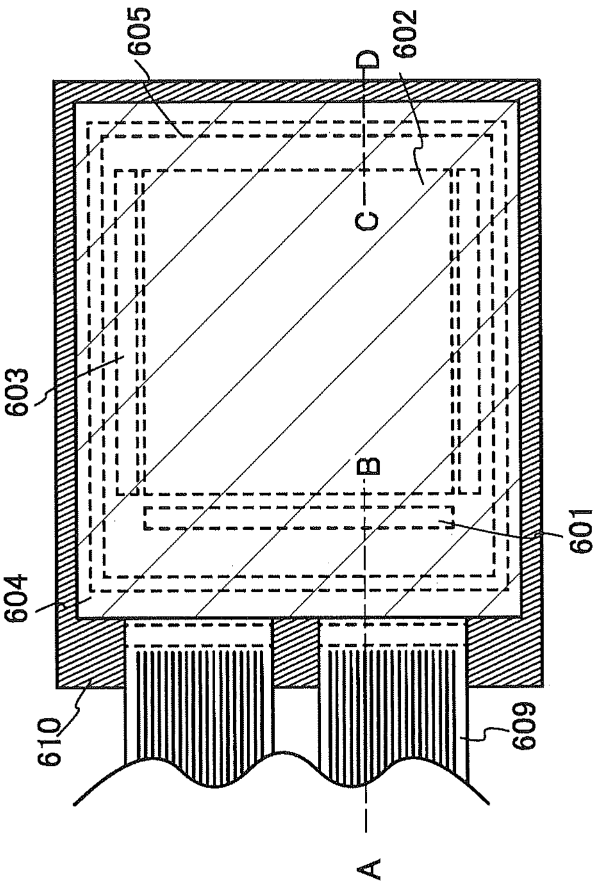
FIGS. 3A-3B are conceptual views of an active matrix light-emitting device of one embodiment of the present invention.
Figure 3B:
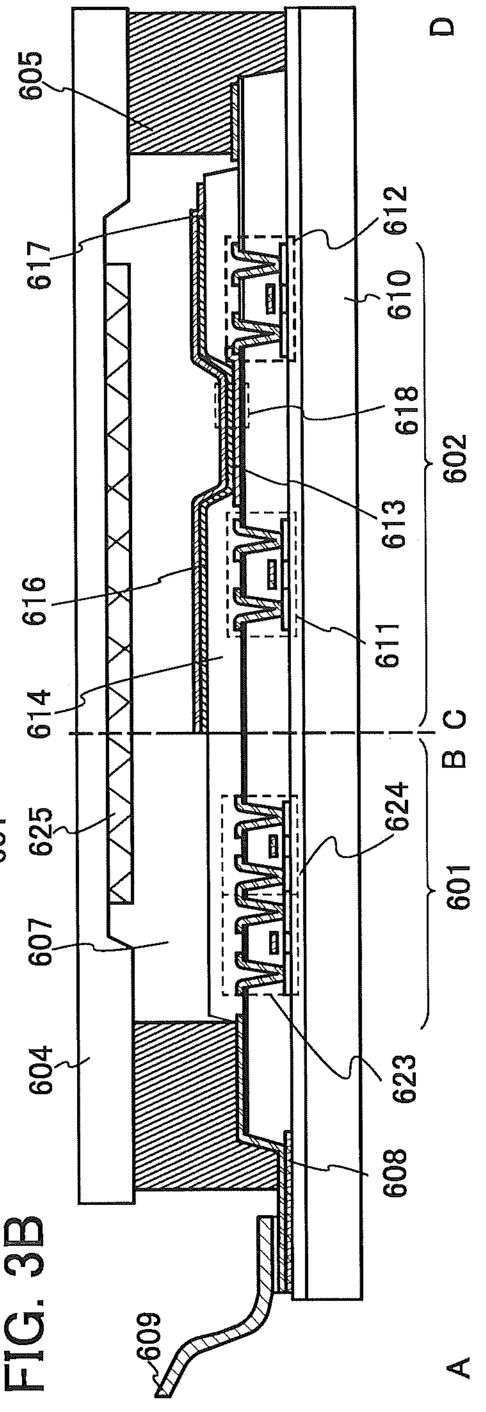

FIG. 3(A) is a top view of a light-emitting device, and FIG. 3(B) is a cross-sectional view taken along A-B and C-D in FIG. 3(A). This light-emitting device includes a driver circuit portion (a source side driver circuit) 601, a pixel portion 602, and a driver circuit portion (a gate side driver circuit) 603 which are indicated by dotted lines as components controlling light emission from a light-emitting element. Furthermore, 604 denotes a sealing substrate, 625 denotes a desiccant, 605 denotes a sealing material, and a portion surrounded by the sealing material 605 is a space 607.

Note that a lead wiring 608 is a wiring for transmitting signals to be input to the source side driver circuit 601 and the gate side driver circuit 603 and receives a video signal, a clock signal, a start signal, a reset signal, and the like from an FPC (flexible printed circuit) 609 serving as an external input terminal. Although only the FPC is shown here, a printed wiring board (PWB) may be attached to the FPC. The light-emitting device in this specification includes not only the light-emitting device itself but also the state where the FPC or the PWB is attached thereto.

Next, a cross-sectional structure of the above light-emitting device is described with reference to FIG. 3(B). The driver circuit portion and the pixel portion are formed over an element substrate 610; here, the source side driver circuit 601, which is the driver circuit portion, and one pixel of the pixel portion 602 are illustrated.

Note that in the source side driver circuit 601, a CMOS circuit in which an n-channel TFT 623 and a p-channel TFT 624 are combined is formed. The driver circuit may be formed of various CMOS circuits, PMOS circuits, or NMOS circuits. Although a driver-integrated type where the driver circuit is formed over the substrate is described in this embodiment, the driver circuit is not necessarily integrated and can be formed not over the substrate but outside the substrate.

The pixel portion 602 is formed of pixels including a switching TFT 611, a current controlling TFT 612, and a first electrode 613 electrically connected to a drain thereof. Note that an insulator 614 is formed to cover an end portion of the first electrode 613. The insulator 614 can be formed using a positive photosensitive resin film.

In order to improve the coverage of a film formed over the insulator 614, the insulator 614 is formed to have a surface with curvature at its upper end portion or lower end portion. For example, in the case where a photosensitive acrylic is used as a material of the insulator 614, only the upper end portion of the insulator 614 preferably has a curved surface. The radius of curvature of the curved surface is preferably greater than or equal to 0.2 μm and less than or equal to 0.3 μm. Either a negative or positive photosensitive material can be used as the insulator 614.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at 2 wt % or higher and 20 wt % or lower, a titanium nitride film, a chromium film, a tungsten film, a Zn film, a Pt film, or the like, a stacked layer of titanium nitride and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. A material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof, such as MgAg, MgIn, or AlLi) is preferably used. Note that in the case where light generated in the EL layer 616 passes through the second electrode 617, a stacked layer of a thin metal film and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that a light-emitting element 618 is formed with the first electrode 613, the EL layer 616, and the second electrode 617. The light-emitting element 618 is preferably a light-emitting element having any of the structures described in Embodiment 3 and Embodiment 4. The pixel portion includes a plurality of light-emitting elements, and the light-emitting device of this embodiment may include both the light-emitting element with the structure described in Embodiment 3 and Embodiment 4 and a light-emitting element with a different structure.

When the sealing substrate 604 and the element substrate 610 are attached to each other with the sealing material 605, a structure in which the light-emitting element 618 is provided in the space 607 surrounded by the element substrate 610, the sealing substrate 604, and the sealing material 605 is obtained. Note that the space 607 is filled with a filler, and may be filled with an inert gas (nitrogen, argon, or the like) or a resin and/or a desiccant.

Note that an epoxy-based resin or glass frit is preferably used for the sealing material 605. Such a material is desirably a material that transmits moisture or oxygen as little as possible. As a material used for the sealing substrate 604, in addition to a glass substrate and a quartz substrate, a plastic substrate formed of FRP (Fiber Reinforced Plastics), PVF (polyvinyl fluoride), polyester, acrylic, or the like can be used.

As described above, the light-emitting device including the light-emitting element described in Embodiment 3 and Embodiment 4 can be obtained.

Structure Example 1 of Light-Emitting Device

As an example of a display device, FIG. 4 shows a light-emitting device including a light-emitting element exhibiting white light emission and a coloring layer (a color filter).

Figure 4A:
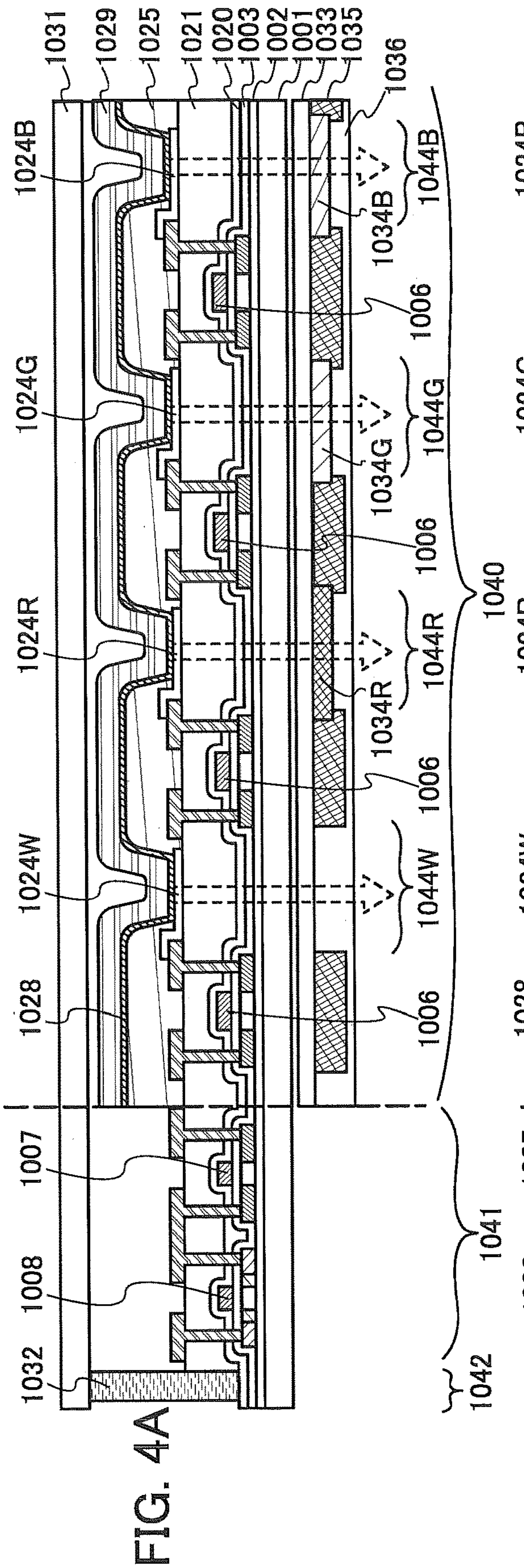
FIGS. 4A-4B are conceptual views of an active matrix light-emitting device of one embodiment of the present invention.

FIG. 4(A) illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of the light-emitting elements, a partition 1025, an EL layer 1028, a second electrode 1029 of the light-emitting elements, a sealing substrate 1031, a sealing material 1032, and the like.

Figure 4B:
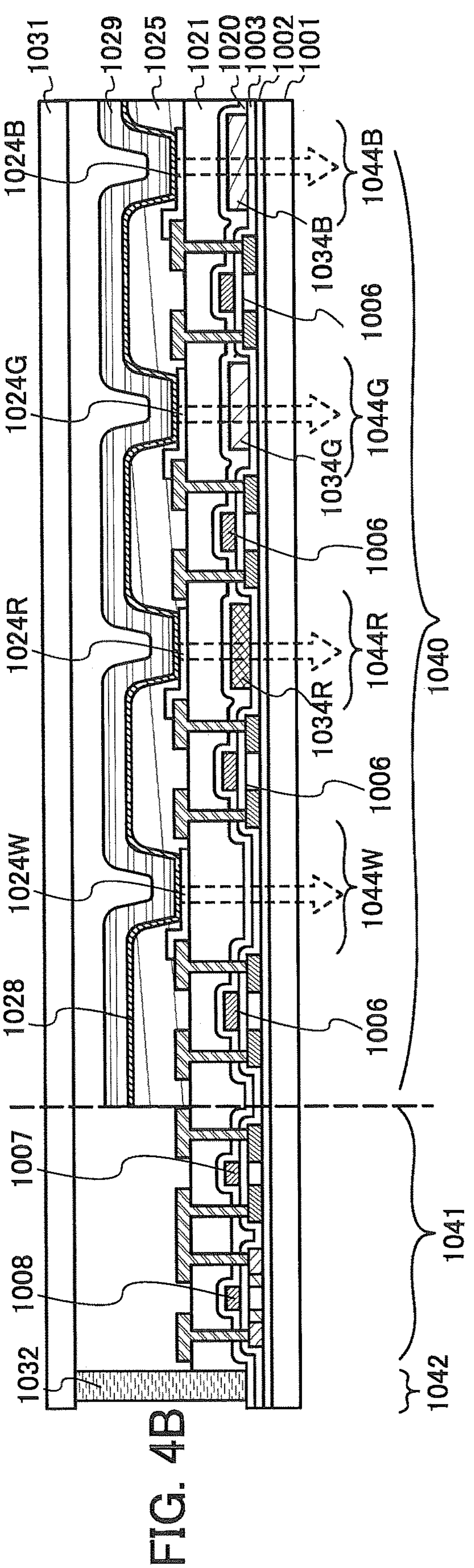

In FIG. 4(A) and FIG. 4(B), coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 4(A), light emitted from some of the light-emitting layers does not pass through the coloring layers and is extracted to the outside, while light emitted from the other light-emitting layers passes through the coloring layers and is extracted to the outside. Since light that does not pass through the coloring layers is white and light that passes through the coloring layers is red, blue, or green, an image can be displayed by pixels of the four colors.

FIG. 4(B) shows an example in which the red coloring layer 1034R, the green coloring layer 1034G, and the blue coloring layer 1034B) are formed between the gate insulating film 1003 and the first interlayer insulating film 1020. As illustrated in FIG. 4(B), the coloring layers may be provided between the substrate 1001 and the sealing substrate 1031.

The above-described light-emitting device is a light-emitting device having a structure in which light is extracted on the substrate 1001 side where the TFTs are formed (a bottom emission type), but may be a light-emitting device having a structure in which light is extracted on the sealing substrate 1031 side (a top emission type).

Structure Example 2 of Light-Emitting Device

Figure 5:
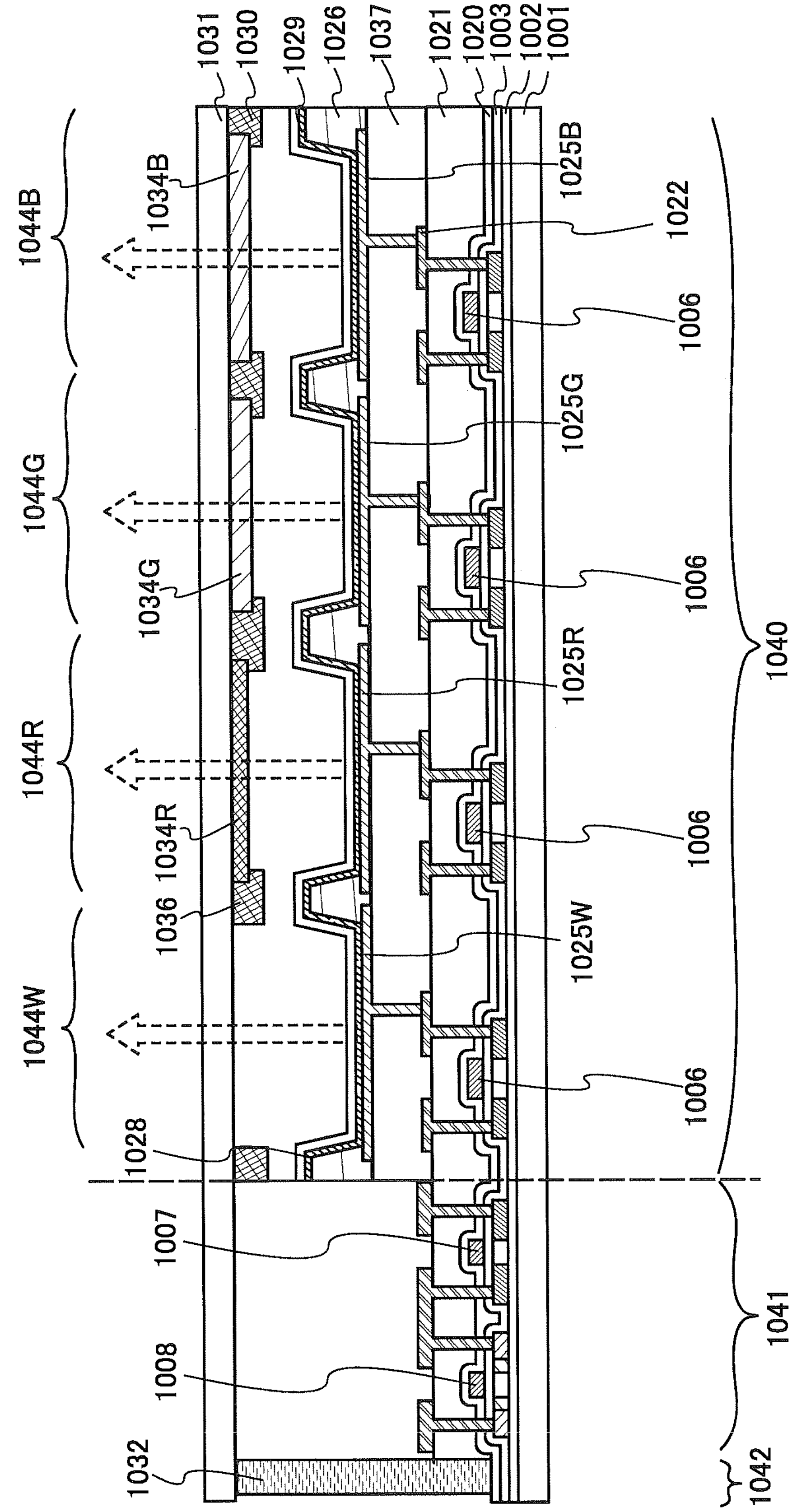
FIG. 5 is a conceptual view of an active matrix light-emitting device of one embodiment of the present invention.

FIG. 5 shows a cross-sectional view of a top-emission light-emitting device. In that case, a substrate that does not transmit light can be used as the substrate 1001. The process up to the formation of a connection electrode that connects the TFT and the anode of the light-emitting element is performed in a manner similar to that of a bottom-emission light-emitting device. Then, a third interlayer insulating film 1037 is formed to cover an electrode 1022. This insulating film may have a planarization function. The third interlayer insulating film 1037 can be formed using a material similar to that of the second interlayer insulating film 1021 or using other various materials.

A first lower electrode 1025W, a lower electrode 1025R, a lower electrode 1025G, and a lower electrode 1025B of the light-emitting element are anodes here, but may be cathodes. Furthermore, in the case of the top-emission light-emitting device as illustrated in FIG. 6, the lower electrode 1025W, the lower electrode 1025R, the lower electrode 1025G, and the lower electrode 1025B are preferably reflective electrodes. Note that the second electrode 1029 preferably has a function of reflecting light and a function of transmitting light. It is preferable that a microcavity structure be used between the second electrode 1029, and the lower electrode 1025W, the lower electrode 1025R, the lower electrode 1025G, and the lower electrode 1025B, in which case light with a specific wavelength is amplified. The EL layer 1028 has a structure similar to the structures described in Embodiment 3 and Embodiment 4, with which white light emission can be obtained.

In FIG. 4(A), FIG. 4(B), and FIG. 5, the structure of the EL layer for providing white light emission can be achieved by, for example, using a plurality of light-emitting layers or using a plurality of light-emitting units. Note that the structure for providing white light emission is not limited thereto.

In a top emission structure as illustrated in FIG. 5, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (black matrix) 1030 positioned between pixels. The coloring layers (the red coloring layer 1034R, the green coloring layer 1034G, and the blue coloring layer 1034B) and the black layer (black matrix) may be covered with the overcoat layer. Note that a substrate having a light-transmitting property is used as the sealing substrate 1031.

Although an example in which full color display is performed using four colors of red, green, blue, and white is shown here, there is no particular limitation and full color display using three colors of red, green, and blue may be performed. Alternatively, full color display using four colors of red, green, blue, and yellow may be performed.

As described above, the light-emitting device including the light-emitting element described in Embodiment 3 and Embodiment 4 can be obtained.

Note that this embodiment can be combined as appropriate with any of the other embodiments.

Embodiment 6

In this embodiment, electronic apparatuses of embodiments of the present invention will be described.

One embodiment of the present invention is a light-emitting element using organic EL, and thus, an electronic apparatus with a flat surface, high emission efficiency, and high reliability can be manufactured. An electronic apparatus with a curved surface, high emission efficiency, and high reliability can be manufactured according to one embodiment of the present invention. In addition, with the use of an organic compound of one embodiment of the present invention for the electronic apparatus, an electronic apparatus with high emission efficiency and high reliability can be manufactured.

Examples of the electronic apparatuses include a television device, a desktop or laptop personal computer, a monitor of a computer or the like, a digital camera, a digital video camera, a digital photo frame, a mobile phone, a portable game machine, a portable information terminal, an audio reproducing device, and a large game machine such as a pachinko machine.

Figure 6A:
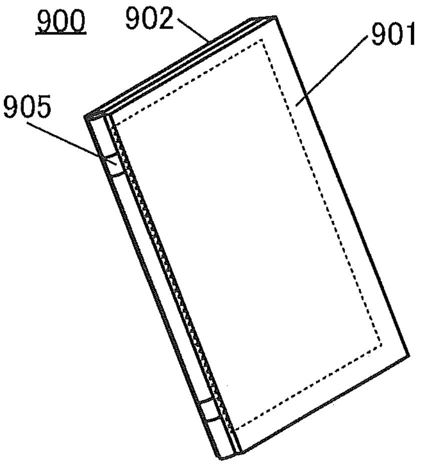
FIGS. 6A-6D are views illustrating electronic apparatuses of one embodiment of the present invention.
Figure 6B:
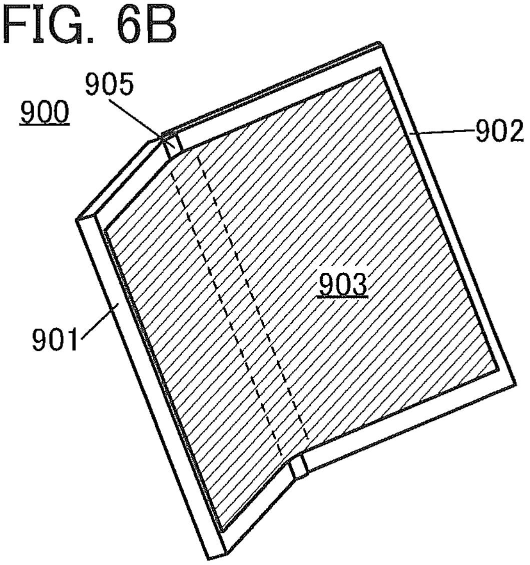

A portable information terminal 900 illustrated in FIGS. 6(A) and 6(B) includes a housing 901, a housing 902, a display portion 903, a hinge portion 905, and the like.

The housing 901 and the housing 902 are joined together by the hinge portion 905. The portable information terminal 900 can be opened as illustrated in FIG. 6(B) from a folded state (FIG. 6(A)). Thus, the portable information terminal 900 has high portability when carried and excellent visibility when used because of its large display region.

In the portable information terminal 900, the flexible display portion 903 is provided across the housing 901 and the housing 902 which are joined together by the hinge portion 905.

The light-emitting device manufactured using one embodiment of the present invention can be used for the display portion 903. Thus, a highly reliable portable information terminal can be manufactured.

The display portion 903 can display at least one of text information, a still image, a moving image, and the like. When text information is displayed on the display portion, the portable information terminal 900 can be used as an e-book reader.

When the portable information terminal 900 is opened, the display portion 903 is held while being in a significantly curved form. For example, the display portion 903 is held while including a curved portion with a radius of curvature of greater than or equal to 1 mm and less than or equal to 50 mm, preferably greater than or equal to 5 mm and less than or equal to 30 mm. Part of the display portion 903 can display an image while being curved since pixels are continuously arranged from the housing 901 to the housing 902.

The display portion 903 functions as a touch panel and can be controlled with a finger, a stylus, or the like.

The display portion 903 is preferably formed using one flexible display. Thus, a seamless continuous image can be displayed between the housing 901 and the housing 902. Note that each of the housing 901 and the housing 902 may be provided with a display.

The hinge portion 905 preferably includes a locking mechanism so that an angle formed between the housing 901 and the housing 902 does not become larger than a predetermined angle when the portable information terminal 900 is opened. For example, an angle at which they become locked (they are not opened any further) is preferably greater than or equal to 90° and less than 180° and can be typically 90°, 120°, 135°, 150°, 175°, or the like. In that case, the convenience, safety, and reliability of the portable information terminal 900 can be improved.

When the hinge portion 905 includes a locking mechanism, excessive force is not applied to the display portion 903; thus, breakage of the display portion 903 can be prevented. Therefore, a highly reliable portable information terminal can be achieved.

A power button, an operation button, an external connection port, a speaker, a microphone, or the like may be provided for the housing 901 and the housing 902.

One of the housing 901 and the housing 902 is provided with a wireless communication module, and data can be transmitted and received through a computer network such as the Internet, a LAN (Local Area Network), or Wi-Fi (registered trademark).

Figure 6C:
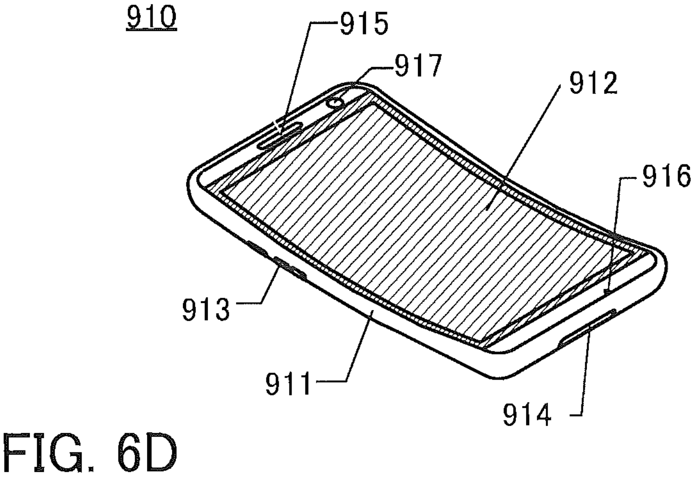

A portable information terminal 910 illustrated in FIG. 6(C) includes a housing 911, a display portion 912, an operation button 913, an external connection port 914, a speaker 915, a microphone 916, a camera 917, and the like.

The light-emitting device manufactured using one embodiment of the present invention can be used for the display portion 912. Thus, the portable information terminal can be manufactured with a high yield.

The portable information terminal 910 includes a touch sensor in the display portion 912. A variety of operations such as making a call and inputting a character can be performed by touch on the display portion 912 with a finger, a stylus, or the like.

In addition, the operation of the operation button 913 can switch the power ON and OFF operations and types of images displayed on the display portion 912. For example, switching from a mail creation screen to a main menu screen can be performed.

When a sensing device such as a gyroscope sensor or an acceleration sensor is provided inside the portable information terminal 910, the direction of display on the screen of the display portion 912 can be automatically switched by determining the orientation (horizontal or vertical) of the portable information terminal 910. Furthermore, the direction of display on the screen can be switched by touch on the display portion 912, operation of the operation button 913, sound input using the microphone 916, or the like.

The portable information terminal 910 has, for example, one or more functions selected from a telephone set, a notebook, an information browsing system, and the like. Specifically, the portable information terminal 910 can be used as a smartphone. The portable information terminal 910 is capable of executing a variety of applications such as mobile phone calls, e-mailing, text viewing and writing, music replay, video replay, Internet communication, and games, for example.

Figure 6D:
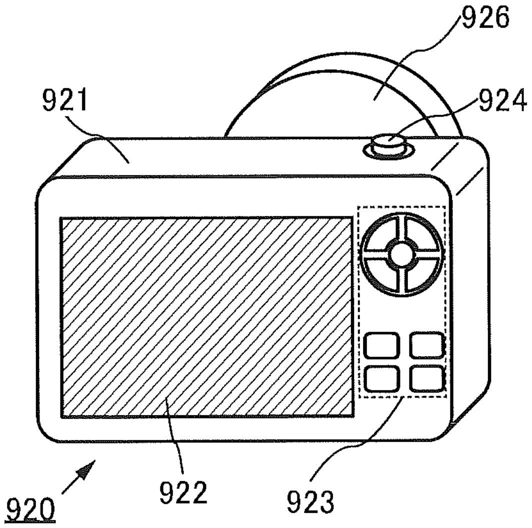

A camera 920 illustrated in FIG. 6(D) includes a housing 921, a display portion 922, operation buttons 923, a shutter button 924, and the like. Furthermore, a detachable lens 926 is attached to the camera 920.

The light-emitting device manufactured using one embodiment of the present invention can be used for the display portion 922. Thus, a highly reliable camera can be manufactured.

Although the camera 920 here is configured such that the lens 926 is detachable from the housing 921 for replacement, the lens 926 may be integrated with the housing 921.

A still image or a moving image can be taken with the camera 920 at the press of the shutter button 924. In addition, the display portion 922 has a function of a touch panel, and images can also be taken by the touch on the display portion 922.

Note that a stroboscope, a viewfinder, or the like can be additionally attached to the camera 920. Alternatively, these may be incorporated into the housing 921.

Figure 7A:
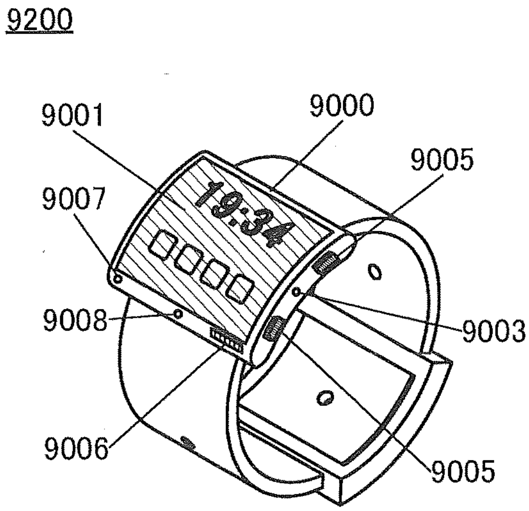
FIGS. 7A-7E are views illustrating electronic apparatuses of one embodiment of the present invention.
Figure 7B:
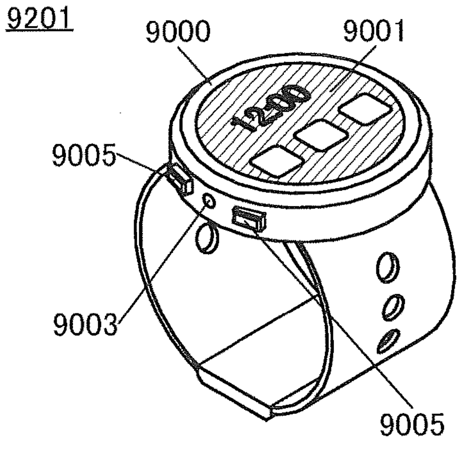

FIG. 7(A) is a perspective view of a wristwatch-type portable information terminal 9200, and FIG. 7(B) is a perspective view of a wristwatch-type portable information terminal 9201.

The portable information terminal 9200 illustrated in FIG. 7(A) is capable of executing a variety of applications such as mobile phone calls, e-mailing, text viewing and writing, music replay, Internet communication, and computer games. The display surface of the display portion 9001 is curved, and an image can be displayed on the curved display surface. The portable information terminal 9200 can perform near field communication conformable to a communication standard. For example, mutual communication between the portable information terminal 9200 and a headset capable of wireless communication can be performed, and thus hands-free calling is possible. The portable information terminal 9200 includes the connection terminal 9006, and data can be directly transmitted to and received from another information terminal via a connector. Power charging through the connection terminal 9006 is also possible. Note that the charging operation may be performed by wireless power feeding without through the connection terminal 9006.

Unlike in the portable information terminal illustrated in FIG. 7(A), the display surface of the display portion 9001 is not curved in the portable information terminal 9201 illustrated in FIG. 7(B). Furthermore, the external shape of the display portion of the portable information terminal 9201 is a non-rectangular shape (a circular shape in FIG. 7(B)).

Figure 7C:
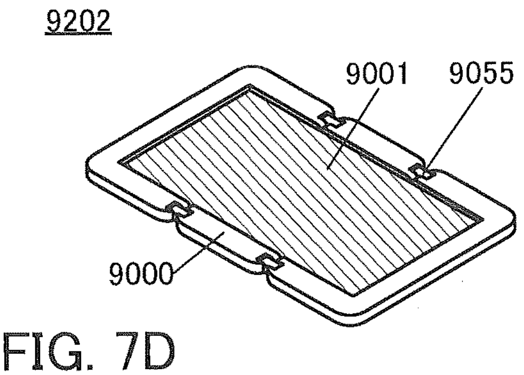
Figure 7D:
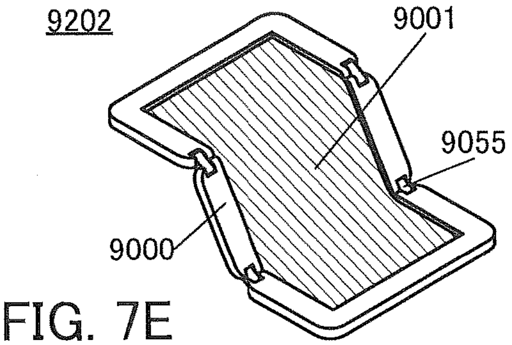
Figure 7E:
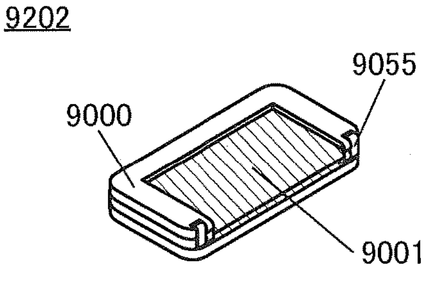

FIGS. 7(C) to 7(E) are perspective views of a foldable portable information terminal 9202. Note that FIG. 7(C) is a perspective view of the portable information terminal 9202 that is opened; FIG. 7(D) is a perspective view of the portable information terminal 9202 that is being changed from one of an opened state and a folded state to the other; and FIG. 7(E) is a perspective view of the portable information terminal 9202 that is folded.

The portable information terminal 9202 is highly portable in the folded state, and is highly browsable in the opened state due to a seamless large display region. The display portion 9001 of the portable information terminal 9202 is supported by three housings 9000 joined together by hinges 9055. By being bent between two housings 9000 with the hinges 9055, the portable information terminal 9202 can be reversibly changed in shape from the opened state to the folded state. For example, the portable information terminal 9202 can be bent with a radius of curvature of greater than or equal to 1 mm and less than or equal to 150 mm.

Figure 8A:
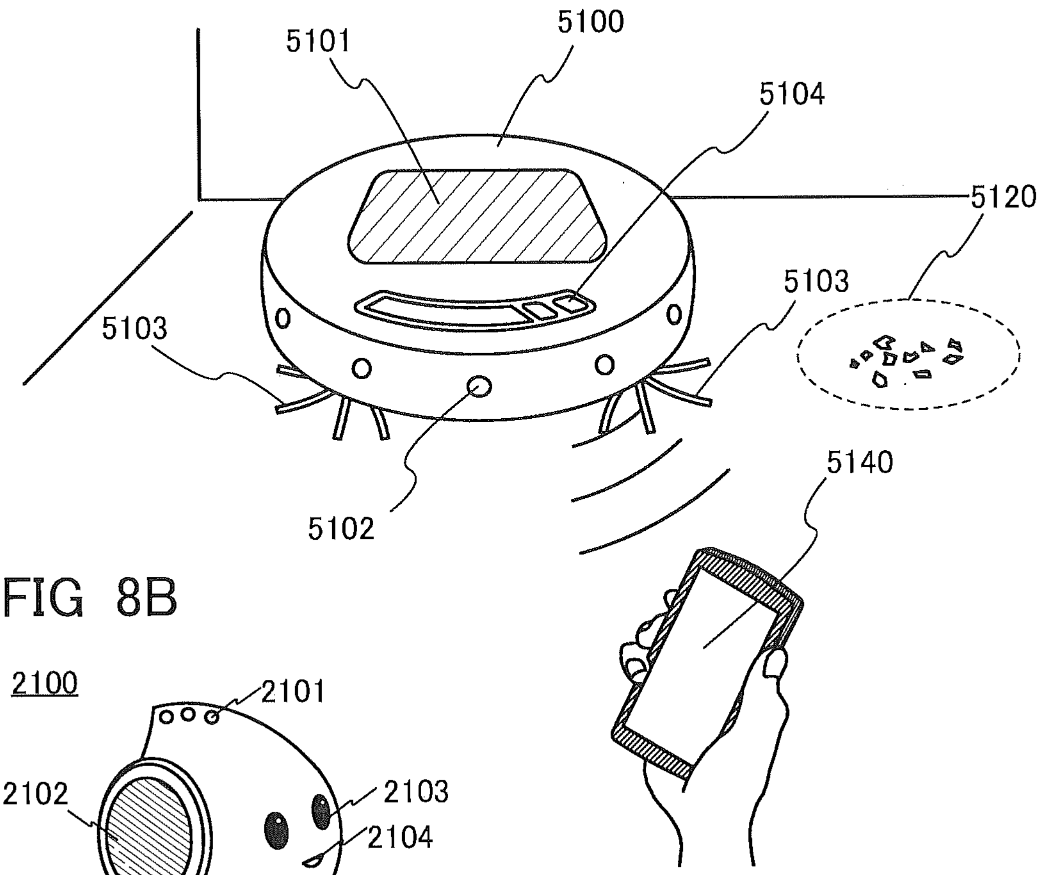
FIGS. 8A-8C are views illustrating electronic apparatuses of one embodiment of the present invention.

FIG. 8(A) is a schematic view showing an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic apparatus 5140 such as a smartphone. The portable electronic apparatus 5140 can display images taken by the cameras 5102. Accordingly, an owner of the cleaning robot 5100 can monitor the room even from the outside. The display on the display 5101 can be checked by the portable electronic apparatus such as a smartphone.

The light-emitting device of one embodiment of the present invention can be used for the display 5101.

Figure 8B:
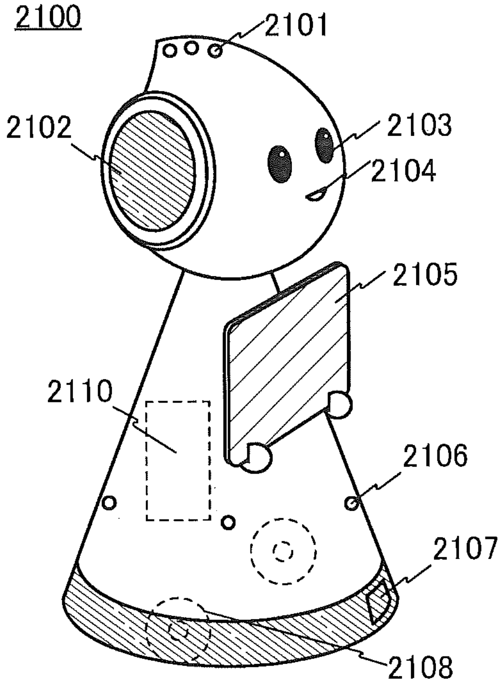

A robot 2100 illustrated in FIG. 8(B) includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107.

The light-emitting device of one embodiment of the present invention can be used for the display 2105.

Figure 8C:
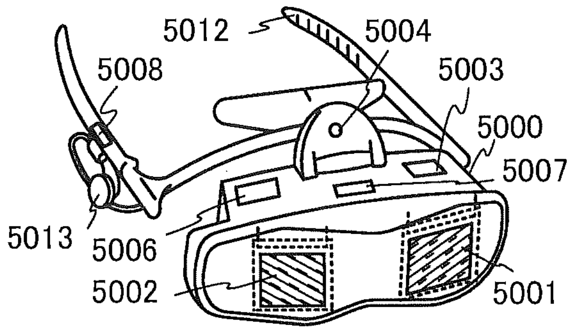

FIG. 8(C) shows an example of a goggle-type display. The goggle-type display includes, for example, a housing 5000, a display portion 5001, a speaker 5003, an LED lamp 5004, operation keys 5005 (including a power switch and an operation switch), a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 5008, a second display portion 5002, a support 5012, and an earphone 5013.

The light-emitting device of one embodiment of the present invention can be used for the display portion 5001 and the second display portion 5002.

Figure 9A:
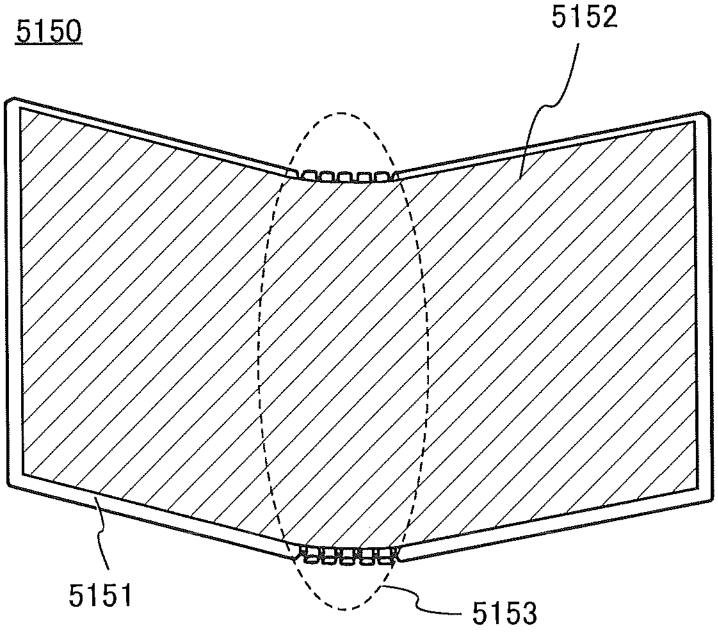
FIGS. 9A-9B are views illustrating an electronic apparatus of one embodiment of the present invention.
Figure 9B:
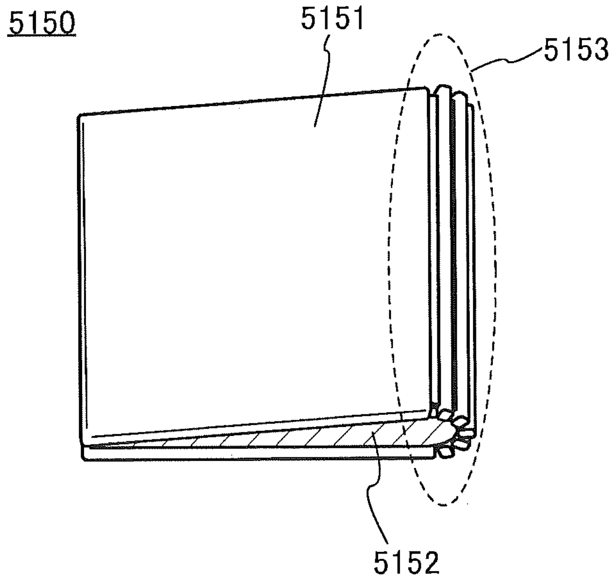

FIGS. 9(A) and 9(B) illustrate a foldable portable information terminal 5150. The foldable portable information terminal 5150 includes a housing 5151, a display region 5152, and a bend portion 5153. FIG. 9(A) illustrates the portable information terminal 5150 that is opened. FIG. 9(B) illustrates the portable information terminal 5150 that is folded. Despite its large display region 5152, the portable information terminal 5150 is compact in size and has excellent portability when folded.

The display region 5152 can be folded in half with the bend portion 5153. The bend portion 5153 includes a flexible member and a plurality of supporting members, and when the display region is folded, the flexible member expands and the bend portion 5153 has a radius of curvature of 2 mm or more, preferably 5 mm or more.

Note that the display region 5152 may be a touch panel (an input/output device) including a touch sensor (an input device). The light-emitting device of one embodiment of the present invention can be used for the display region 5152.

This embodiment can be combined as appropriate with any of the other embodiments.

Embodiment 7

In this embodiment, examples in which the light-emitting element of one embodiment of the present invention is used for various lighting devices will be described with reference to FIG. 10 and FIG. 11. With the use of the light-emitting element of one embodiment of the present invention, a highly reliable lighting device with high emission efficiency can be manufactured.

Fabricating the light-emitting element of one embodiment of the present invention over a substrate having flexibility enables an electronic apparatus or a lighting device that has a light-emitting region with a curved surface to be achieved.

Furthermore, a light-emitting device in which the light-emitting element of one embodiment of the present invention is used can also be used for lighting for motor vehicles; for example, such lighting can be provided on a windshield, a ceiling, and the like.

Figure 10A:
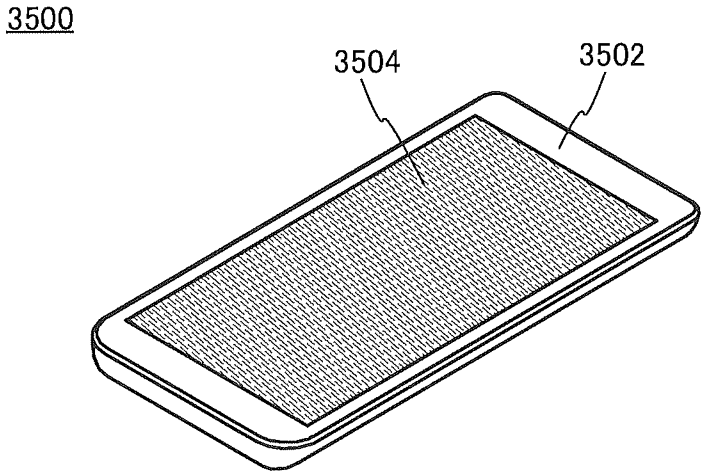
FIGS. 10A-10C are views illustrating lighting devices of one embodiment of the present invention.
Figure 10B:
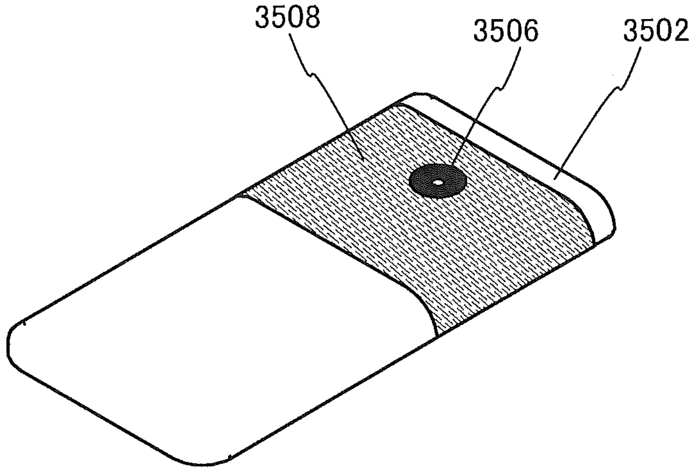

FIG. 10(A) is a perspective view of one surface of a multifunction terminal 3500, and FIG. 10(B) is a perspective view of the other surface of the multifunction terminal 3500. In a housing 3502 of the multifunction terminal 3500, a display portion 3504, a camera 3506, lighting 3508, and the like are incorporated. The light-emitting device of one embodiment of the present invention can be used for the lighting 3508.

The lighting 3508 that includes the light-emitting device of one embodiment of the present invention functions as a planar light source. Thus, unlike a point light source typified by an LED, the lighting 3508 can provide light emission with low directivity. When the lighting 3508 and the camera 3506 are used in combination, for example, an image can be taken by the camera 3506 with the lighting 3508 lighting or flashing. Because the lighting 3508 functions as a planar light source, a photograph as if taken under natural light can be taken.

Note that the multifunction terminal 3500 illustrated in FIGS. 10(A) and 10(B) can have a variety of functions as in the electronic apparatuses illustrated in FIG. 7(A) to FIG. 7(C).

The housing 3502 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone, and the like. When a detection device including a sensor for detecting inclination, such as a gyroscope sensor or an acceleration sensor, is provided inside the multifunction terminal 3500, display on the screen of the display portion 3504 can be automatically changed by determining the orientation (horizontal or vertical) of the multifunction terminal 3500.

The display portion 3504 can function as an image sensor. For example, an image of a palm print, a fingerprint, or the like is taken when the display portion 3504 is touched with the palm or the finger, whereby personal authentication can be performed. Furthermore, with the use of a backlight which emits near-infrared light or a sensing light source which emits near-infrared light in the display portion 3504, an image of a finger vein, a palm vein, or the like can be taken. Note that the light-emitting device of one embodiment of the present invention may be used for the display portion 3504.

Figure 10C:
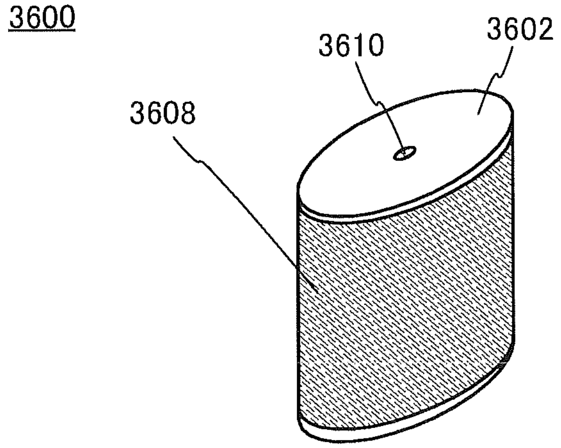

FIG. 10(C) is a perspective view of a security light 3600. The light 3600 includes lighting 3608 on the outside of the housing 3602, and a speaker 3610 and the like are incorporated in the housing 3602. The light-emitting element of one embodiment of the present invention can be used for the lighting 3608.

The light 3600 emits light when the lighting 3608 is gripped or held, for example. An electronic circuit that can control the manner of light emission from the light 3600 may be provided in the housing 3602. The electronic circuit may be a circuit that enables light emission once or intermittently a plurality of times or may be a circuit that can adjust the amount of emitted light by controlling the current value for light emission. A circuit with which a loud audible alarm is output from the speaker 3610 at the same time as light emission from the lighting 3608 may be incorporated.

The light 3600 can emit light in various directions; therefore, it is possible to intimidate a thug or the like with light, or light and sound. Moreover, the light 3600 may include a camera such as a digital still camera to have a photography function.

Figure 11:
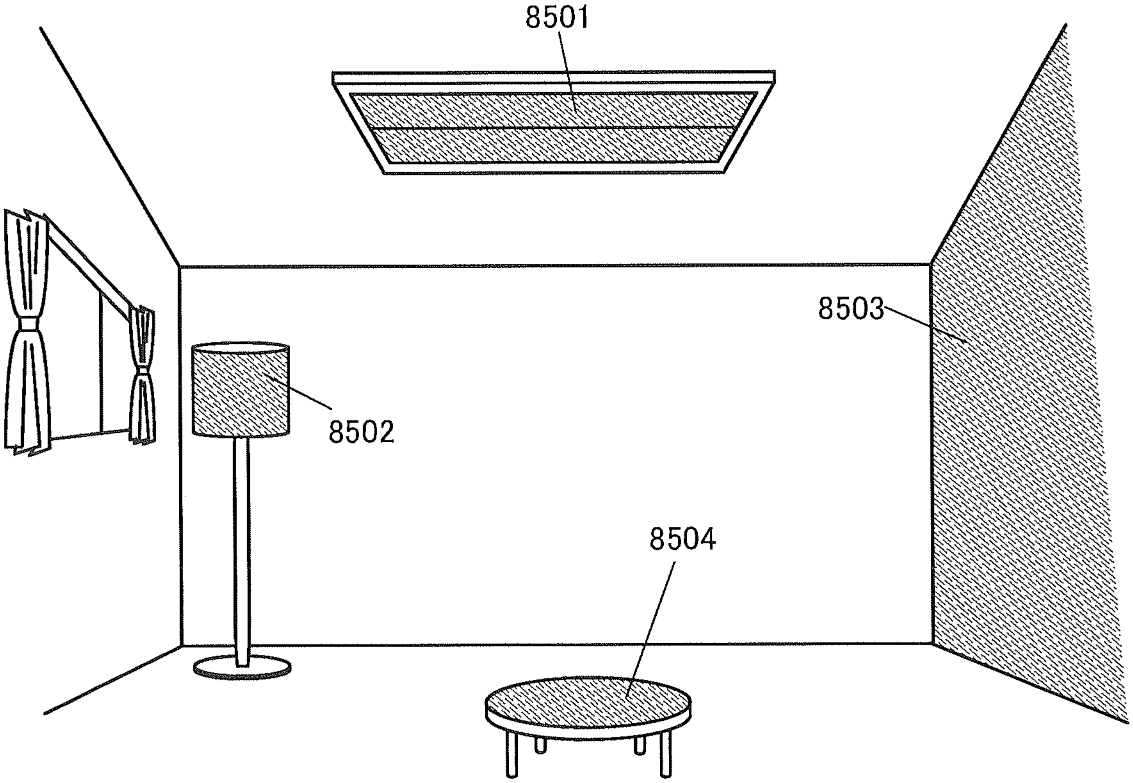
FIG. 11 is a view illustrating a lighting device of one embodiment of the present invention.

FIG. 11 shows an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with the use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to turn the power on or off.

Moreover, when the light-emitting element is used on the surface side of a table, a lighting device 8504 which has a function as a table can be obtained. When the light-emitting element is used as part of other furniture, a lighting device which has a function as the furniture can be obtained.

As described above, lighting devices and electronic apparatuses can be obtained by application of the light-emitting device of one embodiment of the present invention. Note that the light-emitting device can be used for electronic apparatuses in a variety of fields without being limited to the lighting devices and the electronic apparatuses described in this embodiment.

The structure described above in this embodiment can be used in combination as appropriate with any of the structures described in the other embodiments.

Example 1

In this example, a method for synthesizing 5,9-bis[N-phenyl-N-(4-biphenyl)amino]-7-phenyl-7H-dibenzo[c,g]carbazole (abbreviation: 5,9BPA2PcgDBC) (Structural Formula (100)), which is one of the compounds of one embodiment of the present invention, represented by General Formula (G0), and characteristics of the compound will be described.

Step 1: Synthesis of 5,9BPA2PcgDBC

In a 200-mL three-neck flask were put 1.5 g (3.0 mmol) of 5,9-dibromo-7-phenyl-7H-dibenzo[c,g]carbazole, 2.2 g (9.0 mmol) of 4-phenyldiphenylamine, and 1.7 g (18 mmol) of sodium tert-butoxide. To this mixture was added 30 mL of toluene and 0.2 mL of a 10% hexane solution of tri(tert-butyl)phosphine, and this mixture was degassed by being stirred while the pressure was being reduced. To this mixture was added 17 mg (30 μmol) of bis(dibenzylideneacetone) palladium(0), and the mixture was heated and stirred at 120° C. for seven hours under a nitrogen stream. After the stirring, toluene was added to the mixture and the resulting mixture was suction-filtered through Florisil, Celite, and alumina, so that a filtrate was obtained. The obtained filtrate was concentrated and a solid was obtained. This solid was purified by silica gel column chromatography (developing solvent: hexane:toluene=7:3), and the obtained fraction was concentrated to give a solid. The obtained solid was reprecipitated with toluene/ethanol, whereby 1.8 g of a yellow solid was obtained in a yield of 74%. The synthesis scheme is shown in (A-1) below.

[Chemical Formula 33]

(A-1)

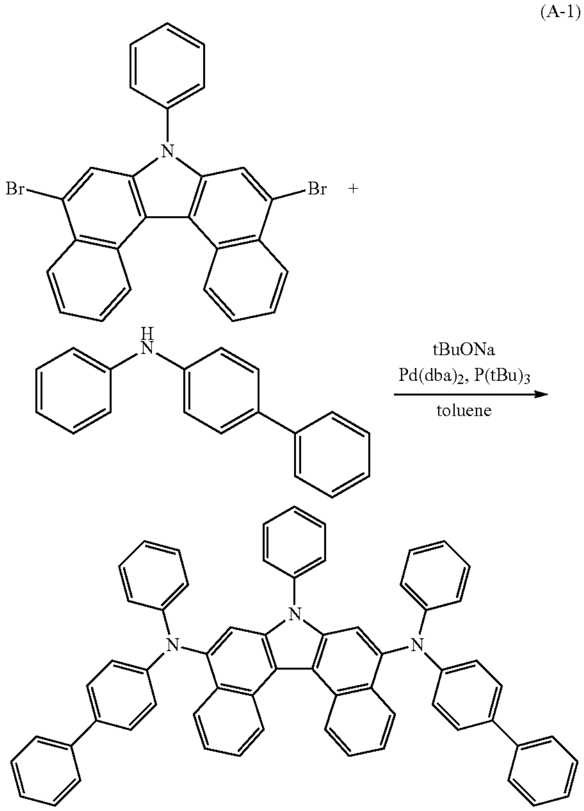

(100)

By a train sublimation method, 1.5 g of the obtained solid was sublimated and purified. Heating was performed at 320° C. under conditions where the pressure was $2.2\times10^{-2}$ Pa and the flow rate of argon was 0 mL/min. After the sublimation purification, 0.70 g of a yellow solid was obtained in a collection rate of 45%.

Analysis data of the obtained solid by nuclear magnetic resonance ($^1$H NMR) spectroscopy are shown below.

$^1$H NMR (DMSO-$d_6$, 300 MHz): δ=6.97 (t, J1=7.2 Hz, 2H), 7.03-7.10 (m, 8H), 7.23-7.31 (m, 6H), 7.38-7.43 (m, 6H), 7.50-7.66 (m, 15H), 7.79 (d, J1=7.2 Hz, 2H), 8.15 (dd, J1=8.7 Hz, J2=1.5 Hz, 2H), 9.22 (d, J1=8.7 Hz, 2H).

Figure 12A:
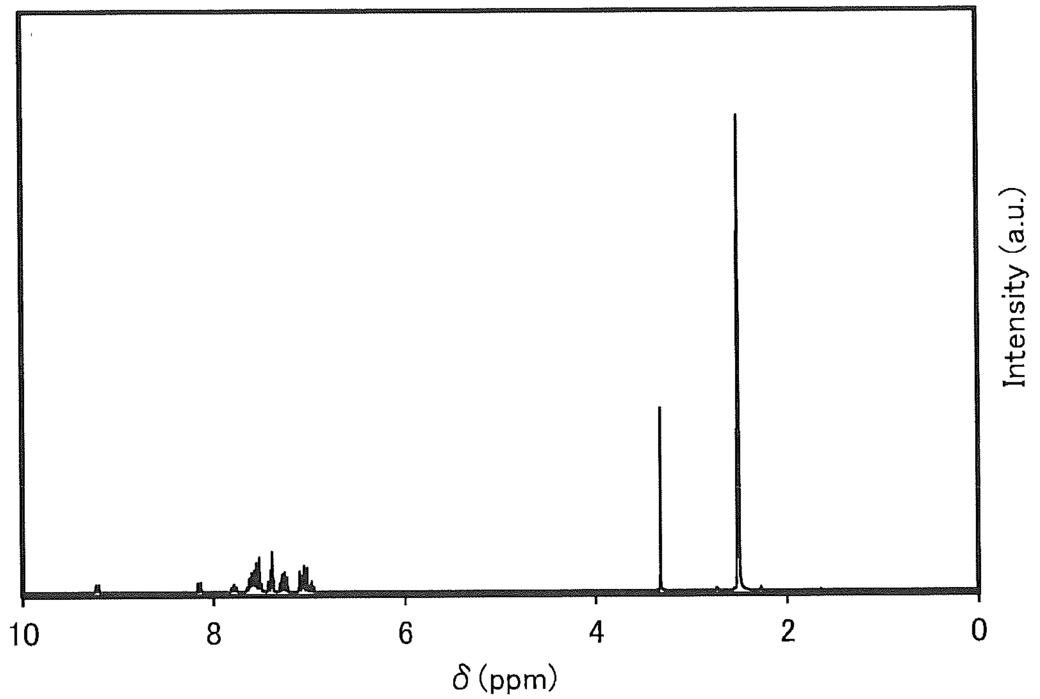
FIGS. 12A-12B are diagrams showing NMR charts of a compound in Example.
Figure 12B:
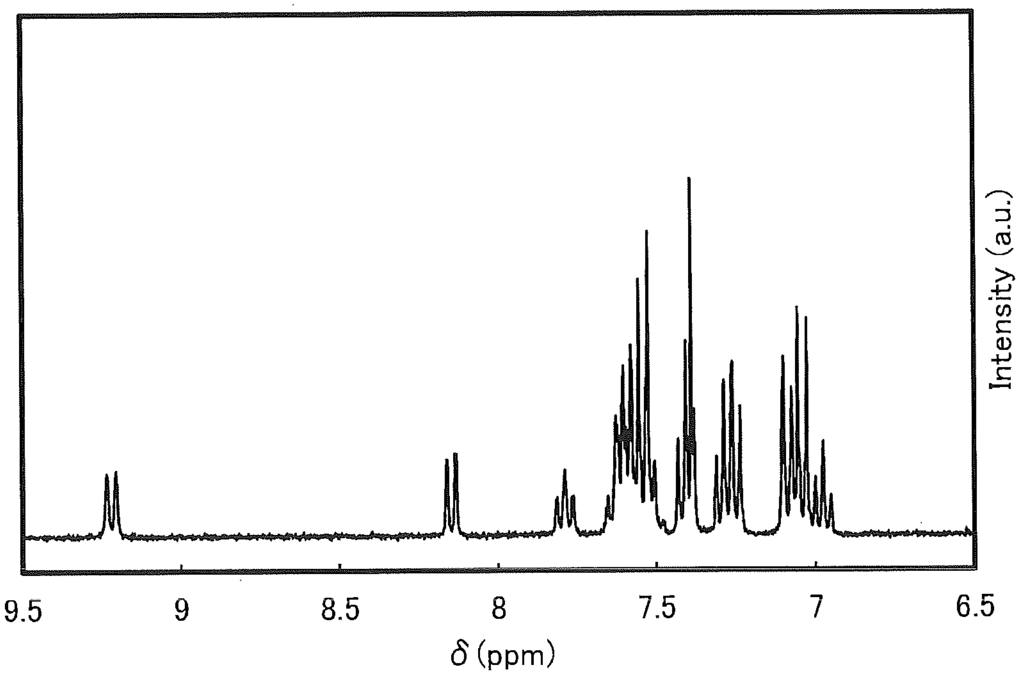

FIGS. 12(A) and 12(B) show $^1$H NMR charts of the obtained solid. Note that FIG. 12(B) is an enlarged diagram of the range of 6.0 ppm to 9.5 ppm of FIG. 12(A). The measurement results indicate that 5,9BPA2PcgDBC, which was the target substance, was obtained.

<Characteristics of 5,9BPA2PcgDBC>

Figure 13:
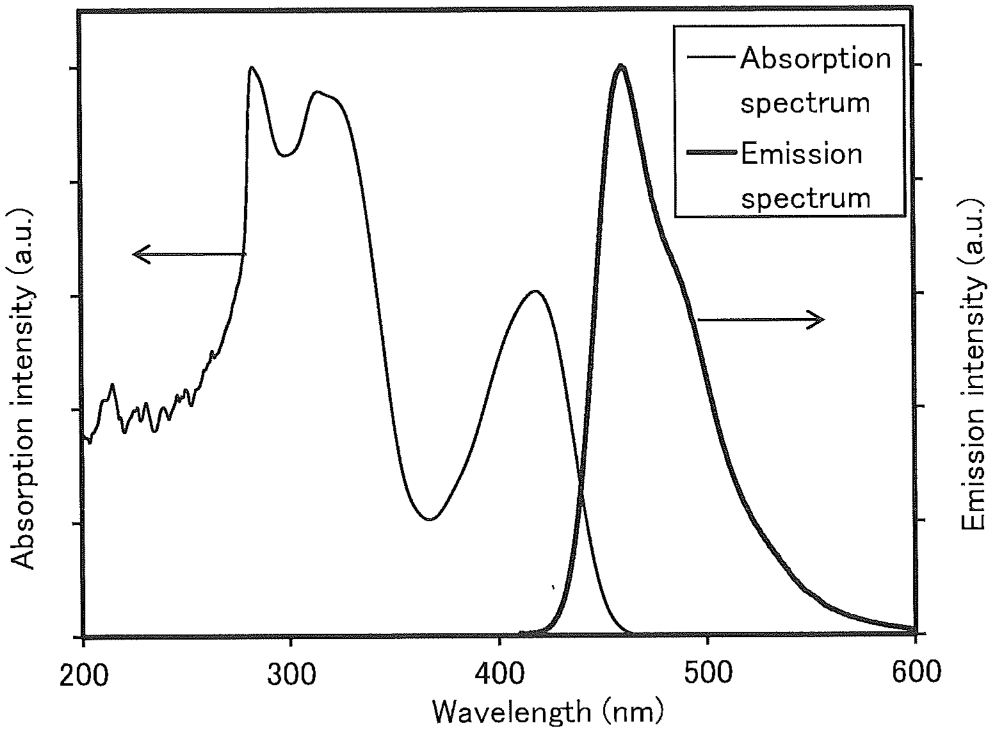
FIG. 13 is a diagram showing an absorption spectrum and an emission spectrum of a compound in Example.
Figure 14:
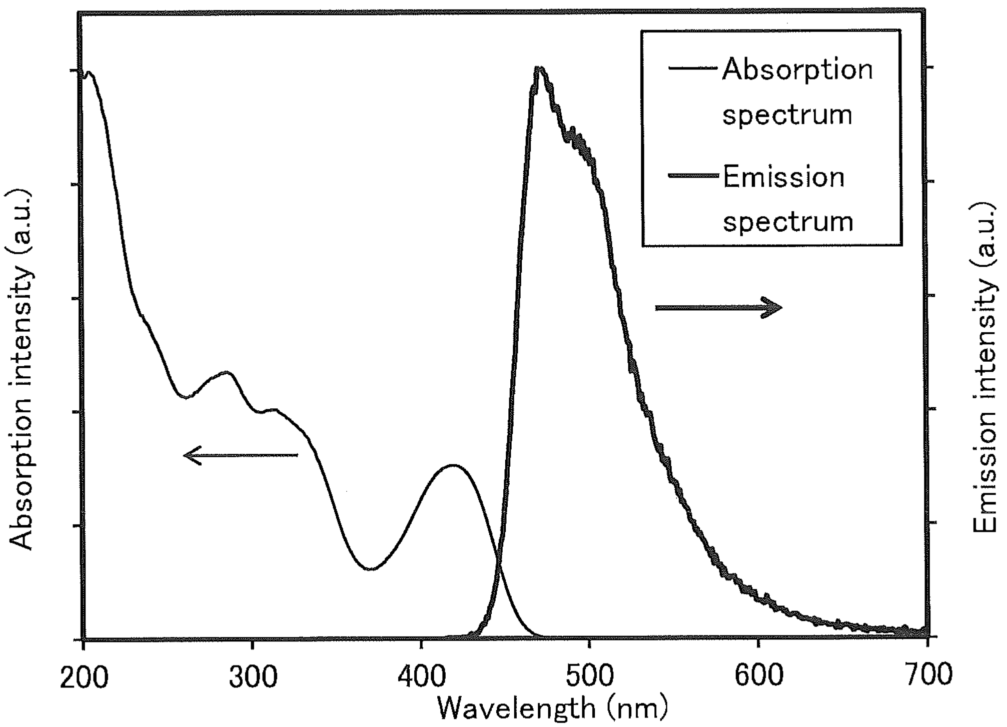
FIG. 14 is a diagram showing an absorption spectrum and an emission spectrum of a compound in Example.

Next, FIG. 13 shows the measurement results of the absorption spectrum and the emission spectrum of 5,9BPA2PcgDBC in a toluene solution. FIG. 14 shows the absorption spectrum and the emission spectrum of a thin film thereof. The solid thin film was fabricated over a quartz substrate by a vacuum evaporation method. The absorption spectrum of the toluene solution was measured with an ultraviolet-visible light spectrophotometer (V550, manufactured by JASCO Corporation), and the spectrum from which the measured spectrum of toluene alone put in a quartz cell was subtracted was shown. For the absorption spectrum of the thin film, a spectrophotometer (U-4100 Spectrophotometer, manufactured by Hitachi High-Technologies Corporation) was used. The emission spectrum of the thin film was measured with a fluorescence spectrophotometer (FS920, manufactured by Hamamatsu Photonics K.K.). For the emission spectrum in the solution and the quantum yields, an absolute PL quantum yield measurement system (Quantaurus-QY, manufactured by Hamamatsu Photonics K.K.) was used.

As shown in FIG. 13, in the case of 5,9BPA2PcgDBC in the toluene solution, absorption peaks were observed at around 419 nm, 324 nm, 314 nm, and 283 nm, and an emission wavelength peak was around 460 nm (excitation wavelength: 400 nm). As shown in FIG. 14, in the case of the thin film of 5,9BPA2PcgDBC, absorption peaks were observed at around 419 nm, 331 nm, 313 nm, and 284 nm, and emission wavelength peaks were observed at around 473 nm and 496 nm (excitation wavelength: 410 nm). These results indicate that 5,9BPA2PcgDBC emits blue light. Furthermore, it is found that 5,9BPA2PcgDBC can be used as a host for a fluorescent substance.

It is found that the quantum yield in the toluene solution is favorably 81%, which is suitable for a light-emitting material.

Next, 5,9BPA2PcgDBC obtained in this example was analyzed by liquid chromatography mass spectrometry (abbreviation: LC/MS analysis).

In the LC/MS analysis, LC (liquid chromatography) separation was performed with Ultimate 3000 manufactured by Thermo Fisher Scientific K.K., and MS analysis (mass spectrometry) was performed with Q Exactive manufactured by Thermo Fisher Scientific K.K.

In the LC separation, a given column was used at a column temperature of 40° C., and the solution sending conditions were that an appropriate solvent was selected, the sample was adjusted by dissolving 5,9BPA2PcgDBC in an organic solvent at a given concentration, and the injection amount was 5.0 μL.

$MS^2$ measurement of m/z=829.35, which is an ion derived from 5,9BPA2PcgDBC, was performed by a Targeted-$MS^2$ method. For setting of the Targeted-$MS^2$, the mass range of a target ion was set to m/z=829.35±2.0 (isolation window=4) and detection was performed in a positive mode. The measurement was performed with energy NCE (Normalized Collision Energy) for accelerating a target ion in a collision cell set to 50. The obtained MS spectrum is shown in FIG. 15.

Figure 15:
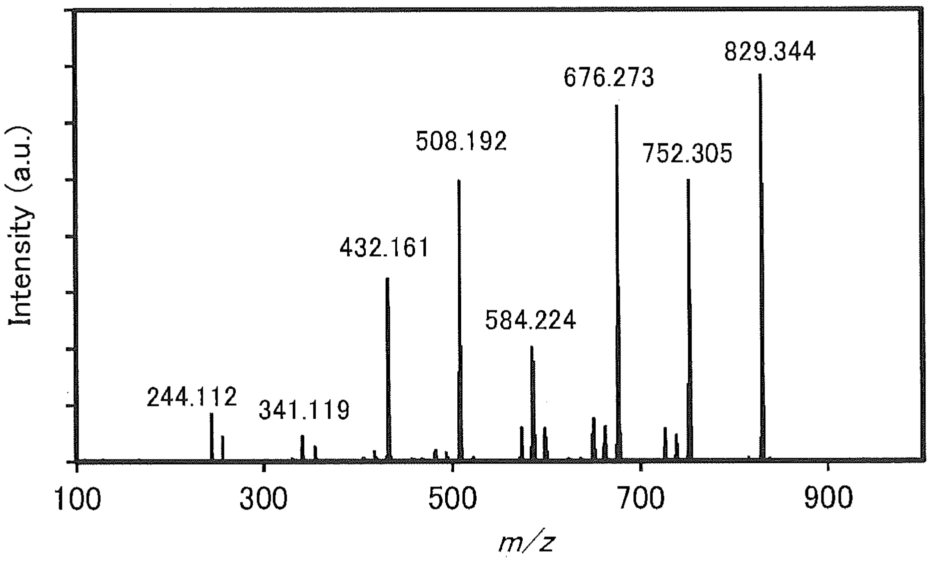
FIG. 15 is a diagram showing $MS^2$ spectra of a compound in Example.

The results in FIG. 15 show that product ions of 5,9BPA2PcgDBC are mainly detected around m/z=752, 676, 584, 508, 432, 341, and 244. Note that the results in the figure show characteristics derived from 5,9BPA2PcgDBC and therefore can be regarded as important data for identifying 5,9BPA2PcgDBC contained in a mixture.

Note that the product ion around m/z=752 is presumed to be a cation in the state where a phenyl group was eliminated from 5,9BPA2PcgDBC, which suggests that 5,9BPA2PcgDBC includes a phenyl group.

Note that the product ion around m/z=676 is presumed to be a cation in the state where a biphenyl group was eliminated from 5,9BPA2PcgDBC, which suggests that 5,9BPA2PcgDBC includes a biphenyl group.

Note that the product ion around m/z=584 is presumed to be a cation in the state where a 4-phenyldiphenylamino group was eliminated from 5,9BPA2PcgDBC, which suggests that 5,9BPA2PcgDBC includes a 4-phenyldiphenylamino group.

Note that the product ion around m/z=341 is presumed to be a cation in the state where two 4-phenyldiphenylamino groups were eliminated from 5,9BPA2PcgDBC, which suggests that 5,9BPA2PcgDBC includes 7-phenyl-7H-dibenzo[c,g]carbazole and two 4-phenyldiphenylamino groups.

Example 2

In this example, a method for synthesizing N,N'-bis(3-methylphenyl)-N,N'-bis[3-(9-phenyl-9H-fluoren-9-yl)phenyl]-7-phenyl-7H-dibenzo[c,g]carbazol-5,9-diamine (abbreviation: 5,9mMemFLPA2PcgDBC) (Structural Formula (101)), which is one of the compounds of one embodiment of the present invention, represented by General Formula (G0), and characteristics of the compound will be described.

Step 1: Synthesis of 5,9mMemFLPA2PcgDBC

In a 200-mL three-neck flask were put 1.1 g (2.1 mmol) of 5,9-dibromo-7-phenyl-7H-dibenzo[c,g]carbazole, 2.7 g (6.3 mmol) of N-(3-methylphenyl)-3-(9-phenyl-9H-fluoren-9-yl)phenylamine, and 1.2 g (13 mmol) of sodium tert-butoxide. To this mixture was added 25 mL of toluene and 0.2 mL of a 10% hexane solution of tri(tert-butyl)phosphine, and this mixture was degassed by being stirred while the pressure was being reduced. To this mixture was added 24 mg (42 μmol) of bis(dibenzylideneacetone)palladium(0), and the mixture was heated and stirred at 110° C. for 13 hours under a nitrogen stream. After the stirring, toluene was added to the mixture and the resulting mixture was suction-filtered through Florisil, Celite, and alumina, so that a filtrate was obtained. The obtained filtrate was concentrated and a solid was obtained. This solid was purified by silica gel column chromatography (developing solvent: hexane:toluene=1:1), and the obtained fraction was concentrated to give a solid. The obtained solid was recrystallized with toluene/ethanol, whereby 1.7 g of a yellow solid was obtained in a yield of 68%. The synthesis scheme of Step 1 is shown in (A-2) below.

[Chemical Formula 34]

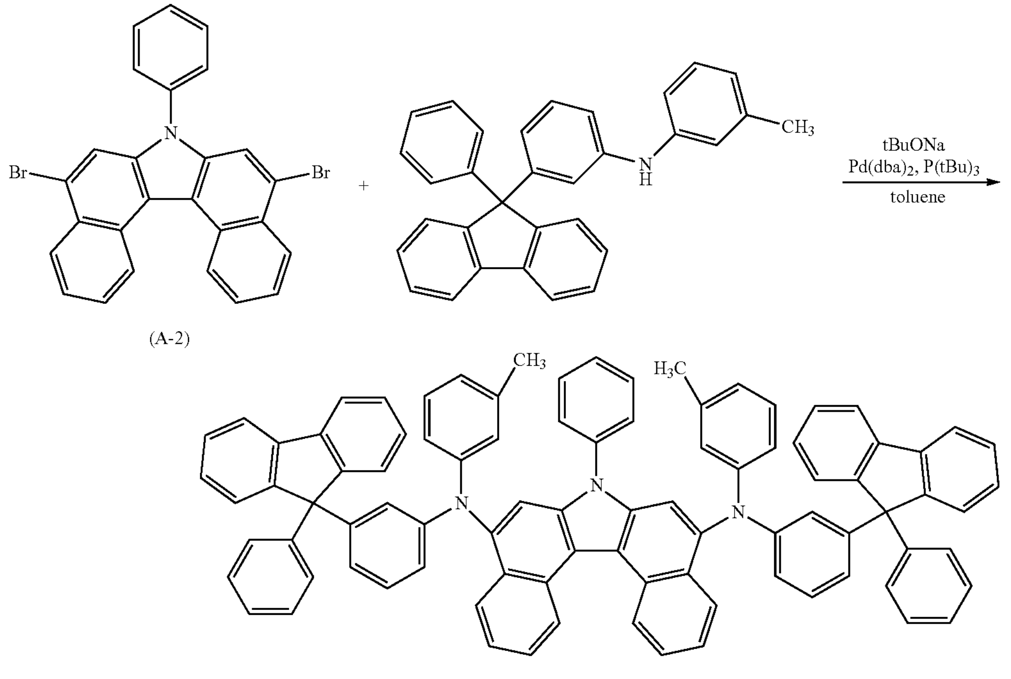

(A-2)

(101)

By a train sublimation method, 1.0 g of the obtained solid was sublimated and purified. Heating was performed at 350° C. under conditions where the pressure was $1.5\times10^{-2}$ Pa and the flow rate of argon was 0 mL/min. After the sublimation purification, 0.60 g of a yellow solid was obtained in a collection rate of 58%.

Analysis data of the obtained solid by nuclear magnetic resonance ($^1$H NMR) spectroscopy are shown below.

$^1$H NMR (DMSO-$d_6$, 300 MHz): δ=2.15 (s, 6H), 6.54 (dd, J1=6.6 Hz, J1=0.9 Hz, 2H), 6.71 (d, J1=8.4 Hz, 4H), 6.79-6.83 (m, 4H), 6.89-6.96 (m, 6H), 7.02-7.16 (m, 18H), 7.22 (s, 2H), 7.25-7.32 (m, 4H), 7.42-7.61 (m, 7H), 7.77-7.85 (m, 6H), 8.02 (dd, J1=8.4 Hz, J2=1.2 Hz, 2H), 9.19 (d, J1=8.1 Hz, 2H).

Figure 16A:
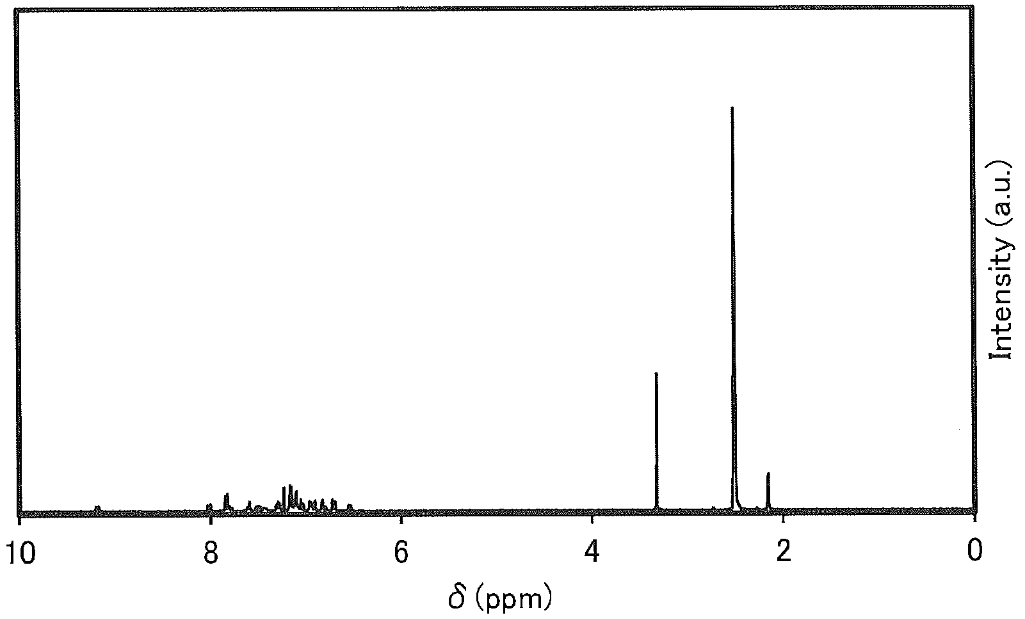
FIGS. 16A-16B are diagrams showing NMR charts of a compound in Example.
Figure 16B:
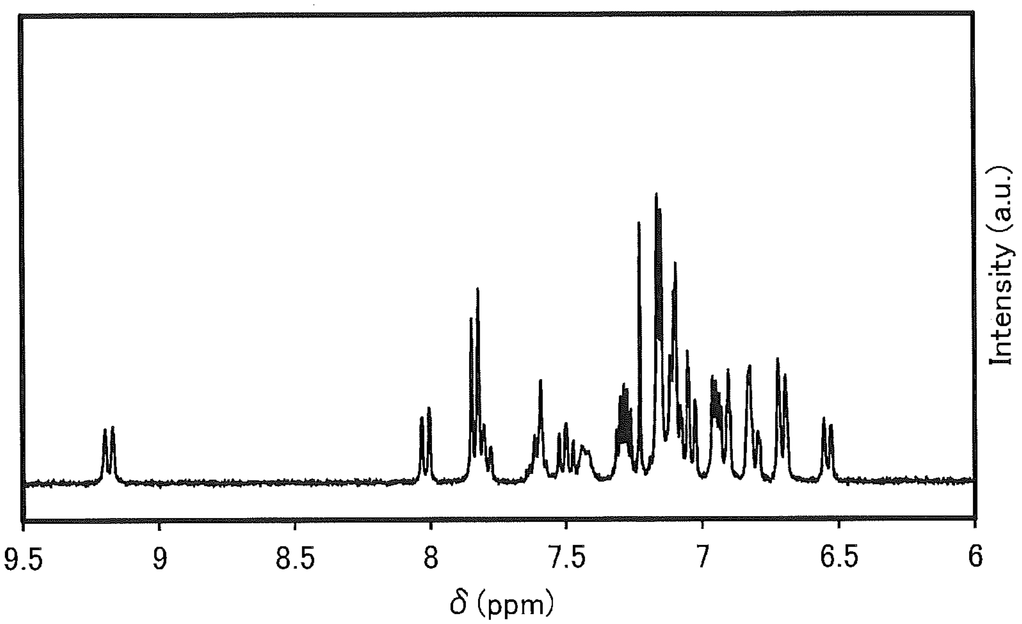

FIGS. 16(A) and 16(B) show $^1$H NMR charts of the obtained solid. Note that FIG. 16(B) is an enlarged diagram of the range of 6.0 ppm to 9.5 ppm of FIG. 16(A). The measurement results reveal that 5,9mMemFLPA2PcgDBC, which was the target substance, was obtained.

<Characteristics of 5,9mMemFLPA2PcgDBC>

Figure 17:
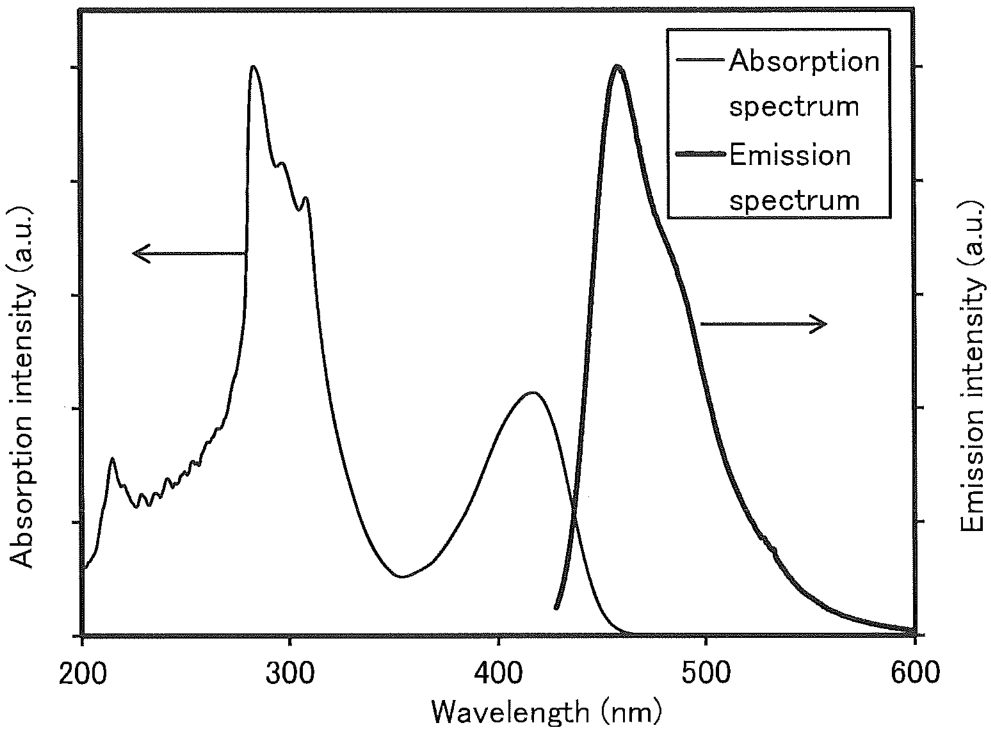
FIG. 17 is a diagram showing an absorption spectrum and an emission spectrum of a compound in Example.
Figure 18:
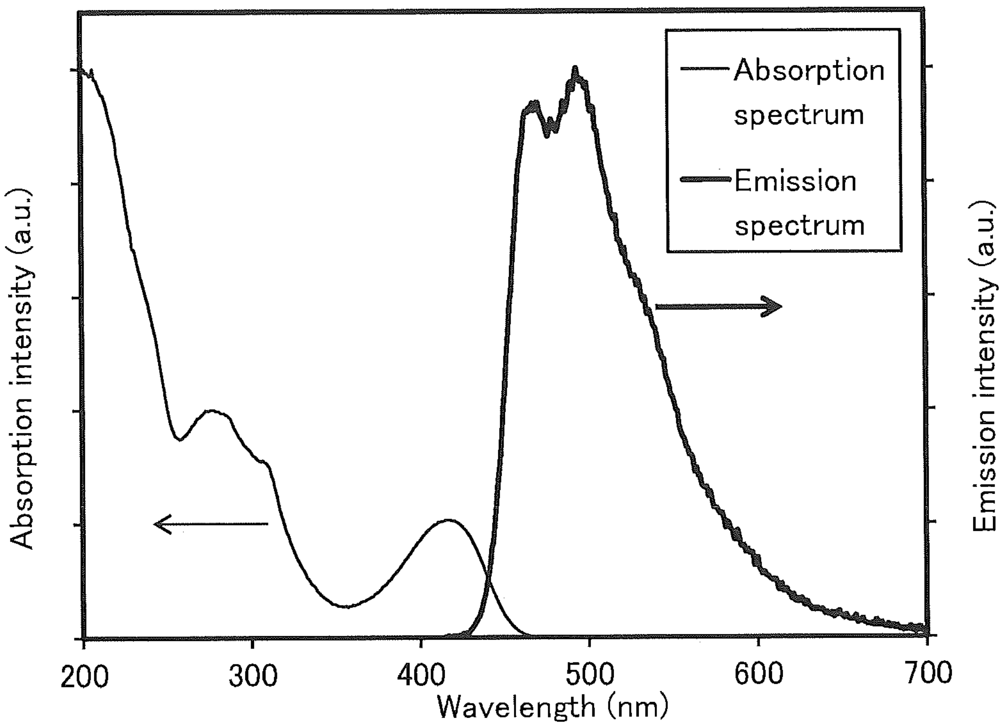
FIG. 18 is a diagram showing an absorption spectrum and an emission spectrum of a compound in Example.

Next, FIG. 17 shows the measurement results of the absorption spectrum and the emission spectrum of 5,9mMemFLPA2PcgDBC in a toluene solution. FIG. 18 shows the absorption spectrum and the emission spectrum of a thin film thereof. The measurement was performed in a manner similar to that in Example 1.

As shown in FIG. 17, in the case of 5,9mMemFLPA2PcgDBC in the toluene solution, absorption peaks were observed at around 417 nm, 308 nm, 297 nm, and 284 nm, and an emission wavelength peak was around 458 nm (excitation wavelength: 420 nm). As shown in FIG. 18, in the case of the thin film of 5,9mMemFLPA2PcgDBC, absorption peaks were observed at around 417 nm, 308 nm, and 278 nm, and emission wavelength peaks were observed at around 470 nm, 494 nm, and 535 nm (excitation wavelength: 410 nm). These results indicate that 5,9mMemFLPA2PcgDBC emits blue light and can be used as a host for a light-emitting substance or a fluorescent substance in the visible region.

It is found that the quantum yield in the toluene solution is favorably 79%, which is suitable for a light-emitting material.

Next, 5,9mMemFLPA2PcgDBC obtained in this example was analyzed by LC/MS analysis. The analysis method was performed in a manner similar to that in Example 1. The obtained MS spectrum is shown in FIG. 19.

Figure 19:
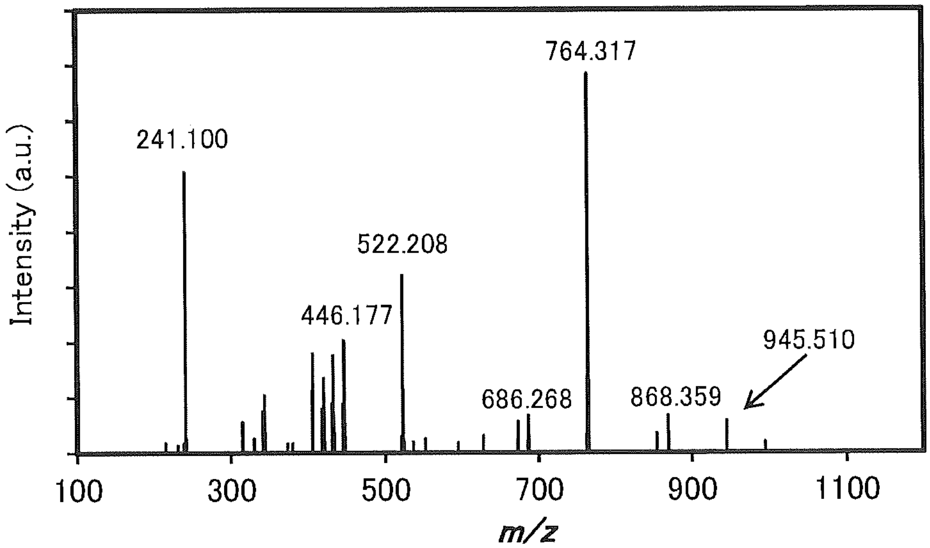
FIG. 19 is a diagram showing $MS^2$ spectra of a compound in Example.

The results in FIG. 19 show that product ions of 5,9mMemFLPA2PcgDBC are mainly detected around m/z=945, 868, 764, 686, 522, 446, and 241. Note that the results in the figure show characteristics derived from 5,9mMemFLPA2PcgDBC and therefore can be regarded as important data for identifying 5,9mMemFLPA2PcgDBC contained in a mixture.

Note that the product ion around m/z=945 is presumed to be a cation in the state where a 9-phenyl-9H-fluorenyl group was eliminated from 5,9mMemFLPA2PcgDBC, which suggests that 5,9mMemFLPA2PcgDBC includes a 9-phenyl-9H-fluorenyl group.

Note that the product ion around m/z=868 is presumed to be a cation in the state where a (9-phenyl-9H-fluoren-9-yl) phenyl group was eliminated from 5,9mMemFLPA2PcgDBC, which suggests that 5,9mMemFLPA2PcgDBC includes a (9-phenyl-9H-fluoren-9-yl)phenyl group.

Note that the product ion around m/z=764 is presumed to be a cation in the state where an N-3-methylphenyl)-N-[3-(9-phenyl-9H-fluoren-9-yl)phenyl]amino group was eliminated from 5,9mMemFLPA2PcgDBC, which suggests that 5,9mMemFLPA2PcgDBC includes an N-3-methylphenyl)-N-[3-(9-phenyl-9H-fluoren-9-yl)phenyl]amino group.

Example 3

In this example, a method for synthesizing N,N'-bis(6-phenyl-benzo[b]naphtho[1,2-d]furan-8-yl)-N,N'-diphenyl-7-phenyl-7H-dibenzo[c,g]carbazol-5,9-diamine (abbreviation: 5,9BnfA2PcgDBC) (Structural Formula (102)), which is one of the compounds of one embodiment of the present invention, represented by General Formula (G0), and characteristics of the compound will be described.

<Step 1: Synthesis of 5,9BnfA2PcgDBC>

In a 200-mL three-neck flask were put 1.1 g (2.3 mmol) of 5,9-dibromo-7-phenyl-7H-dibenzo[c,g]carbazole, 2.2 g (5.6 mmol) of N-(6-phenylbenzo[b]naphtho[1,2-d]furan-8-yl)phenylamine, and 1.3 g (14 mmol) of sodium tert-butoxide. To this mixture was added 25 mL of toluene and 0.2 mL of a 10% hexane solution of tri(tert-butyl)phosphine, and this mixture was degassed by being stirred while the pressure was being reduced. To this mixture was added 26 mg (45 μmol) of bis(dibenzylideneacetone)palladium(0), and the mixture was heated and stirred at 110° C. for 7 hours under a nitrogen stream. After the stirring, toluene was added to the mixture and the resulting mixture was suction-filtered through Florisil, Celite, and alumina, so that a filtrate was obtained. The obtained filtrate was concentrated and a solid was obtained. This solid was purified by silica gel column chromatography (developing solvent: hexane:toluene=2:1 and then hexane:toluene=3:2), and the obtained fraction was concentrated to give a solid. The obtained solid was recrystallized with ethyl acetate/ethanol, whereby 2.2 g of a yellow solid was obtained in a yield of 86%. The synthesis scheme of Step 1 is shown in (A-3) below.

[Chemical Formula 35]

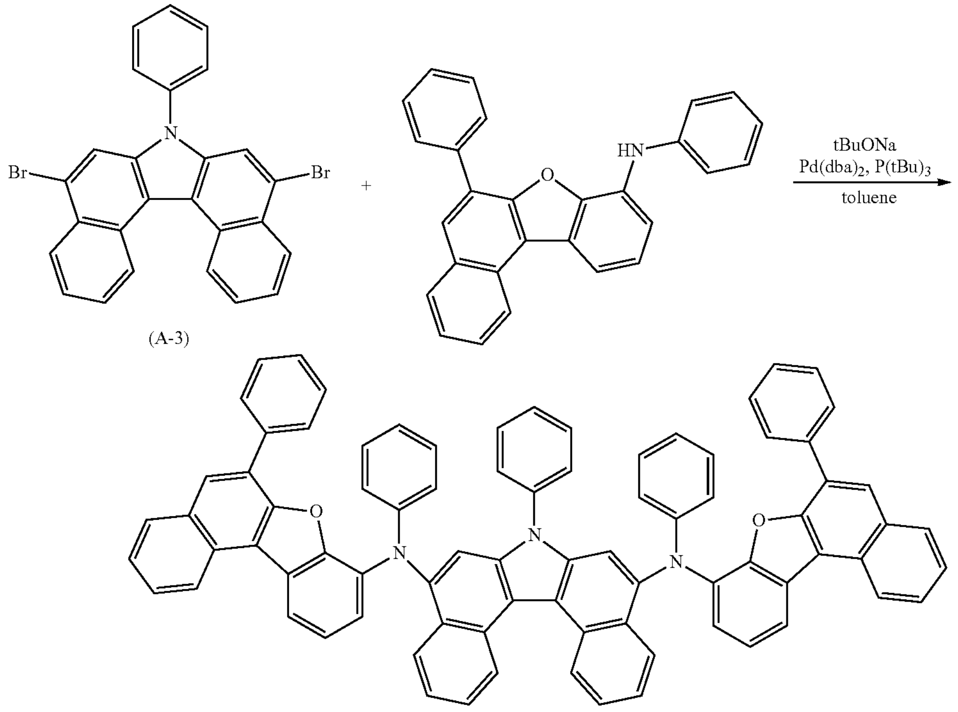

(A-3)

(102)

By a train sublimation method, 1.2 g of the obtained solid was sublimated and purified. Heating was performed at 375° C. under conditions where the pressure was $8.6\times10^{-3}$ Pa and the flow rate of argon was 0 mL/min. After the sublimation purification, 0.55 g of a yellow solid was obtained in a collection rate of 47%.

Analysis data of the obtained solid by nuclear magnetic resonance ($^1H$ NMR) spectroscopy are shown below.

$^1H$ NMR (DMSO-$d_6$, 300 MHz): δ=6.96 (d, J1=7.8 Hz, 4H), 7.02-7.12 (m, 8H), 7.21 (t, J1=7.2 Hz, 2H), 7.28-7.44 (m, 19H), 7.64 (t, J1=7.8 Hz, 2H), 7.73-7.82 (m, 4H), 8.12 (d, J1=8.4 Hz, 2H), 8.21 (d, J1=7.8 Hz, 2H), 8.28 (s, 2H), 8.36 (d, J1=7.8 Hz, 2H), 8.78 (d, J1=8.7 Hz, 2H), 9.22 (d, J1=8.4 Hz, 2H).

Figure 20A:
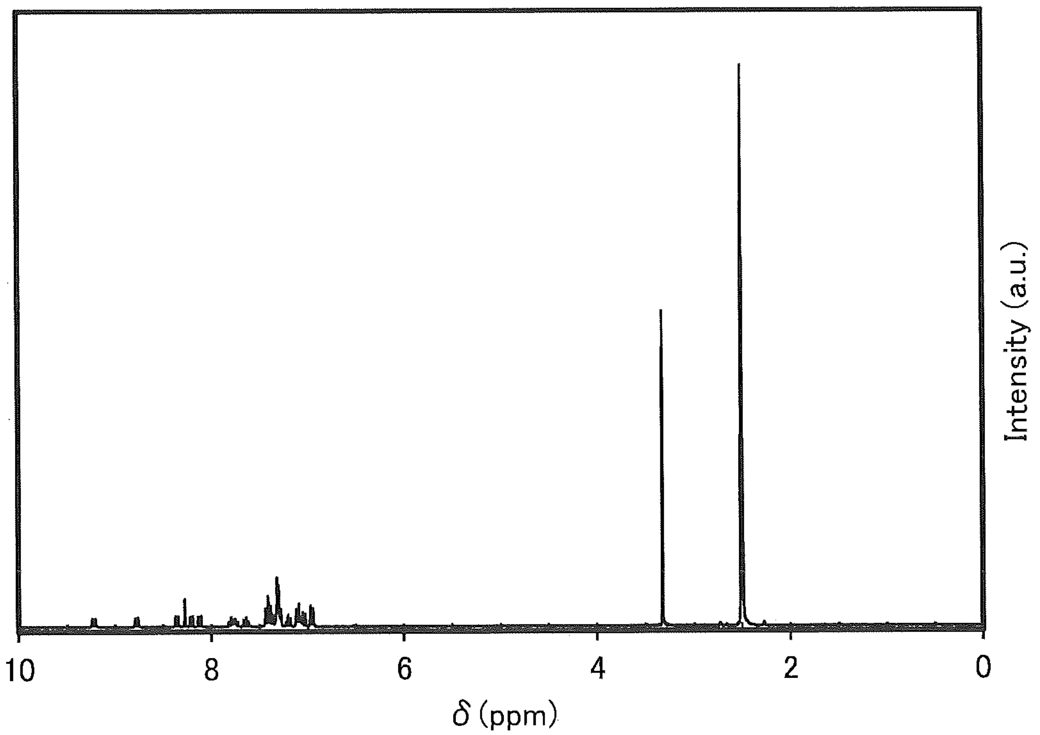
FIGS. 20A-20B are diagrams showing NMR charts of a compound in Example.
Figure 20B:
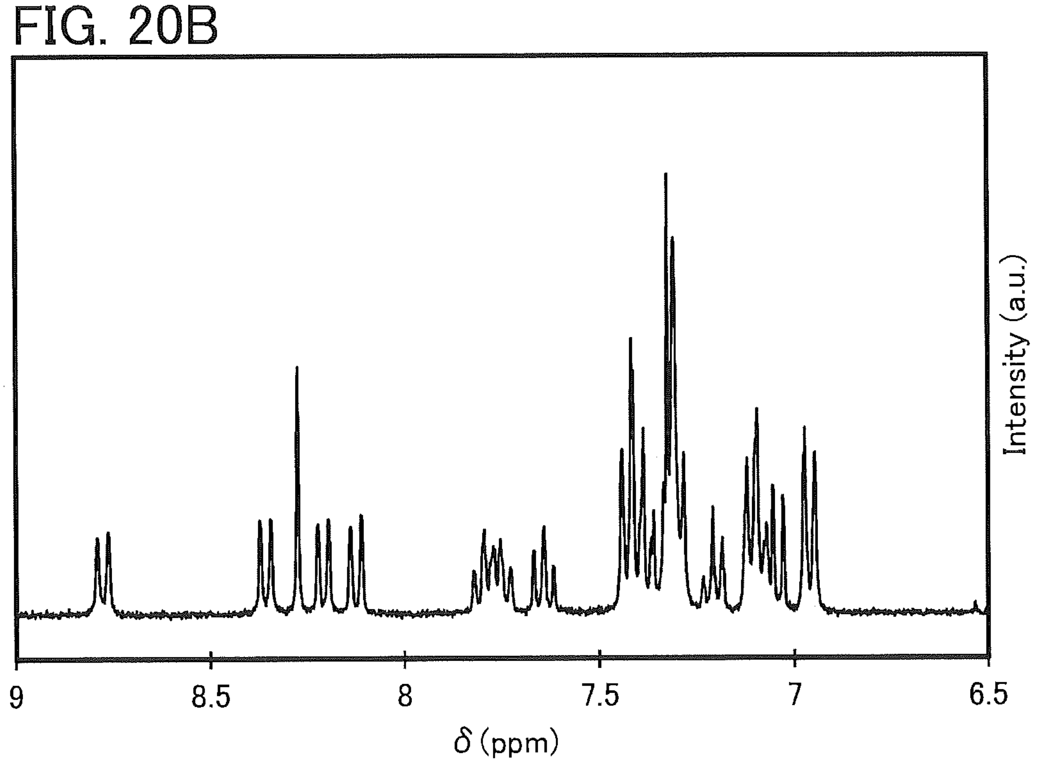

FIGS. 20(A) and 20(B) show $^1H$ NMR charts of the obtained solid. Note that FIG. 20(B) is an enlarged diagram of the range of 6.5 ppm to 9.0 ppm of FIG. 20(A). The measurement results indicate that 5,9BnfA2PcgDBC, which was the target substance, was obtained.

<Characteristics of 5,9BnfA2PcgDBC>

Figure 21:
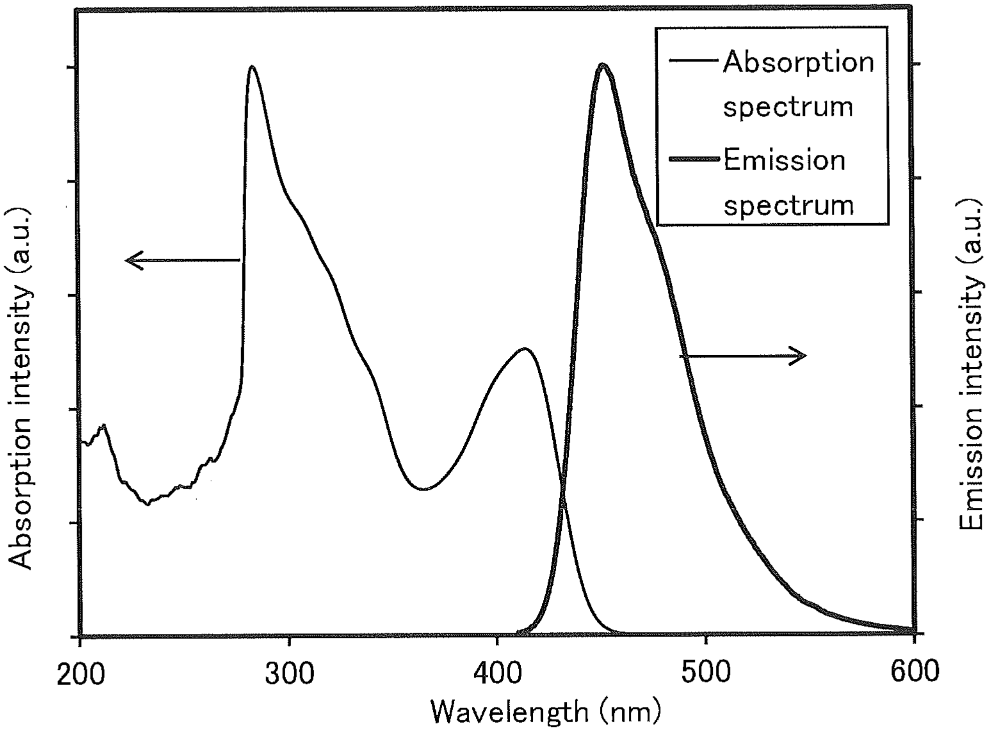
FIG. 21 is a diagram showing an absorption spectrum and an emission spectrum of a compound in Example.
Figure 22:
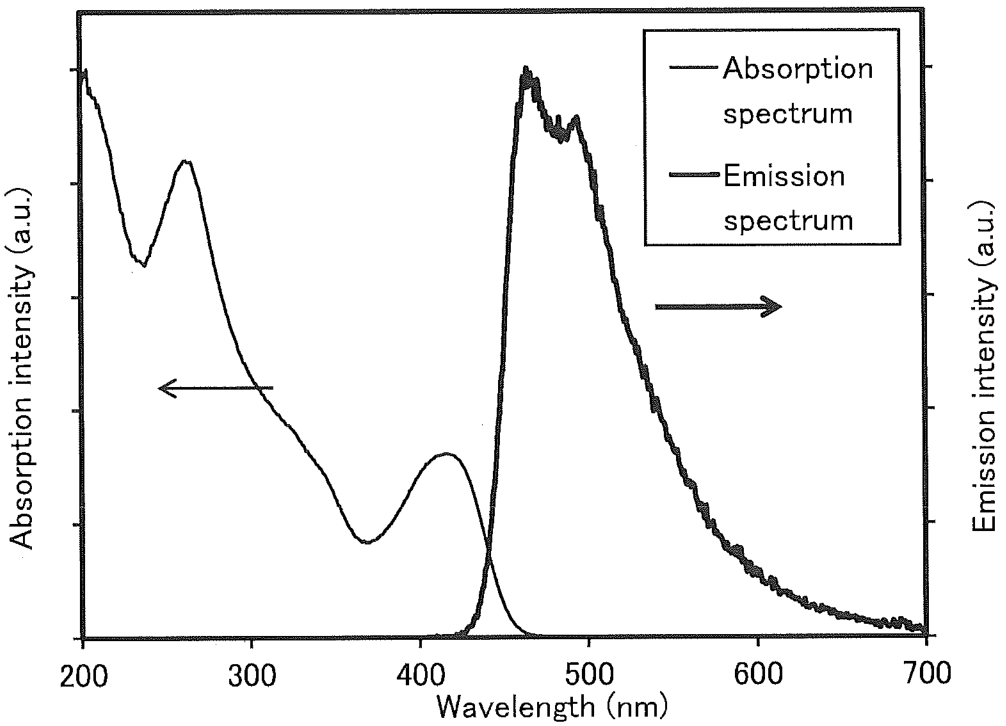
FIG. 22 is a diagram showing an absorption spectrum and an emission spectrum of a compound in Example.

Next, FIG. 21 shows the measurement results of the absorption spectrum and the emission spectrum of 5,9BnfA2PcgDBC in a toluene solution. FIG. 22 shows the absorption spectrum and the emission spectrum of a thin film thereof. The measurement was performed in a manner similar to that in Example 1.

As shown in FIG. 21, in the case of 5,9BnfA2PcgDBC in the toluene solution, absorption peaks were observed at around 414 nm and 284 nm, and emission wavelength peaks were around 451 nm and 477 nm (excitation wavelength: 360 nm). As shown in FIG. 22, in the case of the thin film of 5,9BnfA2PcgDBC, absorption peaks were observed at around 416 nm, 346 nm, 325 nm, and 262 nm, and emission wavelength peaks were observed at around 466 nm and 494 nm (excitation wavelength: 400 nm). These results indicate that 5,9BnfA2PcgDBC emits blue light and can be used as a host for a light-emitting substance or a fluorescent substance in the visible region.

It is found that the quantum yield in the toluene solution is favorably 87%, which is suitable for a light-emitting material.

Next, 5,9BnfA2PcgDBC obtained in this example was analyzed by LC/MS analysis. The analysis method was performed in a manner similar to that in Example 1. The obtained MS spectrum is shown in FIG. 23.

Figure 23:
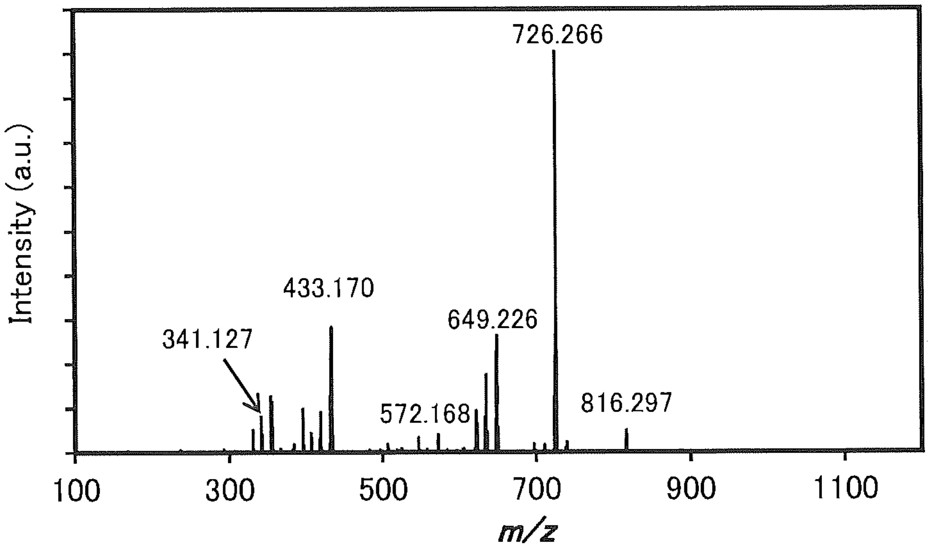
FIG. 23 is a diagram showing $MS^2$ spectra of a compound in Example.

The results in FIG. 23 show that product ions of 5,9BnfA2PcgDBC are mainly detected around m/z=816, 726, 649, 572, 433, and 341. Note that the results in the figure show characteristics derived from 5,9BnfA2PcgDBC and therefore can be regarded as important data for identifying 5,9BnfA2PcgDBC contained in a mixture.

Note that the product ion around m/z=816 is presumed to be a cation in the state where a 6-phenyl-benzo[b]naphtho[1,2-d]furanyl group was eliminated from 5,9BnfA2PcgDBC, which suggests that 5,9BnfA2PcgDBC includes a 6-phenyl-benzo[b]naphtho[1,2-d]furanyl group.

Note that the product ion around m/z=726 is presumed to be a cation in the state where an N-(6-phenyl-benzo[b]naphtho[1,2-d]furan-8-yl)-N-phenylamino group was eliminated from 5,9BnfA2PcgDBC, which suggests that 5,9BnfA2PcgDBC includes an N-(6-phenyl-benzo[b]naphtho[1,2-d]furan-8-yl)-N-phenylamino group.

Note that the product ion around m/z=341 is presumed to be a cation in the state where two N-(6-phenyl-benzo[b]naphtho[1,2-d]furan-8-yl)-N-phenylamino groups were eliminated from 5,9BnfA2PcgDBC, which suggests that 5,9BnfA2PcgDBC includes 7-phenyl-7H-dibenzo[c,g]carbazole and two N-(6-phenyl-benzo[b]naphtho[1,2-d]furan-8-yl)-N-phenylamino groups.

Example 4

In this example, a method for synthesizing N,N'-di(dibenzofuran-4-yl)-N,N'-diphenyl-7-phenyl-7H-dibenzo[c,g]carbazol-5,9-diamine (abbreviation: 5,9FrA2PcgDBC-II) (Structural Formula (103)), which is one of the compounds of one embodiment of the present invention, represented by General Formula (G0), and characteristics of the compound will be described.

Step 1: Synthesis of 5,9FrA2PcgDBC-II

In a 200-mL three-neck flask were put 1.5 g (2.9 mmol) of 5,9-dibromo-7-phenyl-7H-dibenzo[c,g]carbazole, 2.4 g (9.3 mmol) of 4-anilinodibenzofuran, and 1.7 g (17 mmol) of sodium tert-butoxide. To this mixture was added 30 mL of toluene and 0.2 mL of a 10% hexane solution of tri(tert-butyl)phosphine, and this mixture was degassed by being stirred while the pressure was being reduced. To this mixture was added 33 mg (58.2 μmol) of bis(dibenzylideneacetone)palladium(0), and the mixture was heated and stirred at 110° C. for eight hours under a nitrogen stream. After the stirring, toluene was added to the mixture and the resulting mixture was suction-filtered through Florisil, Celite, and alumina, so that a filtrate was obtained. The obtained filtrate was concentrated and a solid was obtained. This solid was purified by silica gel column chromatography (developing solvent: hexane:toluene=2:1 and then hexane:toluene=3:2), and the obtained fraction was concentrated to give a solid. The obtained solid was recrystallized with toluene/ethyl acetate, whereby 1.5 g of a pale yellow solid was obtained in a yield of 60%. The synthesis scheme of Step 1 is shown in (A-4) below.

[Chemical Formula 36]

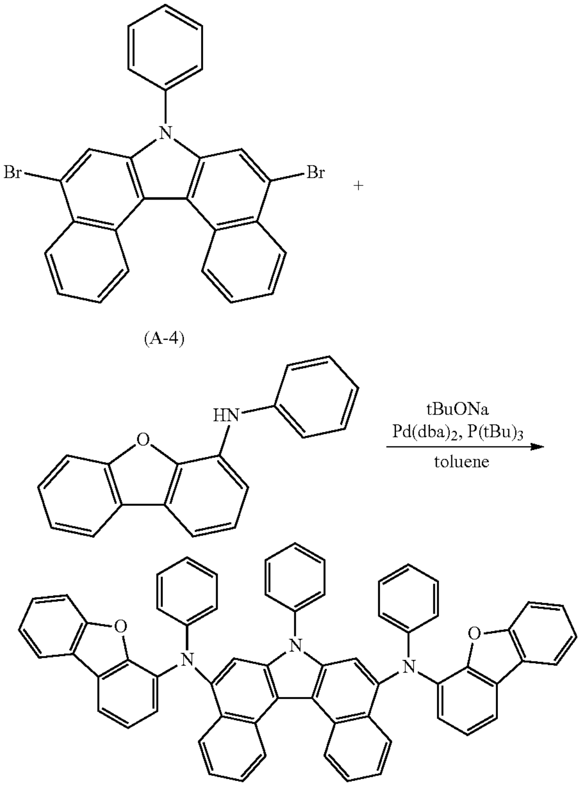

(103)

By a train sublimation method, 1.3 g of the obtained solid was sublimated and purified. Heating was performed at 310° C. under conditions where the pressure was $9.8\times10^{-3}$ Pa and the flow rate of argon was 0 mL/min. After the sublimation purification, 0.75 g of a yellow solid was obtained in a collection rate of 59%.

Analysis data of the obtained solid by nuclear magnetic resonance ($^1$H NMR) spectroscopy are shown below.

$^1$H NMR (DMSO-$d_6$, 300 MHz): δ=6.72 (d, J1=7.5 Hz, 4H), 6.89 (t, J1=7.5 Hz, 2H), 7.14-7.19 (m, 6H), 7.28 (t, J1=7.8 Hz, 2H), 7.38-7.51 (m, 15H), 7.77 (t, J1=8.7 Hz, 2H), 7.93 (dd, J1=7.2 Hz, J2=0.90 Hz, 2H), 8.16 (dd, J1=7.2 Hz, J2=1.2 Hz, 2H), 8.24 (dd, J1=8.4 Hz, J2=1.2 Hz, 2H), 9.20 (d, J1=8.7 Hz, 2H).

Figure 24A:
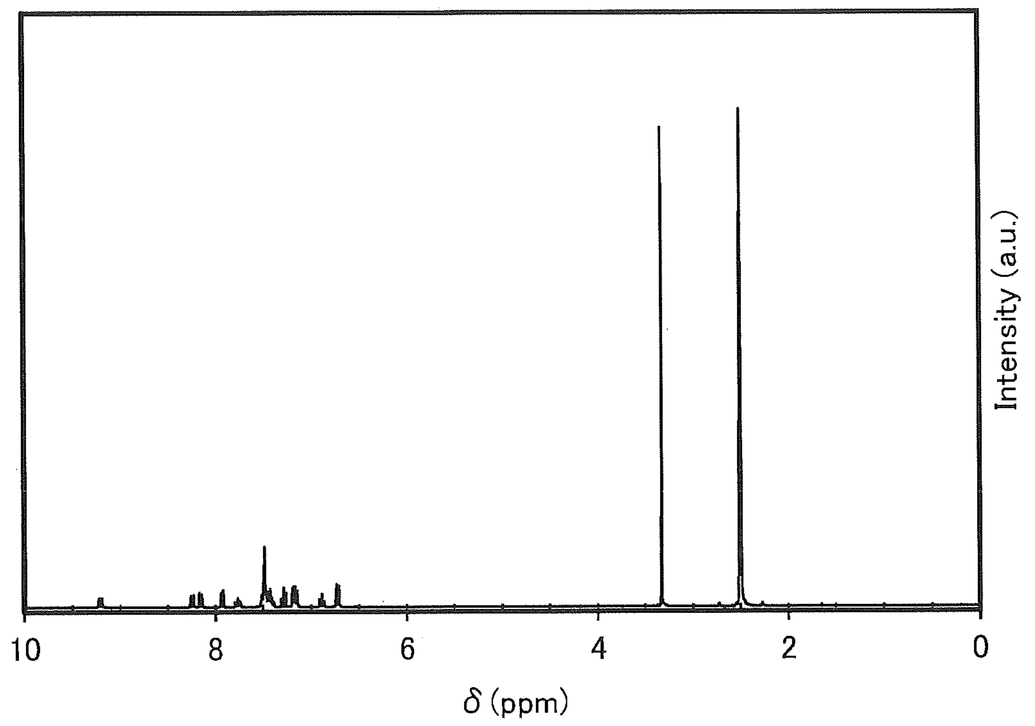
FIGS. 24A-24B are diagrams showing NMR charts of a compound in Example.
Figure 24B:
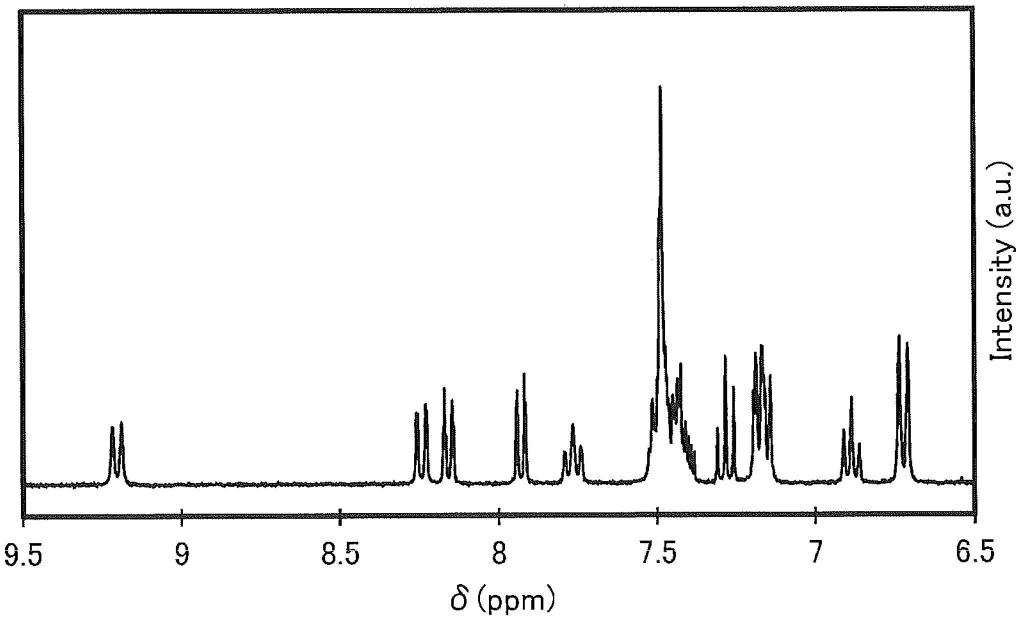

FIGS. 24(A) and 24(B) show $^1$H NMR charts of the obtained solid. Note that FIG. 24(B) is an enlarged diagram of the range of 6.5 ppm to 8.5 ppm of FIG. 24(A). The measurement results indicate that 5,9FrA2PcgDBC-II, which was the target substance, was obtained.

<Characteristics of 5,9FrA2PcgDBC-II>

Figure 25:
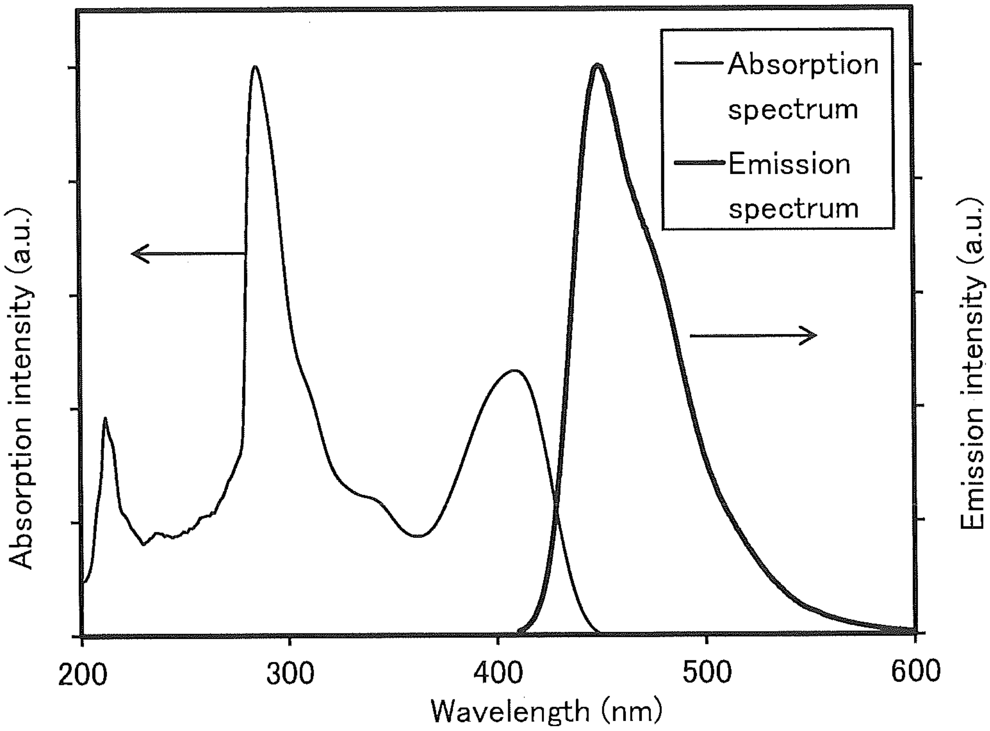
FIG. 25 is a diagram showing an absorption spectrum and an emission spectrum of a compound in Example.
Figure 26:
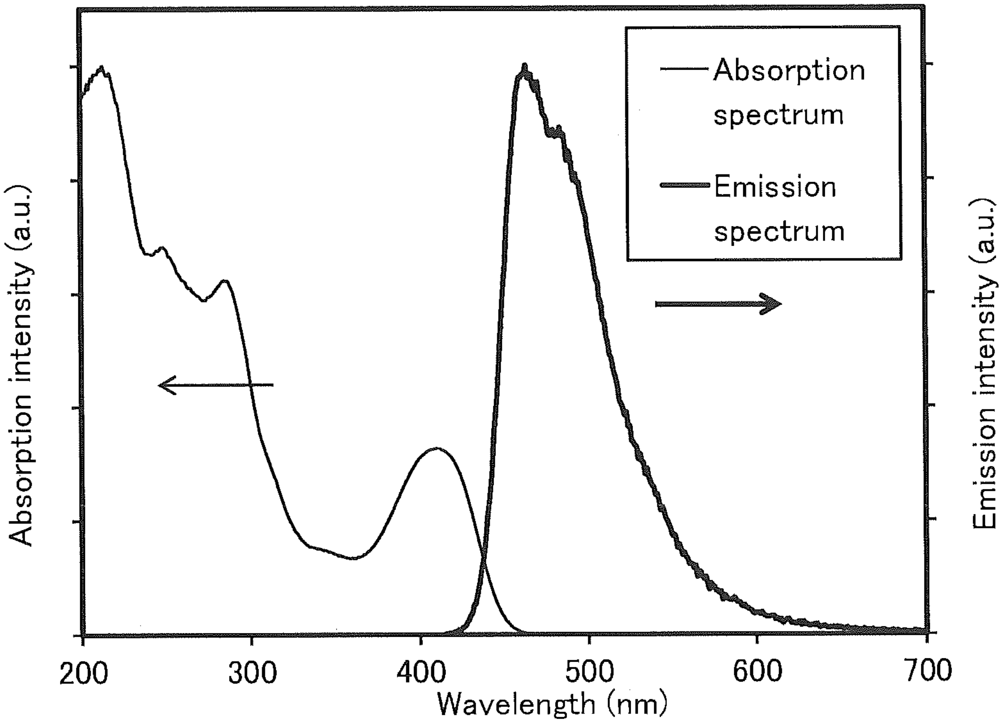
FIG. 26 is a diagram showing an absorption spectrum and an emission spectrum of a compound in Example.

Next, FIG. 25 shows the measurement results of the absorption spectrum and the emission spectrum of 5,9FrA2PcgDBC-II in a toluene solution. FIG. 26 shows the absorption spectrum and the emission spectrum of a thin film thereof. The measurement was performed in a manner similar to that in Example 1.

As shown in FIG. 25, in the case of 5,9FrA2PcgDBC-II in the toluene solution, absorption peaks were observed at around 409 nm, 342 nm, and 285 nm, and an emission wavelength peak was around 449 nm (excitation wavelength: 400 nm). As shown in FIG. 26, in the case of the thin film of 5,9FrA2PcgDBC-II, absorption peaks were observed at around 410 nm, 346 nm, 314 nm, 285 nm, and 248 nm, and emission wavelength peaks were observed at around 464 nm and 483 nm (excitation wavelength: 410 nm). These results indicate that 5,9FrA2PcgDBC-II emits blue light. Furthermore, it is found that 5,9FrA2PcgDBC-II can be used as a host for a fluorescent substance.

It is found that the quantum yield in the toluene solution is favorably 86%, which is suitable for a light-emitting material.

Next, 5,9FrA2PcgDBC-II obtained in this example was analyzed by LC/MS analysis. The analysis method was performed in a manner similar to that in Example 1. The obtained MS spectrum is shown in FIG. 27.

Figure 27:
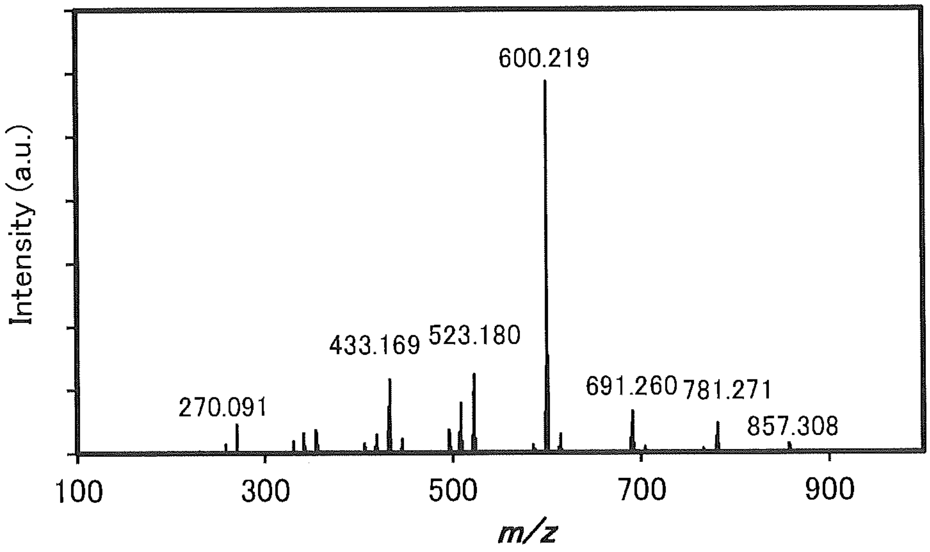
FIG. 27 is a diagram showing $MS^2$ spectra of a compound in Example.

The results in FIG. 27 show that product ions of 5,9FrA2PcgDBC-II are mainly detected around m/z=781, 691, 600, 523, 433, and 270. Note that the results in the figure show characteristics derived from 5,9FrA2PcgDBC-II and therefore can be regarded as important data for identifying 5,9FrA2PcgDBC-II contained in a mixture.

Note that the product ion around m/z=781 is presumed to be a cation in the state where a phenyl group was eliminated from 5,9FrA2PcgDBC-II, which suggests that 5,9FrA2PcgDBC-II includes a phenyl group.

Note that the product ion around m/z=691 is presumed to be a cation in the state where a dibenzofuranyl group was eliminated from 5,9FrA2PcgDBC-II, which suggests that 5,9FrA2PcgDBC-II includes a dibenzofuranyl group.

Note that the product ion around m/z=600 is presumed to be a cation in the state where an N-(dibenzofuran-4-yl)-N-phenylamino group was eliminated from 5,9FrA2PcgDBC-II, which suggests that 5,9FrA2PcgDBC-II includes an N-(dibenzofuran-4-yl)-N-phenylamino group.

Note that the product ion around m/z=270 is presumed to be a cation in the state where a 5-[N-(dibenzofuran-4-yl)-N-phenylamino]-7-phenyl-7H-dibenzo[c,g]carbazolyl group was eliminated from 5,9FrA2PcgDBC-II, which suggests that 5,9FrA2PcgDBC-II includes a 5-[N-(dibenzofuran-4-yl)-N-phenylamino]-7-phenyl-7H-dibenzo[c,g]carbazolyl group.

Example 5

In this example, a method for synthesizing 5,9-bis[N-(2,5-dimethylphenyl)-N-(4-biphenyl)amino]-7-phenyl-7H-dibenzo[c,g]carbazole (abbreviation: 5,9oDMeBPA2PcgDBC) (Structural Formula (104)), which is one of the compounds of one embodiment of the present invention, represented by General Formula (G0), and characteristics of the compound will be described.

Step 1: Synthesis of 5,9oDMeBPA2PcgDBC

In a 200-mL three-neck flask were put 1.4 g (2.8 mmol) of 5,9-dibromo-7-phenyl-7H-dibenzo[c,g]carbazole, 1.9 g (7.1 mmol) of N-(2,6-dimethylphenyl)-4-diphenylamine, and 1.6 g (17 mmol) of sodium tert-butoxide. To this mixture was added 30 mL of toluene and 0.2 mL of a 10% hexane solution of tri(tert-butyl)phosphine, and this mixture was degassed by being stirred while the pressure was being reduced. To this mixture was added 32 mg (56 μmol) of bis(dibenzylideneacetone)palladium(0), and the mixture was heated and stirred at 110° C. for 7.5 hours under a nitrogen stream. After the stirring, toluene was added to the mixture and the resulting mixture was suction-filtered through Florisil, Celite, and alumina, so that a filtrate was obtained. The obtained filtrate was concentrated and a solid was obtained. This solid was purified by silica gel column chromatography (developing solvent: hexane:toluene=2:1 and then hexane:toluene=3:2), and the obtained fraction was concentrated to give a solid. The obtained solid was recrystallized with toluene/ethyl acetate, whereby 1.0 g of a yellow solid was obtained in a yield of 40%. The synthesis scheme of Step 1 is shown in (A-5) below.

[Chemical Formula 37]

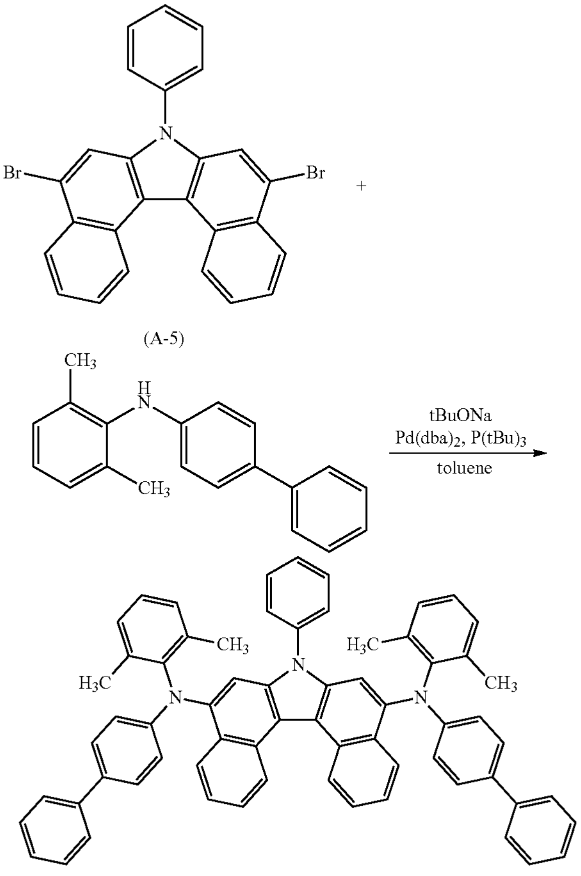

(104)

By a train sublimation method, 1.0 g of the obtained solid was sublimated and purified. Heating was performed at 310° C. under conditions where the pressure was $2.3\times10^{-2}$ Pa and the flow rate of argon was 0 mL/min. After the sublimation purification, 0.80 g of a yellow solid was obtained in a collection rate of 79%.

Analysis data of the obtained solid by nuclear magnetic resonance ($^1$H NMR) spectroscopy are shown below.

$^1$H NMR (DMSO-$d_6$, 300 MHz): δ=2.00 (s, 12H), 6.59 (d, J1=9.0 Hz, 4H), 7.03 (s, 2H), 7.13 (s, 6H), 7.27 (t, J1=7.2 Hz, 2H), 7.37-7.53 (m, 15H), 7.60 (d, J1=6.9 Hz, 4H), 7.73 (t, J1=7.2 Hz, 2H), 8.11 (dd, J1=8.7 Hz, J2=0.9 Hz, 2H), 9.19 (d, J1=8.4 Hz, 2H).

Figure 28A:
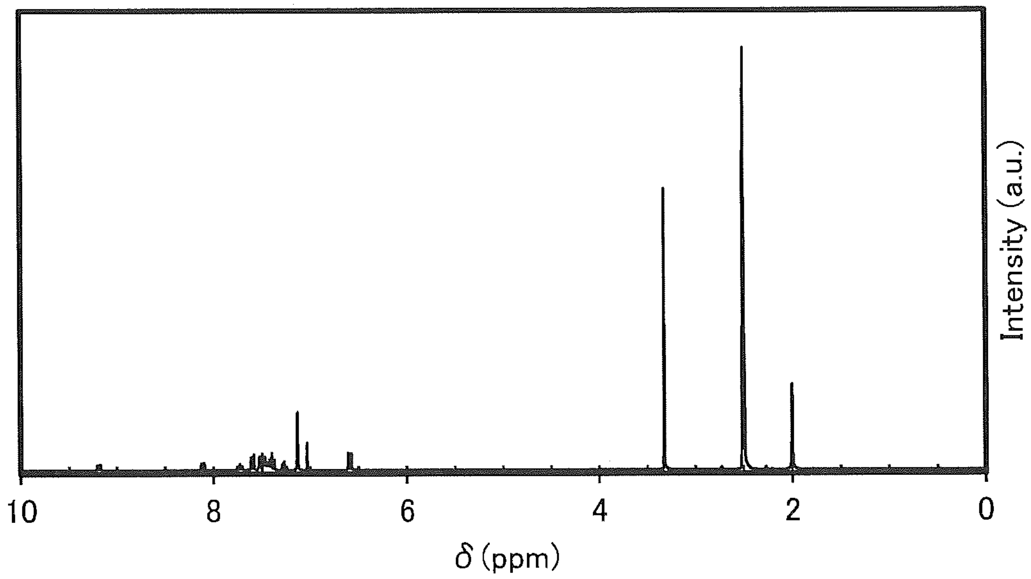
FIGS. 28A-28B are diagrams showing NMR charts of a compound in Example.
Figure 28B:
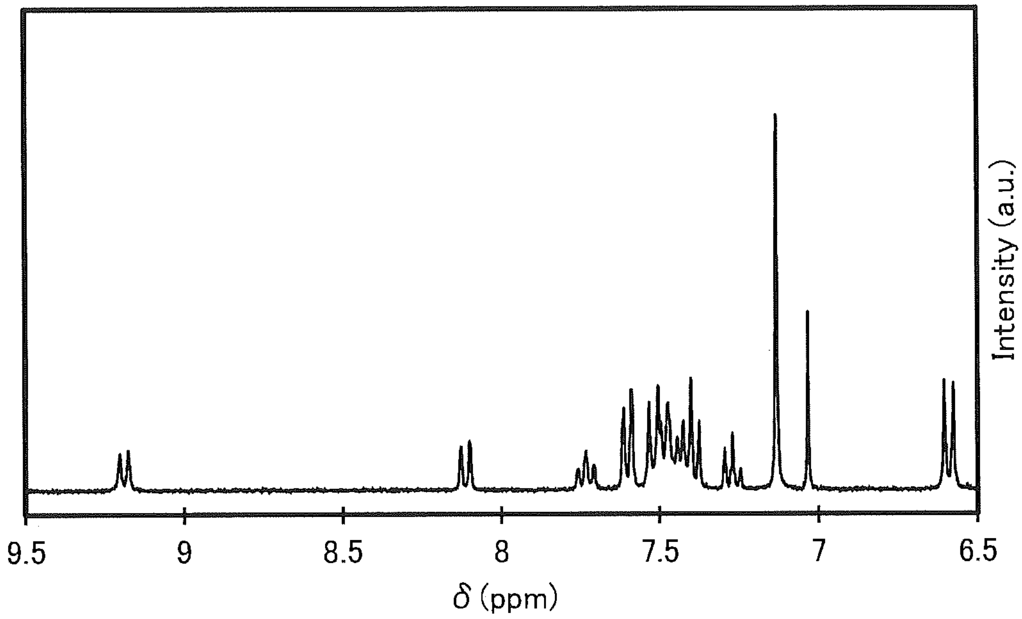

FIGS. 28(A) and 28(B) show $^1$H NMR charts of the obtained solid. Note that FIG. 28(B) is an enlarged diagram of the range of 6.5 ppm to 9.5 ppm of FIG. 28(A). The measurement results indicate that 5,9oDMeBPA2PcgDBC, which was the target substance, was obtained.

<Characteristics of 5,9oDMeBPA2PcgDBC>

Figure 29:
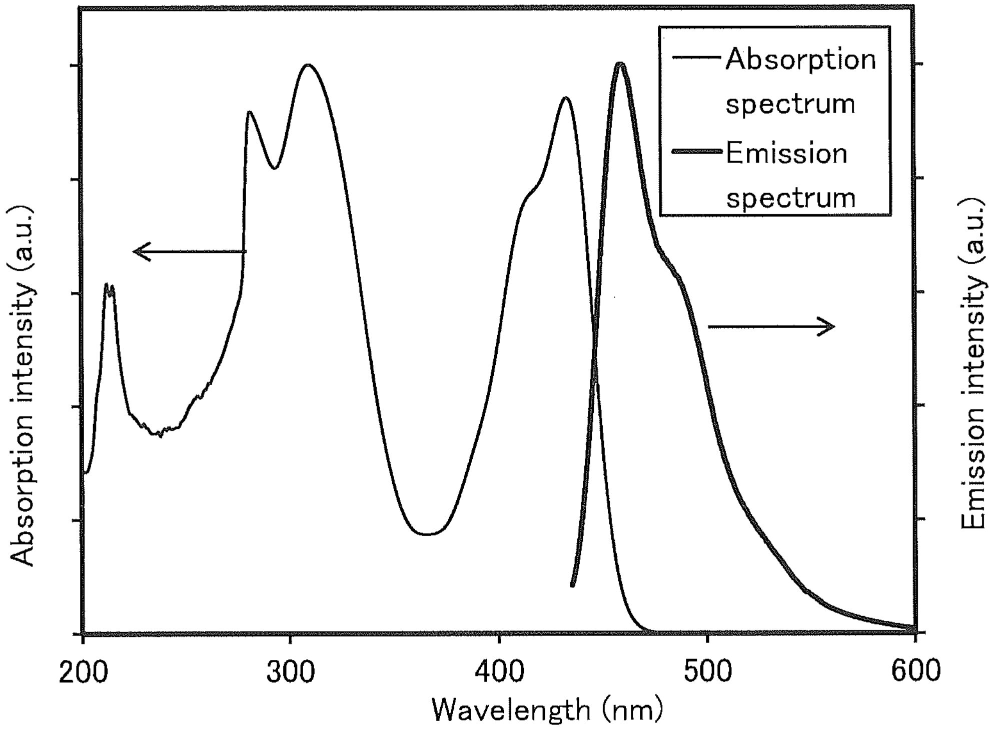
FIG. 29 is a diagram showing an absorption spectrum and an emission spectrum of a compound in Example.
Figure 30:
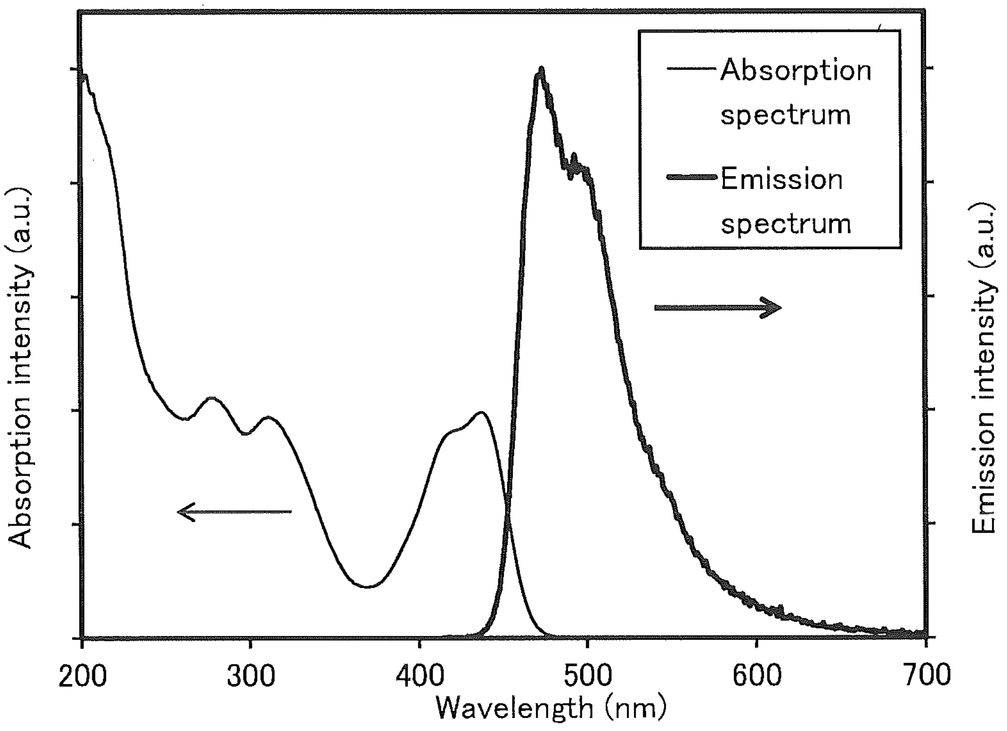
FIG. 30 is a diagram showing an absorption spectrum and an emission spectrum of a compound in Example.

Next, FIG. 29 shows the measurement results of the absorption spectrum and the emission spectrum of 5,9oDMeBPA2PcgDBC in a toluene solution. FIG. 30 shows the absorption spectrum and the emission spectrum of a thin film thereof. The measurement was performed in a manner similar to that in Example 1.

As shown in FIG. 29, in the case of 5,9oDMeBPA2PcgDBC in the toluene solution, absorption peaks were observed at around 433 nm, 415 nm, 310 nm, and 282 nm, and emission wavelength peaks were around 458 nm and 487 nm (excitation wavelength: 430 nm). As shown in FIG. 30, in the case of the thin film of 5,9oDMeBPA2PcgDBC, absorption peaks were observed at around 437 nm, 418 nm, 390 nm, 310 nm, and 276 nm, and emission wavelength peaks were observed at around 473 nm and 497 nm (excitation wavelength: 410 nm). These results indicate that 5,9oDMeBPA2PcgDBC emits blue light and can be used as a host for a light-emitting substance or a fluorescent substance in the visible region.

It is found that the quantum yield in the toluene solution is favorably 85%, which is suitable for a light-emitting material.

Next, 5,9oDMeBPA2PcgDBC obtained in this example was analyzed by LC/MS analysis. The analysis method was performed in a manner similar to that in Example 1. The obtained MS spectrum is shown in FIG. 31.

Figure 31:
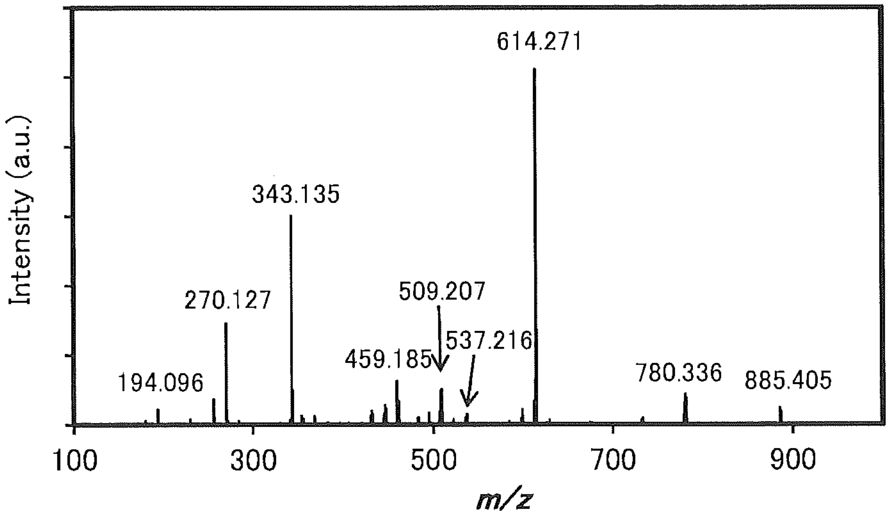
FIG. 31 is a diagram showing $MS^2$ spectra of a compound in Example.

The results in FIG. 31 show that product ions of 5,9oDMeBPA2PcgDBC are mainly detected around m/z=780, 614, 537, 509, 459, 343, 270, and 194. Note that the results in the figure show characteristics derived from 5,9oDMeBPA2PcgDBC and therefore can be regarded as important data for identifying 5,9oDMeBPA2PcgDBC contained in a mixture.

Note that the product ion around m/z=780 is presumed to be a cation in the state where a 2,5-dimethylphenyl group was eliminated from 5,9oDMeBPA2PcgDBC, which suggests that 5,9oDMeBPA2PcgDBC includes a 2,5-dimethylphenyl group.

Note that the product ion around m/z=614 is presumed to be a cation in the state where an N-(2,5-dimethylphenyl)-N-(4-biphenyl)amino group was eliminated from 5,9oDMeBPA2PcgDBC, which suggests that 5,9oDMeBPA2PcgDBC includes an N-(2,5-dimethylphenyl)-N-(4-biphenyl)amino group.

Note that the product ion around m/z=537 is presumed to be a cation in the state where an N-(2,5-dimethylphenyl)-N-(4-biphenyl)amino group and a phenyl group were eliminated from 5,9oDMeBPA2PcgDBC, which suggests that 5,9oDMeBPA2PcgDBC includes an N-(2,5-dimethylphenyl)-N-(4-biphenyl)amino group and a phenyl group.

Note that the product ion around m/z=343 is presumed to be a cation in the state where two N-(2,5-dimethylphenyl)-N-(4-biphenyl)amino groups were eliminated from 5,9oDMeBPA2PcgDBC, which suggests that 5,9oDMeBPA2PcgDBC includes two N-(2,5-dimethylphenyl)-N-(4-biphenyl)amino groups and a 7-phenyl-7H-dibenzo[c,g]carbazole.

Example 6

In this example, a method for synthesizing 5,9-bis[di(4-biphenyl)amino]-7-phenyl-7H-dibenzo[c,g]carbazole (abbreviation: 5,9BBA2PcgDBC) (Structural Formula (105)), which is one of the compounds of one embodiment of the present invention, represented by General Formula (G0), and characteristics of the compound will be described.

Step 1: Synthesis of 5,9BBA2PcgDBC

In a 200-mL three-neck flask were put 1.3 g (2.6 mmol) of 5,9-dibromo-7-phenyl-7H-dibenzo[c,g]carbazole, 2.1 g (6.4 mmol) of bis(4-biphenylyl)amine, and 1.5 g (15 mmol) of sodium tert-butoxide. To this mixture was added 26 mL of toluene and 0.2 mL of a 10% hexane solution of tri(tert-butyl)phosphine, and this mixture was degassed by being stirred while the pressure was being reduced. To this mixture was added 29 mg (51 μmol) of bis(dibenzylideneacetone)palladium(0), and the mixture was heated and stirred at 110° C. for 15 hours under a nitrogen stream. After the stirring, toluene was added to the mixture and the resulting mixture was suction-filtered through Florisil, Celite, and alumina, so that a filtrate was obtained. The obtained filtrate was concentrated and a solid was obtained. This solid was purified by silica gel column chromatography (developing solvent: hexane:toluene=2:1 and then hexane:toluene=3:2), and the obtained fraction was concentrated to give a solid. The obtained solid was reprecipated with toluene/ethanol, whereby 2.2 g of a yellow solid was obtained in a yield of 90%. The synthesis scheme of Step 1 is shown in (A-6) below.

[Chemical Formula 38]

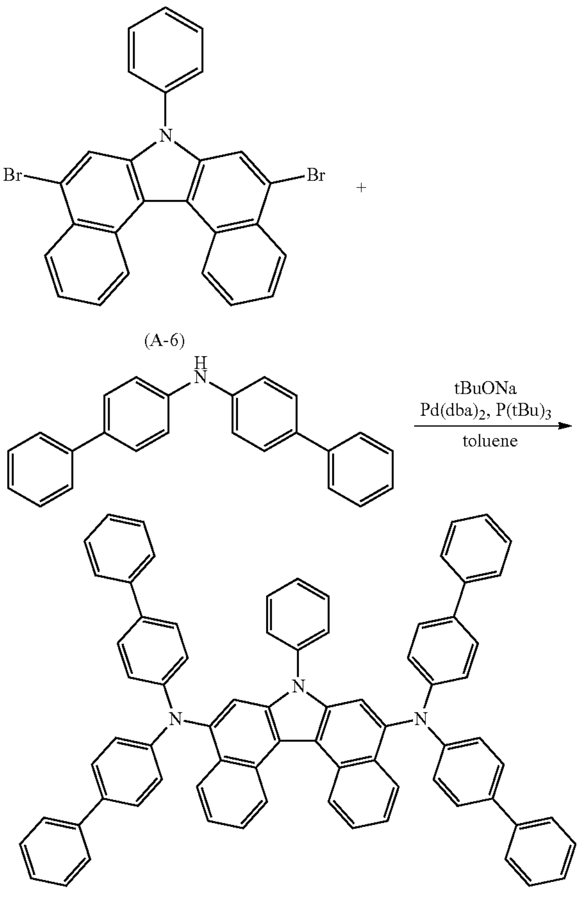

(105)

By a train sublimation method, 1.1 g of the obtained solid was sublimated and purified. Heating was performed at 310° C. under conditions where the pressure was $2.2\times10^{-2}$ Pa and the flow rate of argon was 0 mL/min. After the sublimation purification, 0.51 g of a yellow solid was obtained in a collection rate of 45%.

Analysis data of the obtained solid by nuclear magnetic resonance ($^1$H NMR) spectroscopy are shown below.

$^1$H-NMR δ ($CDCl_3$): $^1$H NMR (DMSO-$d_6$, 300 MHz): δ=7.14 (d, J1=8.7 Hz, 8H), 7.27-7.32 (m, 4H), 7.39-7.63 (m, 31H), 7.69 (d, J1=6.6 Hz, 2H), 7.82 (t, J1=7.2 Hz, 2H), 8.18 (d, J1=9.3 Hz, 2H), 9.25 (d, J1=8.1 Hz, 2H).

Figure 32A:
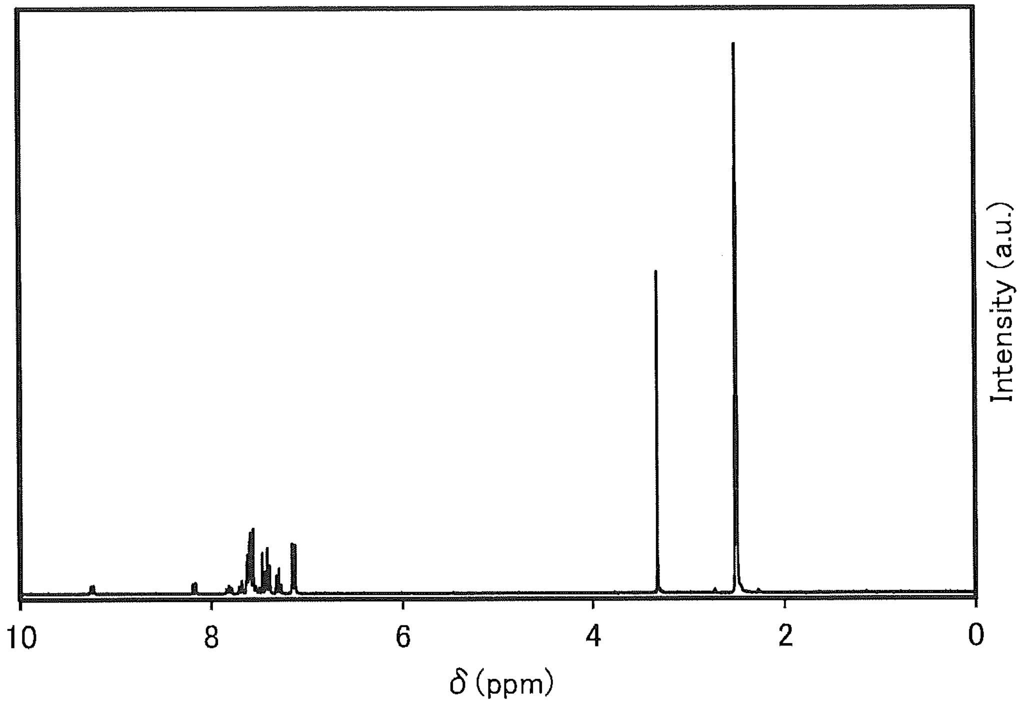
FIGS. 32A-32B are diagrams showing NMR charts of a compound in Example.
Figure 32B:
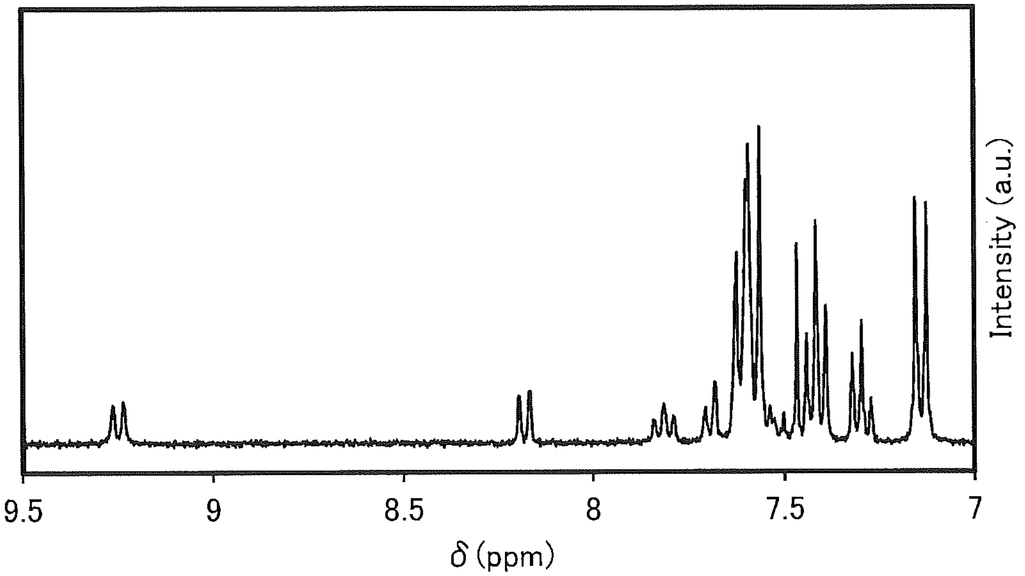

FIGS. 32(A) and 32(B) show $^1$H NMR charts of the obtained solid. Note that FIG. 32(B) is an enlarged diagram of the range of 7.0 ppm to 9.5 ppm of FIG. 32(A). The measurement results indicate that 5,9BBA2PcgDBC, which was the target substance, was obtained.

<Characteristics of 5,9BBA2PcgDBC>

Figure 33:
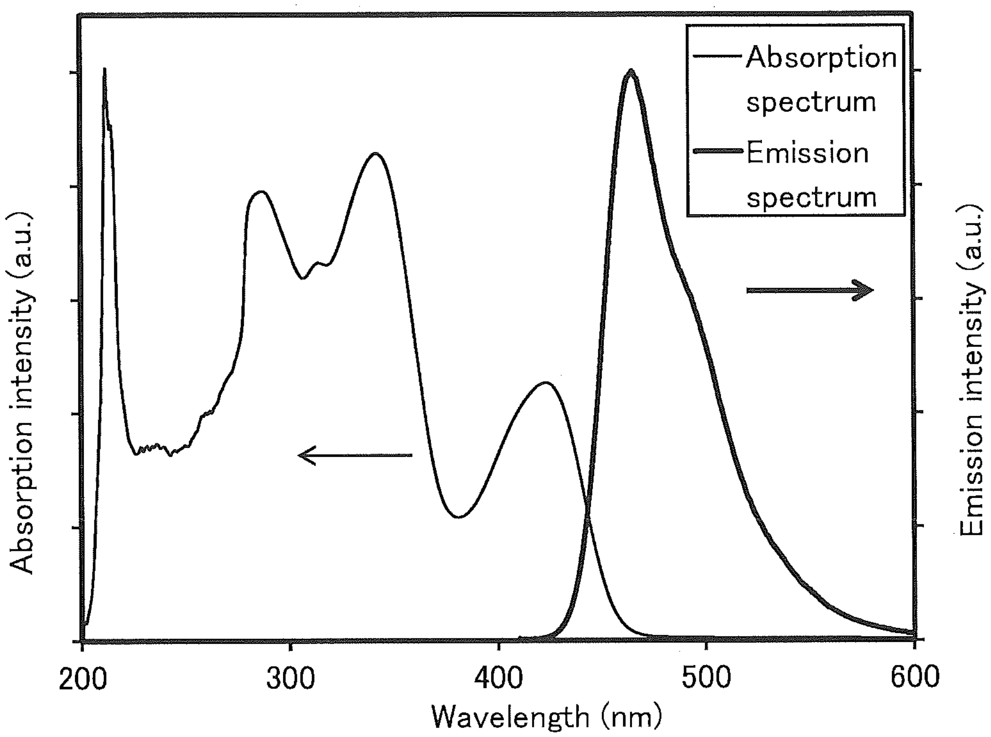
FIG. 33 is a diagram showing an absorption spectrum and an emission spectrum of a compound in Example.
Figure 34:
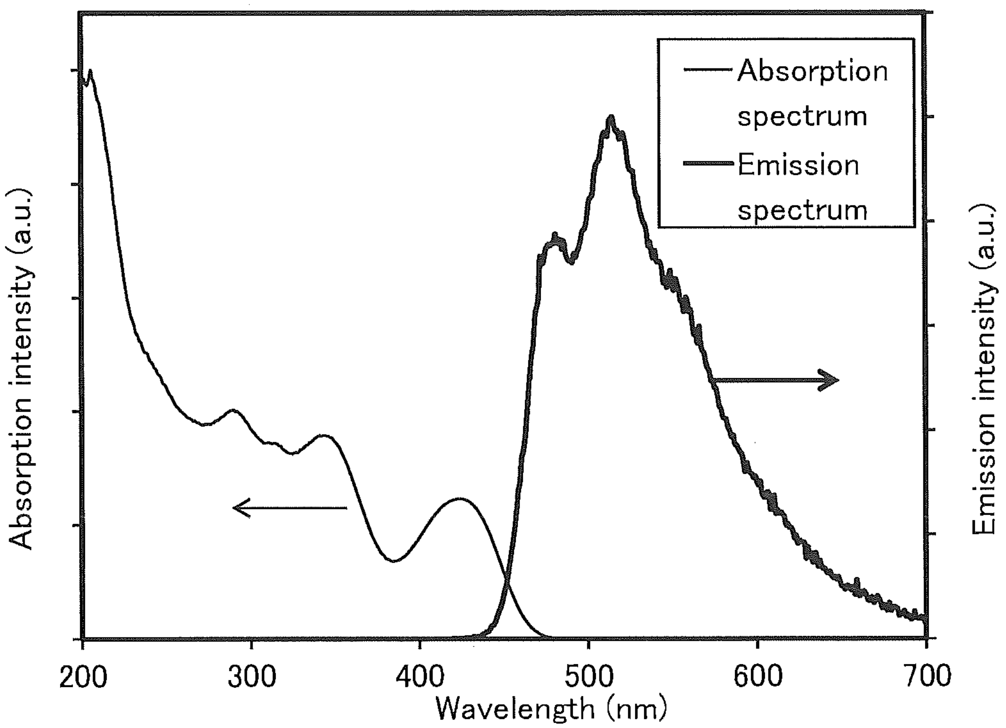
FIG. 34 is a diagram showing an absorption spectrum and an emission spectrum of a compound in Example.

Next, FIG. 33 shows the measurement results of the absorption spectrum and the emission spectrum of 5,9BBA2PcgDBC in a toluene solution. FIG. 34 shows the absorption spectrum and the emission spectrum of a thin film thereof. The measurement was performed in a manner similar to that in Example 1.

As shown in FIG. 33, in the case of 5,9BBA2PcgDBC in the toluene solution, absorption peaks were observed at around 423 nm, 342 nm, 314 nm, and 287 nm, and an emission wavelength peak was around 465 nm (excitation wavelength: 400 nm). As shown in FIG. 34, in the case of the thin film of 5,9BBA2PcgDBC, absorption peaks were observed at around 423 nm, 344 nm, 313 nm, 290 nm, and 246 nm, and emission wavelength peaks were observed at around 482 nm, 514 nm, and 548 nm (excitation wavelength: 410 nm). These results indicate that 5,9BBA2PcgDBC emits blue light. Furthermore, it is found that 5,9BBA2PcgDBC can be used as a host for a fluorescent substance.

It is found that the quantum yield in the toluene solution is favorably 75%, which is suitable for a light-emitting material.

Next, 5,9BBA2PcgDBC obtained in this example was analyzed by LC/MS analysis. The analysis method was performed in a manner similar to that in Example 1. The obtained MS spectrum is shown in FIG. 35.

Figure 35:
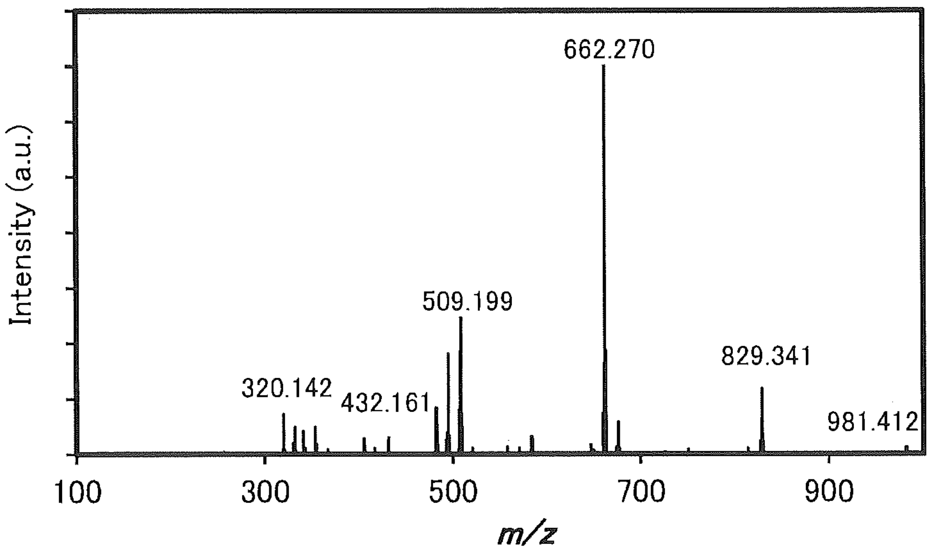
FIG. 35 is a diagram showing $MS^2$ spectra of a compound in Example.

The results in FIG. 35 show that product ions of 5,9BBA2PcgDBC are mainly detected around m/z=829, 662, 509, 432, and 320. Note that the results in the figure show characteristics derived from 5,9BBA2PcgDBC and therefore can be regarded as important data for identifying 5,9BBA2PcgDBC contained in a mixture.

Note that the product ion around m/z=829 is presumed to be a cation in the state where a biphenyl group was eliminated from 5,9BBA2PcgDBC, which suggests that 5,9BBA2PcgDBC includes a biphenyl group.

Note that the product ion around m/z=662 is presumed to be a cation in the state where a di(4-biphenyl)amino group was eliminated from 5,9BBA2PcgDBC, which suggests that 5,9BBA2PcgDBC includes a di(4-biphenyl)amino group.

Note that the product ion around m/z=320 is presumed to be a cation in the state where a di(4-biphenyl)amino]-7-phenyl-7H-dibenzo[c,g]carbazole group was eliminated from 5,9BBA2PcgDBC, which suggests that 5,9BBA2PcgDBC includes a di(4-biphenyl)amino]-7-phenyl-7H-dibenzo[c,g]carbazole group.

Example 7

In this example, a method for synthesizing 5,9-bis{4-[N-(4-biphenyl)-N-phenylamino]phenyl}-7-phenyl-7H-dibenzo[c,g]carbazole (abbreviation: 5,9BPAP2PcgDBC) (Structural Formula (168)), which is one of the compounds of one embodiment of the present invention, represented by General Formula (G0), and characteristics of the compound will be described.

Step 1: Synthesis of 5,9BPAP2PcgDBC

In a 200-mL three-neck flask were put 1.3 g (2.6 mmol) of 5,9-dibromo-7-phenyldibenzo[c,g]carbazole, 2.3 g (6.4 mmol) of 4'-phenyltriphenylamine-4-boronic acid, 68 mg (0.23 mmol) of tris(2-methylphenyl)phosphine, and 1.8 g (13 mmol) of potassium carbonate. To this mixture was added 15 mL of toluene, 5 mL of ethanol, and 5 mL of water. This mixture was degassed by being stirred while the pressure was being reduced. To the degassed mixture was added 10 mg (45 μmol) of palladium(II) acetate, and the mixture was stirred at 90° C. for 12.5 hours under a nitrogen stream. After the stirring, water and ethanol were added to the obtained reaction mixture, and after the irradiation with ultrasonic waves, the resulting mixture was filtered to give a solid. This solid was purified by silica gel column chromatography (developing solvent: hexane:toluene=2:1 and then hexane:toluene=1:1), and the obtained fraction was concentrated to give a solid. The obtained solid was recrystallized with toluene, whereby 2.1 g of a yellow solid was obtained in a yield of 86%. The synthesis scheme of Step 1 is shown in (A-7) below.

[Chemical Formula 42]

(A-7)

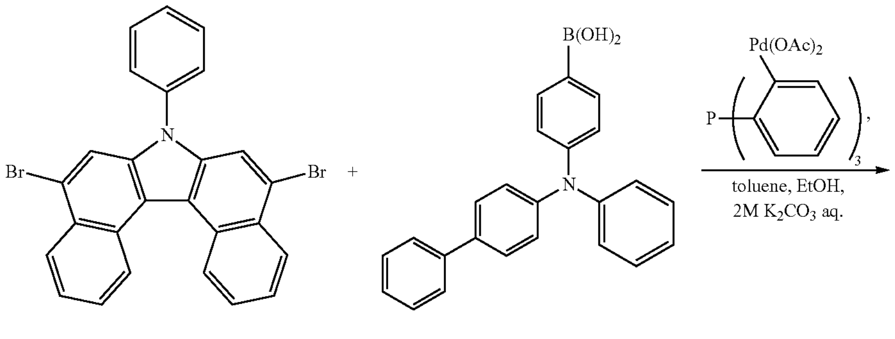

-continued

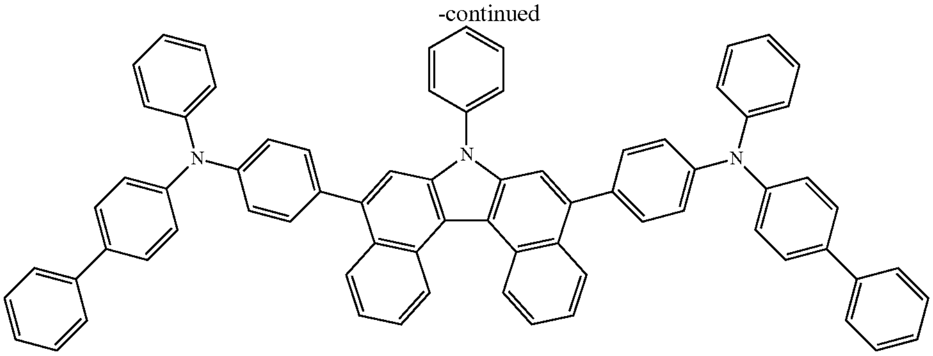

By a train sublimation method, 1.1 g of the obtained yellow solid was sublimated and purified. Heating was performed at 380° C. under conditions where the pressure was $2.4\times10^{-2}$ Pa and the flow rate of argon was 0 mL/min. After the sublimation purification, 0.89 g of a yellow solid was obtained in a collection rate of 82%.

Analysis data of the obtained solid by nuclear magnetic resonance ($^1$H NMR) spectroscopy are shown below.

$^1$H-NMR: $^1$H NMR ($CD_2Cl_2$, 300 MHz): δ=7.09 (t, J1=7.2 Hz, 2H), 7.21-7.76 (m, 45H), 8.20 (d, J1=6.9 Hz, 2H), 9.32 (d, J1=9.0 Hz, 2H).

Figure 47A:
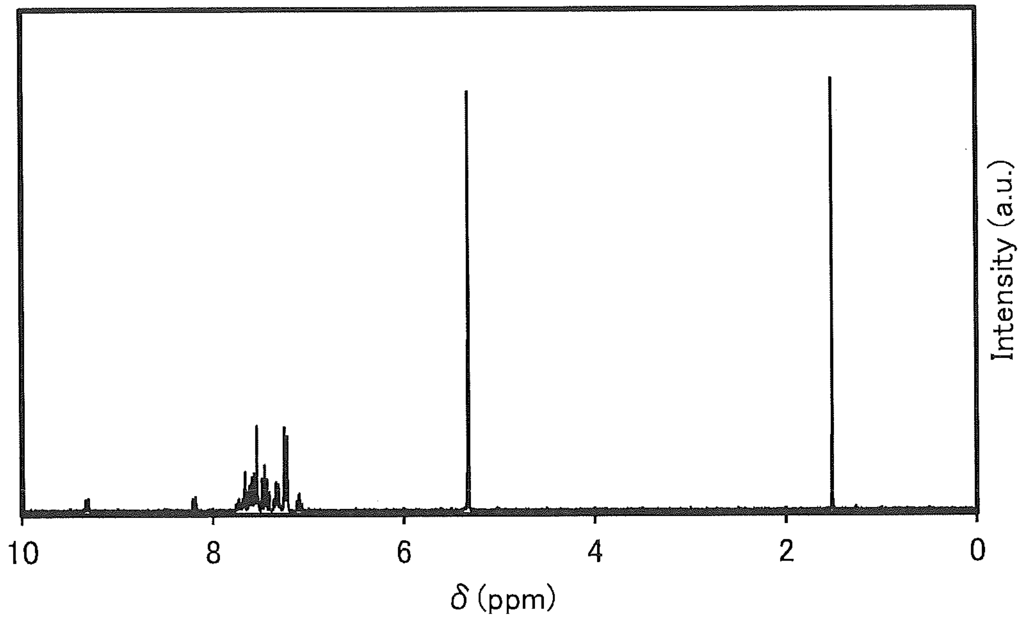
FIGS. 47A-47B are diagrams showing NMR charts of a compound in Example.
Figure 47B:
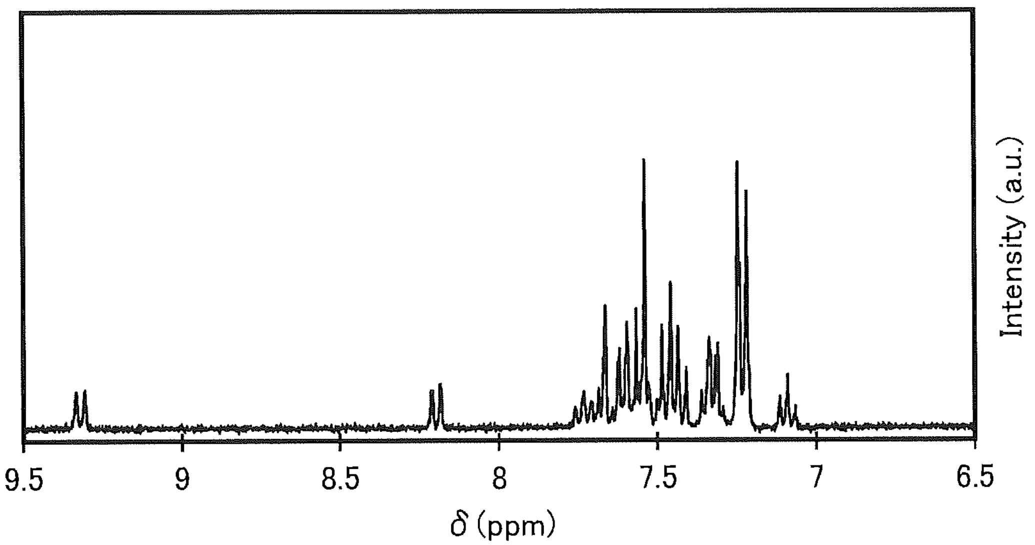

FIGS. 47(A) and 47(B) show $^1$H NMR charts of the obtained solid. Note that FIG. 47(B) is an enlarged diagram of the range of 6.5 ppm to 9.5 ppm of FIG. 47(A). The measurement results indicate that the yellow solid was 5,9BPAP2PcgDBC, which was the target substance.

<Characteristics of 5,9BPAP2PcgDBC>

Figure 48:
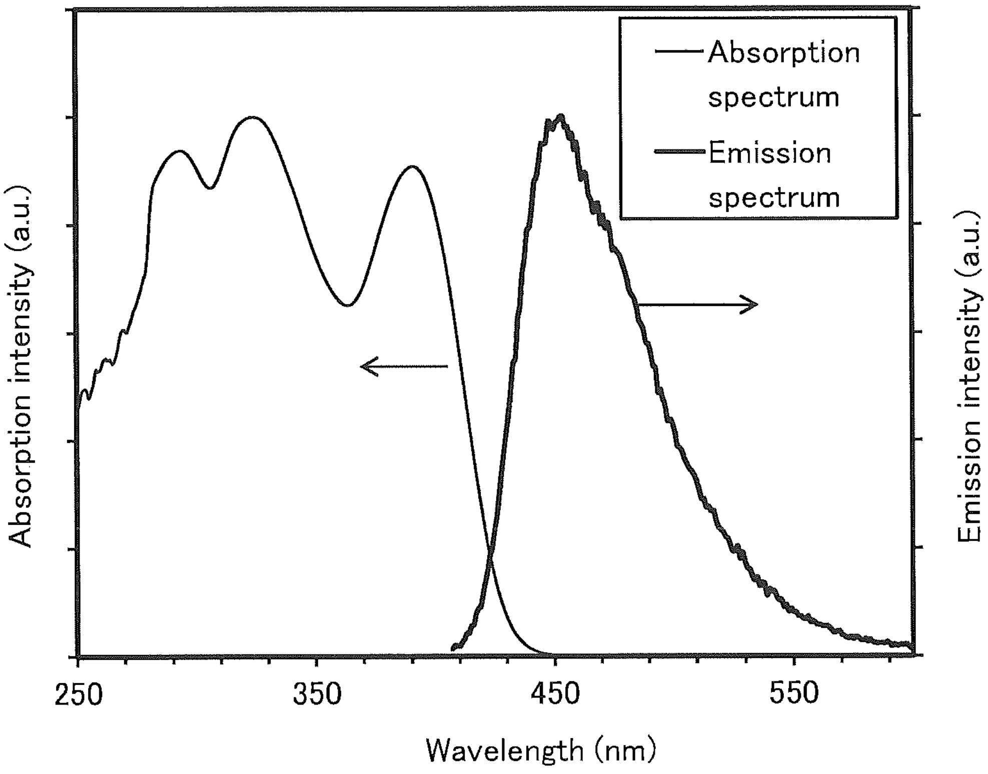
FIG. 48 is a diagram showing an absorption spectrum and an emission spectrum of a compound in Example.
Figure 49:
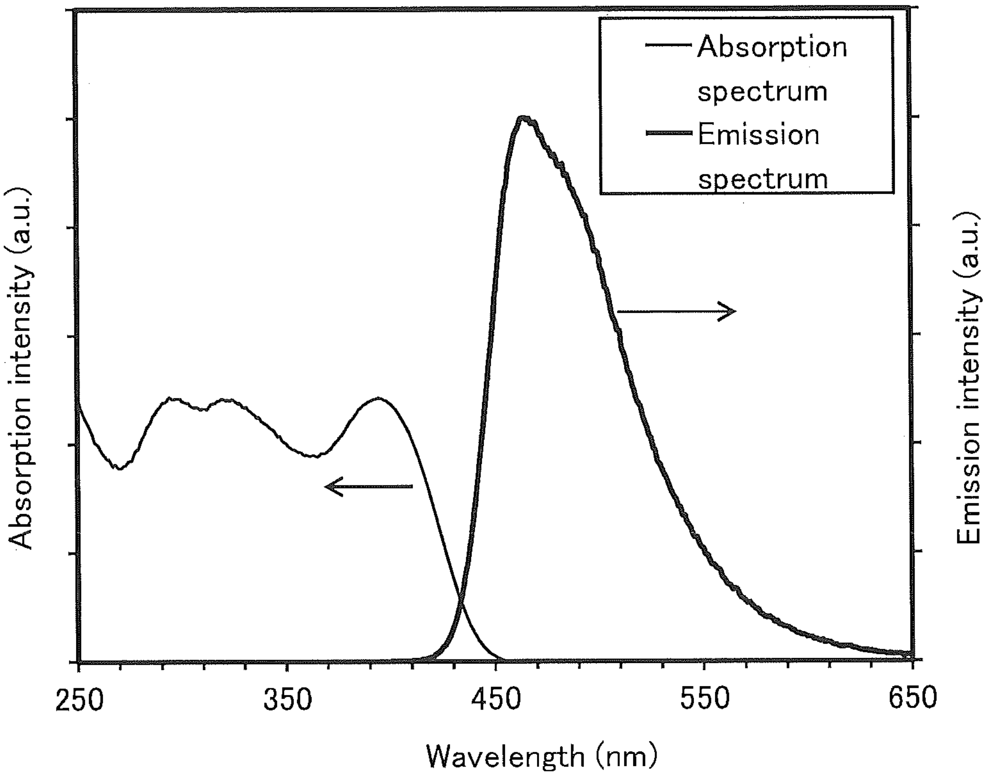
FIG. 49 is a diagram showing an absorption spectrum and an emission spectrum of a compound in Example.

Next, FIG. 48 shows the measurement results of the absorption spectrum and the emission spectrum of 5,9BPAP2PcgDBC in a toluene solution. FIG. 49 shows the absorption spectrum and the emission spectrum of a thin film thereof. The measurement was performed in a manner similar to that in Example 1.

As shown in FIG. 48, in the case of 5,9BPAP2PcgDBC in the toluene solution, absorption peaks were observed at around 391 nm, 324 nm, and 291 nm, and an emission wavelength peak was around 453 nm (excitation wavelength: 397 nm). As shown in FIG. 49, in the case of the thin film of 5,9BPAP2PcgDBC, absorption peaks were observed at around 394 nm, 322 nm, and 294 nm, and an emission wavelength peak was observed at around 465 nm (excitation wavelength: 390 nm). These results indicate that 5,9BPAP2PcgDBC emits blue light and can be used as a host for a light-emitting substance or a fluorescent substance in the visible region.

It is found that the quantum yield in the toluene solution is extremely favorably 95%, which is suitable for a light-emitting material.

As described above, it is found that 5,9BPAP2PcgDBC which is an organic compound of one embodiment of the present invention, in which an arylene group is introduced between a dibenzocarbazole skeleton and amine, the wavelengths of the absorption peak and the emission peak become shorter than those in a compound in which an arylene group is not introduced. It is also found that the quantum yield becomes higher.

Next, 5,9BPAP2PcgDBC obtained in this example was analyzed by LC/MS analysis. The LC separation was performed in a manner similar to that in Example 1. $MS^2$ measurement of m/z=981.41, which is an ion derived from 5,9BPAP2PcgDBC, was performed by a Targeted-$MS^2$ method. For setting of the Targeted-$MS^2$, the mass range of a target ion was set to m/z=981.41±2.0 (isolation window=4) and detection was performed in a positive mode. The measurement was performed with energy NCE for accelerating a target ion in a collision cell set to 60. The obtained MS spectrum is shown in FIG. 50.

Figure 50:
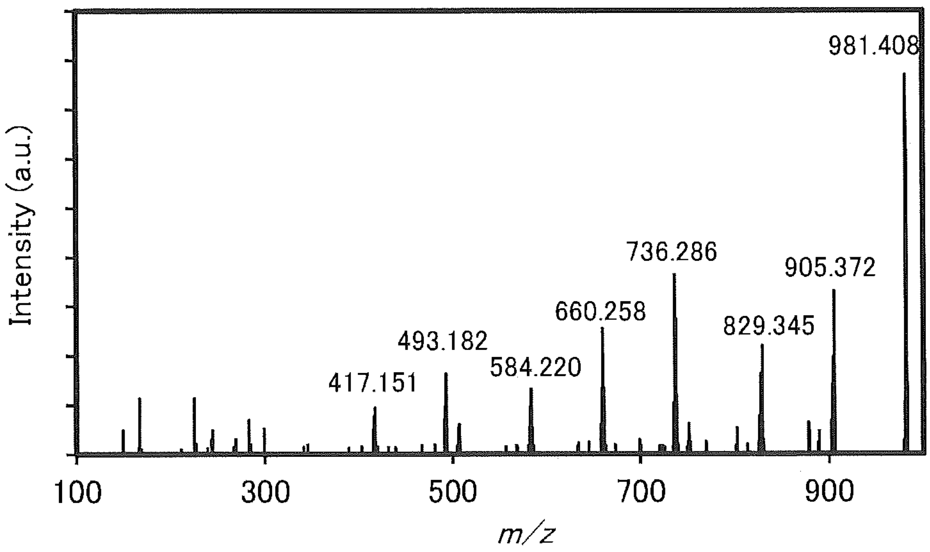
FIG. 50 is a diagram showing $MS^2$ spectra of a compound in Example.

The results in FIG. 50 show that product ions of 5,9BPAP2PcgDBC are mainly detected around m/z=905, 829, 736, 660, 584, 507, 493, and 417. Note that the results in the figure show characteristics derived from 5,9BPAP2PcgDBC and therefore can be regarded as important data for identifying 5,9BPAP2PcgDBC contained in a mixture.

Note that the product ion around m/z=905 is presumed to be a cation in the state where a phenyl group was eliminated from 5,9BPAP2PcgDBC, which suggests that 5,9BPAP2PcgDBC includes a phenyl group.

Note that the product ion around m/z=829 is presumed to be a cation in the state where a biphenyl group was eliminated from 5,9BPAP2PcgDBC, which suggests that 5,9BPAP2PcgDBC includes a biphenyl group.

Note that the product ion around m/z=736 is presumed to be a cation in the state where an N-biphenyl-4-phenylamino group was eliminated from 5,9BPAP2PcgDBC, which suggests that 5,9BPAP2PcgDBC includes an N-biphenyl-4-phenylamino group.

Note that the product ion around m/z=493 is presumed to be a cation in the state where two N-biphenyl-4-biphenylamino groups were eliminated from 5,9BPAP2PcgDBC, which suggests that 5,9BPAP2PcgDBC includes two N-biphenyl-4-phenylamino groups.

Example 8

In this example, fabrication examples of a light-emitting element including the organic compound of one embodiment of the present invention and a comparative light-emitting element and the characteristics of the light-emitting elements are described. FIG. 1(A) illustrates a stacked-layer structure of the light-emitting elements fabricated in this example. Table 1 and Table 2 show details of the element structures. The organic compounds used in this example are shown below. Note that other embodiments or examples can be referred to for other organic compounds.

[Chemical Formula 39]

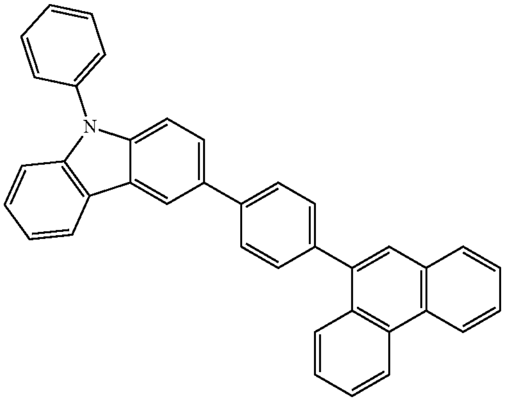

PCPPn

-continued

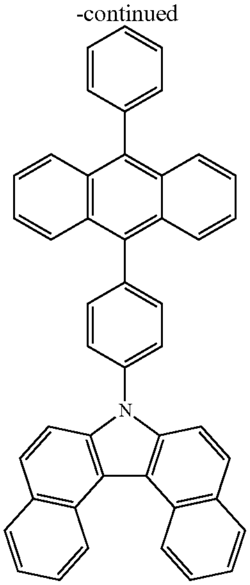

cgDBCzPA

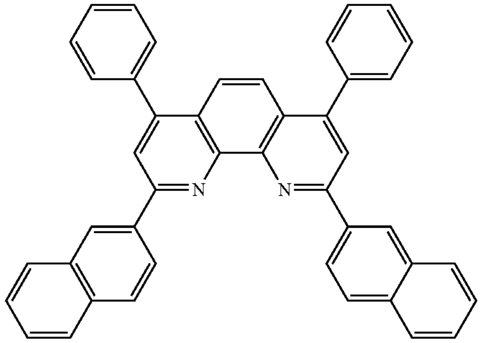

NBPhen

TABLE 1

| | Layer | Reference numeral | Thickness (nm) | Material | Weight ratio |
|---|---|---|---|---|---|
| Light-emitting element 1 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | cgDBCzPA | — |
| | Light-emitting layer | 130 | 25 | cgDBCzPA:5,9BPA2PcgDBC | 1:0.03 |
| | Hole-transport layer | 112 | 30 | PCPPn | — |
| | Hole-injection layer | 111 | 10 | PCPPn:$MoO_3$ | 1:0.5 |
| | Electrode | 101 | 70 | ITSO | — |
| Light-emitting element 2 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | cgDBCzPA | — |
| | Light-emitting layer | 130 | 25 | cgDBCzPA:5,9mMemFLPA2PcgDBC | 1:0.03 |
| | Hole-transport layer | 112 | 30 | PCPPn | — |
| | Hole-injection layer | 111 | 10 | PCPPn:$MoO_3$ | 1:0.5 |
| | Electrode | 101 | 70 | ITSO | — |
| Light-emitting element 3 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | cgDBCzPA | — |
| | Light-emitting layer | 130 | 25 | cgDBCzPA:5,9BnfA2PcgDBC | 1:0.03 |
| | Hole-transport layer | 112 | 30 | PCPPn | — |
| | Hole-injection layer | 111 | 10 | PCPPn:$MoO_3$ | 1:0.5 |
| | Electrode | 101 | 70 | ITSO | — |
| Light-emitting | Electrode | 102 | 200 | Al | — |
| | Electron-injection layer | 119 | 1 | LiF | — |

TABLE 1-continued

| | Layer | Reference numeral | Thickness (nm) | Material | Weight ratio |
|---|---|---|---|---|---|
| element 4 | Electron-transport layer | 118(2) | 10 | NBPhen | — |
| | | 118(1) | 15 | cgDBCzPA | — |
| | Light-emitting layer | 130 | 25 | cgDBCzPA:5,9FrA2PcgDBC-II | 1:0.03 |
| | Hole-transport layer | 112 | 30 | PCPPn | — |
| | Hole-injection layer | 111 | 10 | PCPPn:$MoO_3$ | 1:0.5 |
| | Electrode | 101 | 70 | ITSO | — |

TABLE 2

| | Layer | Reference numeral | Thickness (nm) | Material | Weight ratio |
|---|---|---|---|---|---|
| Light-emitting element 5 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | cgDBCzPA | — |
| | Light-emitting layer | 130 | 25 | cgDBCzPA:5,9oDMeBPA2PcgDBC | 1:0.03 |
| | Hole-transport layer | 112 | 30 | PCPPn | — |
| | Hole-injection layer | 111 | 10 | PCPPn:$MoO_3$ | 1:0.5 |
| | Electrode | 101 | 70 | ITSO | — |
| Light-emitting element 6 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | cgDBCzPA | — |
| | Light-emitting layer | 130 | 25 | cgDBCzPA:5,9BBA2PcgDBC | 1:0.03 |
| | Hole-transport layer | 112 | 30 | PCPPn | — |
| | Hole-injection layer | 111 | 10 | PCPPn:$MoO_3$ | 1:0.5 |
| | Electrode | 101 | 70 | ITSO | — |
| Light-emitting element 9 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | cgDBCzPA | — |
| | Light-emitting layer | 130 | 25 | cgDBCzPA:5,9BPAP2PcgDBC | 1:0.03 |
| | Hole-transport layer | 112 | 30 | PCPPn | — |
| | Hole-injection layer | 111 | 10 | PCPPn:$MoO_3$ | 1:0.5 |
| | Electrode | 101 | 70 | ITSO | — |
| Comparative light-emitting element 7 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | cgDBCzPA | — |
| | Light-emitting layer | 130 | 25 | cgDBCzPA:BPAPcgDBC | 1:0.03 |
| | Hole-transport layer | 112 | 30 | PCPPn | — |
| | Hole-injection layer | 111 | 10 | PCPPn:$MoO_3$ | 1:0.5 |
| | Electrode | 101 | 70 | ITSO | — |

<<Fabrication of Light-Emitting Element 1>>

As the electrode 101, an ITSO film was formed to a thickness of 70 nm over a glass substrate by a sputtering method. Note that the electrode area of the electrode 101 was set to 4 $mm^2$ (2 mm×2 mm). Next, as pretreatment for forming a light-emitting element over the substrate, a surface of the substrate was washed with water, drying was performed at 200° C. for one hour, and then UV ozone treatment was performed for 370 seconds. After that, the substrate was transferred into a vacuum evaporation apparatus where a degree of vacuum was kept at approximately $1\times10^{-4}$ Pa, and baking was performed at 170° C. for 30 minutes. Then, the substrate was allowed to cool for approximately 30 minutes.

Next, as the hole-injection layer 111, PCPPn and molybdenum(VI) oxide ($MoO_3$) were deposited over the electrode 101 by co-evaporation in a weight ratio (PCPPn:$MoO_3$) of 1:0.5 to a thickness of 10 nm.

Next, as the hole-transport layer 112, PCPPn was deposited over the hole-injection layer 111 by evaporation to a thickness of 30 nm.

Next, as the light-emitting layer 130, over the hole-transport layer 112, cgDBCzPA and 5,9BPA2PcgDBC were deposited by co-evaporation in a weight ratio (cgDBCzPA:5,9BPA2PcgDBC) of 1:0.03 to a thickness of 25 nm. Note that in the light-emitting layer 130, 5,9BPA2PcgDBC is a guest material that emits fluorescence.

Next, as an electron-transport layer 118(1), cgDBCzPA was deposited over the light-emitting layer 130 by evaporation to a thickness of 15 nm. Then, as an electron-transport layer 118(2), NBPhen was sequentially deposited over the electron-transport layer 118(1) by evaporation to a thickness of 10 nm.

Then, as the electron-injection layer 119, LiF was deposited over the electron-transport layer 118 by evaporation to a thickness of 1 nm.

Next, as the electrode 102, aluminum (Al) was formed over the electron-injection layer 119 to a thickness of 200 nm.

Figure 37:
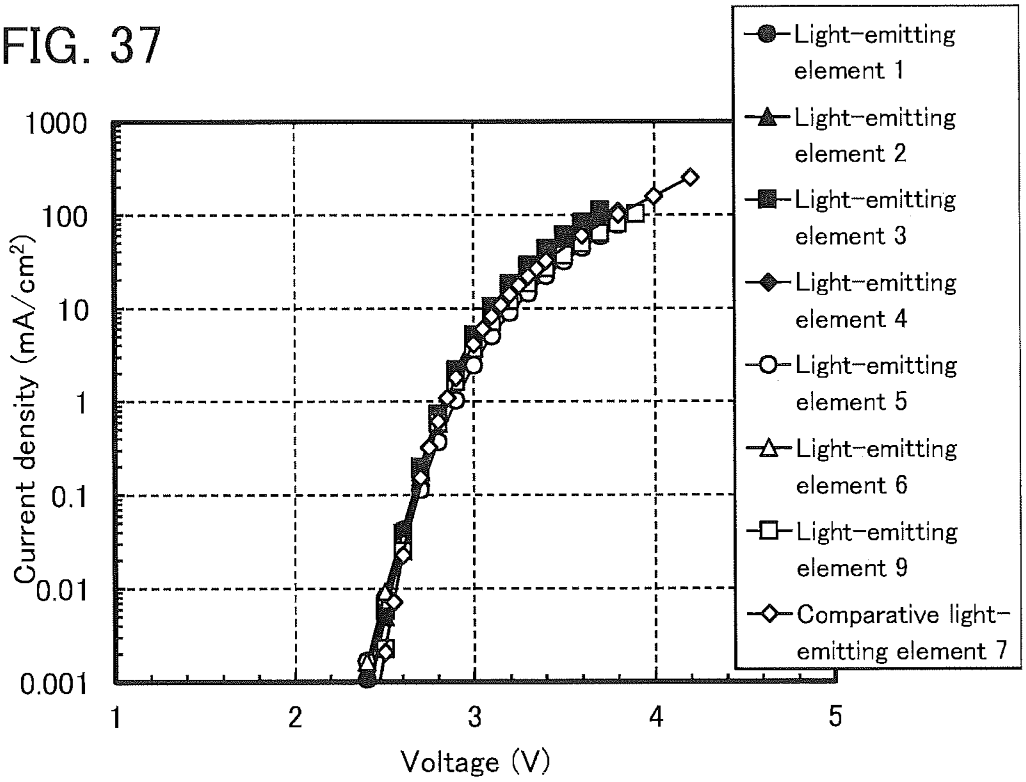
FIG. 37 is a diagram showing current density-voltage characteristics of light-emitting elements in Example.
Figure 38:
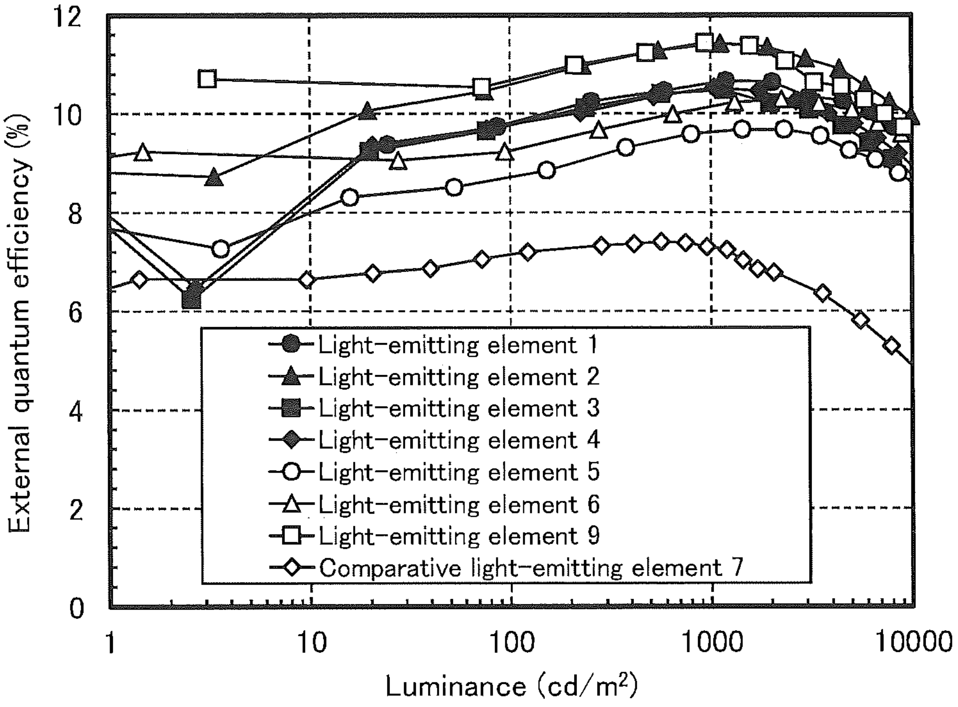
FIG. 38 is a diagram showing external quantum efficiency-luminance characteristics of light-emitting elements in Example.

Next, in a glove box containing a nitrogen atmosphere, the substrate over which the light-emitting element was formed was fixed to a substrate (a counter substrate) which differs from the substrate over which the light-emitting element was formed for sealing with a sealant, whereby the light-emitting element 1 was sealed. Specifically, a drying agent was attached to the counter substrate, and the counter substrate in which the sealant was applied to the surrounding of a portion where the light-emitting element was formed and the glass substrate over which the light-emitting element was formed were further bonded to each other. Then, irradiation with ultraviolet light having a wavelength of 365 nm at 6 $J/cm^2$ and heat treatment at 80° C. for one hour were performed. Through the above steps, the light-emitting element 1 was obtained.

element 6, the light-emitting element 9, and the comparative light-emitting element 7. FIG. 37 shows the current density-voltage characteristics. FIG. 38 shows the external quantum efficiency-luminance characteristics. Note that the measurements of the light-emitting elements were performed at room temperature (in an atmosphere maintained at 23° C.).

Table 3 shows the element characteristics of the light-emitting element 1 to the light-emitting element 6, the light-emitting element 9, and the comparative light-emitting element 7 at around 1000 $cd/m^2$.

TABLE 3

| | Voltage (V) | Current density ($mA/cm^2$) | CIE chromaticity (x, y) | Luminance ($cd/m^2$) | Current efficiency (cd/A) | Power efficiency (lm/W) | External quantum efficiency (%) |
|---|---|---|---|---|---|---|---|
| Light-emitting element 1 | 3.10 | 8.04 | (0.143, 0.205) | 1190 | 14.8 | 15.0 | 10.7 |
| Light-emitting element 2 | 3.10 | 7.95 | (0.143, 0.170) | 1125 | 14.2 | 14.3 | 11.4 |
| Light-emitting element 3 | 3.10 | 10.4 | (0.143, 0.137) | 1168 | 11.3 | 11.4 | 10.5 |
| Light-emitting element 4 | 3.10 | 8.74 | (0.143, 0.148) | 1042 | 11.9 | 12.1 | 10.5 |
| Light-emitting element 5 | 3.10 | 5.01 | (0.150, 0.266) | 799 | 15.9 | 16.1 | 9.59 |
| Light-emitting element 6 | 3.10 | 7.41 | (0.149, 0.291) | 1318 | 17.8 | 18.0 | 10.2 |
| Light-emitting element 9 | 3.10 | 7.09 | (0.143, 0.153) | 945 | 13.3 | 13.5 | 11.4 |
| Comparative light-emitting element 7 | 3.20 | 14.0 | (0.143, 0.112) | 959 | 6.87 | 6.75 | 7.30 |

<<Fabrication of Light-Emitting Element 2 to Light-Emitting Element 6, Light-Emitting Element 9, and Comparative Light-Emitting Element 7>>

The fabrication processes of a light-emitting element 2 to a light-emitting element 6, a light-emitting element 9, and a comparative light-emitting element 7 are different from that of the light-emitting element 1 described above only in the fabrication process of the light-emitting layer 130 and other fabrication processes are similar to those of the light-emitting element 1 and are thus not described in detail here. Table 1 and Table 2 can be referred to for the details of the element structure.

Note that for the light-emitting element 1 to the light-emitting element 6 and the light-emitting element 9 of one embodiment of the present invention, the organic compound of one embodiment of the present invention in which two amine skeletons are bonded to a dibenzocarbazole skeleton was used. In contrast, for the comparative light-emitting element 7, the organic compound in which one amine skeleton is bonded to a dibenzocarbazole skeleton was used.

<Characteristics of Light-Emitting Elements>

Next, the characteristics of the fabricated light-emitting element 1 to the light-emitting element 6, the light-emitting element 9, and the comparative light-emitting element 7 were measured. Luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 36:
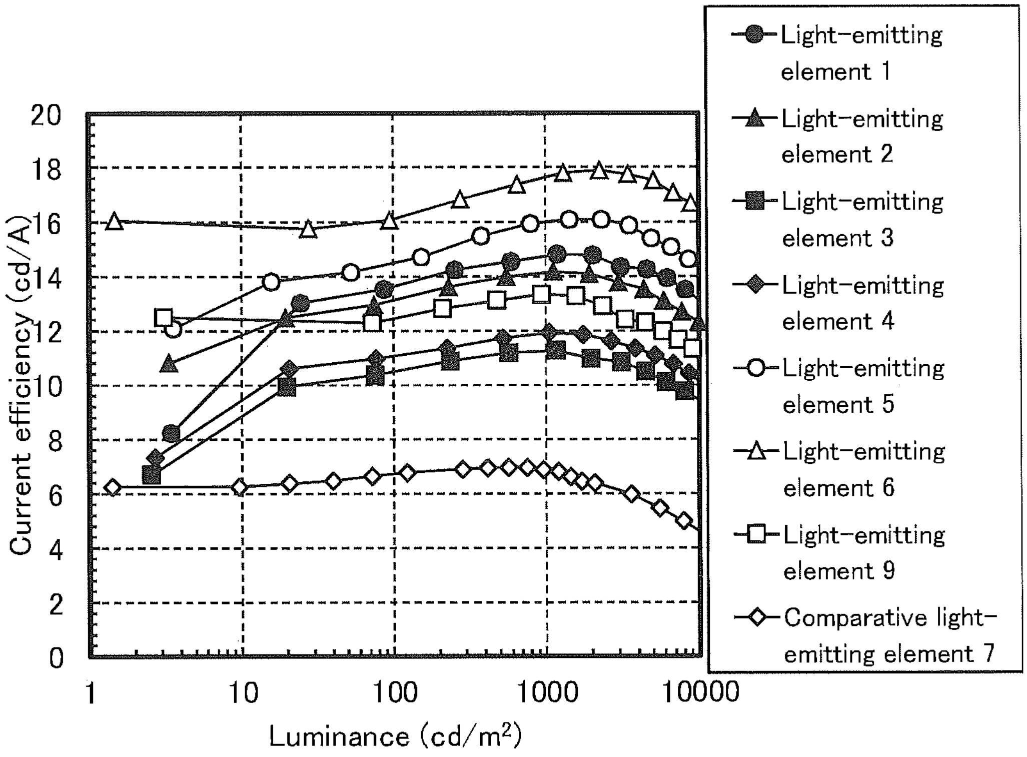
FIG. 36 is a diagram showing current efficiency-luminance characteristics of light-emitting elements in Example.
Figure 39:
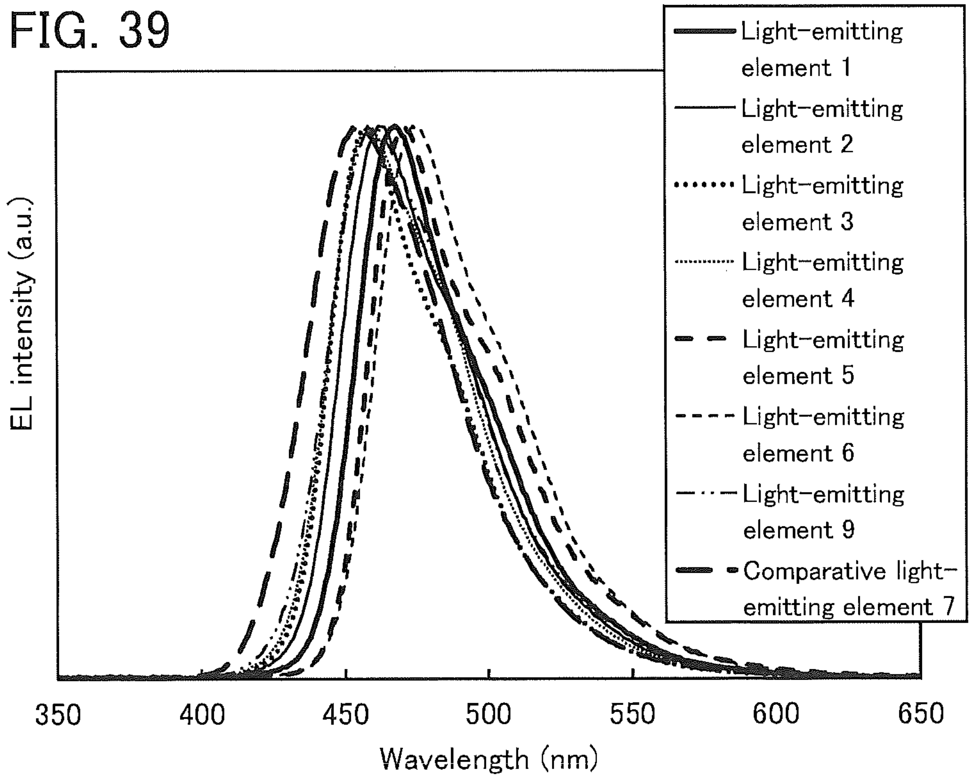
FIG. 39 is a diagram showing emission spectra of light-emitting elements in Example.

FIG. 36 shows current efficiency-luminance characteristics of the light-emitting element 1 to the light-emitting FIG. 39 shows emission spectra when current at a current density of 12.5 $mA/cm^2$ was applied to the light-emitting element 1 to the light-emitting element 6, the light-emitting element 9, and the comparative light-emitting element 7.

As shown in FIG. 36 and Table 3, the light-emitting element 1 to the light-emitting element 6, the light-emitting element 9, and the comparative light-emitting element 7 exhibited high current efficiency. In particular, each of the light-emitting element 1 to the light-emitting element 6, and the light-emitting element 9 using the organic compound of one embodiment of the present invention exhibited extremely high current efficiency as a blue fluorescent element, which exceeds 10 cd/A. In addition, each of the light-emitting element 1 to the light-emitting element 6 and the light-emitting element 9 exhibited higher current efficiency than the comparative light-emitting element 7. Therefore, it is found that the light-emitting element having a structure in which two amine skeletons are bonded to a dibenzocarbazole skeleton has higher emission efficiency than the light-emitting element having a structure in which one amine skeleton is bonded to a dibenzocarbazole skeleton.

As shown in FIG. 38 and Table 3, the light-emitting element 1 to the light-emitting element 6, the light-emitting element 9, and the comparative light-emitting element 7 exhibited high external quantum efficiency. In particular, each of the light-emitting element 1 to the light-emitting element 6 and the light-emitting element 9 using the organic compound of one embodiment of the present invention exhibited extremely high external quantum efficiency as a fluorescent element, which exceeds 9%. In addition, each of the light-emitting element 1 to the light-emitting element 6 and the light-emitting element 9 exhibited higher external quantum efficiency than the comparative light-emitting element 7. Therefore, it is found that the light-emitting element has higher emission efficiency in the case of an organic compound having a structure in which two amine skeletons are bonded to a dibenzocarbazole skeleton than the case of an organic compound having a structure in which one amine skeleton is bonded to a dibenzocarbazole skeleton. This is probably because the organic compound of one embodiment of the present invention, which is a diamine compound, used as a light-emitting material in the light-emitting element 1 to the light-emitting element 6 and the light-emitting element 9 has a higher luminescence quantum yield than the case of a monoamine compound used in the comparative light-emitting element 7.

In particular, the light-emitting element using 5,9mMemFLPA2PcgDBC or 5,9BPAP2PcgDBC, which is the organic compound of one embodiment of the present invention, as a light-emitting material exhibited extremely high external quantum efficiency that is higher than or equal to 11%. Accordingly, it is found that a light-emitting element with high external quantum efficiency can be obtained particularly when a fluorenyl group is introduced as a substituent into arylamine bonded to the dibenzocarbazole skeleton or an arylene group is introduced between the dibenzocarbazole skeleton and an arylamine group.

It is found that high external quantum efficiency can be obtained particularly when, in an element in which the compound of one embodiment of the present invention is used as a light-emitting material, a material having high S1 (the bandgap obtained from the absorption edge is 3.3 eV or more) and a low LUMO level (higher than −2.7 eV) is used as the hole-transport layer.

Note that since the generation probability of singlet excitons which are generated by recombination of carriers (holes and electrons) injected from the pair of electrodes is 25%, the theoretical external quantum efficiency of a fluorescent element in the case where the light extraction efficiency to the outside is 25% is at most 6.25%. Each of the light-emitting element 1 to the light-emitting element 6, the light-emitting element 9, and the comparative light-emitting element 7 can obtain higher efficiency than the theoretical limit value. This is probably because in the light-emitting element 1 to the light-emitting element 6, the light-emitting element 9, and the comparative light-emitting element 7, some of the triplet excitons are converted into singlet excitons by TTA described in Embodiment 3 and contribute to fluorescence in addition to light emission derived from the singlet excitons generated by recombination of carriers injected from the pair of electrodes. Although not described in this example, transient fluorescence was measured, whereby delayed fluorescence was observed in each of the light-emitting element 3 to the light-emitting element 6. In the same manner, delayed fluorescence is probably observed from the other light-emitting elements. Accordingly, it is found that external quantum efficiency higher than or equal to the theoretical limit value was obtained by TTA in each of the light-emitting element 1 to the light-emitting element 6, the light-emitting element 9, and the comparative light-emitting element 7.

As shown in FIG. 37 and Table 3, it is found that the light-emitting element 1 to the light-emitting element 6, the light-emitting element 9, and the comparative light-emitting element 7 each have favorable driving voltage.

As shown in FIG. 39, the emission spectra of the light-emitting element 1 to the light-emitting element 6, the light-emitting element 9, and the comparative light-emitting element 7 respectively have spectrum peaks at around 468 nm, 462 nm, 459 nm, 458 nm, 471 nm, 474 nm, 461 nm, and 456 nm and full widths at half maximum of approximately 50 nm, 52 nm, 50 nm, 54 nm, 51 nm, 53 nm, 57 nm, and 57 nm, indicating that the light-emitting element 1 to the light-emitting element 6, the light-emitting element 9, and the comparative light-emitting element 7 exhibited favorable blue light emission derived from their guest materials. In addition, in the light-emitting element 2 to the light-emitting element 4, the values of chromaticity γ are particularly low. The organic compound of one embodiment of the present invention used as a guest material of each of the light-emitting element 2 to the light-emitting element 4 includes a substituent having a high volume in an amine skeleton. Accordingly, the steric hindrance with the other aryl group bonded to the same nitrogen atom is increased; thus, the bonding length between a nitrogen atom and an aryl group is increased and a distribution range of the conjugation is decreased. As a result, it is probable that the light emission is shifted to the shorter wavelength side and the chromaticity γ is reduced.

<Reliability of Light-Emitting Elements>

Figure 40:
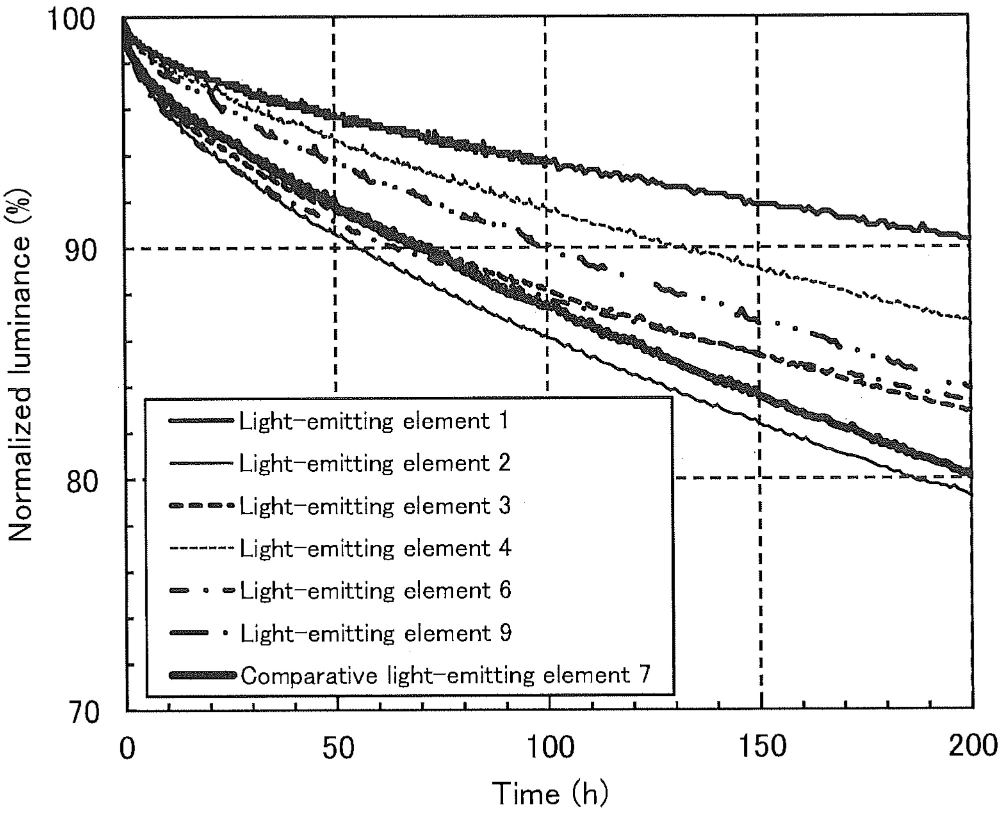
FIG. 40 is a diagram showing results of reliability tests of light-emitting elements in Example.

Next, driving tests at a constant current of 2 mA were performed on the light-emitting element 1 to the light-emitting element 4, the light-emitting element 6, the light-emitting element 9, and the comparative light-emitting element 7. FIG. 40 shows the results. As shown in FIG. 40, it is found that the light-emitting element 1 to the light-emitting element 4, the light-emitting element 6, the light-emitting element 9, and the comparative light-emitting element 7 have favorable reliability. In particular, it is found that an $LT_{90}$ (time for which luminance is reduced by 10%) of each of the light-emitting element 1, and the light-emitting element 4 to the light-emitting element 9 exceeds 100 hours, which particularly exhibits favorable reliability. It is further found from FIG. 40 that each of the light-emitting element 1 to the light-emitting element 6 and the light-emitting element 9 has comparable or higher reliability than the comparative light-emitting element 7. In particular, it is found that the light-emitting element 1, the light-emitting element 3, the light-emitting element 4, and the light-emitting element 9 have higher reliability than the comparative light-emitting element 7. Accordingly, it is suggested that the reliability gets higher when an unsubstituted phenyl group is introduced into a substituent included in the amine skeleton of the organic compound of one embodiment of the present invention. Since each of the light-emitting element 2 and the light-emitting element 6 having comparable reliability to the comparative light-emitting element 7 has higher current efficiency than the comparative light-emitting element 7, the light-emitting element 2 and the light-emitting element 6 have higher luminance than the comparative light-emitting element 7 in the case where current is applied to each element at the same value. It can be said that the light-emitting element 2 and the light-emitting element 6 that emit light with higher luminance in the driving tests at the same current have higher reliability than the comparative light-emitting element 7. That is, it can be said that in the case where the light-emitting element 2 and the light-emitting element 6 are driven with the same luminance, they have higher reliability than the comparative light-emitting element 7.

As described above, a light-emitting element that exhibits blue light emission with high color purity, high emission efficiency, favorable driving voltage, and high reliability can be fabricated with the use of the compound of one embodiment of the present invention for the light-emitting layer. It is further found that the light-emitting element using the organic compound of one embodiment of the present invention has higher emission efficiency and higher reliability than an organic compound having a structure in which one amine skeleton is bonded to a dibenzocarbazole skeleton.

Example 9

In this example, a fabrication example of a light-emitting element including the organic compound of one embodiment of the present invention, which differs from that in Example 8, is described. FIG. 1(A) illustrates a stacked-layer structure of the light-emitting element fabricated in this example. Table 4 shows details of the element structure. The organic compounds used in this example are shown below. Note that other embodiments or examples can be referred to for other organic compounds.

[Chemical Formula 40]

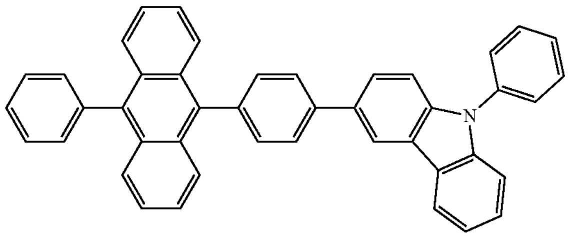

PCzPA

TABLE 4

| | Layer | Reference numeral | Thickness (nm) | Material | Weight ratio |
|---|---|---|---|---|---|
| Light-emitting element 8 | Electrode | 102 | 200 | Al | — |
| | Electron-injection layer | 119 | 1 | LiF | — |
| | Electron-transport layer | 118(2) | 10 | NBPhen | — |
| | | 118(1) | 15 | cgDBCzPA | — |
| | Light-emitting layer | 130 | 25 | cgDBCzPA:5,9BPA2PcgDBC | 1:0.03 |
| | Hole-transport layer | 112 | 30 | PCzPA | — |
| | Hole-injection layer | 111 | 10 | $PCzPA:MoO_3$ | 1:0.5 |
| | Electrode | 101 | 70 | ITSO | — |

<<Fabrication of Light-Emitting Element 8>>

The fabrication process of a light-emitting element 8 is different from that of the light-emitting element 1 described above only in the fabrication process of the electron-injection layer 111 and the electron-transport layer 112 and other fabrication processes are similar to those of the light-emitting element 1 and is thus not described in detail here. Table 4 can be referred to for the details of the element structure.

<<Fabrication of Light-Emitting Element 8>>

As the hole-injection layer 111 of the light-emitting element 8, PCzPA and molybdenum(VI) oxide ($MoO_3$) were deposited over the electrode 101 by co-evaporation in a weight ratio ($PCzPA:MoO_3$) of 1:0.5 to a thickness of 10 nm.

Next, as the hole-transport layer 112, PCzPA was deposited over the hole-injection layer 111 by evaporation to a thickness of 30 nm.

<Characteristics of Light-Emitting Element>

Next, the characteristics of the fabricated light-emitting element 8 were measured. The measurement conditions of the light-emitting element were similar to those described in the above example.

Figure 41:
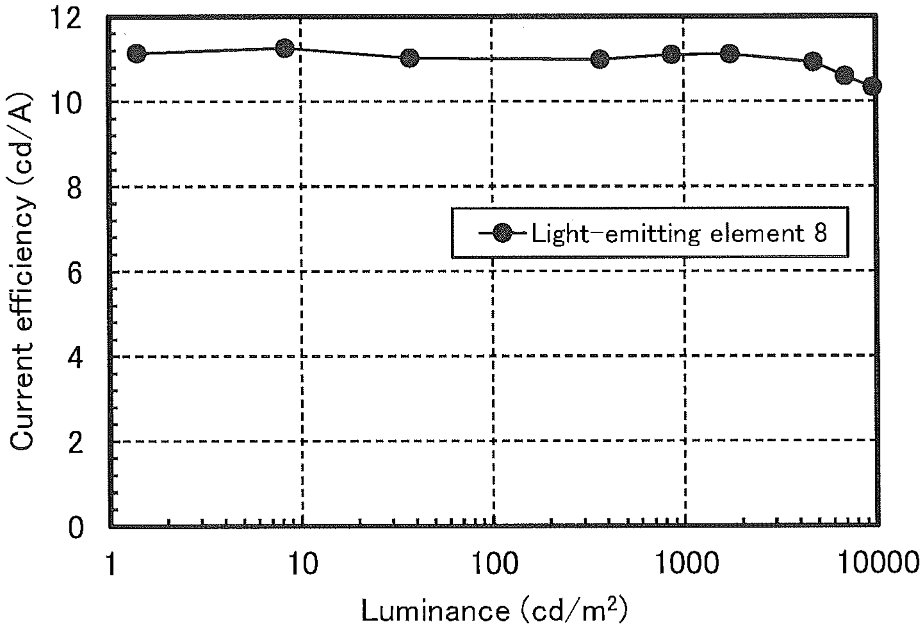
FIG. 41 is a diagram showing current efficiency-luminance characteristics of a light-emitting element in Example.
Figure 42:
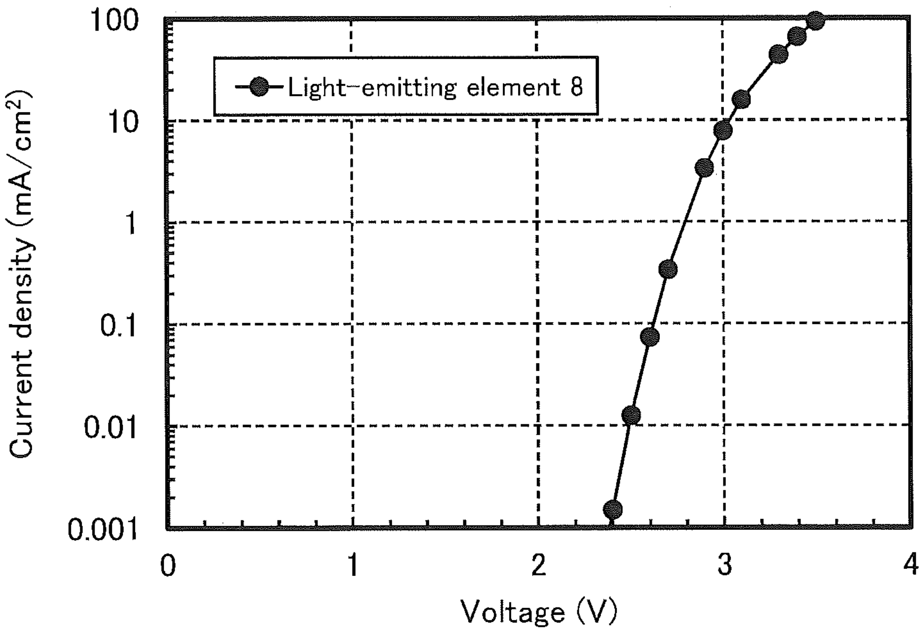
FIG. 42 is a diagram showing current density-voltage characteristics of a light-emitting element in Example.
Figure 43:
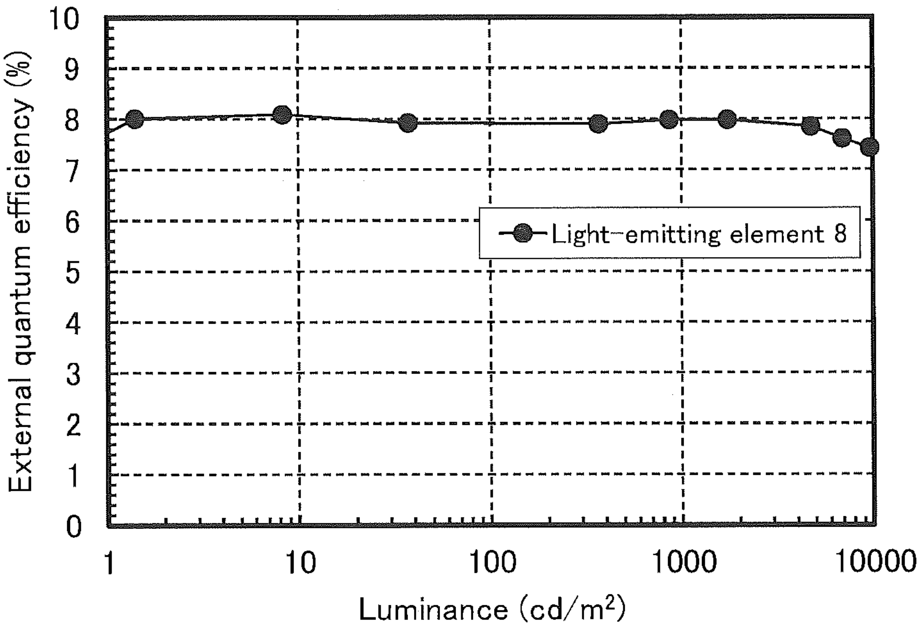
FIG. 43 is a diagram showing external quantum efficiency-luminance characteristics of a light-emitting element in Example.

FIG. 41 shows current efficiency-luminance characteristics of the light-emitting element 8. FIG. 42 shows the current density-voltage characteristics. FIG. 43 shows the external quantum efficiency-luminance characteristics.

Table 5 shows the element characteristics of the light-emitting element 8 at around 1000 cd/m$^2$.

TABLE 5

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 8 | 3.00 | 7.80 | (0.143, 0.208) | 865 | 11.1 | 11.6 | 8.0 |

Figure 44:
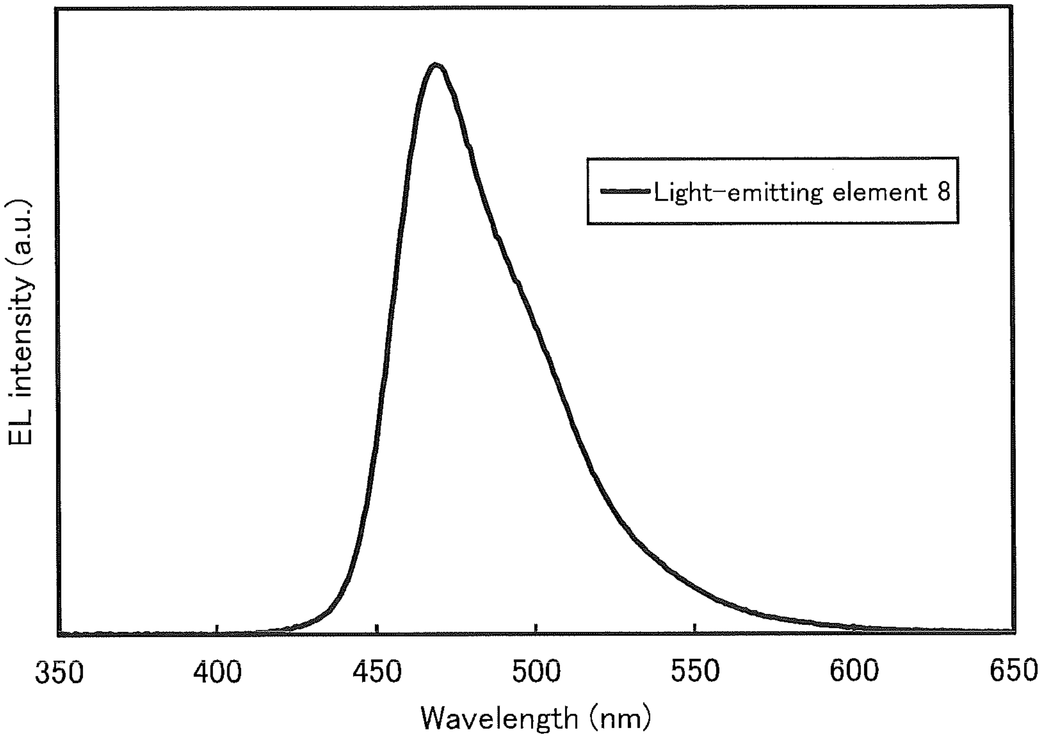
FIG. 44 is a diagram showing an emission spectrum of a light-emitting element in Example.

FIG. 44 shows emission spectra when current at a current density of 12.5 mA/cm$^2$ was applied to the light-emitting element 8.

As shown in FIG. 41 and Table 5, the light-emitting element 8 exhibited extremely high current efficiency as a blue fluorescent element, which exceeds 10 cd/A. In addition, as shown in FIG. 43, the maximum value of the external quantum efficiency exceeds 8.0%, which largely exceeds the theoretical limit value of the fluorescent element. This is probably because of the effect of TTA as described above.

As shown in FIG. 42 and Table 5, it is found that the light-emitting element 8 has favorable driving voltage.

As shown in FIG. 44, the emission spectrum of the light-emitting element 8 has a spectrum peak at around 468 nm and a full width at half maximum of approximately 50 nm, indicating that the light-emitting element 8 exhibited favorable blue light emission derived from its guest material.

<Reliability of Light-Emitting Element>

Figure 45:
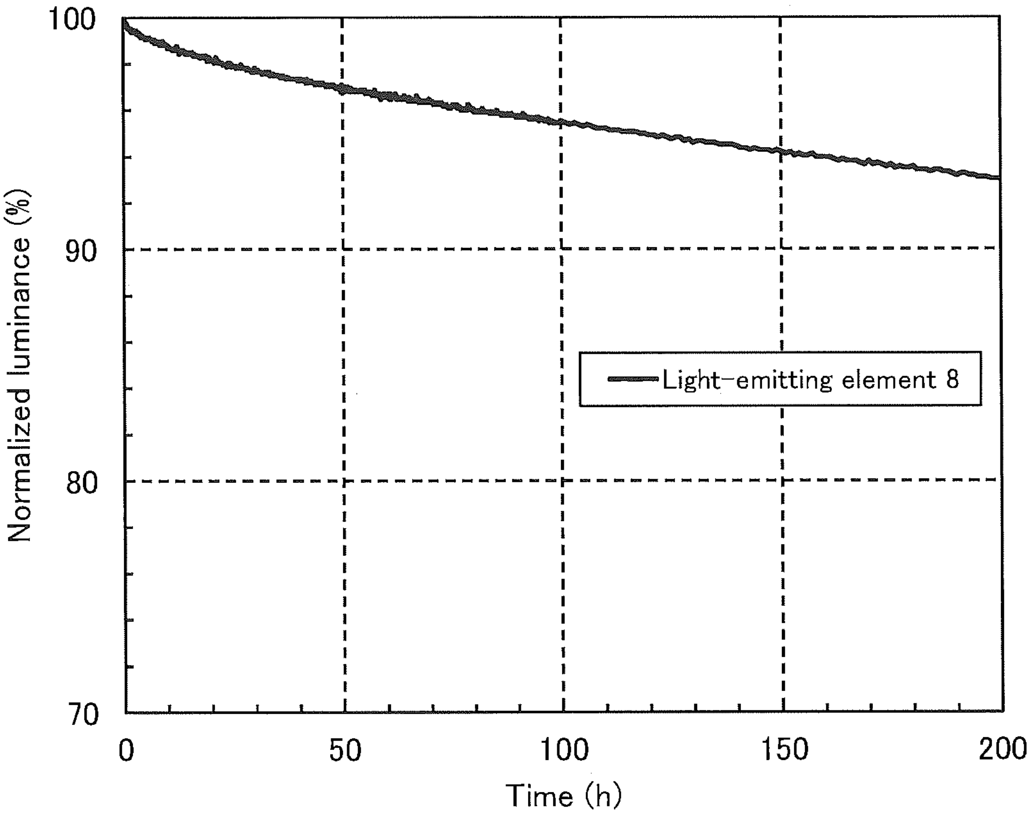
FIG. 45 is a diagram showing a result of a reliability test of a light-emitting element in Example.

Next, a driving test at a constant current of 2 mA was performed on the light-emitting element 8. FIG. 45 shows the result. As shown in FIG. 45, the light-emitting element 8 exhibited extremely favorable reliability with an $LT_{90}$ exceeding 250 hours. As compared to the above light-emitting element 1, the light-emitting element 8 exhibited higher reliability. The light-emitting element 8 differs from the light-emitting element 1 only in the materials used for the hole-injection layer 111 and the hole-transport layer 112.

It is found that the reliability of the light-emitting element of one embodiment of the present invention changes owing to the materials used for the hole-injection layer 111 and the hole-transport layer 112.

Reference Example 1

In this reference example, a method for synthesizing BPAPcgDBC, which was used in Example 8, will be described.

<Step 1: Synthesis of BPAPcgDBC>

In a 200-mL three-neck flask were put 2.2 g (5.1 mmol) of 5-bromo-7-phenyl-7H-dibenzo[c,g]carbazole, 1.9 g (7.7 mmol) of 4-phenyldiphenylamine, and 1.5 g (15 mmol) of sodium tert-butoxide. To this mixture was added 30 mL of toluene and 0.2 mL of a 10% hexane solution of tri(tert-butyl)phosphine, and this mixture was degassed by being stirred while the pressure was being reduced. To this mixture was added 29 mg (51 μmol) of bis(dibenzylideneacetone) palladium(0), and the mixture was heated and stirred at 110° C. for 7 hours under a nitrogen stream. After the stirring, toluene was added to the mixture and the resulting mixture was suction-filtered through Florisil, Celite, and alumina, so that a filtrate was obtained. The obtained filtrate was concentrated and a solid was obtained. This solid was purified by silica gel column chromatography (developing solvent: hexane:toluene=5:1 and then hexane:toluene=3:1) to give a solid. The obtained solid was recrystallized with ethyl acetate/ethanol, whereby 2.0 g of a pale yellow solid was obtained in a yield of 65%. The synthesis scheme of Step 1 is shown in (B-1) below.

[Chemical Formulae 41]

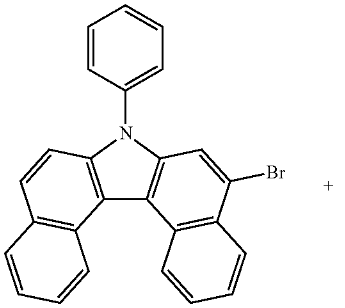

(B-1)

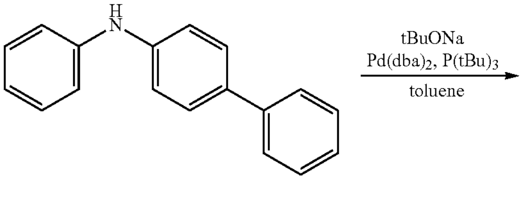

-continued

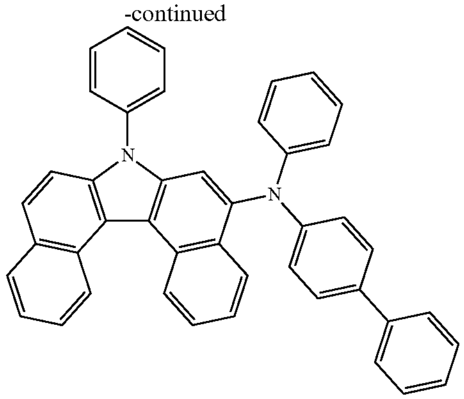

By a train sublimation method, 1.9 g of the obtained solid was sublimated and purified. Heating was performed at 265° C. under conditions where the pressure was 4.0 Pa and the flow rate of argon was 5 mL/min. After the sublimation purification, 1.8 g of a pale yellow solid was obtained in a collection rate of 92%.

Analysis data of the obtained solid by nuclear magnetic resonance ($^{1}$H NMR) spectroscopy are shown below.

$^{1}$H NMR (DMSO-$d_6$, 300 MHz): δ=6.97 (t, J1=7.2 Hz, 1H), 7.03-7.10 (m, 4H), 7.23-7.31 (m, 3H), 7.38-7.43 (m, 3H), 7.49-7.62 (m, 8H), 7.65-7.69 (m, 4H), 7.76-7.82 (m, 2H), 8.00 (d, J1=8.7 Hz, 1H), 8.15 (t, J1=7.8 Hz, 2H), 9.13 (d, J1=8.4 Hz, 1H), 9.21 (d, J1=7.8 Hz, 1H).

Figure 46A:
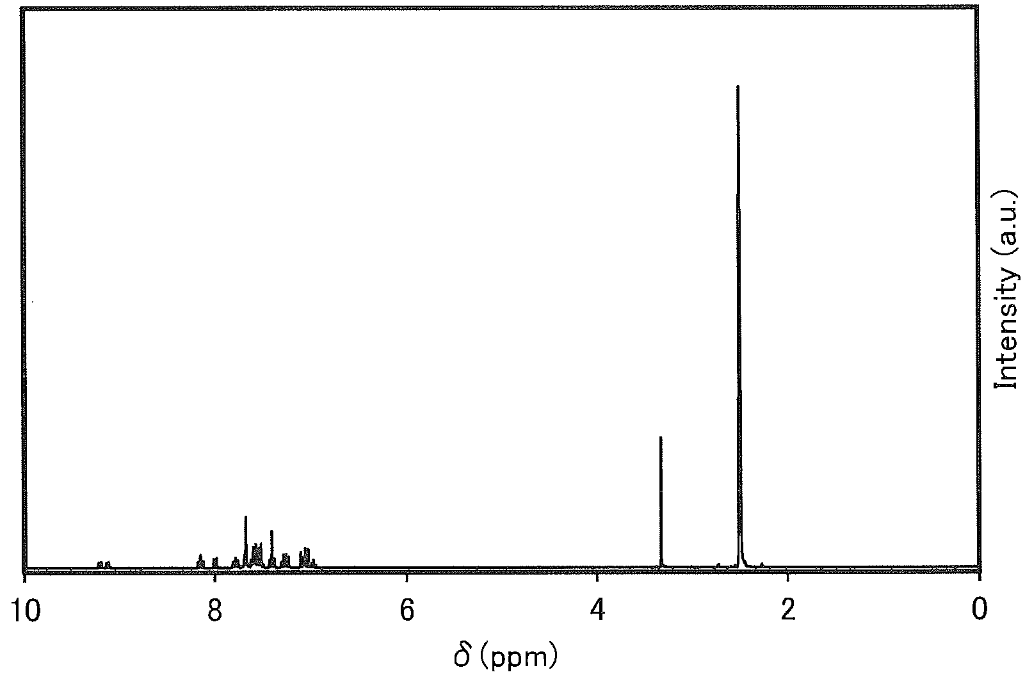
FIGS. 46A-46B are diagrams showing NMR charts of a comparative compound in Example.
Figure 46B:
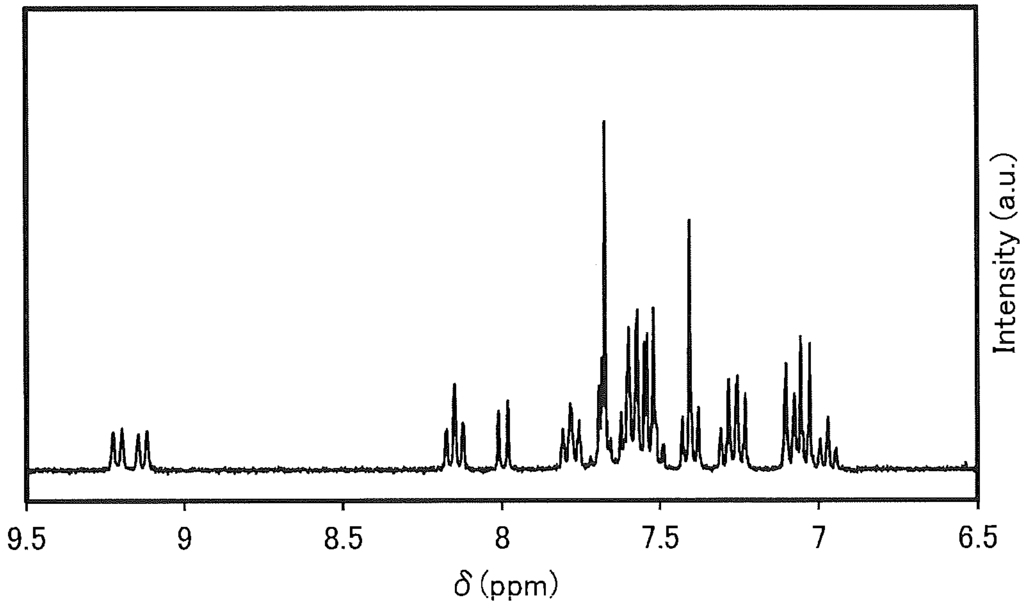

FIGS. 46(A) and 46(B) show $^{1}$H NMR charts of the obtained solid. Note that FIG. 46(B) is an enlarged diagram of the range of 6.5 ppm to 8.5 ppm of FIG. 46(A). The measurement results indicate that BPAPcgDBC, which was the target substance, was obtained.

<Characteristics of BPAPcgDBC>

It is found that the quantum yield of BPAPcgDBC in the toluene solution is 69% and the organic compound of one embodiment of the present compound, which is a diamine compound, has higher quantum yield than the case of the monoamine compound.

REFERENCE NUMERALS

100: EL layer, 101: electrode, 102: electrode, 106: light-emitting unit, 108: light-emitting unit, 110, light-emitting element, 111: hole-injection layer, 112: hole-transport layer, 113: electron-transport layer, 114: electron-injection layer, 115: charge-generation layer, 116: hole-injection layer, 117: hole-transport layer, 118: electron-transport layer, 119: electron-injection layer, 120, light-emitting layer, 121: host material, 122: guest material, 130: light-emitting layer, 131: host material, 132: guest material, 150: light-emitting element, 170: light-emitting layer, 250: light-emitting element, 601: source side driver circuit, 602: pixel portion, 603: gate side driver circuit, 604: sealing substrate, 605: sealing material, 607: space, 608: wiring, 610: element substrate, 611: switching TFT, 612: current controlling, 613: electrode, 614: insulator, 616: EL layer, 617: electrode, 618: light-emitting element, 623: n-channel TFT, 624: p-channel TFT, 900: portable information terminal, 901: housing, 902: housing, 903: display portion, 905: hinge portion, 910: portable information terminal, 911: housing, 912: display portion, 913: operation button, 914: external connection port, 915: speaker, 916: microphone, 917: camera, 920: camera, 921: housing, 922: display portion, 923: operation buttons, 924: shutter button, 926: lens, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1024B: electrode, 1024G: electrode, 1024R: electrode, 1024W: electrode, 1025B: lower electrode, 1025G: lower electrode, 1025R: lower electrode, 1025W: lower electrode, 1026: partition, 1028: EL layer, 1029: electrode, 1031: sealing substrate, 1032: sealing material, 1033: base material, 1034B: coloring layer, 1034G: coloring layer, 1034R: coloring layer, 1036: overcoat layer, 1037: interlayer insulating film, 1040: pixel portion, 1041: driver circuit portion, 1042: peripheral portion, 2100: robot, 2101: illuminance sensor, 2102: microphone, 2103: upper camera, 2104: speaker, 2105: display, 2106: lower camera, 2107: obstacle sensor, 2108: moving mechanism, 2110: arithmetic device, 3500: multifunction terminal, 3502: housing, 3504: display portion, 3506: camera, 3508: lighting, 3600: light, 3602: housing, 3608: lighting, 3610: speaker, 5000: housing, 5001: display portion, 5002: display portion, 5003: speaker, 5004: LED lamp, 5005: operation keys, 5006: connection terminal, 5007: sensor, 5008: microphone, 5012: support, 5013: earphone, 5100: cleaning robot, 5101: display, 5102: camera, 5103: brush, 5104: operation buttons, 5120: dust, 5140: portable electronic apparatus, 5150: portable information terminal, 5151: housing, 5152: display region, 5153: bend portion, 8501: lighting device, 8502: lighting device, 8503: lighting device, 8504: lighting device, 9000: housing, 9001: display portion, 9006: connection terminal, 9055: hinges, 9200: portable information terminal, 9201: portable information terminal, 9202: portable information terminal This application is based on Japanese Patent Application Serial No. 2017-155324 filed with Japan Patent Office on Aug. 10, 2017, the entire contents of which are hereby incorporated herein by reference.

The invention claimed is:

1. A light-emitting element comprising a light-emitting layer between a pair of electrodes, wherein the light-emitting layer comprises a host material and a guest material, wherein the light-emitting layer emits light derived from the guest material, wherein the guest material is an organic compound represented by General Formula (G2), and (G2)

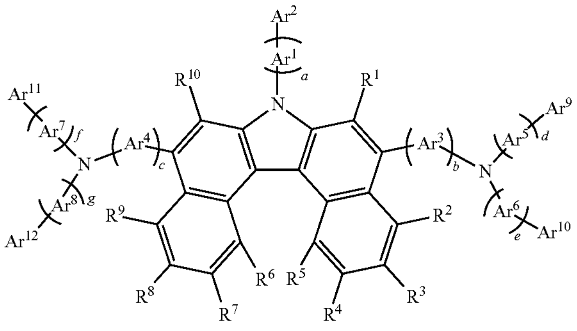

wherein in General Formula (G2):

each of $Ar^1$ and $Ar^3$ to $Ar^8$ independently represents a substituted or unsubstituted arylene group having 6 to 25 carbon atoms;

$Ar^2$ represents a substituted or unsubstituted aryl group having 6 to 25 carbon atoms;

each of a, d, e, f, and g independently represents an integer of 0 to 3, and each of b and c independently represents an integer of 1 to 3;

each of $Ar^9$ to $Ar^{12}$ independently represents a substituted or unsubstituted aryl group having 6 to 100 carbon atoms or a substituted or unsubstituted heteroaryl group having 3 to 100 carbon atoms; and each of $R^1$ to $R^{10}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

2. The light-emitting element according to claim 1, wherein the guest material is an organic compound represented by General Formula (G3), and (G3)

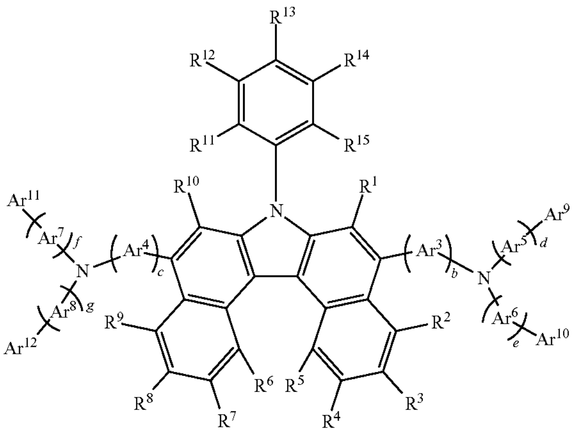

wherein:

each of $R^{11}$ to $R^{15}$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

3. The light-emitting element according to claim 1, wherein each of $Ar^9$ and $Ar^{11}$ is independently any one of a substituted or unsubstituted phenyl group, biphenyl group, naphthyl group, triphenylyl group, fluorenyl group, carbazolyl group, dibenzothiophenyl group, dibenzofuranyl group, benzofluorenyl group, benzocarbazolyl group, naphthobenzothiophenyl group, naphthobenzofuranyl group, dibenzofluorenyl group, dibenzocarbazolyl group, dinaphthothiophenyl group, dinaphthofuranyl group, and phenanthryl group.

4. The light-emitting element according to claim 1, wherein each of $Ar^{10}$ and $Ar^{12}$ independently represents any one of substituents represented by General Formulae (Ht-1) to (Ht-7), (Ht-1)

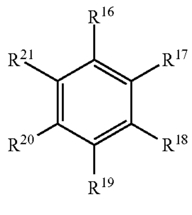

-continued (Ht-2)

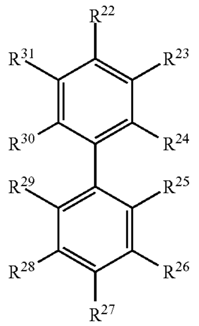

(Ht-3)

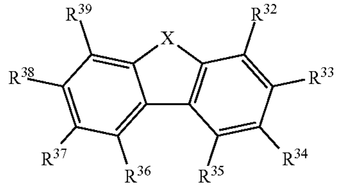

(Ht-4)

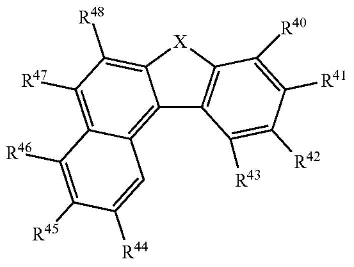

(Ht-5)

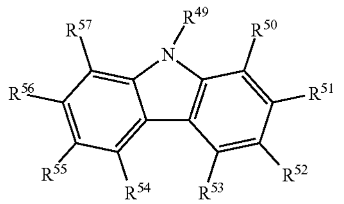

-continued (Ht-6)

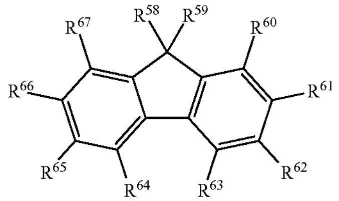

(Ht-7)

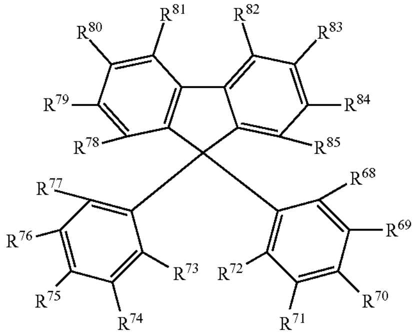

wherein in General Formulae (Ht-3) and (Ht-4):

X represents oxygen or sulfur, and wherein in General Formulae (Ht-1) to (Ht-7):

any one of $R^{16}$ to $R^{21}$, any one of $R^{22}$ to $R^{31}$, any one of $R^{32}$ to $R^{39}$, any one of $R^{40}$ to $R^{48}$, any one of $R^{49}$ to $R^{57}$, any one of $R^{58}$ to $R^{67}$, and any one of $R^{68}$ to $R^{77}$ each represent a single bond to $Ar^6$ or $Ar^8$; and the other $R^{16}$ to $R^{85}$ each independently represent hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

5. A electronic device comprising:

the light-emitting element according to claim 1.

6. A display device comprising:

the electronic device according to claim 5; and at least one of a color filter and a transistor.

7. A light-emitting element comprising a light-emitting layer between a pair of electrodes, wherein the light-emitting layer comprises a host material and a guest material, wherein the light-emitting layer emits light derived from the guest material, and wherein the guest material is an organic compound represented by Structural Formula (168), (168)
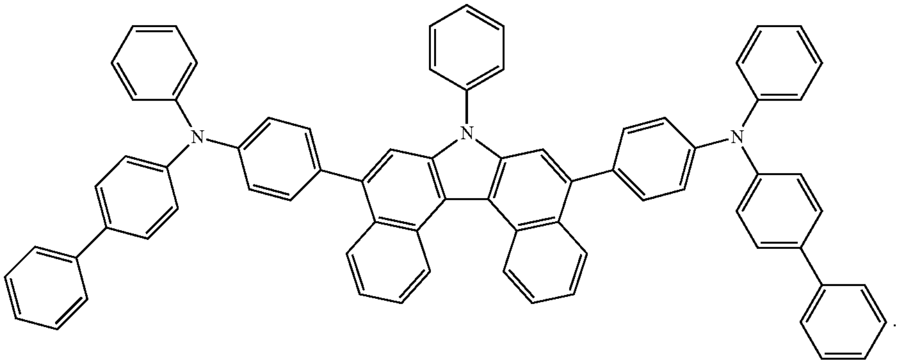
8. A electronic device comprising:
the light-emitting element according to claim 7.
9. A display device comprising:
the electronic device according to claim 8; and
at least one of a color filter and a transistor.
* * * * *